(12) United States Patent
Jakobovits et al.

(10) Patent No.: US 12,364,714 B2
(45) Date of Patent: Jul. 22, 2025

(54) METHODS FOR SELECTIVE EXPANSION OF GAMMA DELTA T-CELL POPULATIONS AND COMPOSITIONS THEREOF

(71) Applicant: ADICET THERAPEUTICS, INC., Redwood City, CA (US)

(72) Inventors: Aya Jakobovits, Beverly Hills, CA (US); Orit Foord, Foster City, CA (US); Andy An-deh Lin, Palo Alto, CA (US); Marianne Theresa Santaguida, Belmont, CA (US); Radhika Chetan Desai, Brisbane, CA (US); Yifeng Frank Jing, Hayward, CA (US); Daulet Kadyl Satpayev, Redwood City, CA (US); Yan Li, San Carlos, CA (US)

(73) Assignee: ADICET THERAPEUTICS, INC., Redwood City, CA (US)

( * ) Notice: Subject to any disclaimer, the term of this patent is extended or adjusted under 35 U.S.C. 154(b) by 748 days.

(21) Appl. No.: 17/718,152

(22) Filed: Apr. 11, 2022

(65) Prior Publication Data
US 2022/0372439 A1 Nov. 24, 2022

Related U.S. Application Data

(62) Division of application No. 15/563,830, filed as application No. PCT/US2017/032530 on May 12, 2017, now Pat. No. 11,299,708.

(60) Provisional application No. 62/335,572, filed on May 12, 2016.

(51) Int. Cl.
| | |
|---|---|
| C07K 16/28 | (2006.01) |
| A61K 35/17 | (2015.01) |
| A61K 40/11 | (2025.01) |
| A61K 40/24 | (2025.01) |
| A61K 40/31 | (2025.01) |
| A61K 40/32 | (2025.01) |
| A61K 40/42 | (2025.01) |
| C12N 5/0783 | (2010.01) |

(52) U.S. Cl.
CPC ............. *A61K 35/17* (2013.01); *A61K 40/11* (2025.01); *A61K 40/24* (2025.01); *A61K 40/31* (2025.01); *A61K 40/32* (2025.01); *A61K 40/42* (2025.01); *C07K 16/2809* (2013.01); *C12N 5/0636* (2013.01); *A61K 2239/31* (2023.05); *A61K 2239/38* (2023.05); *C07K 2317/74* (2013.01); *C07K 2317/75* (2013.01)

(58) Field of Classification Search
None
See application file for complete search history.

(56) References Cited

U.S. PATENT DOCUMENTS

| | | |
|---|---|---|
| 5,185,250 A | 2/1993 | Brenner et al. |
| 5,260,223 A | 11/1993 | Brenner et al. |
| 7,728,114 B2 | 6/2010 | Mach et al. |
| 7,985,739 B2 | 7/2011 | Kay et al. |
| 9,540,448 B2 | 1/2017 | Scheinberg et al. |
| 2003/0138433 A1 | 7/2003 | Newell et al. |
| 2006/0122130 A1 | 6/2006 | Rabbani |
| 2006/0205089 A1 | 9/2006 | Dratz et al. |
| 2008/0026986 A1 | 1/2008 | Wang et al. |
| 2008/0171014 A1 | 7/2008 | Wu et al. |
| 2010/0272739 A1 | 10/2010 | Gelfand et al. |
| 2012/0034221 A1 | 2/2012 | Bonvini et al. |
| 2014/0141513 A1 | 5/2014 | De Carvalho Silva Santos et al. |
| 2015/0259645 A1 | 9/2015 | Poupot et al. |
| 2018/0169147 A1 | 6/2018 | Anjos et al. |

FOREIGN PATENT DOCUMENTS

| | | |
|---|---|---|
| CN | 1506456 A | 6/2004 |
| CN | 102994448 A | 3/2012 |
| WO | WO 1993/020221 A1 | 10/1993 |
| WO | WO 2001/022816 A1 | 4/2001 |
| WO | WO 2003/087341 A2 | 10/2003 |
| WO | WO 2011/090804 A1 | 7/2011 |
| WO | WO 2012/012667 A2 | 1/2012 |
| WO | WO 2012/156958 A | 11/2012 |
| WO | WO 2013/074916 A | 5/2013 |
| WO | WO 2013/079174 A1 | 6/2013 |
| WO | WO 2014/009370 A2 | 1/2014 |
| WO | WO 2014/134412 A1 | 9/2014 |
| WO | WO 2015/061694 A2 | 4/2015 |
| WO | WO 2015/156673 A2 | 10/2015 |
| WO | WO 2016/081518 A2 | 5/2016 |
| WO | WO 2016/198480 A1 | 12/2016 |
| WO | WO 2017/011804 A1 | 1/2017 |
| WO | WO 2017/197347 A1 | 11/2017 |

OTHER PUBLICATIONS

Ali et al., "γδ T Cell Immune Manipulatino during Chroinic Phase of Simian HIV Infection Confers Immunological Benefits", J. Immunol., vol. 183, No. 8, pp. 5407-5417 (2009).

(Continued)

*Primary Examiner* — Zachary S Skelding
(74) *Attorney, Agent, or Firm* — Todd Lorenz

(57) ABSTRACT

The present invention relates to methods for the selective expansion of γδ T-cell population(s), compositions and admixtures thereof and methods for using the same as a therapeutic. Non-engineered and engineered, enriched γδ T-cell populations of the disclosure are useful in the treatment of various cancers, infectious diseases, and immune disorders.

31 Claims, 55 Drawing Sheets

Specification includes a Sequence Listing.

(56) References Cited

OTHER PUBLICATIONS

Appay et al., "Memory CD8+ T cells vary in differentiation phenotype in different persistent virus infections," Nature Medicine, vol. 8, pp. 379-385 (2002).
Avdalovic et al., "Adhesion and costimulation of proliferative responses of human γδ T cells by interaction of VLA-4 and VLA-5 with fibronectin", Immunology Letters, vol. 35, No. 2, pp. 101-108 (1993).
Bauer et al., Gene Therapey for HIV: From Inception 49 to a Possible Cure, SpringBriefs in Biochemistry and Molecular Biology, Chapter 7, pp. 49-54 (2014).
Biocompare, "Monoclonal Antibody Anti-Human TCR PAN [gamma]/[delta] PN IM1349—Purified—Freeze-dried—0.1 mg—Clone IMMU510 for Research Use Only. Not for use in diagnostic procedures", Beckman Coulter: Jan. 1, 2006, p. 1, left-hand column paragraph 1, Retrieved from the Internet: at URL:https://www.bc-cytometry.com/PDF/DataSheet/IM1349.pdf [on Apr. 8, 2019].
Bornstein et al., "Development of a new fully human anti-CD20 monoclonal antibody for the treatment of B-cell malignancies," Investigational New Drugs., Vo. 28, Issue 5, pp. 561-574 (2010).
Boucherma et al., "HLA-A*01:03, HLA-A*24-02, HLA-B8:08-01, HLA-B*27:05, HLA-B*35:01, HLA-B*44:02, and HLA-C*07:01 Monochain Transgenic/H-2 Class I Null Mice: Novel Versatile Preclinical Models of Human T Cell Responses," J. Immunol., vol. 191, pp. 583-593 (2013).
Carding and Egan, "γδ Tcells: Functional Plasticity and Heterogeneity," Nat Rev Immunol vol. 2, pp. 336-345 (2002).
Cheever et al., "The Prioritization of Cancer Antigens: A National Cancer Institute Pilot Project for the Acceleration of Translational Research, "Clin. Cancer Res., vol. 15(17), pp. 5323-5337 (2009).
Chen et al., "Selection and analysis of an optimized anti-VEGF antibody: crystal structure of an affinity-matured Fab in complex with antigen," J. Mol. Biol. vol. 293, pp. 865-881 (1999).
Chothia and Lesk, "Canonical Structures for the Hypervariable Regions of Immunoglobulins," J. Mol. Biol., vol. 196, pp. 901-917 (1987).
Chothia et al., "Conformations of immunoglobulin hypervariable regions, "Nature, vol. 342, pp. 878-883 (1989).
Ciccone, "A monoclonal antibody specific for a common determinant of the human T cell receptor gamma/delta directly activates CD3+WT31- lymphocytes to express their functional program(s)", The Journal of Experimental Medicine, vol. 168, pp. 1-11 (1988).
Dao et al. "Targeting the intracellular WT1 oncogene product with a therapeutic human antibody" Science translational medicine, vol. 5(176): 176ra33, pp. 1-22 (2013).
Damschroder et al., "Analysis of human and primate CD2 molecules by protein sequence and epitope mapping with anti-human CD2 antibodies," Mol Immunol, vol. 41(10) pp. 985-1000 (2004).
Daubenberger et al., "Functional and Structural Similarity of Vγ9Vδ2 T Cells in Humans and Aotus Monkeys, a Primate Infection Model for Plasmodium falciparum Malaria," J Immunol, vol. 167, pp. 6421-6430 (2001).
Davis and Merwe, "The structure and ligand interactions of CD2: implications for T-cell function," Immunol. Today, vol. 17, Issue 4, pp. 177-187 (1996).
Deniger et al., "Bispecific T-cells Expressing Polyclonal Repertoire of Endogenous γδ T-cell Receptors and Introduced CD19-specific Chimeric Antigen Receptor," Molecular Therapy, vol. 21, No. 3, pp. 638-647 (2013).
Deniger et al., "Clinical applications of gamma delta T cells with multivalent immunity " Front. & Immunology, vol. 5, pp. 1-12 (2014).
Dohan & Reiter, "T-cell-receptor-like antibodies -generation, function and applications, "Expert Rev Mol Med., vol. 14(e6), pp. 1-17 (2012).
Dokouhaki et al., Adoptive immunotherapy of cancer using ex vivo expanded human γδ T cells: A new approach, Cancer Letters, vol. 297, pp. 126-136 (2010).
Edwards et al., "The Remarkable Flexibility of theHuman Antibody Repertoire; Isolation of Over One Thousand Different Antibodies to a Single Protein, BLyS", J. Mol. Biol., vol. 334, pp. 102-118 (2003).
Ehl et al., "A variant of SCID with specific immune responses and predominance of gamma delta T cells", J. of Clinical Investigation, vol. 115, No. 11, pp. 3140-3148 (2005).
Fisher et al., "Neuroblastoma Killing Properties of Vδ2 and Vδ2-Negative γδT Cells Following Expansion by Artificial Antigen-Presenting Cells," Clinical Cancer Research, vol. 20, No. 22, pp. 5720-5732 (2014).
Gonzalez et al., "Humanized mice: novel model for studying mechanisms of human immune-based therapies," Immunol. Res. vol. 57, pp. 326-334 (2013).
Gra et al., "Analysis of T-Cell Receptor-γ Gene Rearrangements Using Oligonucleotide Microchip: A Novel Approach for the Determination of T-Cell Clonality," Journal of Molecular Diagnostics, vol. 9, No. 2 pp. 249-257 (2007).
Green, et al., "Recognition of nonpeptide antigens by human V gamma 9V delta 2 T cells requires contact with cells of human origin", Clin Exp Immunol., vol. 136(3), pp. 472-482 (2004).
Groh et al., "Broad tumor-associated expression and recognition by tumor-derived gamma delta T cells of MICA and MICB," PNAS, vol. 96, pp. 6879-6884 (1999).
Hamers-Casterman et al., "Naturally occurring antibodies devoid of light chains," Nature, vol. 63, pp. 446-448 (1993).
Harlow et al. Antibodies, A Laboratory Manual, Cold Spring Harbor laboratory, pp. 37-47 (1988).
Hayday A.C., "γδ Cells: A Right Time and Right Place for a Conserved Third Way of Protection," Annu Rev Immunol. vol. 18, pp. 975-1026 (2000).
Hayday and Pennington, "Key factors in the organized chaos of early T cell development," Nature Immunology. vol. 8, No. pages 137-144 (2007).
Hiasa et al., "Dual specificity of αβ-γδ TCR T cells: transformation of Vγ9Vδ2 T cells with MAGE-A4143-151 specific αβ type TCR genes," Annual Meeting of the Japanese Cancer Association, vol. 66, p. 423 (2007).
Hua et al., "Potentinal regulatory role of in vitro-expanded Vδ1 T cells from human peripheral blood," Immunol Res. vol. 56, pp. 172-180 (2013).
Jakobovits et al., "Production of fully human antibodies by transgenic mice," Curr. Opin. Biotechnol., vol. 6, Issue 5, pp. 561-566 (1995).
Janssens et al., "Generation of heavy-chain-only antibodies in mice," PNAS, vol. 103, No. 41, p. 15130-15135 (2006).
Jin et al., "Oligoclonal expansion of TCR Vδ T cells may be a potential immune biomarker for clinical outcome of acute myeloid leukemia, "Journal of Hematology & Oncology vol. 9:126, pp. 1-7 (2016).
Kabelitz et al., "The primary response of human gamma/delta+ T cells to Mycobacterium tuberculosis is restricted to Vgamma 9-bearing cells.", The Journal of experimental medicine 173.6, pp. 1331-1338 (1991).
Kabelitz and He, "The Multifunctionality of Human Vγ9Vδ2 γδ T Cells: Clonal Plasticity or Distinct Subsets? : Plasticity of Human γδ T Cells," Scandinavian Journal of Immunology, vol. 76, pp. 213-222 (2012).
Kang et al., "Adoptive immunotherapy of lung cancer with immobilized anti-TCRγδ antibody-expanded human γδ T-cells in peripheral blood," Cancer Biology & Therapy, vol. 8, Issue 16, pp. 1540-1549 (2009).
Kim and Hong, "Humanization by CDR Grafting and Specificity-Determining Residue Grafting," Methods in Molecular Biology, vol. 907, pp. 237-245 (2012).
Klebanoff et al., "CD8+ T-cell memory in tumor immunology and immunotherapy, "Immunol Rev., vol. 211, pp. 214-224 (2006).
Kress et al., Distinct gene expression in human Vδ1 and Vδ2 γδ T cells following non-TCR agonist stimulation, Molecular Immunology, vol. 43, pp. 2002-2011 (2006).
Kondo et al., "Zoledronate facilitates large-scale ex vivo expansion of functional γδ T cells from cancer patients for use in adoptive immunotherapy," Cytotherapy, vol. 10, No. 8, pp. 842-856 (2008).

(56) References Cited

OTHER PUBLICATIONS

Lamb and Lopez, "γδ T cells: A New Frontier for Immunotherapy?," Biology of Blood and Marrow Transplantation, vol. 11, pp. 161-168 (2005).

Lang et al., "Pilot trial of interleukin-2 and zoledronic acid to augment γδ T cells as treatment for patients with refractory renal cell carcinoma," Cancer Immunol Immunother, vol. 60, pp. 1447-1460 (2011).

Lefranc et al., "IMGT unique numbering for immunoglobulin and T cell receptor variable domains and Ig superfamily V-like domains," Developmental & Comparative Immunology, vol. 27, pp. 55-77 (2003).

Li et al, "Transgenic mice with a diverse human T cell antigen receptor repertoire," Nature Med.Vol. 16, pp. 1029-1035 (2010).

Linguiti et al., "Genomic and expression analyses of T cell receptor gamma (TRG) and alph/delta (TRA/TRD) loci reveal a similar basic public γδ repertoire in dolphin and human," MBC Genomics, vol. 17, No. 634, pp. 1-17 (2016).

Lloyd et al., "Modelling the human immune response: perfomance of a $10^{11}$ human antibody reperoire against a broad panel of therapeutically relevant antigens", Protein Engineering, Design & Selection, vol. 22, No. 3, pp. 1590168 (2009).

Lopez et al., "CD2-mediated IL0120dependent signals render human -T cells resistant to mitogen-induced apoptosis, permitting the large-scale ex vivo expansion of functionally distinct lymphocytes: implications for the development of adoptive immunotherapy strategies," Blood, vol. 96, pp. 3827-3837 (2000).

Luoma et al., "γδ T cell surveillance via CD1 molecules," Trens in Immunolgoy, vol. 35, No. 12, pp. 613-621 (2014).

Malmborg et al., "BIAcore as a tool in antibody engineering," J. Immunol. Methods, vol. 183, pp. 7-13 (1995).

Mangan et al., "Cutting Edge: CD1d Restriction and Th1/Th2/Th17 Cytokine Secretion by Human V 3 T Cells," J. of Immunol., vol. 191, pp. 30-34 (2013).

Michie et al., "Lifespan of human lymphocyte subsets defined by CD45 isoforms," Nature, vol. 360, pp. 364-365 (1992).

Moonka and Loh, "A consensus primer to amplify both α and β chains of the human T cell receptor," Journal of Immunological Methods, vol. 169, pp. 41-51 (1994).

Nagamine et al., Induction of γδ T Cells Using Zoledronate Plus Interleukin-2 in Patients with Metastatic Cancer, Hiroshima J. Med. Sci, vol. 58, No. 2, pp. 37-44 (2009).

Nakajima et al., "A phase I study of adoptive immunotherapy for recurrent non-small-cell lung cancer patients with autologous γδ T cells," European Journal of Cardio-thoracic Surgery, vol. 37, pp. 1191-1197 (2010).

Nicol et al., "Clinical evaluation of autologous gamma delta T cell-based immunotherapy for metastatic solid tumours," British Journal of Cancer, vol. 105, pp. 778-786 (2011).

Nussbaumer et al., "Essential Requirements of Zoledronate-Induced Cytokine and γδ T Cell Proliferative Responses,", J. of Immunol., vol. 191, No. 3, pp. 1346-1355 (2013).

Oberg et al., "γδ T cell activation by bispecific antibodies," Cellular Immunology, vol. 296, pp. 41-49 (2015).

Petros et al., "Improved analysis of TCR γδ variable region expression in humans," Journal of Immunological Methods, vol. 434, pp. 66-72 (2016).

Peyrat et al., "Repertoire analysis of human peripheral blood lymphocytes using a human V delta 3 region-specific monoclonal antibody. Characterization of dual T cell receptor (TCR) delta-chain expressors and alpha beta T cells expressing V delta 3J alpha C alpha-encoded TCR chains", J of Immunology, vol. 155, pp. 3060-3067 (1995).

Qi et al., "Immobilized MICA Could Expand Human Vδ1 γδT Cells In Vitro that Displayed Major Histocompatibility Complex Class I Chain-Related A-Dependent Cytotoxicity to Human Epithelial Carcinomas." Scandinavian Journal of Immunology, vol. 58, No. 2, pp. 211-220 (2003).

Rei et al., "The Emerging Protumor Role of γδ T Lymphocytes: Implications for Cancer Immunotherapy," Cancer Research, vol. 75(5), pp. 798-802 (2015).

Romagne F et al., "Structural analysis of gammadelta TCR using a novel set of TCR gamma and delta chain-specific monoclonal antibodies generated against soluble gammadelta TCR Evidence for a specific conformation adopted by the Jdelta2 region and for a Vdelta1 polymorphism", Journal of Immunological Methods, vol. 189, No. 1, pp. 25-36 (1996).

Sagar et al., "In vivo immunogenicity of Tax(11-19) epitope in HLA-A2/DTR transgenic mice: Implication for dendritic cell-based anti-HTLV-1 vaccine," Vaccine, vol. 32, , pp. 3274-3284 (2014).

Saitoh et al., "Anti-tumor cytotoxicity of γδ T cells expanded from peripheral blood cells of patients with myeloma and lymphoma," Med Oncol., vol. 25, pp. 137-147 (2008).

Sallusto et al., "Two subsets of memory T lymphocytes with distinct homing potentials and effector functions," Nature, vol. 401, p. 708-712 (1999).

Scheinberg et al., "Reaching Un-Drugable Intracellular Targets with the Long Arm of Antibodies," Oncotarget, vol. 4(5), pp. 647-648 (2013).

Scheper et al., "Hunting for clinical translation with innate-like immune cells and their receptors", Leukemia, vol. 28, No. 6, pp. 1181-1190 (2014).

Shang et al., "Rational optimization of tumor epitopes using in silico analysis-assisted substitution of TCR contact residues," European Journal of Immunology, vol. 39, pp. 2248-2258 (2009).

Sheriff and Constantine, "Redefining the minimal antigen-binding fragment," Nature Struct. Biol., vol. 3, No. 9, pp. 733-736 (1996).

Siegers et al., "Human V delta 1 gamma delta T cells expanded from peripheral blood exhibit specific cytotoxicity against B-cell chronic lymphocytic leukemia-derived cells", Cytoherapy, vol. 13, No. 6, pp. 753-764 (2011).

Siegers et al., "Extensive expansion of primary human gamma delta T cells generates cytotoxic effector memory cells that can be labeled with Feraheme for cellular MRI", Cancer Immunol. Immunother, vol. 62(3), pp. 571-583 (2012).

Taupin et al., "An enlarged subpopulation of T lymphocytes bearing two distinct [gamma][delta] TCR in an HIV-positive patient", International Immunology, vol. 11, No. 4, pp. 545-552 (1999).

TermoFisher Cientific—Useful Numbers for Cell Culture— obtained from www.thermofisher.com/us/en/home/references/gibo-cell-culture-basics/cell-culture-protocols/cell-culture-useful-numbers.html on Apr. 5, 2016 via the WayBackMachine, p. 1 (2016).

Vantourout et al., "Specific requirements for Vγ9Vδ2 T cell stimulation by a natural adenylated photphoantigen", J. Immunol., vol. 183(6), pp. 3848-3857 (2009).

Weidanz et al., "TCR-Like Biomolecules Target Peptide/MHC Class I Complexes on the Surface of Infected and Cancerous Cells," Int. Rev. Immunol., vol. 30, pp. 328-340 (2011).

Wild et al., "Dependence of T Cell Antigen Recognition on the Dimensions of an Accessory Receptor-Ligand Complex," J. Exp. Med, vol. 190, No. 1, pp. 31-41 (1999).

Wilhelm et al., "γδ T cells for immune therapy of patients with lymphoid malignancies," Blood, vol. 102, No. 1, pp. 200-206 (2003).

Wilhelm et al., "Successful adoptive transfer and in vivo expansion of haploidentical γδ T Cells," J Transl Med., vol. 12, pp. 1-6 (2014).

Wistuba-Hamprecht K, Pawelec G, Derhovanessian E. OMIP-020: phenotypic characterization of human γδ T-cells by multicolor flow cytometry. Cytometry A., vol. 85(6) pp. 522-524 (2014).

Wu et al., "Ex vivo expanded human circulating Vδ1 γδ T cells exhibit favorable therapeutic potential for colon cancer," Oncoimmunology, vol. 4:3, pp. e992749-13 (2015).

Xu et al., "Diversity in the CDR3 region of V(H) is sufficient for most antibody specificities," Immunity, vol. 13, pp. 37-45 (2000).

Yin, et al., "Hyperactivation and in situ recruitment of inflammatory Vδ2 T cells contributes to disease pathogensissi in systemic lupus erythematosus,", Scientific Reports 5:14432, pp. 1-12 (2015).

Yoon et al., "The Cell Cycle Time of CD8+ T Cells Responding in Vivo Is Controlled by the Type of Antigenic Stimulus," PLOS One, vol. 5(11), pp. 1-12 (2010).

(56) References Cited

OTHER PUBLICATIONS

Yu et al., "Expansion and Immunological Study of Human Tumor Infiltrating Gamma-Delta T Lymphocytes in vitro," Int Arch Allergy Immunol, vol. 119, pp. 31-37 (1999).
Zapata et al., "Engineering linear F(ab')2 fragments for efficient production in *Escherichia coli* and enhanced antiproliferative activity," Protein Eng. vol. 8, No. 10, pp. 1057-1062 (1995).
Zhou et al., "Anti-γδ TCR antibody-expanded γδ T cells: a better choice for the adoptive immunotherapy of lymphoid malignancies," Cellular & Molecular Immunology, vol. 9, pp. 34-44 (2012).

V delta 1

```
                                                                CDR1-IMGT
  1   2   3   4   5   6   7   8   9  10  11  12  13  14  15  16  17  18  19  20    21  22  23  24  25  26  27  28  29  30  31  32  33  34  35  36  37  38  39  40
  A   Q   K   V   T   Q   A   Q   S   S   V   S   M   P   V   R   K   A   V   T     L   N   C   L   Y   E   T   S   W   W   S   Y   Y   .   .   .   .   .   I   F
 GCC CAG AAG GTT ACT CAA GCC CAG TCA TCA GTA TCC ATG CCA GTG AGG AAA GCA GTC ACC   CTG AAC TGC CTG TAT GAA ACA AGT TGG TGG TCA TAT TAT . . . . . ATT TTT

CDR2-
 41  42  43  44  45  46  47  48  49  50  51  52  53  54  55  56  57  58  59  60    61  62  63  64  65  66  67  68  69  70  71  72  73  74  75  76  77  78  79  80
  W   Y   K   Q   L   P   S   K   E   M   I   F   L   I   R   Q   G   S   .   .     .   .   .   .   .   D   E   Q   N   A   K   S   .   G   R   Y   S   V   N   F
 TGG TAC AAG CAA CTT CCC AGC AAA GAG ATG ATT TTC CTT ATT CGC CAG GGT TCT . .       . . . . . GAT GAA CAG AAT GCA AAA AGT . GGT CGC TAT TCT GTC AAC TTC

CDR3-IMGT
 81  82  83  84  85  86  87  88  89  90  91  92  93  94  95  96  97  98  99 100   101 102 103 104 105 106 107 108
  K   K   A   A   K   S   V   A   L   T   I   S   A   L   Q   L   E   D   S   A     K   Y   F   C   A   L   G   E
 AAA AAA GCA GCG AAA TCC GTC GCC TTA ACC ATT TCA GCC TTA CAG CTA GAA GAT TCA GCA   AAG TAC TTT TGT GCT CTT GGG GAA CT
```

FIG. 14

V delta 2

```
       1    2    3    4    5    6    7    8    9    10   11   12   13   14   15   16   17   18   19   20
       A    I    E    L    V    P    E    H    Q    T    V    P    V    S    I    G    V    P    A    T
       GCC  ATT  GAG  TTG  GTC  CCT  GAA  CAC  CAA  ACA  GTG  CCT  GTG  TCA  ATA  GGG  GTC  CCT  GCC  ACC
                                                                                    I
                                                                               A--  A--  A--

CDR1-IMGT
       21   22   23   24   25   26   27   28   29   30   31   32   33   34   35   36   37   38   39   40
       L    R    C    S    M    K    G    E    A    I                        G    N    Y    Y    I    N
       CTC  AGG  TGC  TCC  ATG  AAA  GGA  GAA  GCG  ATC  ...  ...  ...  ...  GGT  AAC  TAC  TAT  ATC  AAC

CDR2-
       41   42   43   44   45   46   47   48   49   50   51   52   53   54   55   56   57   58   59   60
       W    Y    R    K    T    Q    N    G    T    I    T    F    I    Y    R    E    K    D
       TGG  TAC  AGG  AAG  ACC  CAA  AAC  GGT  ACA  ATC  ACT  TTC  ATA  TAC  CGA  GAA  AAG  GAC  ...  ...
                                                   M
                                                   -G

IMGT
       61   62   63   64   65   66   67   68   69   70   71   72   73   74   75   76   77   78   79   80
                                     I    Y    G    P    G    E    K    D    N    F    Q    G    D    I
       ...  ...  ...  ...  ...  ...  ATC  TAT  GGC  CCT  GGT  TTC  AAA  GAC  AAT  TTC  CAA  GGT  GAC  ATT 81   82   83   84   85   86   87   88   89   90   91   92   93   94   95   96   97   98   99   100
       D    I    A    K    N    L    A    V    L    K    I    L    A    P    S    E    R    D    E    G
       GAT  ATT  GCA  AAA  AAC  CTG  GCT  GTA  CTT  AAG  ATA  CTT  GCA  CCA  TCA  GAG  AGA  GAT  GAA  GGG

CDR3-IMGT
       101  102  103  104  105  106  107  108
       S    Y    Y    C    A    C    D    T
       TCT  TAC  TAC  TGT  GCC  TGT  GAC  ACC
```

FIG. 15

| | Vδ1 | N-D-N | J | TS1 | TS8.2 | R9.12 |
|---|---|---|---|---|---|---|
| BE-13 | AKYFCALG--TGVRGLQD---TDKLIFGKGTRVTVEPRSQPHT | | | + | + | + |
| δ1J1 | AKYFCALLPFLPSDWGIP--VTDKLIFGKGTRVTVEPRSQPHT | | | + | + | + |
| δ1J2 | AKYFCALG--EAPSAWGKH--LTAQLFFGKGTQLIVEPRSQPHT | | | + | + | + |
| δ1J3 | AKYFCALG-EAPSAWGKHSWDTRQMFFGKGTIKLFVEPRSQPHT | | | − | − | + |

Site Directed Mutagenesis

| | | | | | | |
|---|---|---|---|---|---|---|
| BE-13 | AKYFCALG--TGVRGLQD---TDKLIFGTGTRVTVEPRSQPHT | | | − | − | + |
| δ1J3 | AKYFCALG-EAPSAWGKHSWDTRQMFFGKGIKLFVEPRSQPHT | | | + | + | + |

FIG. 24

| | |
|---|---|
| Human Vδ1 | AQKVTQAQSSVSMPVRKAVTLNCLYETSWWSYYIFWYKQLPSKEMIFLIR |
| Human Vδ1 Mut1 | AQKVTQAQSSVSMPVRKAVTLNCLYETSWWSYYIFWYKQLPSKEMIFLIR |
| Human Vδ1 Mut2 | AQKVTQAQSSVSMPVRKAVTLNCLYETSWWSYYIFWYKQLPSGQMTYLIR |
| Human Vδ1 Mut3 | AQKVTQAQSSVSMPVRKAVTLNCLYETSWWSYYIFWYKQLPSKEMIFLIR |
| Human Vδ1 Mut4 | AQKVTQAQPDVSMPVRKAVTLNCLYETSWWSYYIFWYKQLPSKEMIFLIR |
| Human Vδ1 Mut5 | AQKVTQAQSSVSMPVRKAVTLNCLYETSWWSYYIFWYKQLPSKEMIFLIR |
| Human Vδ1 Mut6 | AQKVTQAQSSVSMPVRKAVTLNCLYETSWWSYYIFWYKQLPSKEMIFLIR |

| | |
|---|---|
| Human Vδ1 | QGSDEQNAKSGRYSVNFKKAAKSVALTISALQLEDSAKYFCALGTGVRGL |
| Human Vδ1 Mut1 | QYSDDGNARDGRYSVNFQKAQKSINLTISALQLEDSAKYFCALGTGVRGL |
| Human Vδ1 Mut2 | QGSDEQNAKSGRYSVNFQKAQKSALTISALQLEDSAKYFCALGTGVRGL |
| Human Vδ1 Mut3 | QGSDEQNAKSGRYSVNFKKAAKSVALTISALELEDSAKYFCVLGTGVRGL |
| Human Vδ1 Mut4 | QGSDEQNAKSGRYSVNFKKAAKSVALTISALELEDSAKYFCALGTGVRGL |
| Human Vδ1 Mut5 | QGSDDGNAKSGRYSVNFKKAAKSVALTISALQLEDSAKYFCALGTGVRGL |
| Human Vδ1 Mut6 | QGSDEQNARDGRYSVNFKKAAKSVALTISALQLEDSAKYFCALGTGVRGL |

FIG. 26

```
                            Vδ2CDR1
              ┌─┬──────────────┬──┬─────────┬─┬──────────────┬─┬─────┐
Human TRDV2   │A│ELVPEHQTVPVSI │G │VPATI    │R│CSMKGEAIGNYY  │I│NWYRKTQGNT│ITETYR
Macaca mulatta│A│ELVPEHQTVIVS V│G │DPATI    │K│CSMKGEAISNYY  │I│NWYRKTQGNT│MTETYR Vδ2CDR2                                              Vδ2CDR3
      ┌─┬──┬──────────────────┬──┬──────────────────────┐    ┌──┐
Human TRDV2    │E│KD│IYGPGFKDNFQGDID│IA│KN│AVLKILAPSERDEGSYYCA│DT│
Macaca mulatta │E│KG│IYGPGFKDNFQGDID│TE│NQ│AVLKILAPSERDEGSYYCA│SDR│
```

FIG. 29

| mAb | FW1 | CDRH1 | FW2 | CDRH2 |
|---|---|---|---|---|
| δ1-05 | DVQLQESGPGMVKPSQSLSLTCTVTGYSIT | GGYDWH | WIRHFPGNKLEWMA | YISYSGSTDYNPSLKS |
| δ1-08 | QVQLQQSGAELVRPGASVTLSCKASGYTFT | DYEVY | WVKQTPVHGLEWIG | AIDPETGRTAYNQKFKG |
| δ1-18 | EVQLQQSGPELVKPGDSVKMSCKASGYTFT | DYYMD | WVKQSHGRSLEWIG | YIYPKNVGISYNQKFKG |
| δ1-22 | QVQLQQSGPQLVKPGASVKLSCKASGYTFT | SYDIN | WVKQRPGQGLEWIG | WIYPGDGTTDYNGKFKG |
| δ1-26 | SDVQLQESGPGLVKPSQSLSVTCTVTGYSIT | SGYHWN | WIRQFPGNRLEWMG | YIHNSGSTNYNSFLKS |
| δ1-35 | EVQLQQSGTVLARPGSSVKMSCKASGYTFT | TYWMH | WVKQRPGQGLDWIG | AIYPGNSDTNYNQKFRG |
| δ1-37 | QVQLQQPGAELVRPGASVKLSCKAPGYTFT | SYWMN | WVKQRPEQGLEWIG | KIDPYDSETHYNQKFKD |
| δ1-39 | QVQLQQPGADLVRPGTSVKLSCKASGYTFT | SYWMH | WVQQRPGQGLEWIG | VIDPSDSYTNYNQKFKG |
| δ1-113 | EVKLEESGGGLVQPGGSMKLSCAASGFTFS | DAWMD | WVRQSPEKGLEWVA | EIRAEANNHATYYAESVKG |
| δ1-143 | QVQLQQPGAEIVRPGASVKLSCKASGYAFT | DYWMN | WVKQRPGQGLEWIG | TIDPSDSYASYNQKFKG |
| δ1-149 | QVQLQQSGAELVRPGASVKLSCKASDYKFT | DSEMY | WVKQTPVHGLEWIG | AIDPETGITAYNQRFKG |
| δ1-155 | EVQLQQSGAELGRPGASVKLSCTTSGFNIK | DDYMH | WVKQRPEQGLEWIG | WIDPENGDTAYASKFQG |
| δ1-182 | QVQLQQSGAELVRPGASVTLSCKASGYKFI | DYEMH | WVKQTPVHGLEWVG | DLDPGTGVTAYNQKFKG |
| δ1-183 | EVQLQMSGAELVRPGASVKLSCTASGFNIK | DDYMY | WVKQRPEQGLEWIG | WIDPENGDTEYASKFQG |
| δ1-191 | EVQLQQSGAELVRPGASVKLSCTASDFNIK | DDYMH | WVKQRPEQGLEWIG | WIDPENGETEYASKFQG |
| δ1-192 | QIQLVQSGPELKKPGETVKISCKVSGDTFT | TYGMS | WVKQAPGKGLKWMG | WINTYSGVPTYADDFKG |
| δ1-195 | EVKFEESGGGLVQPGGSMKLSCAASGFTFS | DAWMD | WVRQSPEKGLEWVA | EIRAEANNHATYYAESVKG |
| δ1-197 | QVQLQQSGAELVRPGASVTLSCKASGYTFV | DYEMH | WVKQTPVHGLEWIG | AIDPETGITAYNQKFKG |
| δ1-199 | EVQLQQSGAELVRPGASVKLSCTASGFNIK | DDYMS | WVKQRPEQGLEWIG | WIDPENGDTEYASKFQG |
| δ1-201 | QVQLQQSGADLVRPGASVTLSCKASGYTFT | DYEMH | WVKQTPVHGLEWIG | AIDPETGITAYNQNFKG |
| δ1-203 | SDVQLQESGPGLVKPSQSLSLTCSVTGYSIT | SGYYWN | WIRQFPGNNLEWMG | YISHDGSNNYNPALKN |
| δ1-239 | QVQLQQSGAELVRPGASVKLSCKASDYKFT | DSEMY | WVKQTPVHGLEWIG | AIDPETGITAYNQRFKG |
| δ1-253 | EVQLQQSGPELVKPGASVKMSCKASGYTFT | DYYMN | WVKQSHGKSLEWIG | HINPYNGGTSYNQKFKG |
| δ1-257 | QVQLQQSGAELVRPGASVTLSCKASGYRFP | DYEMH | WVKQTPVHGLEWIG | AIDPETGRTAYNQKFRG |
| δ1-278 | SDVQLQESGPGLVKPSQSLSLTCSVTGYSIT | SDYYWN | WIRQFPGNKLEWMG | YITYDGSNNYNPSLKN |
| δ1-282 | EVKLVESGGGLVQPGGSLKLSCATSGFTFS | DSYMY | WVRQTPEKRLEWVA | YISYGGVNTYYPDTVRG |
| δ1-285 | EVQLVESGGGLVQPGGSLKLSCAASGFTFS | DYGMH | WVRQAPEKGLEWVA | YISSGSRTIYYADTVKG |

FIG. 33

| FW3 | CDRH3 | FW4 |
|---|---|---|
| RISVTHDTSKNLFFLNLTSVTTEDTATYYCAR | EGGRGFAY | WGQGTLVTVSA |
| KAILTTDKSSSTAYMALRSLTSEDSAVYYCAR | LKSGRYYGDLFAY | WGQGTLVTVSA |
| KATLTVDKSSSTAYMELHSLTSEDSAVYYCAR | SLLWDALDY | WGQGTSVTVSS |
| KATLTVDTSSSSAYMELHSLTSEDSAVYFCAR | MDDYDDGGAMDY | WGQGTSVTVSS |
| RISITRDTSKNQFFLQLNSVTTEDTATYYCVA | YYSNSREFWYAY | WGQGTLVTVSA |
| KAKLTAVTSASTAYMELSSLTNEDSAVYYCTY | GYYVDYYAMDY | WGQGTSVTVSS |
| KAILTVDKSSSTAYMQLSSLTSEDSAVYYCAR | GGDNYDPFAY | WGQGTLVTVSA |
| KATLTVDTSSSTAYMQLSSLTSEDSAVYYCAR | SDDYDEGYFFDQ | WGQGTTLTVSA |
| RFTISRDDSKSRVFLQMNSLRAEDTGIYYCTG | LDYGSIGFAY | WGQGTLVTVSA |
| KATLTVDTSSNSAYMHLSSLTSEDSAVYFCAR | ESNDVCWYFDV | WGAGTTVTVSS |
| KATLTSDKSSSTAYMELRSLTSEDSAVYYCTR | AVPPWFAY | WGQGTLVTVSA |
| KATITADTSSNTAYLQLSSLTSEDTAVYYCNY | YGFDY | WGQGTTLTVSS |
| KAILTADKSSSTAYMELRSLTSEDSAVYYCTV | WSADF | WGQGTSVTVSS |
| KATITADTSSNTAYLQLSSLTSEDTAVYYCTY | YAMDY | WGQGTSVTVSS |
| KATLTADTSSNTAYLQLSSLTSEDTAVYYCTE | LGFDY | WGQGTTLTVSS |
| RFAFSLETSASTAYLQINNLKNEDTATYFCAR | SSYDYDDAMDY | WGQGTSVTVSS |
| RFTISRDDSKSRVFLQMNSLRAEDTGIYYCTG | LDYGSVGFAY | WGQGTLVTVSA |
| KATLTADKSSSTAYMELSSLTSEDSAVYYCIR | PRGGSHFDY | WGQGTTLTVSS |
| KATITADTSSNTAYLRLSSLTSEDTAVYYCTE | LGFDY | WGQGTTLTVSS |
| KATLTADKSSSTAYMELSSLTSEDSAVYYCTR | PRGGSHFDH | WGQGTPLTVSS |
| RISITRDTSKNQFFLKLNSVTTEDTGTYYCAS | VYYGDYEVWYTY | WGQGTLVTVSA |
| KATLTSDKSSSTAYMELRSLTSEDSAVYYCTR | AVPPWFAY | WGQGTLVTVSA |
| KATLTVDKSSSTAYMQLNSLTSEDSAVYYCAR | NHIYYYDGGYFYYAMDY | WGQGTSVTVSS |
| KAKLTADKSSSTVYMELRSLTSEDSAVYYCTR | GYGIQFPY | WGQGTLVTVSA |
| RISITRDTSKNQFFLKLNSVTTEDTATYYCAR | DDGYFDY | WGQGTTLTVSS |
| RFTISRDNAKSTLYLQMSRLKSEDTAMYYCAS | RGYY | WGQGTSVTVSS |
| RFTISRDNAKNTLFLQMTSLRSEDTAMYYCAR | EGAYSSFDY | WGQGTTLTVSS |

FIG. 33 (Cont.)

| mAb | FW1 | CDRL1 | FW2 |
|---|---|---|---|
| δ1-05 | NIVLTQSPASLAVSLGQRATISC | RASESVDGYGNSFMH | WYQQKPGQPPKLLIY |
| δ1-08 | QIVLTQSPALMSASPGEKVTMTC | SASSSVSYMY | WYQQKPRSSPKPWIY |
| δ1-18 | DIQMTQSPASLSVSGETVTITC | RASENIYSNLA | WYQQKQGKSPQLLVY |
| δ1-22 | DVVMTQTPLTLSVTVGQPASISC | KSSQSLLHSNGKTYLN | WLLQRPGQSPKLLIY |
| δ1-26 | DIVMSQSPSSLAVSVGEKVTMSC | KSSQSLLYSSNQKNSLA | WYQQKPGQSPKLLIY |
| δ1-35 | DIVMTQSHKFMSTSVGDRVSITC | KASQDVSIDVA | WYQQKPGQSPKLLIY |
| δ1-37 | DIQMTQSPASLSVSGETVTITC | RASENIYSNLA | WYQQKQGKSPQLLVY |
| δ1-39 | DVVMTQTPLTLSVTVGQPASISC | KSSQSLLHSNGKTYLN | WLLQRPGQSPKLLIY |
| δ1-113 | DVLMTQTPLSLPVSLGDQASISC | RSSQSVVHRNGNTFLE | WYLQKPGQSPKLLIY |
| δ1-143 | DIQMTQTTSSLSASLGDRVTISC | RASQDISNYLN | WYQQKPDGTVKLLIY |
| δ1-149 | QIVLTQSPALMSASPGEKVTMTC | SASSSVSYMY | WYQQKPRSSPKPWIY |
| δ1-155 | DVLMTQTPLSLPVSLGDQASISC | RSSQSIVHSDGNTFLQ | WYLQKPGQSPKLLIY |
| δ1-182 | SDVVRPTPLSLPVSLGDQASISC | RSSQSLVHSNGNTYLH | WYLQKPGQSPKLLIY |
| δ1-183 | DVVMTQIPVSLPVTLGDQASISC | RSSQSLLHSDGNTYLH | WYLQKPGQSPKLLIY |
| δ1-191 | AVVMTQTPLSLPVSLGDQASISC | RSSQSLVHSDGNTYLH | WYLQKPGQSPKLLIY |
| δ1-192 | DVQITQSPSYLAASPGETITINC | RTSKSISKYLA | WYQEKPGKTNKLLIY |
| δ1-195 | DVLMTQTPLSLPVSLGDQASISC | RSSQSVVHRNGNTFLE | WYLQKPGQSPKLLIY |
| δ1-197 | QIVLSQSPAILSASPGEKVTMTC | RASSSVNYMH | WYQQKPGSSPKPWIY |
| δ1-199 | AVVMTQTPLSLPVSLGDQASISC | RSSQSLVHSDGNTYLH | WYLQKPGQSPKLLIY |
| δ1-201 | QIVLSQSPAILSASPGEKVTMTC | RASSSVRYIH | WYQQKPGSSPKPWIY |
| δ1-203 | DIVMSQSPSSLAVSVGEKVALNC | KSSQSLLYSINQKNYLA | WYQRNPGQSPKLLIY |
| δ1-239 | QIVLTQSPALMSASPGEKVTMTC | SASSSVSYMY | WYQQKPRSSPKPWIY |
| δ1-253 | NIVLTQSPASLAVSLGQRATISC | RPSESVDSYGNSFMH | WYQQKPGQPPKLLIY |
| δ1-257 | QIVLSQSPAILSASPGEKVTMTC | RASSSVSYIH | WFQQKPGSSPKFWIY |
| δ1-278 | QIVLSQSPAILSASPGEKVTMTC | RASSSVNYMH | WHQQKPGSSPKPRIY |
| δ1-282 | DIVLTQSPPSLAVSLGQRATISC | KASQSVDYDGDSYMN | WYQQKPGQPPKLLIY |
| δ1-285 | DIVLTQSPASLAVSLGQRATISC | KASQSVDYDGDSYMN | WYQQKPGQPPKLLIY |

FIG. 34

| CDRL2 | FW3 | CDRL3 | FW4 |
|---|---|---|---|
| LASNLES | GVPARFSGSGSRTDFTLTIDPVESDDAATYYC | QQNNEDPFT | FGSGTKLEIK |
| FTSNLAS | GVPARFSGSGSTSYSLTISSMEAEDAATYYC | QQWSSNPLT | FGAGTKLELK |
| AATYLAD | GVPSRFSGSGSTQYSLKINSLQSEDFGSYYC | QHFWGIPYT | FGGGTKLEIK |
| LVSKLES | GVPDRFSGSGSTDFKLKISRVEAEDLGVYYC | LQATHFPLT | CGAGTKLELK |
| WASTRES | GVPDRFTGSGSTDFTLTISSVKAEDLAVYYC | QQDYSYPL | TFGGGTKLELK |
| SASYRYT | GVPDRFTGSGSTDFTFTISNVQAEDLAVYYC | QQHYSIPCT | FGSGTKLEIK |
| GARNLAD | GVPSRFSGSGSTQYSLKINSLQSEDFGSYFC | QHFWDTTFT | FGSGTKVEIK |
| LVSKVES | GVPDRFSGSGSTDFTLKISRVEAEDLGLYYC | LQVTHFPLT | FGAGTKLELK |
| KVSNRFS | GVPDRFSGSGSTDFTLKISRVEAEDLGLYYC | FQGSHVPYT | FGGGTKLEIKR |
| YTSRLHS | GVPSRFSGSGSTDYSLTISNLEQEDIATYFC | QQGNTLRT | FGGGTKLEIK |
| LTSNLAA | GVPARFSGSGSTSYSLTISSMEAEDAATYYC | QQWSGDPPT | FGGGTKLEIKR |
| KVSNRFS | GVPDRFSGSGSTDFTLKISRVEAEDLGVYYC | FQGSHVPYT | FGGGTKLEIKR |
| KVSNRFS | GVPDRFSGSGSTDFTLKISRVEAEDLGVYFC | SQSTHVPPWT | FGGGTKLEIK |
| KVSNRFS | GVPDRFSGSGSTDFTLKISRVEAEDLGVYFC | SQFTHVPPWT | FGGGTKLEIK |
| KVSNRFS | GVPDRFSGSGSTDFTLKISRVEAEDLGVYFC | SHSTHVPYT | FGGGTKLEIKR |
| SGSTLQS | GIPSRFSGSGSTDFTLTISSLEPEDFAMYYC | QHHNEYPYT | FGGGTRLEIKR |
| KVSNRFS | GVPDRFSGSGSTDFTLKISRVEAEDLGVYYC | FQGSHVPYT | FGGGTKLEIKR |
| ATSNLAS | GVPARFSGSGSTSYSLTISRVEAEDAATYYC | QQWSSHQPT | FGAGTKLELK |
| KVSNRFS | GVPDRFSGSGSTDFTLKISRVEAEDLGVYFC | SHSTHVPYT | FGGGTKLEIKR |
| ATSNLAS | GVPARFSGSGSTSYSLTISRVEAEDAATYHC | QQWYSDTPT | FGAGTKLELK |
| WASTRES | GVPDRFTGSGSTDFTLTISSVKTEDLAVYYC | QQYYSYPWT | FGGGTKLEIK |
| LTSNLAA | GVPARFSGSGSTSYSLTISSMEAEDAATYYC | QQWSGDPPT | FGGGTKLEIKR |
| LASNLES | GVPARFSGSGSRTDLTLTIDPVEADDAATYYC | QQNNEDPWT | FGGGTK |
| GTSNLAS | GVPARFTGSGSTSYSLTISRVEAEDAATYYC | QQWSSDSPT | FGGGTKLEIK |
| GTSNLAS | GVPARFSGSGSTSYSLTISRVEAEDAATYYC | QQWSSNPPT | FGAGTKLELK |
| GASNLES | GIPARFSGSGSGTDFTLNIHPMEEEDAATYYC | QQSNEDPWT | FGGGTKLEIK |
| AASNLES | GIPARFSGSGSGTDFTLNIHPVEEEDAATYYC | QQSNEDPWT | FGGGTKLEIK |

FIG. 34 (Cont.)

| mAb | FW1 | CDRH1 | FW2 | CDRH2 |
|---|---|---|---|---|
| δ2-14 | EVQLQQSGPELVKPGASVKISCKASGYSFT | GYYMN | WVKQSPEKSLEWIG | EINPSTGGTTYNQKFQA |
| δ2-17 | SDVQLQESGPGLVTPSQSLSVTCTVTGYSIT | SGSYWN | WIRQFPGNKLEWMG | YIHNSGSTTYNPSLKS |
| δ2-30 | QVQLQQSGAELVKPGASVKLSCKTSGYTFT | SYWIQ | WVKQRPGQGLGWIG | EIFPGTGTTYYNEKFKG |
| δ2-31 | QVQLLQPGAELVKPGASVKLSCKASGYSFT | NFWIN | WVKLRPGQGLEWIG | NIFPGSSSPNYNEKFKS |
| δ2-32 | EVKLVESGGGLVQPGGSLSLSCAASGFTFT | DYYMS | WVRQPPGKALEWLG | FIRNKANGYTTESSASVKG |
| δ2-33 | EVQLQQSGPELVKPGASVKISCKASGYSFT | GYYMN | WVKQSPEKSLEWIG | EINPSTGGTTYNQKFQA |
| δ2-35 | DVKLVESGGGLVKPGGSLKLSCAASGFTFS | SYYMS | WVRQTPEKRLEWVA | TISNSGGSTYYPDSVKG |
| δ2-36 | QVQLLQPGAELVKPGASVKLSCKASGYTFT | NFWIN | WVKQRPGQGLEWIG | NIYPGSSSPNYNEKFKF |
| δ2-37 | QVQLQQPGAELVKPGASVKLSCKASGYTFT | NHWIS | WVKQRPGQGLEWIG | NIFPGSSSPNYNEKFKS |
| | | | | |

FIG. 35

| mAb | FW1 | CDRL1 | FW2 | CDRL2 |
|---|---|---|---|---|
| δ2-14 | DIVLIQSPATLSVTPGDSVSLSC | RASQSINNNLH | WYQQKSHESPRLLIK | YVSQSIS |
| δ2-17 | NIVLTQSPGSLAVSLGQRATISC | RASESVDNYGNSFMH | WYQQKPGQPPKLLIY | LASNLES |
| δ2-22 | DIQMTQSPASLSVSVGETVTITC | RASENIYSNLA | WYQQKQGKSPQLLVY | AATNLAG |
| δ2-30 | DIQMTQSPASLSVSVGETVTITC | RASENIYSNLA | WYQQKQGKSPQLLVY | AATNLAD |
| δ2-31 | DLKMTQSPSSMYASLGERVTITC | KASQDINSFLS | WFQQIPGKSPKTLIY | RANRLVD |
| δ2-32 | DIQMTQTSSSFSVSLGDRVTITC | KASEDIYNRLA | WYQQKPGNAPRLLIS | GATSLEA |
| δ2-33 | DIVLIQSPATLSVTPGDSVSLSC | RASQSINNNLH | WYQQKSHESPRLLIK | YVSQSIS |
| δ2-35 | DVVMTQTPLSLPVSLGDQASISC | RSSQSLVHSNGNTYLH | WYLQKPGQSPKLLIY | KVSNRFS |
| δ2-36 | DIKMTQSPSSMYASLGERVTITC | KASQDINNFLS | WFQQIPGKSPKTLIY | RANRLVD |
| δ2-37 | QIVLTQSPAIMSASLGEEITLTC | SASSRVNYMH | WYQQKSGTSPKLLIY | STSNLAS |

FIG. 36

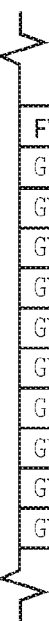

| FW3 | CDRL3 | FW4 |
|---|---|---|
| GIPSRFSGSGSGTDFTLSINSVETEDFGMYFC | QQSNSWPLT | FGAGTKLELK |
| GVPARFSGSGSRTDFTLTIDPVEADDAATYYC | QQNNEDPT | FGSGTKLEMK |
| GVPSRFSGSGSGTQYSLKINSLQSEDFGSYYC | QHFWGTPRT | FGGGTKLEIK |
| GVPSRFSGSGSGTQYSLKINSLQSEDFGSYYC | QHFGDTPYT | FGGGTKLEIKR |
| GVPSRFSGSGSGQDYSLTISSLEYEDMGIYYC | LQSDEFPYT | IGGGTKLEIKR |
| GVPSRFSGSGSGNDYTLSITSLQTEDVATYYC | QQYWYTPWT | FGGGTKLEIK |
| GIPSRFSGSGSGTDFTLSINSVETEDFGMYFC | QQSNSWPLT | FGAGTKLELK |
| GVPDRFSGSGSGTDFTLKISRVEAEDLGVYFC | SQSRHVPYT | FGGGTKLEIKR |
| GVPSRFSGSGSGQDYSLTISSLEYEDMGIYYC | LQSDEFPYT | IGGGTKLEIKR |
| GVPSRFSGSGSGTFYSLTIISVEAEDAADYYC | HQWSSYPT | FGGGTKLEIK |

FIG. 36 (Cont.)

| | δ1γδ | δ2γ9 | δ3γ2 | δ4γδ | δ5γ3 | δ7γδ | δ8γδ | cross reactivity |
|---|---|---|---|---|---|---|---|---|
| TS-1 | 1.754 | 0.080 | 0.061 | 0.064 | 0.059 | 0.067 | 0.066 | |
| | 2.198 | 0.089 | 0.084 | 0.084 | 0.081 | 0.038 | 0.040 | |
| d1-08 | 1.790 | 0.044 | 0.045 | 0.049 | 0.046 | 0.042 | 0.044 | |
| | 2.099 | 0.051 | 0.048 | 0.051 | 0.053 | 0.037 | 0.037 | |
| d1-18 | 1.081 | 0.048 | 0.051 | 0.983 | 0.043 | 0.043 | 0.044 | δ1, δ4 |
| | 1.491 | 0.051 | 0.048 | 0.872 | 0.052 | 0.037 | 0.038 | |
| d1-26 | 1.387 | 0.097 | 0.059 | 0.054 | 0.062 | 0.043 | 0.038 | |
| | 1.587 | 0.128 | 0.078 | 0.067 | 0.069 | 0.041 | 0.043 | |
| d1-35 | 1.278 | 0.084 | 0.048 | 1.249 | 0.044 | 0.053 | 0.037 | δ1, δ4 |
| | 1.741 | 0.062 | 0.052 | 1.005 | 0.052 | 0.043 | 0.044 | |
| d1-37 | 1.525 | 0.052 | 0.044 | 0.043 | 0.043 | 0.056 | 0.037 | |
| | 2.013 | 0.052 | 0.050 | 0.051 | 0.057 | 0.039 | 0.038 | |
| d1-39 | 1.167 | 0.072 | 0.734 | 0.824 | 0.646 | 0.076 | 0.067 | δ1, δ3, δ4, δ5 |
| | 1.282 | 0.080 | 0.758 | 0.694 | 0.469 | 0.044 | 0.037 | |
| B1 | 2.263 | 1.307 | 1.711 | 1.582 | 1.381 | 0.922 | 1.828 | |
| γδ pan | 2.117 | 1.668 | 1.669 | 1.722 | 1.176 | 0.644 | 1.604 | | d1-18 and d1-35 were found to cross reacts with δ4
d1-39 cross reacts with δ3, δ4 and δ5 subsets

FIG. 37

```
              CDR1
Human Vd1    AQKVTQAQSSVSMPVRKAVTLNCLYE TSWWSYYI FWYKQLPSKEMIFLIR
Dolphin Vd1  -----V-RAM-SQLGE----S-Q---  LSW-D---  ---------G--T---H CDR2
Human Vd1    QGS DEQNAKSGRYSVNFKKAAKSVALTISALQLEDSAKYFCALGE-------
Dolphin Vd1  --- I-SD---N-------QERH-FIS-----LV----N------TGVRGL
```

FIG. 38

| | δ1γ8 | δ2γ9 | δ3γ2 | d1 Dolphin δi-11 | δi-21 | δi-28 | δi-47 | δi-70 | δi-80 | δi-95 | J1 | J2 | J3 | K120A | BIN |
|---|---|---|---|---|---|---|---|---|---|---|---|---|---|---|---|
| TS-1 | 1.46 | 0.07 | 0.07 | 0.09 | 1.27 | 2.17 | 1.88 | 1.77 | 0.54 | 0.64 | 0.50 | 1.14 | 0.77 | 0.05 | 0.07 | 47-70 J1,J2,K120 1 |
| | 2.27 | 0.09 | 0.09 | 0.14 | 1.74 | 2.29 | 1.95 | 2.06 | 0.95 | 0.91 | 0.82 | 1.08 | 0.74 | 0.05 | 0.06 | |
| TS8.2 | 1.36 | 0.05 | 0.05 | 0.05 | 0.91 | 1.09 | 0.23 | 0.24 | 0.06 | 0.05 | 0.09 | 0.93 | 0.76 | 0.04 | 0.15 | 21-28 J1,J2 6 |
| | 2.04 | 0.04 | 0.04 | 0.06 | 1.02 | 1.92 | 0.39 | 0.33 | 0.10 | 0.05 | 0.17 | 1.00 | 0.77 | 0.04 | 0.20 | |
| R9.12 | 1.76 | 0.06 | 0.06 | 0.06 | 1.19 | 0.06 | 0.06 | 0.06 | 0.09 | 0.05 | 0.07 | 0.95 | 0.94 | 0.94 | 0.82 | 11 to 21 Arg16 2b |
| | 1.95 | 0.05 | 0.05 | 0.07 | 1.68 | 0.06 | 0.06 | 0.06 | 0.11 | 0.06 | 0.10 | 1.11 | 0.92 | 0.99 | 1.11 | |
| d1-08 | 1.70 | 0.05 | 0.05 | 0.08 | 1.34 | 1.68 | 1.77 | 1.90 | 0.92 | 0.49 | 0.12 | 0.99 | 0.94 | 0.94 | 0.93 | 80 to 95 3 |
| | 2.08 | 0.05 | 0.06 | 0.07 | 1.65 | 1.91 | 2.03 | 2.05 | 1.63 | 0.72 | 0.15 | 1.20 | 1.18 | 0.95 | 1.23 | |
| d1-35 | 1.49 | 0.07 | 0.06 | 0.09 | 0.06 | 0.06 | 0.06 | 0.07 | 0.07 | 0.06 | 0.11 | 0.86 | 0.96 | 0.04 | 0.49 | 1 to 11 J1,J2 4 |
| | 1.87 | 0.09 | 0.07 | 0.12 | 0.07 | 0.07 | 0.08 | 0.08 | 0.09 | 0.07 | 0.13 | 1.01 | 1.08 | 0.05 | 0.70 | |
| d1-37 | 1.71 | 0.05 | 0.05 | 0.05 | 1.13 | 1.72 | 0.75 | 0.96 | 0.20 | 0.08 | 0.10 | 0.98 | 0.05 | 0.04 | 0.04 | 47-70 J1 K120 1b |
| | 1.91 | 0.04 | 0.05 | 0.05 | 1.96 | 1.89 | 1.57 | 1.65 | 0.24 | 0.06 | 0.30 | 1.26 | 0.12 | 0.05 | 0.04 | |
| d1-39 | 1.84 | 0.06 | 0.35 | 0.06 | 0.82 | 0.07 | 0.07 | 0.07 | 0.08 | 0.06 | 0.07 | 0.81 | 0.97 | 0.32 | 0.59 | 11 to 21 2c |
| | 1.83 | 0.05 | 0.37 | 0.07 | 1.43 | 0.07 | 0.07 | 0.07 | 0.15 | 0.06 | 0.09 | 1.12 | 0.89 | 0.53 | 1.01 | |
| d1-113 | 2.58 | 0.13 | 0.14 | 0.48 | 2.42 | 2.18 | 2.71 | 0.31 | 0.74 | 0.24 | 0.65 | 0.99 | 0.07 | 0.05 | 0.36 | 28-47 J1 5 |
| | 2.44 | 0.22 | 0.22 | 0.65 | 2.52 | 2.57 | 2.61 | 0.42 | 1.12 | 0.39 | 0.60 | 1.07 | 0.04 | 0.05 | 0.51 | |
| d1-143 | 2.31 | 0.08 | 0.09 | 0.17 | 1.70 | 2.17 | 0.12 | 0.09 | 0.12 | 0.12 | 0.25 | 0.90 | 0.98 | 0.25 | 0.81 | 21 to 28 J1,J2 6 |
| | 2.29 | 0.12 | 0.12 | 0.30 | 2.29 | 2.25 | 0.17 | 0.12 | 0.24 | 0.18 | 0.30 | 1.04 | 1.05 | 0.37 | 0.95 | |
| d1-149 | 1.84 | 0.06 | 0.07 | 0.08 | 1.57 | 2.14 | 2.08 | 1.28 | 0.16 | 0.06 | 0.07 | 0.59 | 0.64 | 0.10 | 0.51 | 47-70 J1,J2 7 |
| | 2.12 | 0.06 | 0.06 | 0.08 | 1.85 | 2.22 | 2.33 | 1.89 | 0.24 | 0.21 | 0.08 | 0.78 | 0.54 | 0.15 | 0.66 | |
| d1-155 | 2.17 | 0.09 | 0.13 | 0.21 | 2.22 | 2.34 | 2.44 | 0.10 | 0.48 | 0.16 | 0.27 | 0.90 | 0.04 | 0.04 | 0.44 | 28-47 J1 5 |
| | 2.41 | 0.10 | 0.11 | 0.27 | 2.02 | 2.24 | 2.23 | 0.18 | 0.56 | 0.21 | 0.27 | 1.07 | 0.04 | 0.05 | 0.73 | |
| d1-182 | 2.66 | 0.13 | 0.16 | 0.74 | 2.68 | 2.77 | 2.82 | 2.47 | 0.83 | 0.51 | 0.98 | 1.11 | 0.06 | 0.06 | 0.93 | |
| | 2.71 | 0.14 | 0.21 | 0.89 | 2.48 | 2.48 | 2.57 | 2.28 | 1.56 | 0.49 | 0.89 | 1.52 | 0.06 | 0.07 | 1.25 | |
| d1-183 | 2.46 | 0.10 | 0.12 | 0.31 | 2.26 | 2.59 | 2.62 | 0.15 | 0.56 | 0.19 | 0.45 | 0.99 | 0.05 | 0.05 | 0.78 | 28-47 J1 5 |
| | 2.56 | 0.11 | 0.14 | 0.35 | 2.42 | 2.41 | 2.53 | 0.16 | 0.74 | 0.24 | 0.39 | 1.39 | 0.07 | 0.05 | 1.10 | |
| d1-191 | 2.42 | 0.11 | 0.11 | 0.27 | 2.25 | 2.49 | 2.53 | 0.16 | 0.54 | 0.16 | 0.31 | 0.95 | 0.04 | 0.04 | 0.70 | 28-47 J1 5 |
| | 2.43 | 0.14 | 0.16 | 0.33 | 2.30 | 2.36 | 2.35 | 0.19 | 0.56 | 0.24 | 0.39 | 1.34 | 0.04 | 0.05 | 1.13 | |

| Label | C1 | C2 | C3 | C4 | C5 | C6 | C7 | C8 | C9 | C10 | C11 | C12 | C13 | C14 | C15 | Annotation |
|---|---|---|---|---|---|---|---|---|---|---|---|---|---|---|---|---|
| d1-192 | 2.54 | 0.06 | 0.06 | 0.08 | 2.44 | 2.79 | 2.70 | 2.68 | 0.65 | 0.09 | 0.13 | 1.01 | 1.00 | 0.39 | 0.90 | 70-80 + J1,J2 + + + 8 |
|  | 2.61 | 0.06 | 0.07 | 0.09 | 2.35 | 2.55 | 2.55 | 2.62 | 0.75 | 0.10 | 0.14 | 1.56 | 1.46 | 0.73 | 1.51 |  |
| d1-201 | 1.66 | 0.08 | 0.12 | 0.22 | 1.73 | 2.02 | 2.04 | 1.92 | 1.27 | 0.61 | 0.37 | 1.18 | 1.08 | 0.86 | 1.16 | 80-95 ... 9 |
|  | 2.14 | 0.14 | 0.27 | 0.48 | 1.92 | 1.93 | 2.13 | 2.07 | 1.89 | 1.10 | 0.63 | 1.31 | 1.30 | 1.12 | 1.29 |  |
| d1-203 | 1.80 | 0.04 | 0.04 | 0.19 | 0.05 | 0.06 | 0.06 | 0.06 | 0.05 | 0.05 | 0.05 | 0.58 | 0.33 | 0.04 | 0.18 | 1 to 11 + J1,J2 + K120:4 |
|  | 1.30 | 0.05 | 0.05 | 0.05 | 0.05 | 0.06 | 0.06 | 0.06 | 0.05 | 0.05 | 0.05 | 0.59 | 0.34 | 0.04 | 0.10 |  |
| d1-253 | 1.42 | 0.04 | 0.04 | 0.06 | 1.07 | 1.70 | 0.63 | 0.11 | 0.17 | 0.06 | 0.07 | 0.93 | 0.91 | 0.30 | 0.87 | 47-70 + J1,J2 + + + 7 |
|  | 1.91 | 0.05 | 0.05 | 0.07 | 1.76 | 1.81 | 0.66 | 0.72 | 0.34 | 0.08 | 0.08 | 1.17 | 0.98 | 0.42 | 1.07 |  |
| d1-257 | 0.99 | 0.05 | 0.05 | 0.06 | 0.98 | 1.43 | 1.42 | 1.27 | 0.35 | 0.07 | 0.06 | 0.78 | 0.83 | 0.29 | 0.69 | 47-70 + J1 + + + 7 |
|  | 1.41 | 0.05 | 0.05 | 0.06 | 1.38 | 1.66 | 1.61 | 1.58 | 0.09 | 0.08 | 0.06 | 1.00 | 0.89 | 0.48 | 0.86 |  |
| d1-278 | 0.97 | 0.05 | 0.04 | 0.05 | 0.62 | 0.71 | 0.86 | 0.05 | 0.12 | 0.06 | 0.07 | 0.70 | 0.04 | 0.04 | 0.40 | 28-47 + J1 + + + 5 |
|  | 1.00 | 0.06 | 0.06 | 0.09 | 1.35 | 1.16 | 1.39 | 0.06 | 0.12 | 0.06 | 0.08 | 1.08 | 0.04 | 0.05 | 0.57 |  |
| d1-282 | 1.46 | 0.04 | 0.04 | 0.15 | 1.36 | 1.63 | 1.68 | 0.13 | 0.28 | 0.13 | 0.23 | 0.97 | 0.08 | 0.06 | 0.87 | 28-47 + J1 + + + 5 |
|  | 1.91 | 0.05 | 0.05 | 0.30 | 1.78 | 1.84 | 1.81 | 0.12 | 0.48 | 0.14 | 0.34 | 1.54 | 0.09 | 0.08 | 1.00 |  |
| d1-285 | 1.52 | 0.04 | 0.04 | 0.05 | 1.11 | 0.06 | 0.06 | 0.05 | 0.07 | 0.05 | 0.06 | 0.95 | 0.96 | 0.34 | 0.84 | 11 to 21 + ... 2 |
|  | 1.97 | 0.05 | 0.05 | 0.07 | 1.57 | 0.06 | 0.06 | 0.06 | 0.09 | 0.05 | 0.06 | 1.31 | 0.99 | 0.52 | 1.21 |  |
| B1 | 1.38 | 1.15 | 0.94 | 0.89 | 1.25 | 1.48 | 1.70 | 1.59 | 0.92 | 0.84 | 0.74 | 0.97 | 0.97 | 0.98 | 0.95 |  |
|  | 1.88 | 1.75 | 1.55 | 0.81 | 1.64 | 1.66 | 1.70 | 1.57 | 1.42 | 1.21 | 1.18 | 1.51 | 1.28 | 1.02 | 1.42 |  |
| IMM510 | 1.59 | 1.31 | 1.09 | 0.56 | 1.27 | 1.61 | 1.72 | 1.63 | 0.86 | 0.90 | 0.91 | 1.03 | 0.99 | 0.92 | 0.81 |  |
|  | 1.53 | 1.43 | 1.41 | 0.69 | 1.59 | 2.00 | 1.80 | 1.87 | 1.00 | 0.96 | 0.88 | 1.30 | 1.15 | 0.88 | 1.32 |  |

| | Dolphinδ1 | Dolph-11 | Dolph-21 | Dolph-28 | Dolph-47 | Dolph-70 | Dolph-80 | Dolph-95 | δ1-Arg16 | K120A | K120T | J2-M | Epitope |
|---|---|---|---|---|---|---|---|---|---|---|---|---|---|
| D1-113 | 0.053 | 1.444 | 1.384 | 1.556 | 0.081 | 0.060 | 0.053 | 0.054 | 1.574 | 1.634 | 0.059 | 0.051 | 28-47 |
| D1-143 | 0.048 | 0.790 | 0.941 | 0.055 | 0.046 | 0.047 | 0.047 | 0.042 | 1.178 | 1.100 | 1.124 | 1.172 | 21-28 |
| D1-155 | 0.053 | 0.933 | 1.201 | 1.282 | 0.051 | 0.050 | 0.050 | 0.049 | 1.107 | 1.093 | 0.053 | 0.050 | 28-47 |
| D1-182 | 0.079 | 1.322 | 1.362 | 1.348 | 1.099 | 0.248 | 0.104 | 0.088 | 1.378 | 1.393 | 0.086 | 0.090 | 47-70 |
| D1-183 | 0.048 | 1.077 | 1.012 | 1.154 | 0.046 | 0.048 | 0.048 | 0.046 | 1.202 | 1.060 | 0.088 | 0.065 | 28-47 |
| D1-191 | 0.051 | 1.043 | 1.125 | 1.157 | 0.055 | 0.056 | 0.055 | 0.053 | 1.167 | 1.204 | 0.053 | 0.051 | 28-47 |
| D1-192 | 0.049 | 0.926 | 1.195 | 1.020 | 0.973 | 0.199 | 0.092 | 0.047 | 1.173 | 1.207 | 1.157 | 0.995 | 47-70 |
| D1-201 | 0.062 | 1.030 | 1.161 | 1.223 | 0.990 | 0.979 | 0.769 | 0.051 | 1.191 | 1.036 | 1.306 | 1.116 | 80-95 |
| D1-203 | 0.053 | 0.046 | 0.051 | 0.061 | 0.072 | 0.058 | 0.055 | 0.050 | 0.972 | 0.267 | 0.241 | 0.491 | 1-11 |
| D1-253 | 0.047 | 1.100 | 1.612 | 0.629 | 0.409 | 0.100 | 0.053 | 0.050 | 1.500 | 1.132 | 1.343 | 1.180 | 47-70 |
| D1-257 | 0.053 | 0.871 | 1.359 | 1.181 | 0.812 | 0.115 | 0.075 | 0.055 | 1.252 | 0.928 | 1.179 | 0.882 | 47-70 |
| D1-278 | 0.054 | 0.931 | 1.114 | 1.271 | 0.054 | 0.050 | 0.051 | 0.056 | 1.014 | 0.825 | 0.056 | 0.055 | 28-47 |
| D1-282 | 0.116 | 1.354 | 1.460 | 1.575 | 0.105 | 0.099 | 0.114 | 0.104 | 1.599 | 1.370 | 0.173 | 0.220 | 28-47 |
| D1-285 | 0.052 | 1.089 | 0.053 | 0.062 | 0.054 | 0.047 | 0.051 | 0.053 | 1.341 | 1.330 | 1.441 | 1.271 | 11 to 21 |
| TS-1 | 0.111 | 1.036 | 1.642 | 0.910 | 0.561 | 0.081 | 0.103 | 0.329 | 1.649 | 0.492 | 0.658 | 1.002 | |

FIG. 47B

| | Dolphin (1-94) | Dolphin (28-94) | Dolphin (44-94) | Dolphin (72-94) | Dolphin (83-94) | CDR1(S) | CDR2(G) | CDR3(S) | Epitope | critical |
|---|---|---|---|---|---|---|---|---|---|---|
| Isotype | - | - | - | - | - | - | - | - | | |
| δ2-14 | - | + | + | + | + | + | + | + | 1-27 | |
| δ2-17 | - | - | - | - | - | + | + | + | 83-94 | |
| δ2-22 | - | + | + | + | + | + | + | + | 1-27 | |
| δ2-30 | - | + | + | + | + | + | + | + | 1-27 | |
| δ2-31 | - | - | + | + | + | + | + | + | 1-27 | |
| δ2-32 | - | + | + | - | + | + | + | + | 72-83 | |
| δ2-33 | - | + | + | + | + | + | + | + | 1-27 | |
| δ2-36 | - | + | + | + | + | + | + | + | 1-27 | |
| δ2-37 | - | + | + | + | + | + | + | + | 1-27 | |
| B6 | - | - | - | - | - | + | + | + | 83-94 | |
| 15D | - | + | + | + | + | - | + | + | 28-38 | G35 |
| 7A5 | + | + | + | + | + | + | + | + | γ9 binder | |
| IMM510 | + | + | + | + | + | + | + | + | γδ pan | |
| B1 | + | + | + | + | + | + | + | + | γδ pan | |

FIG. 48

SEQUENCE LISTING

```
<160> NUMBER OF SEQ ID NOS: 227

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgctgttct ccagcctgct gtgtgtattt                                   30

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgcagagga tctcctccct catccatct                                    29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgattctta ctgtgggctt tagcttttg                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttggggtag aattccttca ccagacaagc                                   30
```

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Gln Arg Arg Lys Asn Pro Gln Glu Gly Leu Tyr Asn Glu Leu Gln
1               5                   10                  15

Lys Asp Lys Met Ala Glu Ala Tyr Ser Glu Ile Gly Met
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Arg Arg Arg Gly Lys Gly His Asp Gly Leu Tyr Gln Gly Leu Ser
1               5                   10                  15

Thr Ala Thr Lys Asp Thr Tyr Asp Ala Leu His Met Gln
            20                  25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agagtgaagt tcagcaggag cgca                                           24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcgagtggc tgttagccag a                                              21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ggtgcttcta gctttcctgt ctcctgc                                27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atgctgttgg ctctagctct gcttcta                                27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
atgctgtcac tgctccacac atcaacg                                27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggaagaaaaa tagtgggctt gggggaa                                27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
atgacaacac ccagaaattc agtaaatgg                              29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tcaaggagag ctgtcatttt ctattggtg                              29

<210> SEQ ID NO 16

```
<211> LENGTH: 9
<212> TYPE: PRT
<213> ORGANISM: Homo sapiens

<400> SEQUENCE: 16

Ser Leu Leu Met Trp Ile Thr Gln Cys
1               5

<210> SEQ ID NO 17
<211> LENGTH: 17
<212> TYPE: PRT
<213> ORGANISM: Homo sapiens

<400> SEQUENCE: 17

Ser Lys Glu Met Ile Phe Leu Ile Arg Gln Gly Ser Asp Glu Gln Asn
1               5                   10                  15

Ala

<210> SEQ ID NO 18
<211> LENGTH: 16
<212> TYPE: PRT
<213> ORGANISM: Homo sapiens

<400> SEQUENCE: 18

Thr Asp Lys Leu Ile Phe Gly Lys Gly Thr Arg Val Thr Val Glu Pro
1               5                   10                  15

<210> SEQ ID NO 19
<211> LENGTH: 17
<212> TYPE: PRT
<213> ORGANISM: Homo sapiens

<400> SEQUENCE: 19

Leu Thr Ala Gln Leu Phe Phe Gly Lys Gly Thr Gln Leu Ile Val Glu
1               5                   10                  15

Pro

<210> SEQ ID NO 20
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Lys Glu Met Ile Phe Leu Ile Arg Gln Gly Ser Asp Glu Gln Asn
1               5                   10                  15

Ala Lys Ser Gly Arg Tyr Ser Val Asn Phe Lys Lys Ala Ala Lys Ser
                20                  25                  30

Val Ala Leu Thr Ile Ser Ala Leu Gln Leu Glu Asp Ser Ala Lys Tyr
            35                  40                  45

Phe Cys Ala Leu Gly Thr Gly Val Arg Gly Leu Gln Asp Thr Asp Lys
        50                  55                  60

Leu Ile Phe Gly Lys Gly Thr Arg Val Thr Val Glu Pro
65                  70                  75

<210> SEQ ID NO 21
<211> LENGTH: 79
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 21

Ser Lys Glu Met Ile Phe Leu Ile Arg Gln Gly Ser Asp Glu Gln Asn
1               5                   10                  15

Ala Lys Ser Gly Arg Tyr Ser Val Asn Phe Lys Lys Ala Ala Lys Ser
            20                  25                  30

Val Ala Leu Thr Ile Ser Ala Leu Gln Leu Glu Asp Ser Ala Lys Tyr
        35                  40                  45

Phe Cys Ala Leu Gly Glu Ala Pro Ser Ala Trp Gly Lys His Leu Thr
    50                  55                  60

Ala Gln Leu Phe Phe Gly Lys Gly Thr Gln Leu Ile Val Glu Pro
65                  70                  75

<210> SEQ ID NO 22
<211> LENGTH: 118
<212> TYPE: PRT
<213> ORGANISM: Homo sapiens

<400> SEQUENCE: 22

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

```
Val Arg Gly Leu Gln Asp Ser Trp Asp Thr Arg Gln Met Phe Phe Gly
            100                 105                 110

Thr Gly Ile Lys Leu Phe Val Glu Pro
        115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Ala
                85                  90                  95

Pro Ser Ala Trp Gly Lys His Leu Thr Ala Gln Leu Phe Phe Gly Lys
            100                 105                 110

Gly Thr Gln Leu Ile Val Glu Pro
        115                 120

<210> SEQ ID NO 25
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Gln Lys Val Thr Gln Val Gln Arg Ala Met Ser Ser Gln Leu Gly
1               5                   10                  15

Glu Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro Arg Ser Gln Pro His Thr Lys Pro Ser Val
        115                 120                 125

Phe Val Met Lys Asn Gly Thr Asn Val Ala Cys Leu Val Lys Glu Phe
    130                 135                 140
```

<210> SEQ ID NO 26
<211> LENGTH: 11
<212> TYPE: PRT
<213> ORGANISM: Homo sapiens

<400> SEQUENCE: 26

Val Ser Met Pro Val Arg Lys Ala Val Thr Leu
1               5                   10

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Gln Lys Val Thr Gln Ala Gln Ser Ser Val Ser Met Pro Val Asn
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115

<210> SEQ ID NO 28
<211> LENGTH: 16
<212> TYPE: PRT
<213> ORGANISM: Homo sapiens

<400> SEQUENCE: 28

Phe Lys Lys Ala Ala Lys Ser Val Ala Leu Thr Ile Ser Ala Leu Gln
1               5                   10                  15

<210> SEQ ID NO 29
<211> LENGTH: 25
<212> TYPE: PRT
<213> ORGANISM: Homo sapiens

<400> SEQUENCE: 29

Ala Lys Ser Gly Arg Tyr Ser Val Asn Phe Lys Lys Ala Ala Lys Ser
1               5                   10                  15

Val Ala Leu Thr Ile Ser Ala Leu Gln
            20                  25

<210> SEQ ID NO 30
<211> LENGTH: 148
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ala Gln Lys Val Thr Gln Val Gln Arg Ala Met Ser Ser Gln Leu Gly
1               5                   10                  15

Glu Ala Val Thr Leu Ser Cys Gln Tyr Glu Thr Ser Leu Ser Trp Tyr
                20                  25                  30

Asp Ile Phe Trp Tyr Lys Gln Leu Pro Ser Gly Glu Met Thr Phe Leu
            35                  40                  45

Ile His Gln Ile Ser Ser Asp Gln Asn Ala Lys Asn Gly Arg Tyr Ser
        50                  55                  60

Val Asn Phe Gln Glu Arg His Lys Phe Ile Ser Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro Arg Ser Gln Pro His Thr Lys Pro Ser Val
        115                 120                 125

Phe Val Met Lys Asn Gly Thr Asn Val Ala Cys Leu Val Lys Glu Phe
    130                 135                 140

Tyr Pro Lys Asp
145

<210> SEQ ID NO 31
<211> LENGTH: 15
<212> TYPE: PRT
<213> ORGANISM: Homo sapiens

<400> SEQUENCE: 31

Ser Trp Trp Ser Tyr Tyr Ile Phe Trp Tyr Lys Gln Leu Pro Ser
1               5                   10                  15

<210> SEQ ID NO 32
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Trp Trp Ser Tyr Tyr Ile Phe Trp Tyr Lys Gln Leu Pro Ser Lys
1               5                   10                  15

Glu Met Ile Phe Leu Ile Arg Gln Gly Ser Asp Glu Gln Asn Ala Lys
                20                  25                  30

Ser Gly Arg Tyr Ser Val Asn Phe Lys Lys Ala Ala Lys Ser Val Ala
            35                  40                  45

Leu Thr Ile Ser Ala Leu Gln Leu Glu Asp Ser Ala Lys Tyr Phe Cys
        50                  55                  60

Ala Leu Gly Thr Gly Val Arg Gly Leu Gln Asp Thr Asp Lys Leu Ile
65                  70                  75                  80

Phe Gly Lys Gly Thr Arg Val Thr Val Glu Pro
                85                  90

<210> SEQ ID NO 33
<211> LENGTH: 8
<212> TYPE: PRT
<213> ORGANISM: Homo sapiens

<400> SEQUENCE: 33

Leu Asn Cys Leu Tyr Glu Thr Ser
1               5

<210> SEQ ID NO 34
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Leu Asn Cys Leu Tyr Glu Thr Ser Trp Trp Ser Tyr Tyr Ile Phe Trp
1               5                   10                  15

Tyr Lys Gln Leu Pro Ser Lys Glu Met Ile Phe Leu Ile Arg Gln Gly
                20                  25                  30

Ser Asp Glu Gln Asn Ala Lys Ser Gly Arg Tyr Ser Val Asn Phe Lys
            35                  40                  45

Lys Ala Ala Lys Ser Val Ala Leu Thr Ile Ser Ala Leu Gln Leu Glu
50                  55                  60

Asp Ser Ala Lys Tyr Phe Cys Ala Leu Gly Thr Gly Val Arg Gly Leu
65                  70                  75                  80

Gln Asp Thr Asp Lys Leu Ile Phe Gly Lys Gly Thr Arg Val Thr Val
                85                  90                  95

Glu Pro

<210> SEQ ID NO 35
<211> LENGTH: 10
<212> TYPE: PRT
<213> ORGANISM: Homo sapiens

<400> SEQUENCE: 35

Ala Lys Ser Gly Arg Tyr Ser Val Asn Phe
1               5                   10

<210> SEQ ID NO 36
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Lys Ser Gly Arg Tyr Ser Val Asn Phe Lys Lys Ala Ala Lys Ser
1               5                   10                  15

Val Ala Leu Thr Ile Ser Ala Leu Gln Leu Glu Asp Ser Ala Lys Tyr
                20                  25                  30

Phe Cys Ala Leu Gly Thr Gly Val Arg Gly Leu Gln Asp Thr Asp Lys
            35                  40                  45

Leu Ile Phe Gly Lys Gly Thr Arg Val Thr Val Glu Pro
50                  55                  60

<210> SEQ ID NO 37
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Lys Ser Gly Arg Tyr Ser Val Asn Phe Lys Ala Lys Ser
1               5                   10                  15

Val Ala Leu Thr Ile Ser Ala Leu Gln Leu Glu Asp Ser Ala Lys Tyr
            20                  25                  30

Phe Cys Ala Leu Gly Glu Ala Pro Ser Ala Trp Gly Lys His Leu Thr
        35                  40                  45

Ala Gln Leu Phe Phe Gly Lys Gly Thr Gln Leu Ile Val Glu Pro
    50                  55                  60

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Gln Lys Val Thr Gln Val Gln Arg Ala Met Ser Ser Gln Leu Gly
1               5                   10                  15

Glu Ala Val Thr Leu Ser Cys Gln Tyr Glu Thr Ser Leu Ser Trp Tyr
            20                  25                  30

Asp Ile Phe Trp Tyr Lys Gln Leu Pro Ser Gly Glu Met Thr Phe Leu
        35                  40                  45

Ile His Gln Ile Ser Ser Asp Gln Asn Ala Lys Asn Gly Arg Tyr Ser
    50                  55                  60

Val Asn Phe Gln Glu Arg His Lys Phe Ile Ser Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115

<210> SEQ ID NO 39
<211> LENGTH: 116
<212> TYPE: PRT
<213> ORGANISM: Homo sapiens

<400> SEQUENCE: 39

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Pro
                85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 40
<211> LENGTH: 12
<212> TYPE: PRT
<213> ORGANISM: Homo sapiens

<400> SEQUENCE: 40

Ala Lys Asn Leu Ala Val Leu Lys Ile Leu Ala Pro
1               5                   10

<210> SEQ ID NO 41
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Phe Leu Asn Asn Gln Ala Val Leu Asn Ile Leu
65                  70                  75                  80

Glu Ala Ser Glu Arg Asp Glu Gly Ser Tyr Tyr Cys Ala Cys Asp Pro
                85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 42
<211> LENGTH: 7
<212> TYPE: PRT
<213> ORGANISM: Homo sapiens

<400> SEQUENCE: 42

Glu Ala Ile Gly Asn Tyr Tyr
1               5

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Ile Glu Leu Val Pro Glu His Gln Thr Val Pro Val Ser Ile Gly
1               5                   10                  15

Val Pro Ala Thr Leu Arg Cys Ser Met Lys Gly Asp Ser Ile Ser Asn
            20                  25                  30

Tyr Tyr Thr Phe Trp Tyr Arg Arg Thr Pro Gly Asn Thr Met Thr Leu
        35                  40                  45

```
Ile Tyr Arg Glu Gly Gly Thr Tyr Gly Pro Gly Phe Glu Asp Asn Leu
 50                  55                  60

Gln Gly Glu Ile Asp Phe Leu Asn Asn Gln Ala Val Leu Asn Ile Leu
 65                  70                  75                  80

Glu Ala Ser Glu Arg Asp Glu Gly Ser Tyr Tyr Cys Ala Cys Asp Pro
                 85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 44
<211> LENGTH: 11
<212> TYPE: PRT
<213> ORGANISM: Homo sapiens

<400> SEQUENCE: 44

Lys Asp Asn Phe Gln Gly Asp Ile Asp Ile Ala
 1               5                  10

<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Ile Glu Leu Val Pro Glu His Gln Thr Val Pro Val Ser Ile Gly
 1               5                  10                  15

Val Pro Ala Thr Leu Arg Cys Ser Met Lys Gly Glu Ala Ile Gly Asn
                 20                  25                  30

Tyr Tyr Ile Asn Trp Tyr Arg Lys Thr Gln Gly Asn Thr Met Thr Phe
             35                  40                  45

Ile Tyr Arg Glu Lys Asp Ile Tyr Gly Pro Gly Phe Glu Asp Asn Leu
 50                  55                  60

Gln Gly Glu Ile Asp Phe Leu Asn Asn Gln Ala Val Leu Asn Ile Leu
 65                  70                  75                  80

Glu Ala Ser Glu Arg Asp Glu Gly Ser Tyr Tyr Cys Ala Cys Asp Pro
                 85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 46
<211> LENGTH: 27
<212> TYPE: PRT
<213> ORGANISM: Homo sapiens

<400> SEQUENCE: 46

Ala Ile Glu Leu Val Pro Glu His Gln Thr Val Pro Val Ser Ile Gly
 1               5                  10                  15

Val Pro Ala Thr Leu Arg Cys Ser Met Lys Gly
                 20                  25

<210> SEQ ID NO 47
<211> LENGTH: 116
```

```
<212> TYPE: PRT
<213> ORGANISM: Tursiops truncatus

<400> SEQUENCE: 47

Ala Val Thr Leu Val Pro Gln Asn Gln Ala Arg Ser Val Ser Val Gly
1               5                   10                  15

Glu Ser Val Thr Leu Arg Cys Ser Met Lys Gly Asp Ser Ile Ser Asn
            20                  25                  30

Tyr Tyr Thr Phe Trp Tyr Arg Arg Thr Pro Gly Asn Thr Met Thr Leu
        35                  40                  45

Ile Tyr Arg Glu Gly Gly Thr Tyr Gly Pro Gly Phe Glu Asp Asn Leu
    50                  55                  60

Gln Gly Glu Ile Asp Phe Leu Asn Asn Gln Ala Val Leu Asn Ile Leu
65                  70                  75                  80

Glu Ala Ser Glu Arg Asp Glu Gly Ser Tyr Tyr Cys Ala Cys Asp Pro
                85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcccagaagg ttactcaagc ccagtc                                          26

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccattgagt tggtgcctga acacc                                           25

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttacaagaaa ataacttgg cagtcaagag aaa                                   33

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```

```
tcttccaact tggaagggag aacgaagtc                                          29
```

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
tcttccaact tggaaggggg aacga                                              25
```

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
tcttccaact tggaagggag aacaaagtc                                          29
```

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
gcaggtcacc tagagcaacc tcaaatttcc                                         30
```

<210> SEQ ID NO 55
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Pro Val
                85                  90                  95

Val Ile Pro Lys Gly Lys Leu Ser Phe Gly Lys Gly Thr Arg Val Thr
            100                 105                 110

Val Glu Pro
        115

<210> SEQ ID NO 56
<211> LENGTH: 118

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Leu
                85                  90                  95

Cys Leu Gly Asp Thr Tyr Thr Asp Lys Leu Ile Phe Gly Lys Gly Thr
            100                 105                 110

Arg Val Thr Val Glu Pro
        115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Asp Pro
                85                  90                  95

Lys Val Tyr Trp Gly Cys Thr Asp Lys Leu Ile Phe Gly Lys Gly Thr
            100                 105                 110

Arg Val Thr Val Glu Pro
        115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Ala Gln Lys Val Thr Gln Ala Gln Ser Ser Val Ser Met Pro Val Arg

-continued

```
                1               5                  10                 15
Lys Ala Val Thr Leu Asn Cys Leu Tyr Glu Thr Ser Trp Trp Ser Tyr
                20                 25                 30

Tyr Ile Phe Trp Tyr Lys Gln Leu Pro Ser Lys Glu Met Ile Phe Leu
                35                 40                 45

Ile Arg Gln Gly Ser Asp Glu Gln Asp Ala Lys Ser Gly Arg Tyr Ser
            50                 55                 60

Val Asn Phe Lys Lys Ala Ala Lys Ser Val Ala Leu Thr Ile Ser Ala
 65                 70                 75                 80

Leu Gln Leu Glu Asp Ser Ala Lys Tyr Phe Cys Ala Leu Gly Thr Gly
                85                 90                 95

Val Arg Gly Leu Gln Asp Ala Asp Lys Leu Ile Phe Gly Lys Gly Thr
                100                105                110

Arg Val Thr Val Glu Pro
        115
```

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Ala Gln Lys Val Thr Gln Ala Gln Ser Ser Val Ser Met Pro Val Arg
 1               5                  10                 15

Lys Ala Val Thr Leu Asn Cys Leu Tyr Glu Thr Ser Trp Trp Ser Tyr
                20                 25                 30

Tyr Ile Phe Trp Tyr Lys Gln Leu Pro Ser Lys Glu Met Ile Phe Leu
                35                 40                 45

Ile Arg Gln Gly Ser Asp Glu Gln Asn Ala Lys Ser Gly Arg Tyr Ser
            50                 55                 60

Val Asn Phe Lys Lys Ala Ala Lys Ser Val Ala Leu Thr Ile Ser Ala
 65                 70                 75                 80

Leu Gln Leu Glu Asp Ser Ala Lys Tyr Phe Cys Ala Leu Leu Leu Gly
                85                 90                 95

Asp Thr Ser Phe Tyr Thr Asp Lys Leu Ile Phe Gly Lys Gly Thr Arg
                100                105                110

Val Thr Val Glu Pro
        115
```

<210> SEQ ID NO 60
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Ala Gln Lys Val Thr Gln Ala Gln Ser Ser Val Ser Met Pro Val Arg
 1               5                  10                 15

Lys Ala Val Thr Leu Asn Cys Leu Tyr Glu Thr Ser Trp Trp Ser Tyr
                20                 25                 30

Tyr Ile Phe Trp Tyr Lys Gln Leu Pro Ser Lys Glu Met Ile Phe Leu
                35                 40                 45

Ile Arg Gln Gly Ser Asp Glu Gln Asn Ala Lys Ser Gly Arg Tyr Ser
```

```
                50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Ala Leu Leu Pro
                 85                  90                  95

Phe Leu Pro Ser Asp Trp Gly Ile Pro Val Thr Asp Lys Leu Ile Phe
                100                 105                 110

Gly Lys Gly Thr Arg Val Thr Val Glu Pro
            115                 120

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Gln Lys Val Thr Gln Ala Gln Ser Ser Val Ser Met Pro Val Arg
 1               5                  10                  15

Lys Ala Val Thr Leu Asn Cys Leu Tyr Glu Thr Ser Trp Trp Ser Tyr
                20                  25                  30

Tyr Ile Phe Trp Tyr Lys Gln Leu Pro Ser Lys Glu Met Ile Phe Leu
             35                  40                  45

Ile Arg Gln Gly Ser Asp Glu Gln Asn Ala Lys Ser Gly Arg Tyr Ser
         50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Thr Gly
                 85                  90                  95

Val Arg Gly Leu Gln Asp Thr Asp Lys Leu Ile Phe Gly Thr Gly Thr
                100                 105                 110

Arg Val Thr Val Glu Pro
            115

<210> SEQ ID NO 62
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Gln Lys Val Thr Gln Ala Gln Ser Ser Val Ser Met Pro Val Arg
 1               5                  10                  15

Lys Ala Val Thr Leu Asn Cys Leu Tyr Glu Thr Ser Trp Trp Ser Tyr
                20                  25                  30

Tyr Ile Phe Trp Tyr Lys Gln Leu Pro Ser Lys Glu Met Ile Phe Leu
             35                  40                  45

Ile Arg Gln Gly Ser Asp Glu Gln Asn Ala Lys Ser Gly Arg Tyr Ser
         50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Gly Leu
                 85                  90                  95

Ser Ser Leu Asp Leu Gly Asp Thr Asp Asn His Tyr Thr Asp Lys Leu
```

```
                100                 105                 110

Ile Phe Gly Lys Gly Thr Arg Val Thr Val Glu Pro
        115                 120

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly His Pro
                85                  90                  95

Arg Ser Leu Met Gly Val Tyr Thr Asp Lys Leu Ile Phe Gly Lys Gly
            100                 105                 110

Thr Arg Val Thr Val Glu Pro
        115

<210> SEQ ID NO 64
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Ile
65                  70                  75                  80

Ile Leu Arg Asn Leu Ile Glu Asn Asp Ser Gly Val Tyr Tyr Cys Ala
                85                  90                  95

Thr Trp Asp Asp Gly Lys Lys Leu Phe Gly Ser Gly Thr Thr Leu Val
            100                 105                 110

Val Thr

<210> SEQ ID NO 65
<211> LENGTH: 121
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 65

```
Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Asp Asp Thr Arg Leu Gly Lys Ile Lys Val Phe
            100                 105                 110

Ala Pro Gly Thr Lys Leu Ile Ile Thr
            115                 120
```

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Ser Asp Lys Lys Leu Phe Gly Ser Gly Thr Thr Leu Val Val
            100                 105                 110

Thr
```

<210> SEQ ID NO 67
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
```

```
                    20                  25                  30

Thr Ser Val Tyr Trp Tyr Arg Glu Arg Pro Gly Glu Val Ile Gln Phe
            35                  40                  45

Leu Val Ser Ile Ser Tyr Asp Gly Thr Val Arg Lys Glu Ser Gly Ile
        50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Ile His Lys Lys Leu Phe Gly Ser Gly Thr Thr Leu
            100                 105                 110

Val Val Thr
        115

<210> SEQ ID NO 68
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ser Ser Asn Leu Glu Gly Arg Thr Lys Ser Val Ile Arg Gln Thr Gly
1               5                   10                  15

Ser Ser Ala Glu Asn Thr Cys Asp Leu Ala Glu Gly Ser Asn Gly Tyr
            20                  25                  30

Ile His Trp Tyr Leu His Gln Glu Gly Lys Thr Pro Gln Arg Leu Gln
            35                  40                  45

Tyr Tyr Asp Ser Tyr Asn Ser Lys Val Val Leu Glu Ser Gly Val Ser
        50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Cys His Tyr Lys Lys Leu Phe Gly Ser Gly Thr Thr Leu
            100                 105                 110

Val Val Thr
        115

<210> SEQ ID NO 69
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ser Ser Asn Leu Glu Gly Arg Thr Lys Ser Val Thr Arg Gln Thr Gly
1               5                   10                  15

Ser Ser Ala Glu Ile Thr Cys Asp Leu Thr Val Thr Asn Thr Phe Tyr
            20                  25                  30

Ile His Trp Tyr Leu His Gln Glu Gly Lys Ala Pro Gln Arg Leu Leu
            35                  40                  45

Tyr Tyr Asp Val Ser Thr Ala Arg Asp Val Leu Glu Ser Gly Leu Ser
        50                  55                  60

Pro Gly Lys Tyr Tyr Thr His Thr Pro Arg Arg Trp Ser Trp Ile Leu
```

```
                65                  70                  75                  80
Arg Leu Gln Asn Leu Ile Glu Asn Asp Ser Gly Val Tyr Tyr Cys Ala
                    85                  90                  95

Thr Trp Asp Arg Arg Trp Ile Lys Thr Phe Ala Lys Gly Thr Lys Leu
                100                 105                 110

Ile Val Thr Ser Pro
            115
```

<210> SEQ ID NO 70
<211> LENGTH: 127
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 70

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
                20                  25                  30

Ile His Trp Tyr Leu His Gln Glu Gly Lys Ala Pro Gln Arg Leu Gln
            35                  40                  45

Tyr Tyr Asp Ser Tyr Asn Ser Lys Val Val Leu Glu Ser Gly Val Ser
        50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Gly Leu Asp Ala Thr Cys Gly Val Asp Thr Thr Gly Trp
                100                 105                 110

Phe Lys Ile Phe Ala Glu Gly Thr Lys Leu Ile Val Thr Ser Pro
            115                 120                 125
```

<210> SEQ ID NO 71
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 71

```
Ser Ser Asn Leu Glu Gly Arg Thr Lys Ser Val Thr Arg Pro Thr Gly
1               5                   10                  15

Ser Ser Ala Val Ile Thr Cys Asp Leu Pro Val Glu Asn Ala Val Tyr
                20                  25                  30

Thr His Trp Tyr Leu His Gln Glu Gly Lys Ala Pro Arg Arg Leu Leu
            35                  40                  45

Tyr Tyr Asp Ser Tyr Thr Ser Ser Val Val Leu Glu Ser Gly Ile Ser
        50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Lys Lys Leu Phe Gly Ser Gly Thr Thr Leu Val Val Thr
                100                 105                 110
```

```
<210> SEQ ID NO 72
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Ile Ala Ser Gln Leu Gly Lys Lys Ile Lys Val
            100                 105                 110

Phe Gly Pro Gly Thr Lys Leu Ile Ile Thr
        115                 120

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ser Ser Asn Leu Gly Gly Arg Thr Lys Ser Val Thr Arg Gln Thr Gly
1               5                   10                  15

Ser Ser Ala Glu Ile Thr Cys Asp Leu Thr Val Thr Asn Thr Phe Tyr
            20                  25                  30

Ile His Trp Tyr Leu His Gln Glu Gly Lys Ala Pro Gln Arg Leu Leu
        35                  40                  45

Tyr Tyr Asp Val Ser Thr Ala Arg Asp Val Leu Glu Ser Gly Leu Ser
    50                  55                  60

Pro Gly Lys Tyr Tyr Thr His Thr Pro Arg Arg Trp Ser Trp Ile Leu
65                  70                  75                  80

Arg Leu Gln Asn Leu Ile Glu Asn Asp Ser Gly Val Tyr Tyr Cys Ala
                85                  90                  95

Thr Trp Asp Arg Tyr Tyr Lys Lys Leu Phe Gly Ser Gly Thr Thr
            100                 105                 110

Leu Val Val Thr
        115

<210> SEQ ID NO 74
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

```
Ser Ser Asn Leu Glu Gly Arg Thr Lys Ser Val Thr Arg Gln Thr Gly
1               5                   10                  15

Ser Ser Ala Glu Ile Thr Cys Asp Leu Thr Val Thr Asn Thr Phe Tyr
                20                  25                  30

Ile His Trp Tyr Leu His Gln Glu Gly Lys Ala Pro Gln Arg Leu Leu
            35                  40                  45

Tyr Tyr Asp Val Ser Thr Ala Arg Asp Val Leu Glu Ser Gly Leu Ser
        50                  55                  60

Pro Gly Lys Tyr Tyr Thr His Thr Pro Arg Arg Trp Ser Trp Ile Leu
65              70                  75                  80

Arg Leu Gln Asn Leu Ile Glu Asn Asp Ser Gly Val Tyr Tyr Pro Asn
                85                  90                  95

Ser Ser Asp Trp Ile Lys Thr Phe Ala Lys Gly Thr Lys Leu Ile Val
                100                 105                 110

Thr Ser Pro
        115

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ser Ser Asn Leu Glu Gly Gly Thr Lys Ser Val Thr Arg Pro Thr Arg
1               5                   10                  15

Ser Ser Ala Glu Ile Thr Cys Asp Leu Ala Glu Arg Asn Thr Phe Tyr
                20                  25                  30

Ile His Trp Tyr Leu His Gln Glu Gly Lys Ala Pro Gln Arg Leu Gln
            35                  40                  45

Tyr Tyr Asp Ser Tyr Thr Ser Ser Val Val Leu Glu Ser Gly Ile Ser
        50                  55                  60

Pro Gly Lys Tyr Asp Thr Tyr Gly Ser Thr Arg Lys Asn Leu Arg Met
65              70                  75                  80

Ile Leu Arg Asn Leu Ile Glu Asn Asp Ser Gly Val Tyr Tyr Cys Ala
                85                  90                  95

Thr Arg Asp Val Pro Asn Tyr Tyr Lys Lys Leu Phe Gly Ser Gly Thr
                100                 105                 110

Thr Leu Val Val Thr
        115

<210> SEQ ID NO 76
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
                20                  25                  30

Ile His Trp Tyr Leu His Gln Glu Gly Lys Ala Pro Gln Arg Leu Gln
            35                  40                  45
```

```
Tyr Tyr Asp Ser Tyr Asn Ser Lys Val Val Leu Glu Ser Gly Val Ser
         50                  55                  60

Pro Gly Lys Tyr Tyr Thr Tyr Ala Ser Thr Arg Asn Asn Leu Arg Leu
 65                  70                  75                  80

Ile Leu Arg Asn Leu Ile Glu Asn Asp Ser Gly Val Tyr Tyr Cys Ala
                 85                  90                  95

Thr Trp Asp Gly Arg Val Ser Tyr Thr Thr Gly Trp Phe Lys Ile Phe
                100                 105                 110

Ala Glu Gly Thr Lys Leu Ile Val Thr Ser Pro
                115                 120

<210> SEQ ID NO 77
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ser Ser Asn Leu Glu Gly Arg Thr Lys Ser Val Ile Arg Gln Thr Gly
 1               5                  10                  15

Ser Ser Ala Glu Ile Thr Cys Asp Leu Ala Glu Gly Ser Thr Gly Tyr
                 20                  25                  30

Ile His Trp Tyr Leu His Gln Glu Gly Lys Ala Pro Gln Arg Leu Leu
                 35                  40                  45

Tyr Tyr Asp Ser Tyr Thr Ser Ser Val Val Leu Glu Ser Gly Ile Ser
         50                  55                  60

Pro Gly Lys Tyr Asp Thr Tyr Gly Ser Thr Arg Lys Asn Leu Arg Met
 65                  70                  75                  80

Ile Leu Arg Asn Leu Ile Glu Asn Asp Ser Gly Val Tyr Tyr Cys Ala
                 85                  90                  95

Thr Trp Asp Lys Gly Arg Lys Leu Phe Gly Ser Gly Thr Thr Leu Val
                100                 105                 110

Val Thr

<210> SEQ ID NO 78
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Gly His Leu Glu Gln Pro Gln Ile Ser Ser Thr Lys Thr Leu Ser
 1               5                  10                  15

Lys Thr Ala Arg Leu Glu Cys Val Val Ser Gly Ile Thr Ile Ser Ala
                 20                  25                  30

Thr Ser Val Tyr Trp Tyr Arg Glu Arg Pro Gly Glu Val Ile Gln Phe
                 35                  40                  45

Leu Val Ser Ile Ser Tyr Asp Gly Thr Val Arg Lys Glu Ser Gly Ile
         50                  55                  60

Pro Ser Gly Lys Phe Glu Val Asp Arg Ile Pro Glu Thr Ser Thr Ser
 65                  70                  75                  80

Thr Leu Thr Ile His Asn Val Glu Lys Gln Asp Ile Ala Thr Tyr Tyr
                 85                  90                  95
```

Cys Ala Leu Trp Glu Thr His Tyr Lys Lys Leu Phe Gly Ser Gly Thr
            100                 105                 110

Thr Leu Val Val Thr
        115

<210> SEQ ID NO 79
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
            20                  25                  30

Ile His Trp Tyr Leu His Gln Glu Gly Lys Ala Pro Gln Arg Leu Gln
        35                  40                  45

Tyr Tyr Asp Ser Tyr Asn Ser Lys Val Val Leu Glu Ser Gly Val Ser
    50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Gly Arg Tyr Lys Lys Leu Phe Gly Ser Gly Thr Thr Leu
            100                 105                 110

Val Val Thr
        115

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Gly Thr Thr Gly Trp Phe Lys Ile Phe Ala Glu Gly Thr Lys
            100                 105                 110

Leu Ile Val Thr Ser Pro
        115

<210> SEQ ID NO 81
<211> LENGTH: 122

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Lys
                85                  90                  95

Val Leu Gly Val Pro Thr Ala Ser Tyr Thr Asp Asn Lys Leu Ile Phe
            100                 105                 110

Gly Lys Gly Thr Arg Val Thr Val Glu Pro
        115                 120

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Ser Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95

Val Gly Ile Leu Pro Tyr Asp Lys Leu Ile Phe Gly Lys Gly Thr Arg
            100                 105                 110

Val Thr Val Glu Pro
        115

<210> SEQ ID NO 83
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Ile Glu Leu Val Pro Glu His Gln Thr Val Pro Val Ser Ile Gly
```

```
1               5                   10                  15
Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
            35                  40                  45

Ile Tyr Arg Glu Lys Asp Ile Tyr Gly Pro Gly Phe Lys Asp Asn Phe
        50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Ile
                85                  90                  95

Leu Thr Val Leu Gly Asp Asn Arg Thr Asp Lys Leu Ile Phe Gly Lys
                100                 105                 110

Gly Thr Arg Val Thr Val Glu Pro
            115                 120
```

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
            35                  40                  45

Ile Tyr Arg Glu Lys Asp Ile Tyr Gly Pro Gly Phe Lys Asp Asn Phe
        50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Val
                85                  90                  95

Val Gly Glu Gly Gly Ala Asp Lys Leu Ile Phe Gly Lys Gly Thr Arg
                100                 105                 110

Val Thr Val Glu Pro
        115
```

<210> SEQ ID NO 85
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
            35                  40                  45

Ile Tyr Arg Glu Lys Asp Ile Tyr Gly Pro Gly Phe Lys Asp Asn Phe
```

-continued

```
            50                  55                  60
Gln Gly Asp Ile Asp Ile Ala Lys Asn Leu Ala Val Leu Lys Ile Leu
 65                  70                  75                  80

Ala Pro Ser Glu Arg Asp Glu Gly Ser Tyr Tyr Cys Ala Cys Asp Thr
                 85                  90                  95

Val Gly Gly Gly Glu Tyr Thr Asp Lys Leu Ile Phe Gly Lys Gly Thr
            100                 105                 110

Arg Val Thr Val Glu Pro
        115

<210> SEQ ID NO 86
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ile Glu Leu Val Pro Glu His Gln Thr Val Pro Val Ser Ile Gly
 1               5                  10                  15

Val Pro Ala Thr Leu Arg Cys Ser Met Lys Gly Glu Ala Ile Gly Asn
             20                  25                  30

Tyr Tyr Ile Asn Trp Tyr Arg Lys Thr Gln Gly Asn Thr Met Thr Phe
         35                  40                  45

Ile Tyr Arg Glu Lys Asp Ile Tyr Gly Pro Gly Phe Lys Asp Asn Phe
     50                  55                  60

Gln Gly Asp Ile Asp Ile Ala Lys Asn Leu Ala Val Leu Lys Ile Leu
 65                  70                  75                  80

Ala Pro Ser Glu Arg Asp Glu Gly Ser Tyr Tyr Cys Ala Cys Asp Thr
                 85                  90                  95

Val Gly Thr Gly Asp Ile Arg Thr Tyr Thr Asp Lys Leu Ile Phe Gly
            100                 105                 110

Lys Gly Thr Arg Val Thr Val Glu Pro
        115                 120

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Ile Glu Leu Val Pro Glu His Gln Thr Val Pro Val Ser Ile Gly
 1               5                  10                  15

Val Pro Ala Thr Leu Arg Cys Ser Met Lys Gly Glu Ala Ile Gly Asn
             20                  25                  30

Tyr Tyr Ile Asn Trp Tyr Arg Lys Thr Gln Gly Asn Thr Met Thr Phe
         35                  40                  45

Ile Tyr Arg Glu Lys Asp Ile Tyr Gly Pro Gly Phe Lys Asp Asn Phe
     50                  55                  60

Gln Gly Asp Ile Asp Ile Ala Lys Asn Leu Ala Val Leu Lys Ile Leu
 65                  70                  75                  80

Ala Pro Ser Glu Arg Asp Glu Gly Ser Tyr Tyr Cys Ala Cys Asp Ser
                 85                  90                  95

Leu Thr Gly Gly Ser Gly Leu Thr Asp Lys Leu Ile Phe Gly Lys Gly
```

```
                100                 105                 110
Thr Arg Val Thr Val Glu Pro
            115

<210> SEQ ID NO 88
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Pro Pro Ser Glu Arg Asp Glu Gly Ser Tyr Tyr Cys Ala Cys Asp Thr
                85                  90                  95

Gly Gly Tyr Ser Ser Trp Asp Thr Arg Gln Met Phe Phe Gly Thr Gly
            100                 105                 110

Ile Lys Leu Phe Val Glu Pro
            115

<210> SEQ ID NO 89
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Pro
                85                  90                  95

Leu Lys Thr Leu Gly Thr Tyr Thr Asp Lys Leu Ile Phe Gly Lys Gly
            100                 105                 110

Thr Arg Val Thr Val Glu Pro
            115

<210> SEQ ID NO 90
<211> LENGTH: 119
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 90

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Ala
                85                  90                  95

Val Ile Ala Gly Gly Ser Phe Thr Asp Lys Leu Ile Phe Gly Lys Gly
            100                 105                 110

Thr Arg Val Thr Val Glu Pro
        115

<210> SEQ ID NO 91
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Asp Gln Glu Leu Gly Lys Lys Ile Lys Val Phe
            100                 105                 110

Gly Pro Gly Thr Lys Leu Ile Ile Thr
        115                 120

<210> SEQ ID NO 92
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ala Gly His Leu Glu Gln Pro Gln Ile Ser Ser Thr Lys Thr Leu Ser
1               5                   10                  15
```

Lys Thr Ala Arg Leu Glu Cys Val Val Ser Gly Ile Thr Ile Ser Ala
                20                  25                  30

Thr Ser Val Tyr Trp Tyr Arg Glu Arg Pro Gly Glu Val Ile Gln Phe
            35                  40                  45

Leu Val Ser Ile Ser Tyr Asp Gly Thr Val Arg Lys Glu Ser Gly Ile
 50                  55                  60

Pro Ser Gly Lys Phe Glu Val Asp Arg Ile Pro Glu Thr Ser Thr Ser
 65                  70                  75                  80

Thr Leu Thr Ile His Asn Val Glu Lys Gln Asp Ile Ala Thr Tyr Tyr
                85                  90                  95

Cys Ala Leu Trp Ala Tyr Pro Pro Glu Leu Gly Lys Lys Ile Lys Val
                100                 105                 110

Phe Gly Pro Gly Thr Lys Leu Ile Ile Thr
            115                 120

<210> SEQ ID NO 93
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ala Gly His Leu Glu Gln Pro Gln Ile Ser Ser Thr Lys Thr Leu Ser
 1               5                  10                  15

Lys Thr Ala Arg Leu Glu Cys Ala Val Ser Gly Ile Thr Ile Ser Ala
                20                  25                  30

Thr Ser Val Tyr Trp Tyr Arg Glu Arg Pro Gly Glu Val Ile Gln Phe
            35                  40                  45

Leu Val Ser Ile Ser Tyr Asp Gly Thr Val Arg Lys Glu Ser Gly Ile
 50                  55                  60

Pro Ser Gly Lys Phe Glu Val Asp Arg Ile Pro Glu Thr Ser Thr Ser
 65                  70                  75                  80

Thr Leu Thr Ile His Asn Val Glu Lys Gln Asp Ile Ala Thr Tyr Tyr
                85                  90                  95

Cys Ala Leu Trp Glu Val Gln Glu Leu Gly Lys Lys Ile Lys Val Phe
                100                 105                 110

Gly Pro Gly Thr Lys Leu Ile Ile Thr
            115                 120

<210> SEQ ID NO 94
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Gly His Leu Glu Gln Pro Gln Ile Ser Ser Thr Lys Thr Leu Ser
 1               5                  10                  15

Lys Thr Ala Arg Leu Glu Cys Val Val Ser Gly Ile Thr Ile Ser Ala
                20                  25                  30

Thr Ser Val Cys Trp Tyr Arg Glu Arg Pro Gly Glu Val Ile Gln Phe
            35                  40                  45

Leu Val Ser Ile Ser Tyr Asp Gly Thr Val Arg Lys Glu Ser Gly Ile
 50                  55                  60

```
Pro Ser Gly Lys Phe Glu Val Asp Arg Ile Pro Glu Thr Ser Thr Ser
 65                  70                  75                  80

Thr Leu Thr Ile His Asn Val Glu Lys Gln Asp Ile Ala Thr Tyr Tyr
                 85                  90                  95

Cys Ala Leu Trp Glu Val Leu Gln Glu Leu Gly Lys Lys Ile Lys Val
            100                 105                 110

Phe Gly Pro Gly Thr Lys Leu Ile Ile Thr
        115                 120

<210> SEQ ID NO 95
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Gly His Leu Glu Gln Pro Gln Ile Ser Ser Thr Lys Thr Leu Ser
 1               5                  10                  15

Lys Thr Ala Arg Leu Glu Cys Val Val Ser Gly Ile Thr Ile Ser Ala
                 20                  25                  30

Thr Ser Val Tyr Trp Tyr Arg Glu Arg Pro Gly Glu Val Ile Gln Phe
             35                  40                  45

Leu Val Ser Ile Ser Tyr Asp Gly Thr Val Arg Lys Glu Ser Gly Ile
         50                  55                  60

Pro Ser Gly Lys Phe Glu Val Asp Arg Ile Pro Glu Thr Ser Thr Ser
 65                  70                  75                  80

Thr Leu Thr Ile His Asn Val Lys Lys Gln Asp Ile Ala Thr Tyr Tyr
                 85                  90                  95

Cys Ala Leu Trp Glu Val Arg Glu Leu Gly Lys Lys Ile Lys Val Phe
            100                 105                 110

Gly Pro Gly Thr Lys Leu Ile Ile Thr
        115                 120

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Gly His Leu Glu Gln Pro Gln Ile Ser Ser Thr Lys Thr Leu Ser
 1               5                  10                  15

Lys Thr Ala Arg Leu Glu Cys Val Val Ser Gly Ile Thr Ile Ser Ala
                 20                  25                  30

Thr Ser Val Tyr Trp Tyr Arg Glu Arg Pro Gly Glu Val Ile Gln Phe
             35                  40                  45

Leu Val Ser Ile Ser Tyr Asp Gly Thr Val Arg Lys Glu Ser Gly Ile
         50                  55                  60

Pro Ser Gly Lys Phe Glu Val Asp Arg Ile Pro Glu Thr Ser Thr Ser
 65                  70                  75                  80

Thr Leu Thr Ile His Asn Val Glu Lys Gln Asp Ile Ala Thr Tyr Tyr
                 85                  90                  95

Cys Ala Leu Trp Arg Glu Leu Gly Lys Lys Ile Lys Val Phe Gly Pro
            100                 105                 110
```

Gly Thr Lys Leu Ile Ile Thr
        115

<210> SEQ ID NO 97
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Ala Gln Glu Leu Gly Lys Lys Ile Lys Val Phe
            100                 105                 110

Gly Pro Gly Thr Lys Leu Ile Ile Thr
        115                 120

<210> SEQ ID NO 98
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Thr Glu Leu Gly Lys Lys Ile Lys Val Phe Gly
            100                 105                 110

Pro Gly Thr Lys Leu Ile Ile Thr
        115                 120

<210> SEQ ID NO 99
<211> LENGTH: 121
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 99

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Glu Val Glu Leu Gly Lys Lys Ile Lys Val Phe
            100                 105                 110

Gly Pro Gly Thr Lys Leu Ile Ile Thr
        115                 120

<210> SEQ ID NO 100
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Pro Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Pro Pro Gln Ser Leu Gly Lys Lys Ile Lys Val
            100                 105                 110

Phe Gly Pro Gly Thr Lys Leu Ile Ile Thr
        115                 120

<210> SEQ ID NO 101
<211> LENGTH: 355
<212> TYPE: DNA
<213> ORGANISM: Homo sapiens

<400> SEQUENCE: 101
gcccagaagg ttactcaagc ccagtcatca gtatccatgc cagtgaggaa agcagtcacc       60
ctgaactgcc tgtatgaaac aagttggtgg tcatattata tttttggta caagcaactt      120 cccagcaaag agatgatttt ccttattcgc cagggttctg atgaacagaa tgcaaaaagt      180
```

```
ggtcgctatt ctgtcaactt caagaaagca gcgaaatccg tcgccttaac catttcagcc      240
ttacagctag aagattcagc aaagtacttt tgtgctcttg ggacggggt gagggactc        300 caggacaccg ataaactcat ctttggaaaa ggaacccgtg tgactgtgga accaa           355
```

<210> SEQ ID NO 102
<211> LENGTH: 367
<212> TYPE: DNA
<213> ORGANISM: Tursiops truncatus

<400> SEQUENCE: 102

```
gcccagaaag ttactcaagt ccagcgagcc atgtccagtc agctagggga ggcggtcacc      60
ttgagctgtc agtatgaaac aagcttgagc tggtacgata ttttttggta taagcagctt     120
cccagtggag agatgacttt ccttattcat cagatttctt ctgaccaaaa tgcaaagaat     180
ggccgctatt ctgtaaactt tcaggaaaga cataaattca tcagcctcac catttcagcc     240
ttactggtgg aagattctgc aaactacttc tgtgctctcc gggagcgcgt tgtccacgtc     300
gttttattca atacgcgcaa taagccactg ctattcggca aggaaccta tctgaacgtt      360 gaaccaa                                                                367
```

<210> SEQ ID NO 103
<211> LENGTH: 122
<212> TYPE: PRT
<213> ORGANISM: Tursiops truncatus

<400> SEQUENCE: 103

```
Ala Gln Lys Val Thr Gln Val Gln Arg Ala Met Ser Ser Gln Leu Gly
 1               5                  10                  15

Glu Ala Val Thr Leu Ser Cys Gln Tyr Glu Thr Ser Leu Ser Trp Tyr
                20                  25                  30

Asp Ile Phe Trp Tyr Lys Gln Leu Pro Ser Gly Glu Met Thr Phe Leu
            35                  40                  45

Ile His Gln Ile Ser Ser Asp Gln Asn Ala Lys Asn Gly Arg Tyr Ser
        50                  55                  60

Val Asn Phe Gln Glu Arg His Lys Phe Ile Ser Leu Thr Ile Ser Ala
 65                 70                  75                  80

Leu Leu Val Glu Asp Ser Ala Asn Tyr Phe Cys Ala Leu Arg Glu Arg
                85                  90                  95

Val Val His Val Val Leu Phe Asn Thr Arg Asn Lys Pro Leu Leu Phe
               100                 105                 110

Gly Lys Gly Thr Tyr Leu Asn Val Glu Pro
        115                 120
```

<210> SEQ ID NO 104
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
gcccagaaag ttactcaagt ccagcgagcc atgtccatgc cagtgaggaa agcagtcacc      60
ctgaactgcc tgtatgaaac aagttggtgg tcatattata ttttttggta caagcaactt     120
cccagcaaag agatgatttt ccttattcgc cagggtctg atgaacagaa tgcaaaaagt      180
ggtcgctatt ctgtcaactt caagaaagca gcgaaatccg tcgccttaac catttcagcc     240
```

```
ttacagctag aagattcagc aaagtacttt tgtgctcttg ggacgggggt gaggggactc    300
caggacaccg ataaactcat ctttggaaaa ggaacccgtg tgactgtgga accaa         355
```

<210> SEQ ID NO 105
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Gln Lys Val Thr Gln Val Gln Arg Ala Met Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115

<210> SEQ ID NO 106
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
gcccagaaag ttactcaagt ccagcgagcc atgtccagtc agctagggga ggcggtcacc    60
ttgaactgcc tgtatgaaac aagttggtgg tcatattata ttttttggta caagcaactt   120
cccagcaaag agatgatttt ccttattcgc cagggttctg atgaacagaa tgcaaaaagt   180
ggtcgctatt ctgtcaactt caagaaagca gcgaaatccg tcgccttaac catttcagcc   240
ttacagctag aagattcagc aaagtacttt tgtgctcttg ggacgggggt gaggggactc    300
caggacaccg ataaactcat ctttggaaaa ggaacccgtg tgactgtgga accaa         355
```

<210> SEQ ID NO 107
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Gln Lys Val Thr Gln Val Gln Arg Ala Met Ser Ser Gln Leu Gly
1               5                   10                  15

Glu Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
            35                  40                  45

Ile Arg Gln Gly Ser Asp Glu Gln Asn Ala Lys Ser Gly Arg Tyr Ser
 50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Thr Gly
                 85                  90                  95

Val Arg Gly Leu Gln Asp Thr Asp Lys Leu Ile Phe Gly Lys Gly Thr
                100                 105                 110

Arg Val Thr Val Glu Pro
            115

<210> SEQ ID NO 108
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gcccagaaag ttactcaagt ccagcgagcc atgtccagtc agctagggga ggcggtcacc      60
ttgagctgtc agtatgaaac aagctggtgg tcatattata ttttttggta caagcaactt     120
cccagcaaag agatgatttt ccttattcgc cagggttctg atgaacagaa tgcaaaaagt     180
ggtcgctatt ctgtcaactt caagaaagca gcgaaatccg tcgccttaac catttcagcc     240
ttacagctag aagattcagc aaagtacttt tgtgctcttg gacggggggt gaggggactc     300
caggacaccg ataaactcat ctttggaaaa ggaacccgtg tgactgtgga accaa          355

<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Gln Lys Val Thr Gln Val Gln Arg Ala Met Ser Ser Gln Leu Gly
 1               5                  10                  15

Glu Ala Val Thr Leu Ser Cys Gln Tyr Glu Thr Ser Trp Trp Ser Tyr
                 20                  25                  30

Tyr Ile Phe Trp Tyr Lys Gln Leu Pro Ser Lys Glu Met Ile Phe Leu
            35                  40                  45

Ile Arg Gln Gly Ser Asp Glu Gln Asn Ala Lys Ser Gly Arg Tyr Ser
 50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Thr Gly
                 85                  90                  95

Val Arg Gly Leu Gln Asp Thr Asp Lys Leu Ile Phe Gly Lys Gly Thr
                100                 105                 110

Arg Val Thr Val Glu Pro
            115

<210> SEQ ID NO 110
<211> LENGTH: 355

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gcccagaaag ttactcaagt ccagcgagcc atgtccagtc agctagggga ggcggtcacc      60
ttgagctgtc agtatgaaac aagcttgagc tggtacgata tttttttggta taagcagctt    120 cccagtaaag agatgatttt ccttattcgc cagggttctg atgaacagaa tgcaaaaagt    180
ggtcgctatt ctgtcaactt caagaaagca gcgaaatccg tcgccttaac catttcagcc    240
ttacagctag aagattcagc aaagtacttt tgtgctcttg gacgggggt gaggggactc     300 caggacaccg ataaactcat ctttggaaaa ggaacccgtg tgactgtgga accaa         355

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Gln Lys Val Thr Gln Val Gln Arg Ala Met Ser Ser Gln Leu Gly
1               5                   10                  15

Glu Ala Val Thr Leu Ser Cys Gln Tyr Glu Thr Ser Leu Ser Trp Tyr
            20                  25                  30

Asp Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115

<210> SEQ ID NO 112
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
gcccagaaag ttactcaagt ccagcgagcc atgtccagtc agctagggga ggcggtcacc      60
ttgagctgtc agtatgaaac aagcttgagc tggtacgata tttttttggta taagcagctt    120 cccagtggag agatgacttt ccttattcat cagatttctg atgaacagaa tgcaaaaagt    180
ggtcgctatt ctgtcaactt caagaaagca gcgaaatccg tcgccttaac catttcagcc    240
ttacagctag aagattcagc aaagtacttt tgtgctcttg gacgggggt gaggggactc     300 caggacaccg ataaactcat ctttggaaaa ggaacccgtg tgactgtgga accaa         355
```

<210> SEQ ID NO 113
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Ala Gln Lys Val Thr Gln Val Gln Arg Ala Met Ser Ser Gln Leu Gly
1               5                   10                  15

Glu Ala Val Thr Leu Ser Cys Gln Tyr Glu Thr Ser Leu Ser Trp Tyr
                20                  25                  30

Asp Ile Phe Trp Tyr Lys Gln Leu Pro Ser Gly Glu Met Thr Phe Leu
            35                  40                  45

Ile His Gln Ile Ser Asp Glu Gln Asn Ala Lys Ser Gly Arg Tyr Ser
        50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115
```

<210> SEQ ID NO 114
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
gcccagaaag ttactcaagt ccagcgagcc atgtccagtc agctagggga ggcggtcacc     60
ttgagctgtc agtatgaaac aagcttgagc tggtacgata ttttttggta taagcagctt    120
cccagtggag agatgacttt ccttattcat cagatttctt ctgaccaaaa tgcaaagaat    180
ggccgctatt ctgtaaactt taagaaagca gcgaaatccg tcgccttaac catttcagcc    240
ttacagctag aagattcagc aaagtacttt tgtgctcttg gacgggggt gaggggactc    300 caggacaccg ataaactcat ctttggaaaa ggaacccgtg tgactgtgga accaa          355
```

<210> SEQ ID NO 115
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Ala Gln Lys Val Thr Gln Val Gln Arg Ala Met Ser Ser Gln Leu Gly
1               5                   10                  15

Glu Ala Val Thr Leu Ser Cys Gln Tyr Glu Thr Ser Leu Ser Trp Tyr
                20                  25                  30

Asp Ile Phe Trp Tyr Lys Gln Leu Pro Ser Gly Glu Met Thr Phe Leu
            35                  40                  45

Ile His Gln Ile Ser Ser Asp Gln Asn Ala Lys Asn Gly Arg Tyr Ser
        50                  55                  60
```

Val Asn Phe Lys Lys Ala Ala Lys Ser Val Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu Gln Asp Thr Asp Lys Leu Ile Phe Gly Lys Gly Thr
            100                 105                 110

Arg Val Thr Val Glu Pro
        115

<210> SEQ ID NO 116
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
gcccagaaag ttactcaagt ccagcgagcc atgtccagtc agctagggga ggcggtcacc        60
ttgagctgtc agtatgaaac aagcttgagc tggtacgata ttttttggta taagcagctt      120
cccagtggag agatgacttt ccttattcat cagatttctt ctgaccaaaa tgcaaagaat      180
ggccgctatt ctgtaaactt tcaggaaaga cataaattca tcagcctcac catttcagcc      240
ttacagctag aagattcagc aaagtacttt tgtgctcttg gacgggggt gaggggactc       300 caggacaccg ataaactcat ctttggaaaa ggaacccgtg tgactgtgga accaa           355

<210> SEQ ID NO 117
<211> LENGTH: 367
<212> TYPE: DNA
<213> ORGANISM: Homo sapiens

<400> SEQUENCE: 117
gcaggtcacc tagagcaacc tcaaatttcc agtactaaaa cgctgtcaaa acagcccgc        60 ctggaatgtg tggtgtctgg aataacaatt tctgcaacat ctgtatattg gtatcgagag      120
agacctggtg aagtcataca gttcctggtg tccatttcat atgacggcac tgtcagaaag      180
gaatccggca ttccgtcagg caaatttgag gtggatagga tacctgaaac gtctacatcc      240
actctcacca ttcacaatgt agagaaacag gacatagcta cctactactg tgccttgtgg      300
gaggtaaagc aagagttggg caaaaaaatc aaggtatttg gtcccggaac aaagcttatc      360
attacag                                                                 367

<210> SEQ ID NO 118
<211> LENGTH: 122
<212> TYPE: PRT
<213> ORGANISM: Homo sapiens

<400> SEQUENCE: 118

Ala Gly His Leu Glu Gln Pro Gln Ile Ser Ser Thr Lys Thr Leu Ser
1               5                   10                  15

Lys Thr Ala Arg Leu Glu Cys Val Val Ser Gly Ile Thr Ile Ser Ala
            20                  25                  30

Thr Ser Val Tyr Trp Tyr Arg Glu Arg Pro Gly Glu Val Ile Gln Phe
        35                  40                  45

Leu Val Ser Ile Ser Tyr Asp Gly Thr Val Arg Lys Glu Ser Gly Ile
    50                  55                  60

Pro Ser Gly Lys Phe Glu Val Asp Arg Ile Pro Glu Thr Ser Thr Ser

```
                65                  70                  75                  80
            Thr Leu Thr Ile His Asn Val Glu Lys Gln Asp Ile Ala Thr Tyr Tyr
                                85                  90                  95

Cys Ala Leu Trp Glu Val Lys Gln Glu Leu Gly Lys Lys Ile Lys Val
                            100                 105                 110

Phe Gly Pro Gly Thr Lys Leu Ile Ile Thr
                        115                 120

<210> SEQ ID NO 119
<211> LENGTH: 349
<212> TYPE: DNA
<213> ORGANISM: Homo sapiens

<400> SEQUENCE: 119
gccattgagt tggtgcctga acaccaaaca gtgcctgtgt caatagggt  ccctgccacc      60 ctcaggtgct ccatgaaagg agaagcgatc ggtaactact atatcaactg gtacaggaag    120
acccaaggta acacaatgac tttcatatac gagaaaagg  acatctatgg ccctggtttc    180
aaagacaatt tccaaggtga cattgatatt gcaagaacc  tggctgtact taagatactt    240
gcaccatcag agagagatga aggtcttac  tactgtgcct gtgaccctct tggcggaccc    300
cccgataaac tcatctttgg aaaaggaacc cgtgtgactg tggaaccaa                349

<210> SEQ ID NO 120
<211> LENGTH: 349
<212> TYPE: DNA
<213> ORGANISM: Tursiops truncatus

<400> SEQUENCE: 120
gctgtcacgt tggtgcctca aaaccaagca aggagtgtgt ctgtggggga atctgtcacc      60
ctcaggtgct ccatgaaagg agactccatc agtaactatt ataccttctg gtacaggaga    120
acaccgggta acacaatgac tctcatatac gagaagggg  gcacatatgg ccctggtttc    180
gaagacaacc tccaaggtga aattgatttt ttaaacaacc aggctgtgct gaatatcctg    240
gaggcatcag agagagatga aggatcttac tactgtgcct gtgaccctct tggcggaccc    300
cccgataaac tcatctttgg aaaaggaacc cgtgtgactg tggaaccaa                349

<210> SEQ ID NO 121
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gccattgagt tggtgcctga acaccaaaca gtgcctgtgt caatagggt  ccctgccacc      60 ctcaggtgct ccatgaaagg agactccatc agtaactatt ataccttctg gtacaggaga    120
acaccgggta acacaatgac tctcatatac gagaagggg  gcacatatgg ccctggtttc    180
gaagacaacc tccaaggtga aattgatttt ttaaacaacc aggctgtgct gaatatcctg    240
gaggcatcag agagagatga aggatcttac tactgtgcct gtgaccctct tggcggaccc    300
cccgataaac tcatctttgg aaaaggaacc cgtgtgactg tggaaccaa                349

<210> SEQ ID NO 122
<211> LENGTH: 349
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 122
gccattgagt tggtgcctga acaccaaaca gtgcctgtgt caatagggt ccctgccacc      60 ctcaggtgct ccatgaaagg agaagcgatc ggtaactact atatcaactg gtacaggaga    120
acaccgggta acacaatgac tctcatatac cgagaagggg gcacatatgg ccctggtttc    180
gaagacaacc tccaaggtga aattgatttt ttaaacaacc aggctgtgct gaatatcctg    240
gaggcatcag agagagatga aggatcttac tactgtgcct gtgaccctct tggcggaccc    300
cccgataaac tcatctttgg aaaaggaacc cgtgtgactg tggaaccaa               349

<210> SEQ ID NO 123
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Arg Thr Pro Gly Asn Thr Met Thr Leu
        35                  40                  45

Ile Tyr Arg Glu Gly Gly Thr Tyr Gly Pro Gly Phe Glu Asp Asn Leu
    50                  55                  60

Gln Gly Glu Ile Asp Phe Leu Asn Asn Gln Ala Val Leu Asn Ile Leu
65                  70                  75                  80

Glu Ala Ser Glu Arg Asp Glu Gly Ser Tyr Tyr Cys Ala Cys Asp Pro
                85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 124
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gccattgagt tggtgcctga acaccaaaca gtgcctgtgt caatagggt ccctgccacc      60 ctcaggtgct ccatgaaagg agaagcgatc ggtaactact atatcaactg gtacaggaag    120
acccaaggta acacaatgac tttcatatac cgagaaaagg acatctatgg ccctggtttc    180
gaagacaacc tccaaggtga aattgatttt ttaaacaacc aggctgtgct gaatatcctg    240
gaggcatcag agagagatga aggatcttac tactgtgcct gtgaccctct tggcggaccc    300
cccgataaac tcatctttgg aaaaggaacc cgtgtgactg tggaaccaa               349

<210> SEQ ID NO 125
<211> LENGTH: 349
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gccattgagt tggtgcctga acaccaaaca gtgcctgtgt caatagggt ccctgccacc      60 ctcaggtgct ccatgaaagg agaagcgatc ggtaactact atatcaactg gtacaggaag    120
acccaaggta acacaatgac tttcatatac cgagaaaagg acatctatgg ccctggtttc    180
aaagacaatt tccaaggtga cattgatttt ttaaacaacc aggctgtgct gaatatcctg    240
gaggcatcag agagagatga aggatcttac tactgtgcct gtgaccctct tggcggaccc    300
cccgataaac tcatctttgg aaaaggaacc cgtgtgactg tggaaccaa               349

<210> SEQ ID NO 126
<211> LENGTH: 349
<212> TYPE: DNA
<213> ORGANISM: Homo sapiens

<400> SEQUENCE: 126
gccattgagt tggtgcctga acaccaaaca gtgcctgtgt caatagggt ccctgccacc      60 ctcaggtgct ccatgaaagg agaagcgatc agtaactact atatcaactg gtacaggaag    120
acccaaggta acacaatgac tttcatatac cgagaaaagg acatctatgg ccctggtttc    180
aaagacaatt tccaaggtga cattgatatt gcaagaacc tggctgtact taagatactt    240
gcaccatcag agagagatga aggtcttac tactgtgcct gtgaccctct tggcggaccc    300
cccgataaac tcatctttgg aaaaggaacc cgtgtgactg tggaaccaa               349

<210> SEQ ID NO 127
<211> LENGTH: 116
<212> TYPE: PRT
<213> ORGANISM: Homo sapiens

<400> SEQUENCE: 127

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Ser Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Pro
                85                  90                  95

Leu Gly Gly Pro Pro Asp Lys Leu Ile Phe Gly Lys Gly Thr Arg Val
            100                 105                 110

Thr Val Glu Pro
        115

<210> SEQ ID NO 128
<211> LENGTH: 349
<212> TYPE: DNA
<213> ORGANISM: Homo sapiens

<400> SEQUENCE: 128
```

```
gccattgagt tggtgcctga acaccaaaca gtgcctgtgt caataggggt ccctgccacc      60
ctcaggtgct ccatgaaagg agaagcgatc ggtaactact atatcaactg gtacaggaag     120
acccaaggta acacaatgac tttcatatac gagaaaagg gcatctatgg ccctggtttc     180
aaagacaatt tccaaggtga cattgatatt gcaaagaacc tggctgtact aagatactt     240 gcaccatcag agagagatga agggtcttac tactgtgcct gtgaccctct ggcggaccc     300 cccgataaac tcatctttgg aaaaggaacc cgtgtgactg tggaaccaa                349
```

<210> SEQ ID NO 129
<211> LENGTH: 116
<212> TYPE: PRT
<213> ORGANISM: Homo sapiens

<400> SEQUENCE: 129

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Gly Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Pro
                85                  90                  95

Leu Gly Gly Pro Pro Asp Lys Leu Ile Phe Gly Lys Gly Thr Arg Val
            100                 105                 110

Thr Val Glu Pro
        115
```

<210> SEQ ID NO 130
<211> LENGTH: 349
<212> TYPE: DNA
<213> ORGANISM: Homo sapiens

<400> SEQUENCE: 130

```
gccattgagt tggtgcctga acaccaaaca gtgcctgtgt caataggggt ccctgccacc      60
ctcaggtgct ccatgaaagg agaagcgatc ggtaactact atatcaactg gtacaggaag     120
acccaaggta acacaatgac tttcatatac gagaaaagg acatctatgg ccctggtttc     180
aaagacaatt tccaaggtga cattgatatt gcaaagaacc tggctgtact aagatactt     240 gcaccatcag agagagatga agggtcttac tactgtgcct ctgaccctct ggcggaccc     300 cccgataaac tcatctttgg aaaaggaacc cgtgtgactg tggaaccaa                349
```

<210> SEQ ID NO 131
<211> LENGTH: 116
<212> TYPE: PRT
<213> ORGANISM: Homo sapiens

<400> SEQUENCE: 131

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30
```

```
Tyr Tyr Ile Asn Trp Tyr Arg Lys Thr Gln Gly Asn Thr Met Thr Phe
            35                  40                  45

Ile Tyr Arg Glu Lys Asp Ile Tyr Gly Pro Gly Phe Lys Asp Asn Phe
 50                  55                  60

Gln Gly Asp Ile Asp Ile Ala Lys Asn Leu Ala Val Leu Lys Ile Leu
 65                  70                  75                  80

Ala Pro Ser Glu Arg Asp Glu Gly Ser Tyr Tyr Cys Ala Ser Asp Pro
                 85                  90                  95

Leu Gly Gly Pro Pro Asp Lys Leu Ile Phe Gly Lys Gly Thr Arg Val
                100                 105                 110

Thr Val Glu Pro
        115

<210> SEQ ID NO 132
<211> LENGTH: 287
<212> TYPE: DNA
<213> ORGANISM: Homo sapiens
<220> FEATURE:
<221> NAME/KEY: CDS
<222> LOCATION: (1)..(285)

<400> SEQUENCE: 132 gcc cag aag gtt act caa gcc cag tca tca gta tcc atg cca gtg agg      48
Ala Gln Lys Val Thr Gln Ala Gln Ser Ser Val Ser Met Pro Val Arg
 1               5                  10                  15 aaa gca gtc acc ctg aac tgc ctg tat gaa aca agt tgg tgg tca tat      96
Lys Ala Val Thr Leu Asn Cys Leu Tyr Glu Thr Ser Trp Trp Ser Tyr
                 20                  25                  30 tat att ttt tgg tac aag caa ctt ccc agc aaa gag atg att ttc ctt     144
Tyr Ile Phe Trp Tyr Lys Gln Leu Pro Ser Lys Glu Met Ile Phe Leu
             35                  40                  45 att cgc cag ggt tct gat gaa cag aat gca aaa agt ggt cgc tat tct     192
Ile Arg Gln Gly Ser Asp Glu Gln Asn Ala Lys Ser Gly Arg Tyr Ser
     50                  55                  60 gtc aac ttc aag aaa gca gcg aaa tcc gtc gcc tta acc att tca gcc     240
Val Asn Phe Lys Lys Ala Ala Lys Ser Val Ala Leu Thr Ile Ser Ala
 65                  70                  75                  80 tta cag cta gaa gat tca gca aag tac ttt tgt gct ctt ggg gaa ct      287
Leu Gln Leu Glu Asp Ser Ala Lys Tyr Phe Cys Ala Leu Gly Glu
                 85                  90                  95

<210> SEQ ID NO 133
<211> LENGTH: 95
<212> TYPE: PRT
<213> ORGANISM: Homo sapiens

<400> SEQUENCE: 133

Ala Gln Lys Val Thr Gln Ala Gln Ser Ser Val Ser Met Pro Val Arg
 1               5                  10                  15

Lys Ala Val Thr Leu Asn Cys Leu Tyr Glu Thr Ser Trp Trp Ser Tyr
                 20                  25                  30

Tyr Ile Phe Trp Tyr Lys Gln Leu Pro Ser Lys Glu Met Ile Phe Leu
             35                  40                  45

Ile Arg Gln Gly Ser Asp Glu Gln Asn Ala Lys Ser Gly Arg Tyr Ser
     50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Glu
                 85                  90                  95
```

<210> SEQ ID NO 134
<211> LENGTH: 288
<212> TYPE: DNA
<213> ORGANISM: Homo sapiens
<220> FEATURE:
<221> NAME/KEY: CDS
<222> LOCATION: (1)..(288)

<400> SEQUENCE: 134

```
gcc att gag ttg gtg cct gaa cac caa aca gtg cct gtg tca ata ggg      48
Ala Ile Glu Leu Val Pro Glu His Gln Thr Val Pro Val Ser Ile Gly
1               5                   10                  15 gtc cct gcc acc ctc agg tgc tcc atg aaa gga gaa gcg atc ggt aac      96
Val Pro Ala Thr Leu Arg Cys Ser Met Lys Gly Glu Ala Ile Gly Asn
                20                  25                  30 tac tat atc aac tgg tac agg aag acc caa ggt aac aca atc act ttc     144
Tyr Tyr Ile Asn Trp Tyr Arg Lys Thr Gln Gly Asn Thr Ile Thr Phe
            35                  40                  45 ata tac cga gaa aag gac atc tat ggc cct ggt ttc aaa gac aat ttc     192
Ile Tyr Arg Glu Lys Asp Ile Tyr Gly Pro Gly Phe Lys Asp Asn Phe
        50                  55                  60 caa ggt gac att gat att gca aag aac ctg gct gta ctt aag ata ctt     240
Gln Gly Asp Ile Asp Ile Ala Lys Asn Leu Ala Val Leu Lys Ile Leu
65                  70                  75                  80 gca cca tca gag aga gat gaa ggg tct tac tac tgt gcc tgt gac acc     288
Ala Pro Ser Glu Arg Asp Glu Gly Ser Tyr Tyr Cys Ala Cys Asp Thr
                85                  90                  95
```

<210> SEQ ID NO 135
<211> LENGTH: 96
<212> TYPE: PRT
<213> ORGANISM: Homo sapiens

<400> SEQUENCE: 135

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
                20                  25                  30

Tyr Tyr Ile Asn Trp Tyr Arg Lys Thr Gln Gly Asn Thr Ile Thr Phe
            35                  40                  45

Ile Tyr Arg Glu Lys Asp Ile Tyr Gly Pro Gly Phe Lys Asp Asn Phe
        50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95
```

<210> SEQ ID NO 136
<211> LENGTH: 288
<212> TYPE: DNA
<213> ORGANISM: Homo sapiens
<220> FEATURE:
<221> NAME/KEY: CDS
<222> LOCATION: (1)..(288)

<400> SEQUENCE: 136

```
gcc att gag ttg gtg cct gaa cac caa aca gtg cct gtg tca ata agg      48
Ala Ile Glu Leu Val Pro Glu His Gln Thr Val Pro Val Ser Ile Gly
1               5                   10                  15 atc cct gcc acc ctc agg tgc tcc atg aaa gga gaa gcg atc ggt aac      96
Ile Pro Ala Thr Leu Arg Cys Ser Met Lys Gly Glu Ala Ile Gly Asn
                20                  25                  30
```

```
tac tat atc aac tgg tac agg aag acc caa ggt aac aca atg act ttc      144
Tyr Tyr Ile Asn Trp Tyr Arg Lys Thr Gln Gly Asn Thr Met Thr Phe
            35                  40                  45 ata tac cga gaa aag gac atc tat ggc cct ggt ttc aaa gac aat ttc      192
Ile Tyr Arg Glu Lys Asp Ile Tyr Gly Pro Gly Phe Lys Asp Asn Phe
 50                  55                  60 caa ggt gac att gat att gca aag aac ctg gct gta ctt aag ata ctt      240
Gln Gly Asp Ile Asp Ile Ala Lys Asn Leu Ala Val Leu Lys Ile Leu
 65                  70                  75                  80 gca cca tca gag aga gat gaa ggg tct tac tac tgt gcc tgt gac acc      288
Ala Pro Ser Glu Arg Asp Glu Gly Ser Tyr Tyr Cys Ala Cys Asp Thr
                 85                  90                  95
```

<210> SEQ ID NO 137
<211> LENGTH: 96
<212> TYPE: PRT
<213> ORGANISM: Homo sapiens

<400> SEQUENCE: 137

```
Ala Ile Glu Leu Val Pro Glu His Gln Thr Val Pro Val Ser Ile Gly
 1               5                   10                  15

Ile Pro Ala Thr Leu Arg Cys Ser Met Lys Gly Glu Ala Ile Gly Asn
                20                  25                  30

Tyr Tyr Ile Asn Trp Tyr Arg Lys Thr Gln Gly Asn Thr Met Thr Phe
            35                  40                  45

Ile Tyr Arg Glu Lys Asp Ile Tyr Gly Pro Gly Phe Lys Asp Asn Phe
 50                  55                  60

Gln Gly Asp Ile Asp Ile Ala Lys Asn Leu Ala Val Leu Lys Ile Leu
 65                  70                  75                  80

Ala Pro Ser Glu Arg Asp Glu Gly Ser Tyr Tyr Cys Ala Cys Asp Thr
                 85                  90                  95
```

<210> SEQ ID NO 138
<211> LENGTH: 38
<212> TYPE: PRT
<213> ORGANISM: Homo sapiens

<400> SEQUENCE: 138

```
Ala Lys Tyr Phe Cys Ala Leu Gly Thr Gly Val Arg Gly Leu Gln Asp
 1               5                   10                  15

Thr Asp Lys Leu Ile Phe Gly Lys Gly Thr Arg Val Thr Val Glu Pro
                20                  25                  30

Arg Ser Gln Pro His Thr
            35
```

<210> SEQ ID NO 139
<211> LENGTH: 41
<212> TYPE: PRT
<213> ORGANISM: Homo sapiens

<400> SEQUENCE: 139

```
Ala Lys Tyr Phe Cys Ala Leu Leu Pro Phe Leu Pro Ser Asp Trp Gly
 1               5                   10                  15

Ile Pro Val Thr Asp Lys Leu Ile Phe Gly Lys Gly Thr Arg Val Thr
                20                  25                  30

Val Glu Pro Arg Ser Gln Pro His Thr
            35                  40
```

<210> SEQ ID NO 140

```
<211> LENGTH: 40
<212> TYPE: PRT
<213> ORGANISM: Homo sapiens

<400> SEQUENCE: 140

Ala Lys Tyr Phe Cys Ala Leu Gly Glu Ala Pro Ser Ala Trp Gly Lys
1               5                   10                  15

His Leu Thr Ala Gln Leu Phe Phe Gly Lys Gly Thr Gln Leu Ile Val
            20                  25                  30

Glu Pro Arg Ser Gln Pro His Thr
        35                  40

<210> SEQ ID NO 141
<211> LENGTH: 42
<212> TYPE: PRT
<213> ORGANISM: Homo sapiens

<400> SEQUENCE: 141

Ala Lys Tyr Phe Cys Ala Leu Gly Glu Ala Pro Ser Ala Trp Gly Lys
1               5                   10                  15

His Ser Trp Asp Thr Arg Gln Met Phe Phe Gly Thr Gly Ile Lys Leu
            20                  25                  30

Phe Val Glu Pro Arg Ser Gln Pro His Thr
        35                  40

<210> SEQ ID NO 142
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Lys Tyr Phe Cys Ala Leu Gly Thr Gly Val Arg Gly Leu Gln Asp
1               5                   10                  15

Thr Asp Lys Leu Ile Phe Gly Thr Gly Thr Arg Val Thr Val Glu Pro
            20                  25                  30

Arg Ser Gln Pro His Thr
        35

<210> SEQ ID NO 143
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Lys Tyr Phe Cys Ala Leu Gly Glu Ala Pro Ser Ala Trp Gly Lys
1               5                   10                  15

His Ser Trp Asp Thr Arg Gln Met Phe Phe Gly Lys Gly Ile Lys Leu
            20                  25                  30

Phe Val Glu Pro Arg Ser Gln Pro His Thr
        35                  40

<210> SEQ ID NO 144
<211> LENGTH: 100
<212> TYPE: PRT
<213> ORGANISM: Homo sapiens

<400> SEQUENCE: 144
```

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
                20                  25                  30

Tyr Ile Phe Trp Tyr Lys Gln Leu Pro Ser Lys Glu Met Ile Phe Leu
            35                  40                  45

Ile Arg Gln Gly Ser Asp Glu Gln Asn Ala Lys Ser Gly Arg Tyr Ser
        50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu
            100

<210> SEQ ID NO 145
<211> LENGTH: 100
<212> TYPE: PRT
<213> ORGANISM: Homo sapiens

<400> SEQUENCE: 145

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
                20                  25                  30

Tyr Ile Phe Trp Tyr Lys Gln Leu Pro Ser Lys Glu Met Ile Phe Leu
            35                  40                  45

Ile Arg Gln Tyr Ser Asp Asp Gly Asn Ala Arg Asp Gly Arg Tyr Ser
        50                  55                  60

Val Asn Phe Gln Lys Ala Gln Lys Ser Ile Asn Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu
            100

<210> SEQ ID NO 146
<211> LENGTH: 100
<212> TYPE: PRT
<213> ORGANISM: Homo sapiens

<400> SEQUENCE: 146

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
                20                  25                  30

Tyr Ile Phe Trp Tyr Lys Gln Leu Pro Ser Gly Gln Met Thr Tyr Leu
            35                  40                  45

Ile Arg Gln Gly Ser Asp Glu Gln Asn Ala Lys Ser Gly Arg Tyr Ser
        50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu
            100

<210> SEQ ID NO 147
<211> LENGTH: 100
<212> TYPE: PRT
<213> ORGANISM: Homo sapiens

<400> SEQUENCE: 147

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Glu Leu Glu Asp Ser Ala Met Tyr Phe Cys Val Leu Gly Thr Gly
                85                  90                  95

Val Arg Gly Leu
            100

<210> SEQ ID NO 148
<211> LENGTH: 100
<212> TYPE: PRT
<213> ORGANISM: Homo sapiens

<400> SEQUENCE: 148

Ala Gln Lys Val Thr Gln Ala Gln Pro Asp Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Thr Gly
                85                  90                  95

Val Arg Gly Leu
            100

<210> SEQ ID NO 149
<211> LENGTH: 100
<212> TYPE: PRT
<213> ORGANISM: Homo sapiens

<400> SEQUENCE: 149

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Asp Gly Asn Ala Lys Ser Gly Arg Tyr Ser
    50                  55                  60

```
Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Thr Gly
                 85                  90                  95

Val Arg Gly Leu
            100

<210> SEQ ID NO 150
<211> LENGTH: 100
<212> TYPE: PRT
<213> ORGANISM: Homo sapiens

<400> SEQUENCE: 150

Ala Gln Lys Val Thr Gln Ala Gln Ser Ser Val Ser Met Pro Val Arg
  1               5                  10                  15

Lys Ala Val Thr Leu Asn Cys Leu Tyr Glu Thr Ser Trp Trp Ser Tyr
                 20                  25                  30

Tyr Ile Phe Trp Tyr Lys Gln Leu Pro Ser Lys Glu Met Ile Phe Leu
             35                  40                  45

Ile Arg Gln Gly Ser Asp Glu Gln Asn Ala Arg Asp Gly Arg Tyr Ser
 50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Thr Gly
                 85                  90                  95

Val Arg Gly Leu
            100

<210> SEQ ID NO 151
<211> LENGTH: 96
<212> TYPE: PRT
<213> ORGANISM: Homo sapiens

<400> SEQUENCE: 151

Ala Ile Glu Leu Val Pro Glu His Gln Thr Val Pro Val Ser Ile Gly
  1               5                  10                  15

Val Pro Ala Thr Leu Arg Cys Ser Met Lys Gly Glu Ala Ile Gly Asn
                 20                  25                  30

Tyr Tyr Ile Asn Trp Tyr Arg Lys Thr Gln Gly Asn Thr Ile Thr Phe
             35                  40                  45

Ile Tyr Arg Glu Lys Asp Ile Tyr Gly Pro Gly Phe Lys Asp Asn Phe
 50                  55                  60

Gln Gly Asp Ile Asp Ile Ala Lys Asn Leu Ala Val Leu Lys Ile Leu
 65                  70                  75                  80

Ala Pro Ser Glu Arg Asp Glu Gly Ser Tyr Tyr Cys Ala Cys Asp Thr
                 85                  90                  95

<210> SEQ ID NO 152
<211> LENGTH: 96
<212> TYPE: PRT
<213> ORGANISM: Macaca mulatta

<400> SEQUENCE: 152

Ala Val Glu Leu Val Pro Glu His Gln Thr Val Ile Val Ser Val Gly
  1               5                  10                  15

Asp Pro Ala Thr Leu Lys Cys Ser Met Lys Gly Glu Ala Ile Ser Asn
                 20                  25                  30

Tyr Tyr Ile Asn Trp Tyr Arg Lys Thr Gln Gly Asn Thr Met Thr Phe
```

```
                35                  40                  45
Ile Tyr Arg Glu Lys Gly Ile Tyr Gly Pro Gly Phe Lys Asp Asn Phe
 50                  55                  60

Gln Gly Asp Ile Asp Thr Glu Glu Asn Gln Ala Val Leu Lys Ile Leu
65                  70                  75                  80

Ala Pro Ser Glu Arg Asp Glu Gly Ser Tyr Tyr Cys Ala Ser Asp Arg
                85                  90                  95

<210> SEQ ID NO 153
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Val Gln Leu Gln Glu Ser Gly Pro Gly Met Val Lys Pro Ser Gln
1               5                   10                  15

Ser Leu Ser Leu Thr Cys Thr Val Thr Gly Tyr Ser Ile Thr Gly Gly
                20                  25                  30

Tyr Asp Trp His Trp Ile Arg His Phe Pro Gly Asn Lys Leu Glu Trp
            35                  40                  45

Met Ala Tyr Ile Ser Tyr Ser Gly Ser Thr Asp Tyr Asn Pro Ser Leu
     50                  55                  60

Lys Ser Arg Ile Ser Val Thr His Asp Thr Ser Lys Asn Leu Phe Phe
65                  70                  75                  80

Leu Asn Leu Thr Ser Val Thr Thr Glu Asp Thr Ala Thr Tyr Tyr Cys
                85                  90                  95

Ala Arg Glu Gly Gly Arg Gly Phe Ala Tyr Trp Gly Gln Gly Thr Leu
            100                 105                 110

Val Thr Val Ser Ala
        115

<210> SEQ ID NO 154
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Val Tyr Trp Val Lys Gln Thr Pro Val His Gly Leu Glu Trp Ile
            35                  40                  45

Gly Ala Ile Asp Pro Glu Thr Gly Arg Thr Ala Tyr Asn Gln Lys Phe
     50                  55                  60

Lys Gly Lys Ala Ile Leu Thr Thr Asp Lys Ser Ser Ser Thr Ala Tyr
65                  70                  75                  80

Met Ala Leu Arg Ser Leu Thr Ser Glu Asp Ser Ala Val Tyr Tyr Cys
                85                  90                  95

Ala Arg Leu Lys Ser Gly Arg Tyr Tyr Gly Asp Leu Phe Ala Tyr Trp
            100                 105                 110

Gly Gln Gly Thr Leu Val Thr Val Ser Ala
```

115                 120

<210> SEQ ID NO 155
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Gln Gln Ser Gly Pro Glu Leu Val Lys Pro Gly Asp
1               5                   10                  15

Ser Val Lys Met Ser Cys Lys Ala Ser Gly Tyr Thr Phe Thr Asp Tyr
            20                  25                  30

Tyr Met Asp Trp Val Lys Gln Ser His Gly Arg Ser Leu Glu Trp Ile
        35                  40                  45

Gly Tyr Ile Tyr Pro Lys Asn Val Gly Ile Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Ser Leu Leu Trp Asp Ala Leu Asp Tyr Trp Gly Gln Gly Thr
            100                 105                 110

Ser Val Thr Val Ser Ser
        115

<210> SEQ ID NO 156
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Gln Gln Ser Gly Pro Gln Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Thr Thr Asp Tyr Asn Gly Lys Phe
    50                  55                  60

Lys Gly Lys Ala Thr Leu Thr Val Asp Thr Ser Ser Ser Ser Ala Tyr
65                  70                  75                  80

Met Glu Leu His Ser Leu Thr Ser Glu Asp Ser Ala Val Tyr Phe Cys
                85                  90                  95

Ala Arg Met Asp Asp Tyr Asp Asp Gly Gly Ala Met Asp Tyr Trp Gly
            100                 105                 110

Gln Gly Thr Ser Val Thr Val Ser Ser
        115                 120

<210> SEQ ID NO 157
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Ser Asp Val Gln Leu Gln Glu Ser Gly Pro Gly Leu Val Lys Pro Ser
1               5                   10                  15

Gln Ser Leu Ser Val Thr Cys Thr Val Thr Gly Tyr Ser Ile Thr Ser
            20                  25                  30

Gly Tyr His Trp Asn Trp Ile Arg Gln Phe Pro Gly Asn Arg Leu Glu
        35                  40                  45

Trp Met Gly Tyr Ile His Asn Ser Gly Ser Thr Asn Tyr Asn Ser Phe
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Val Ala Tyr Tyr Ser Asn Ser Arg Glu Phe Trp Tyr Ala Tyr Trp
            100                 105                 110

Gly Gln Gly Thr Leu Val Thr Val Ser Ala
        115                 120

<210> SEQ ID NO 158
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Gln Gln Ser Gly Thr Val Leu Ala Arg Pro Gly Ser
1               5                   10                  15

Ser Val Lys Met Ser Cys Lys Ala Ser Gly Tyr Thr Phe Thr Thr Tyr
            20                  25                  30

Trp Met His Trp Val Lys Gln Arg Pro Gly Gln Gly Leu Asp Trp Ile
        35                  40                  45

Gly Ala Ile Tyr Pro Gly Asn Ser Asp Thr Asn Tyr Asn Gln Lys Phe
    50                  55                  60

Arg Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Tyr Gly Tyr Tyr Val Asp Tyr Tyr Ala Met Asp Tyr Trp Gly Gln
            100                 105                 110

Gly Thr Ser Val Thr Val Ser Ser
        115                 120

<210> SEQ ID NO 159
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Gln Gln Pro Gly Ala Glu Leu Val Arg Pro Gly Ala
1               5                   10                  15

Ser Val Lys Leu Ser Cys Lys Ala Pro Gly Tyr Thr Phe Thr Ser Tyr
            20                  25                  30

```
Trp Met Asn Trp Val Lys Gln Arg Pro Glu Gln Gly Leu Glu Trp Ile
        35                  40                  45

Gly Lys Ile Asp Pro Tyr Asp Ser Glu Thr His Tyr Asn Gln Lys Phe
 50                  55                  60

Lys Asp Lys Ala Ile Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Gly Gly Asp Asn Tyr Asp Pro Phe Ala Tyr Trp Gly Gln Gly
                100                 105                 110

Thr Leu Val Thr Val Ser Ala
        115
```

<210> SEQ ID NO 160
<211> LENGTH: 121
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 160

```
Gln Val Gln Leu Gln Gln Pro Gly Ala Asp Leu Val Arg Pro Gly Thr
 1               5                  10                  15

Ser Val Lys Leu Ser Cys Lys Ala Ser Gly Tyr Thr Phe Thr Ser Tyr
                20                  25                  30

Trp Met His Trp Val Gln Arg Pro Gly Gln Gly Leu Glu Trp Ile
        35                  40                  45

Gly Val Ile Asp Pro Ser Asp Ser Tyr Thr Asn Tyr Asn Gln Lys Phe
 50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Ser Asp Asp Tyr Asp Glu Gly Tyr Phe Phe Asp Gln Trp Gly
                100                 105                 110

Gln Gly Thr Thr Leu Thr Val Ser Ala
        115                 120
```

<210> SEQ ID NO 161
<211> LENGTH: 121
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 161

```
Glu Val Lys Leu Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
        35                  40                  45

Ala Glu Ile Arg Ala Glu Ala Asn Asn His Ala Thr Tyr Tyr Ala Glu
 50                  55                  60

Ser Val Lys Gly Arg Phe Thr Ile Ser Arg Asp Asp Ser Lys Ser Arg
 65                  70                  75                  80
```

```
Val Phe Leu Gln Met Asn Ser Leu Arg Ala Glu Asp Thr Gly Ile Tyr
                85                  90                  95

Tyr Cys Thr Gly Leu Asp Tyr Gly Ser Ile Gly Phe Ala Tyr Trp Gly
            100                 105                 110

Gln Gly Thr Leu Val Thr Val Ser Ala
        115                 120

<210> SEQ ID NO 162
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Gln Gln Pro Gly Ala Glu Ile Val Arg Pro Gly Ala
1               5                   10                  15

Ser Val Lys Leu Ser Cys Lys Ala Ser Gly Tyr Ala Phe Thr Asp Tyr
            20                  25                  30

Trp Met Asn Trp Val Lys Gln Arg Pro Gly Gln Gly Leu Glu Trp Ile
        35                  40                  45

Gly Thr Ile Asp Pro Ser Asp Ser Tyr Ala Ser Tyr Asn Gln Lys Phe
    50                  55                  60

Lys Gly Lys Ala Thr Leu Thr Val Asp Thr Ser Asn Ser Ala Tyr
65                  70                  75                  80

Met His Leu Ser Ser Leu Thr Ser Glu Asp Ser Ala Val Tyr Phe Cys
                85                  90                  95

Ala Arg Glu Ser Asn Asp Val Cys Trp Tyr Phe Asp Val Trp Gly Ala
            100                 105                 110

Gly Thr Thr Val Thr Val Ser Ser
        115                 120

<210> SEQ ID NO 163
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Gln Gln Ser Gly Ala Glu Leu Val Arg Pro Gly Ala
1               5                   10                  15

Ser Val Lys Leu Ser Cys Lys Ala Ser Asp Tyr Lys Phe Thr Asp Ser
            20                  25                  30

Glu Met Tyr Trp Val Lys Gln Thr Pro Val His Gly Leu Glu Trp Ile
        35                  40                  45

Gly Ala Ile Asp Pro Glu Thr Gly Ile Thr Ala Tyr Asn Gln Arg Phe
    50                  55                  60

Lys Gly Lys Ala Thr Leu Thr Ser Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Ala Val Pro Pro Trp Phe Ala Tyr Trp Gly Gln Gly Thr Leu
            100                 105                 110

Val Thr Val Ser Ala
        115
```

<210> SEQ ID NO 164
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Gln Gln Ser Gly Ala Glu Leu Gly Arg Pro Gly Ala
1               5                   10                  15

Ser Val Lys Leu Ser Cys Thr Thr Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Ala Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Tyr Tyr Gly Phe Asp Tyr Trp Gly Gln Gly Thr Thr Leu Thr Val
            100                 105                 110

Ser Ser

<210> SEQ ID NO 165
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Lys Phe Ile Asp Tyr
            20                  25                  30

Glu Met His Trp Val Lys Gln Thr Pro Val His Gly Leu Glu Trp Val
        35                  40                  45

Gly Asp Leu Asp Pro Gly Thr Gly Val Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Val Trp Ser Ala Asp Phe Trp Gly Gln Gly Thr Ser Val Thr Val
            100                 105                 110

Ser Ser

<210> SEQ ID NO 166
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Gln Met Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met Tyr Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Tyr Tyr Ala Met Asp Tyr Trp Gly Gln Gly Thr Ser Val Thr Val
            100                 105                 110

Ser Ser

<210> SEQ ID NO 167
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Gln Leu Gln Gln Ser Gly Ala Glu Leu Val Arg Pro Gly Ala
1               5                   10                  15

Ser Val Lys Leu Ser Cys Thr Ala Ser Asp Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Glu Thr Glu Tyr Ala Ser Lys Phe
    50                  55                  60

Gln Gly Lys Ala Thr Leu Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Glu Leu Gly Phe Asp Tyr Trp Gly Gln Gly Thr Leu Thr Val
            100                 105                 110

Ser Ser

<210> SEQ ID NO 168
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Ile Gln Leu Val Gln Ser Gly Pro Glu Leu Lys Lys Pro Gly Glu
1               5                   10                  15

Thr Val Lys Ile Ser Cys Lys Val Ser Gly Asp Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe

```
            50                  55                  60
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                     85                  90                  95

Ala Arg Ser Ser Tyr Asp Tyr Asp Asp Ala Met Asp Tyr Trp Gly Gln
                    100                 105                 110

Gly Thr Ser Val Thr Val Ser Ser
            115                 120

<210> SEQ ID NO 169
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Val Lys Phe Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ala Glu Ala Asn Asn His Ala Thr Tyr Tyr Ala Glu
 50                  55                  60

Ser Val Lys Gly Arg Phe Thr Ile Ser Arg Asp Asp Ser Lys Ser Arg
 65                  70                  75                  80

Val Phe Leu Gln Met Asn Ser Leu Arg Ala Glu Asp Thr Gly Ile Tyr
                    85                  90                  95

Tyr Cys Thr Gly Leu Asp Tyr Gly Ser Val Gly Phe Ala Tyr Trp Gly
                100                 105                 110

Gln Gly Thr Leu Val Thr Val Ser Ala
            115                 120

<210> SEQ ID NO 170
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Gln Gln Ser Gly Ala Glu Leu Val Arg Pro Gly Ala
 1               5                  10                  15

Ser Val Thr Leu Ser Cys Lys Ala Ser Gly Tyr Thr Phe Val Asp Tyr
                20                  25                  30

Glu Met His Trp Val Lys Gln Thr Pro Val His Gly Leu Glu Trp Ile
            35                  40                  45

Gly Ala Ile Asp Pro Glu Thr Gly Ile Thr Ala Tyr Asn Gln Lys Phe
 50                  55                  60

Lys Gly Lys Ala Thr Leu Thr Ala Asp Lys Ser Ser Ser Thr Ala Tyr
 65                  70                  75                  80

Met Glu Leu Ser Ser Leu Thr Ser Glu Asp Ser Ala Val Tyr Tyr Cys
                    85                  90                  95

Ile Arg Pro Arg Gly Gly Ser His Phe Asp Tyr Trp Gly Gln Gly Thr
```

-continued

```
                100             105                 110

Thr Leu Thr Val Ser Ser
        115

<210> SEQ ID NO 171
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met Ser Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Arg Leu Ser Ser Leu Thr Ser Glu Asp Thr Ala Val Tyr Tyr Cys
                85                  90                  95

Thr Glu Leu Gly Phe Asp Tyr Trp Gly Gln Gly Thr Thr Leu Thr Val
            100                 105                 110

Ser Ser

<210> SEQ ID NO 172
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Gln Gln Ser Gly Ala Asp Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Ile Thr Ala Tyr Asn Gln Asn Phe
    50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Pro Arg Gly Gly Ser His Phe Asp His Trp Gly Gln Gly Thr
            100                 105                 110

Pro Leu Thr Val Ser Ser
        115

<210> SEQ ID NO 173
<211> LENGTH: 122
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 173

Ser Asp Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Tyr Tyr Trp Asn Trp Ile Arg Gln Phe Pro Gly Asn Asn Leu Glu
        35                  40                  45

Trp Met Gly Tyr Ile Ser His Asp Gly Ser Asn Asn Tyr Asn Pro Ala
    50                  55                  60

Leu Lys Asn Arg Ile Ser Ile Thr Arg Asp Thr Ser Lys Asn Gln Phe
65                  70                  75                  80

Phe Leu Lys Leu Asn Ser Val Thr Thr Glu Asp Thr Gly Thr Tyr Tyr
                85                  90                  95

Cys Ala Ser Val Tyr Tyr Gly Asp Tyr Glu Val Trp Tyr Thr Tyr Trp
            100                 105                 110

Gly Gln Gly Thr Leu Val Thr Val Ser Ala
        115                 120

<210> SEQ ID NO 174
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Gln Gln Ser Gly Ala Glu Leu Val Arg Pro Gly Ala
1               5                   10                  15

Ser Val Lys Leu Ser Cys Lys Ala Ser Asp Tyr Lys Phe Thr Asp Ser
            20                  25                  30

Glu Met Tyr Trp Val Lys Gln Thr Pro Val His Gly Leu Glu Trp Ile
        35                  40                  45

Gly Ala Ile Asp Pro Glu Thr Gly Ile Thr Ala Tyr Asn Gln Arg Phe
    50                  55                  60

Lys Gly Lys Ala Thr Leu Thr Thr Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Ala Val Pro Pro Trp Phe Ala Tyr Trp Gly Gln Gly Thr Leu
            100                 105                 110

Val Thr Val Ser Ala
        115

<210> SEQ ID NO 175
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Gln Gln Ser Gly Pro Glu Leu Val Lys Pro Gly Ala
1               5                   10                  15
```

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
            35                  40                  45

Gly His Ile Asn Pro Tyr Asn Gly Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
            85                  90                  95

Ala Arg Asn His Ile Tyr Tyr Tyr Asp Gly Gly Tyr Phe Tyr Tyr Ala
            100                 105                 110

Met Asp Tyr Trp Gly Gln Gly Thr Ser Val Thr Val Ser Ser
            115                 120                 125

<210> SEQ ID NO 176
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Arg Phe Pro Asp Tyr
            20                  25                  30

Glu Met His Trp Val Lys Gln Thr Pro Val His Gly Leu Glu Trp Ile
            35                  40                  45

Gly Ala Ile Asp Pro Glu Thr Gly Arg Thr Ala Tyr Asn Gln Lys Phe
        50                  55                  60

Arg Gly Lys Ala Lys Leu Thr Ala Asp Lys Ser Ser Ser Thr Val Tyr
65                  70                  75                  80

Met Glu Leu Arg Ser Leu Thr Ser Glu Asp Ser Ala Val Tyr Tyr Cys
            85                  90                  95

Thr Arg Gly Tyr Gly Ile Gln Phe Pro Tyr Trp Gly Gln Gly Thr Leu
            100                 105                 110

Val Thr Val Ser Ala
        115

<210> SEQ ID NO 177
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Ser Asp Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Asp Tyr Tyr Trp Asn Trp Ile Arg Gln Phe Pro Gly Asn Lys Leu Glu
            35                  40                  45

Trp Met Gly Tyr Ile Thr Tyr Asp Gly Ser Asn Asn Tyr Asn Pro Ser
        50                  55                  60

Leu Lys Asn Arg Ile Ser Ile Thr Arg Asp Thr Ser Lys Asn Gln Phe
 65                  70                  75                  80

Phe Leu Lys Leu Asn Ser Val Thr Thr Glu Asp Thr Ala Thr Tyr Tyr
                 85                  90                  95

Cys Ala Arg Asp Asp Gly Tyr Phe Asp Tyr Trp Gly Gln Gly Thr Thr
            100                 105                 110

Leu Thr Val Ser Ser
            115

<210> SEQ ID NO 178
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Lys Leu Val Glu Ser Gly Gly Gly Leu Val Gln Pro Gly Gly
 1               5                  10                  15

Ser Leu Lys Leu Ser Cys Ala Thr Ser Gly Phe Thr Phe Ser Asp Ser
                 20                  25                  30

Tyr Met Tyr Trp Val Arg Gln Thr Pro Glu Lys Arg Leu Glu Trp Val
             35                  40                  45

Ala Tyr Ile Ser Tyr Gly Gly Val Asn Thr Tyr Tyr Pro Asp Thr Val
 50                  55                  60

Arg Gly Arg Phe Thr Ile Ser Arg Asp Asn Ala Lys Ser Thr Leu Tyr
 65                  70                  75                  80

Leu Gln Met Ser Arg Leu Lys Ser Glu Asp Thr Ala Met Tyr Tyr Cys
                 85                  90                  95

Ala Ser Arg Gly Tyr Tyr Trp Gly Gln Gly Thr Ser Val Thr Val Ser
            100                 105                 110

Ser

<210> SEQ ID NO 179
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
                 20                  25                  30

Gly Met His Trp Val Arg Gln Ala Pro Glu Lys Gly Leu Glu Trp Val
             35                  40                  45

Ala Tyr Ile Ser Ser Gly Ser Arg Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Glu Gly Ala Tyr Ser Ser Phe Asp Tyr Trp Gly Gln Gly Thr
            100                 105                 110

Thr Leu Thr Val Ser Ser

<210> SEQ ID NO 180
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Gly Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ser Asp Asp Ala Ala Thr Tyr Tyr Cys Gln Gln Asn Asn
                85                  90                  95

Glu Asp Pro Phe Thr Phe Gly Ser Gly Thr Lys Leu Glu Ile Lys
            100                 105                 110

<210> SEQ ID NO 181
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Phe Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 182
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Tyr Leu Ala Asp Gly Val Pro Ser Arg Phe Ser Gly
50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Ile Pro Tyr
                85                  90                  95

Thr Phe Gly Gly Gly Thr Lys Leu Glu Ile Lys
            100                 105

<210> SEQ ID NO 183
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Asp Val Val Met Thr Gln Thr Pro Leu Thr Leu Ser Val Thr Val Gly
1               5                   10                  15

Gln Pro Ala Ser Ile Ser Cys Lys Ser Ser Gln Ser Leu Leu His Ser
            20                  25                  30

Asn Gly Lys Thr Tyr Leu Asn Trp Leu Leu Gln Arg Pro Gly Gln Ser
        35                  40                  45

Pro Lys Leu Leu Ile Tyr Leu Val Ser Lys Leu Glu Ser Gly Val Pro
50                  55                  60

Asp Arg Phe Ser Gly Ser Gly Ser Gly Thr Asp Phe Lys Leu Lys Ile
65                  70                  75                  80

Ser Arg Val Glu Ala Gly Asp Leu Gly Val Tyr Tyr Cys Leu Gln Ala
                85                  90                  95

Thr His Phe Pro Leu Thr Cys Gly Ala Gly Thr Lys Leu Glu Leu Lys
            100                 105                 110

<210> SEQ ID NO 184
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Asp Tyr Ser Tyr Pro Leu Thr Phe Gly Gly Gly Thr Lys Leu Glu Leu
            100                 105                 110

Lys

<210> SEQ ID NO 185
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Asp
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Asn Val Gln Ala
65                  70                  75                  80

Glu Asp Leu Ala Val Tyr Tyr Cys Gln Gln His Tyr Ser Ile Pro Cys
                85                  90                  95

Thr Phe Gly Ser Gly Thr Lys Leu Glu Ile Lys
            100                 105

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Gly Ala Arg Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Phe Cys Gln His Phe Trp Asp Thr Phe
                85                  90                  95

Thr Phe Gly Ser Gly Thr Lys Val Glu Ile Lys
            100                 105

<210> SEQ ID NO 187
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Val Val Met Thr Gln Thr Pro Leu Thr Leu Ser Val Thr Val Gly
1               5                   10                  15

Gln Pro Ala Ser Ile Ser Cys Lys Ser Ser Gln Ser Leu Leu His Ser
            20                  25                  30

Asn Gly Lys Thr Tyr Leu Asn Trp Leu Leu Gln Arg Pro Gly Gln Ser
        35                  40                  45

Pro Lys Leu Leu Ile Tyr Leu Val Ser Lys Val Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Leu Gln Val
                85                  90                  95

Thr His Phe Pro Leu Thr Phe Gly Ala Gly Thr Lys Leu Glu Leu Lys
            100                 105                 110

<210> SEQ ID NO 188
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Val His Arg
            20                  25                  30

Asn Gly Asn Thr Phe Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 189
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Arg Thr
                85                  90                  95

Phe Gly Gly Gly Thr Lys Leu Glu Ile Lys
            100                 105

<210> SEQ ID NO 190
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ala Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asp Pro Pro Thr
                85                  90                  95

Phe Gly Gly Gly Thr Lys Leu Glu Ile Lys Arg
            100                 105

<210> SEQ ID NO 191
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Phe Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 192
<211> LENGTH: 113

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ser Asp Val Val Arg Pro Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys

<210> SEQ ID NO 193
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Val Val Met Thr Gln Ile Pro Val Ser Leu Pro Val Thr Leu Gly
1               5                   10                  15

Asp Gln Ala Ser Ile Ser Cys Arg Ser Ser Gln Ser Leu Leu His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Phe
                85                  90                  95

Thr His Val Pro Pro Trp Thr Phe Gly Gly Gly Thr Lys Leu Glu Ile
            100                 105                 110

Lys

<210> SEQ ID NO 194
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ala Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu His Ser
                 20                  25                  30

Asp Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser His Ser
                 85                  90                  95

Thr His Val Pro Tyr Thr Phe Gly Gly Gly Thr Lys Leu Glu Ile Lys
                100                 105                 110

Arg

<210> SEQ ID NO 195
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Val Gln Ile Thr Gln Ser Pro Ser Tyr Leu Ala Ala Ser Pro Gly
1               5                   10                  15

Glu Thr Ile Thr Ile Asn Cys Arg Thr Ser Lys Ser Ile Ser Lys Tyr
                 20                  25                  30

Leu Ala Trp Tyr Gln Glu Lys Pro Gly Lys Thr Asn Lys Leu Leu Ile
             35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln His His Asn Glu Tyr Pro Tyr
                 85                  90                  95

Thr Phe Gly Gly Gly Thr Arg Leu Glu Ile Lys Arg
                100                 105

<210> SEQ ID NO 196
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Val His Arg
                 20                  25                  30

Asn Gly Asn Thr Phe Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly 85                  90                  95

Ser His Val Pro Tyr Thr Phe Gly Gly Gly Thr Lys Leu Glu Ile Lys
                100                 105                 110

Arg

<210> SEQ ID NO 197
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
                20                  25                  30

His Trp Tyr Gln Gln Lys Pro Gly Ser Ser Pro Lys Pro Trp Ile Tyr
                35                  40                  45

Ala Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser His Gln Pro Thr
                85                  90                  95

Phe Gly Ala Gly Thr Lys Leu Glu Leu Lys
                100                 105

<210> SEQ ID NO 198
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Ala Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asp Gly Asn Thr Tyr Leu His Trp Tyr Leu Gln Lys Pro Gly Gln Ser
                35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser His Ser
                85                  90                  95

Thr His Val Pro Tyr Thr Phe Gly Gly Gly Thr Lys Leu Glu Ile Lys
                100                 105                 110

Arg

<210> SEQ ID NO 199
<211> LENGTH: 106
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 199

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Arg Tyr Ile
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr His Cys Gln Gln Trp Tyr Ser Asp Thr Pro Thr
                85                  90                  95

Phe Gly Ala Gly Thr Lys Leu Glu Leu Lys
            100                 105

<210> SEQ ID NO 200
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 200

Asp Ile Val Met Ser Gln Ser Pro Ser Ser Leu Ala Val Ser Val Gly
1               5                   10                  15

Glu Lys Val Ala Leu Asn Cys Lys Ser Ser Gln Ser Leu Leu Tyr Ser
            20                  25                  30

Ile Asn Gln Lys Asn Tyr Leu Ala Trp Tyr Gln Arg Asn Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Thr Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys

<210> SEQ ID NO 201
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 201

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

```
Leu Thr Ser Asn Leu Ala Ala Gly Val Pro Ala Arg Phe Ser Gly Ser
     50                  55                  60

Gly Ser Gly Thr Ser Tyr Ser Leu Thr Ile Ser Ser Met Glu Ala Glu
 65              70                  75                  80

Asp Ala Ala Thr Tyr Tyr Cys Gln Gln Trp Ser Gly Asp Pro Pro Thr
                 85                  90                  95

Phe Gly Gly Gly Thr Lys Leu Glu Ile Lys Arg
                100                 105

<210> SEQ ID NO 202
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asn Ile Val Leu Thr Gln Ser Pro Ala Ser Leu Ala Val Ser Leu Gly
 1               5                  10                  15

Gln Arg Ala Thr Ile Ser Cys Arg Pro Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
     50                  55                  60

Arg Phe Ser Gly Ser Gly Ser Arg Thr Asp Leu Thr Leu Thr Ile Asp
 65              70                  75                  80

Pro Val Glu Ala Asp Asp Ala Ala Thr Tyr Tyr Cys Gln Gln Asn Asn
                 85                  90                  95

Glu Asp Pro Trp Thr Phe Gly Gly Gly Thr Lys
                100                 105

<210> SEQ ID NO 203
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Phe Trp Ile Tyr
         35                  40                  45

Gly Thr Ser Asn Leu Ala Ser Gly Val Pro Ala Arg Phe Thr Gly Ser
     50                  55                  60

Gly Ser Gly Thr Ser Tyr Ser Leu Thr Ile Ser Arg Val Glu Ala Glu
 65              70                  75                  80

Asp Ala Ala Thr Tyr Tyr Cys Gln Gln Trp Ser Ser Asp Ser Pro Thr
                 85                  90                  95

Phe Gly Gly Gly Thr Lys Leu Glu Ile Lys
                100                 105

<210> SEQ ID NO 204
```

```
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

His Trp His Gln Gln Lys Pro Gly Ser Ser Pro Lys Pro Arg Ile Tyr
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105

<210> SEQ ID NO 205
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Asp Ile Val Leu Thr Gln Ser Pro Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Gly Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Met Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 206
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30
```

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Trp Thr Phe Gly Gly Gly Thr Lys Leu Glu Ile Lys
            100                 105                 110

<210> SEQ ID NO 207
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Gly Tyr
                 20                  25                  30

Tyr Met Asn Trp Val Lys Gln Ser Pro Glu Lys Ser Leu Glu Trp Ile
             35                  40                  45

Gly Glu Ile Asn Pro Ser Thr Gly Gly Thr Thr Tyr Asn Gln Lys Phe
 50                  55                  60

Gln Ala Lys Ala Thr Leu Thr Val Asp Lys Ser Ser Ser Thr Ala Tyr
 65                  70                  75                  80

Met Gln Leu Lys Ser Leu Thr Ser Glu Asp Ser Ala Val Tyr Tyr Cys
                 85                  90                  95

Ser Arg Gly Glu Asp Asp Gly Tyr Phe Pro Tyr Ser Met Asp Phe Trp
            100                 105                 110

Gly Gln Gly Ala Ser Val Thr Val Ser Ser
            115                 120

<210> SEQ ID NO 208
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Ser Asp Val Gln Leu Gln Glu Ser Gly Pro Gly Leu Val Thr Pro Ser
 1               5                  10                  15

Gln Ser Leu Ser Val Thr Cys Thr Val Thr Gly Tyr Ser Ile Thr Ser
                 20                  25                  30

Gly Ser Tyr Trp Asn Trp Ile Arg Gln Phe Pro Gly Asn Lys Leu Glu
             35                  40                  45

Trp Met Gly Tyr Ile His Asn Ser Gly Ser Thr Thr Tyr Asn Pro Ser
 50                  55                  60

Leu Lys Ser Arg Ile Ser Ile Thr Arg Asp Thr Ser Lys Asn Gln Phe
 65                  70                  75                  80

Phe Leu Gln Leu Asn Ser Val Thr Thr Glu Asp Thr Ala Thr Tyr Tyr
                 85                  90                  95

```
Cys Ala Arg Ser Thr Gly Pro Pro Phe Thr Tyr Trp Gly Gln Gly Thr
                100                 105                 110

Leu Val Thr Val Ser Ala
        115

<210> SEQ ID NO 209
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gln Val Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Thr Ser Tyr
                20                  25                  30

Trp Ile Gln Trp Val Lys Gln Arg Pro Gly Gln Gly Leu Gly Trp Ile
            35                  40                  45

Gly Glu Ile Phe Pro Gly Thr Gly Thr Thr Tyr Tyr Asn Glu Lys Phe
    50                  55                  60

Lys Gly Lys Ala Thr Leu Thr Arg Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Val Phe Gly Asn Tyr Ala Met Asp Tyr Trp Gly Gln
                100                 105                 110

Gly Thr Ser Val Thr Val Ser Ser
        115                 120

<210> SEQ ID NO 210
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Gln Leu Leu Gln Pro Gly Ala Glu Leu Val Lys Pro Gly Ala
1               5                   10                  15

Ser Val Lys Leu Ser Cys Lys Ala Ser Gly Tyr Ser Phe Thr Asn Phe
                20                  25                  30

Trp Ile Asn Trp Val Lys Leu Arg Pro Gly Gln Gly Leu Glu Trp Ile
            35                  40                  45

Gly Asn Ile Phe Pro Gly Ser Ser Pro Asn Tyr Asn Glu Lys Phe
    50                  55                  60

Lys Ser Lys Ala Thr Leu Thr Val Asp Ile Ser Ser Thr Ala Tyr
65                  70                  75                  80

Met Gln Leu Ser Ser Leu Thr Ser Asp Gly Ser Ala Val Tyr Tyr Cys
                85                  90                  95

Ala Arg Tyr Gly Ser Tyr Gly Asn Trp Tyr Phe Asp Val Trp Gly Ala
                100                 105                 110

Gly Thr Thr Val Thr Val Ser Ser
        115                 120

<210> SEQ ID NO 211
<211> LENGTH: 120
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Val Lys Leu Val Glu Ser Gly Gly Gly Leu Val Gln Pro Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Ser Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Val Leu Arg Ala Glu Asp Ser Ala Thr Tyr
                85                  90                  95

Tyr Cys Ala Ser Ser Lys Pro Gly Trp Pro Met Asp Tyr Trp Gly Gln
            100                 105                 110

Gly Thr Ser Val Thr Val Ser Ser
        115                 120

<210> SEQ ID NO 212
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met Asn Trp Val Lys Gln Ser Pro Glu Lys Ser Leu Glu Trp Ile
        35                  40                  45

Gly Glu Ile Asn Pro Ser Thr Gly Gly Thr Thr Tyr Asn Gln Lys Phe
    50                  55                  60

Gln Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ser Arg Gly Glu Asp Asp Gly Tyr Phe Pro Tyr Ser Met Asp Phe Trp
            100                 105                 110

Gly Gln Gly Ala Ser Val Thr Val Ser Ser
        115                 120

<210> SEQ ID NO 213
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Asp Val Lys Leu Val Glu Ser Gly Gly Gly Leu Val Lys Pro Gly Gly

```
                1               5                   10                  15
Ser Leu Lys Leu Ser Cys Ala Ala Ser Gly Phe Thr Phe Ser Ser Tyr
                    20                  25                  30

Tyr Met Ser Trp Val Arg Gln Thr Pro Glu Lys Arg Leu Glu Trp Val
            35                  40                  45

Ala Thr Ile Ser Asn Ser Gly Ser Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Ile Ser Ser Leu Asn Ser Glu Asp Thr Ala Val Tyr Tyr Cys
                    85                  90                  95

Ser Arg Glu Tyr Asp Phe Asp Gly Glu Phe Phe Asp Tyr Trp Gly Gln
                    100                 105                 110

Gly Thr Thr Leu Thr Val Ser Ser
            115                 120

<210> SEQ ID NO 214
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Leu Gln Pro Gly Ala Glu Leu Val Lys Pro Gly Ala
1               5                   10                  15

Ser Val Lys Leu Ser Cys Lys Ala Ser Gly Tyr Thr Phe Thr Asn Phe
                20                  25                  30

Trp Ile Asn Trp Val Lys Gln Arg Pro Gly Gln Gly Leu Glu Trp Ile
            35                  40                  45

Gly Asn Ile Tyr Pro Gly Ser Ser Pro Asn Tyr Asn Glu Lys Phe
        50                  55                  60

Lys Phe Lys Ala Thr Leu Thr Val Asp Ile Ser Ser Thr Ala Tyr
65                  70                  75                  80

Ile Gln Leu Ser Ser Leu Pro Ser Asp Asp Ser Ala Val Tyr Tyr Cys
                    85                  90                  95

Ala Arg Tyr Gly Thr Phe Gly Asn Trp Tyr Phe Asp Val Trp Gly Ala
                    100                 105                 110

Gly Thr Thr Val Thr Val Ser Ser
            115                 120

<210> SEQ ID NO 215
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn His
                20                  25                  30

Trp Ile Ser Trp Val Lys Gln Arg Pro Gly Gln Gly Leu Glu Trp Ile
            35                  40                  45

Gly Asn Ile Phe Pro Gly Ser Ser Ser Pro Asn Tyr Asn Glu Lys Phe
```

-continued

```
                50                  55                  60
Lys Ser Lys Ala Thr Leu Thr Val Asp Thr Ser Ser Thr Ala Tyr
 65                  70                  75                  80

Met Gln Leu Ser Ser Leu Thr Ser Asp Ala Ser Ala Val Tyr Tyr Cys
                     85                  90                  95

Thr Arg Trp Gly Asn Tyr Gly Tyr Tyr Tyr Ala Met Asp Tyr Trp Gly
               100                 105                 110

Gln Gly Thr Ser Val Thr Val Ser Ser
           115                 120

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Asp Ile Val Leu Ile Gln Ser Pro Ala Thr Leu Ser Val Thr Pro Gly
  1               5                  10                  15

Asp Ser Val Ser Leu Ser Cys Arg Ala Ser Gln Ser Ile Asn Asn Asn
                 20                  25                  30

Leu His Trp Tyr Gln Gln Lys Ser His Glu Ser Pro Arg Leu Leu Ile
             35                  40                  45

Lys Tyr Val Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Lys
            100                 105

<210> SEQ ID NO 217
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Asn Ile Val Leu Thr Gln Ser Pro Gly Ser Leu Ala Val Ser Leu Gly
  1               5                  10                  15

Gln Arg Ala Thr Ile Ser Cys Arg Ala Ser Glu Ser Val Asp Asn Tyr
                 20                  25                  30

Gly Asn Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Thr Phe Gly Ser Gly Thr Lys Leu Glu Met Lys
            100                 105                 110
```

```
<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Gly Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 219
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Gly Asp Thr Pro Tyr
                85                  90                  95

Thr Phe Gly Gly Gly Thr Lys Leu Glu Ile Lys Arg
            100                 105

<210> SEQ ID NO 220
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Leu Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Phe
            20                  25                  30
```

```
Leu Ser Trp Phe Gln Gln Ile Pro Gly Lys Ser Pro Lys Thr Leu Ile
        35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Ser Asp Glu Phe Pro Tyr
                 85                  90                  95

Thr Ile Gly Gly Gly Thr Lys Leu Glu Ile Lys Arg
            100                 105
```

<210> SEQ ID NO 221
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

```
Asp Ile Gln Met Thr Gln Thr Ser Ser Phe Ser Val Ser Leu Gly
1               5                  10                  15

Asp Arg Val Thr Ile Thr Cys Lys Ala Ser Glu Asp Ile Tyr Asn Arg
                 20                  25                  30

Leu Ala Trp Tyr Gln Gln Lys Pro Gly Asn Ala Pro Arg Leu Leu Ile
        35                  40                  45

Ser Gly Ala Thr Ser Leu Glu Ala Gly Val Pro Ser Arg Phe Ser Gly
 50                  55                  60

Ser Gly Ser Gly Asn Asp Tyr Thr Leu Ser Ile Thr Ser Leu Gln Thr
 65                  70                  75                  80

Glu Asp Val Ala Thr Tyr Tyr Cys Gln Gln Tyr Trp Tyr Thr Pro Trp
                 85                  90                  95

Thr Phe Gly Gly Gly Thr Lys Leu Glu Ile Lys
            100                 105
```

<210> SEQ ID NO 222
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Asp Ile Val Leu Ile Gln Ser Pro Ala Thr Leu Ser Val Thr Pro Gly
1               5                  10                  15

Asp Ser Val Ser Leu Ser Cys Arg Ala Ser Gln Ser Ile Asn Asn Asn
                 20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Lys
            100                 105
```

<210> SEQ ID NO 223
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Arg His Val Pro Tyr Thr Phe Gly Gly Gly Thr Lys Leu Glu Ile Lys
            100                 105                 110

Arg

<210> SEQ ID NO 224
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Phe
            20                  25                  30

Leu Ser Trp Phe Gln Gln Ile Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Ser Asp Glu Phe Pro Tyr
                85                  90                  95

Thr Ile Gly Gly Gly Thr Lys Leu Glu Ile Lys Arg
            100                 105

<210> SEQ ID NO 225
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Ile Val Leu Thr Gln Ser Pro Ala Ile Met Ser Ala Ser Leu Gly

```
1               5                   10                  15
Glu Glu Ile Thr Leu Thr Cys Ser Ala Ser Ser Arg Val Asn Tyr Met
                20                  25                  30

His Trp Tyr Gln Gln Lys Ser Gly Thr Ser Pro Lys Leu Leu Ile Tyr
                35                  40                  45

Ser Thr Ser Asn Leu Ala Ser Gly Val Pro Ser Arg Phe Ser Gly Ser
            50                  55                  60

Gly Ser Gly Thr Phe Tyr Ser Leu Thr Ile Ile Ser Val Glu Ala Glu
65                  70                  75                  80

Asp Ala Ala Asp Tyr Tyr Cys His Gln Trp Ser Ser Tyr Pro Thr Phe
                    85                  90                  95

Gly Gly Gly Thr Lys Leu Glu Ile Lys
                100                 105

<210> SEQ ID NO 226
<211> LENGTH: 100
<212> TYPE: PRT
<213> ORGANISM: Tursiops truncatus

<400> SEQUENCE: 226

Ala Gln Lys Val Thr Gln Val Gln Arg Ala Met Ser Ser Gln Leu Gly
1               5                   10                  15

Glu Ala Val Thr Leu Ser Cys Gln Tyr Glu Thr Ser Leu Ser Trp Tyr
                20                  25                  30

Asp Ile Phe Trp Tyr Lys Gln Leu Pro Ser Gly Glu Met Thr Phe Leu
            35                  40                  45

Ile His Gln Ile Ser Ser Asp Gln Asn Ala Lys Asn Gly Arg Tyr Ser
        50                  55                  60

Val Asn Phe Gln Glu Arg His Lys Phe Ile Ser Leu Thr Ile Ser Ala
65                  70                  75                  80

Leu Leu Val Glu Asp Ser Ala Asn Tyr Phe Cys Ala Leu Gly Thr Gly
                    85                  90                  95

Val Arg Gly Leu
                100

<210> SEQ ID NO 227
<211> LENGTH: 11
<212> TYPE: PRT
<213> ORGANISM: Homo sapiens

<400> SEQUENCE: 227

Ala Gln Lys Val Thr Gln Ala Gln Ser Ser Val
1               5                   10
```

METHODS FOR SELECTIVE EXPANSION OF GAMMA DELTA T-CELL POPULATIONS AND COMPOSITIONS THEREOF

CROSS-REFERENCE TO RELATED APPLICATION

This application is a divisional of U.S. application Ser. No. 15/563,830 filed Oct. 2, 2017, which is a National Stage Entry of PCT/US2017/032530 filed May 12, 2017, which claims priority under Section 119(e) and the benefit of U.S. Provisional Application Ser. No. 62/335,572 filed May 12, 2016, the entire disclosure of which is hereby incorporated by reference in the entirety and for all purposes.

BACKGROUND

Antigen recognition by T lymphocytes may be achieved by highly diverse heterodimeric receptors, the T-cell receptors (TCRs). Approximately 95% of human T-cells in blood and lymphoid organs express a heterodimeric αβ TCR receptor (αβ T-cell lineage). Approximately 5% of human T-cells in the blood and lymphoid organs express heterodimeric γδ TCR receptor (γδ T-cell lineage). These T-cell subsets may be referred to as 'αβ' and 'γδ' T-cells, respectively. αβ and γδ T-cells are different in function. Activation of αβ T-cells then occurs when an antigen presenting cell (APC) presents an antigen in the context of class I/II MHC. In contrast to αβ T-cells, γδ T-cells can recognize an antigen independent of MHC restriction. In addition, γδ T-cells combine both innate and adoptive immune recognition and responses.

γδ T cells utilize a distinct set of somatically rearranged variable (V), diversity (D), joining (J), and constant (C) genes. γδ T cells contain fewer V, D, and J segments than αβ T cells. Although the number of germline Vγ and Vδ genes is more limited than the repertoire of Vα and Vβ TCR genes, more extensive junctional diversification processes during TCR γ and δ chain rearrangement leads to a potential larger γδ TCRs repertoire than that of αβ TCRs (Carding and Egan, Nat Rev Immunol (2002) 2:336).

Human γδ T-cells use 3 main Vδ (Vδ1, Vδ2, Vδ3) and at most six Vγ region genes to make their TCRs (Hayday A C., Annu Rev Immunol. 2000; 18, 975-1026). Two main Vδ subsets are Vδ1 and Vδ2 γδ T cells. Vδ1 T cells with different Vγ predominate in the intraepithelial subset of mucosal γδ T cells where the TCRs appear to recognize stress molecules on epithelial cells (Beagley K W, Husband A J. Crit Rev Immunol. 1998; 18(3):237-254). Vδ2 T cells that generally coexpress Vγ9 are abundant in the peripheral blood and lymphatic system.

The ability of γδ T-cells to recognize an antigen on diseased cells directly and to exhibit inherent ability to kill tumor cells renders γδ T-cells an attractive therapeutic tool. Adoptive transfer of Vγ9Vδ2 T cells has yielded limited objective clinical responses for investigational treatment of cancer (Kondo et al, Cytotherapy, 10:842-856, 2008; Lang et al, Cancer Immunology, Immunotherapy: CII, 60: 1447-1460, 2011; Nagamine et al, 2009; Nicol et al, British Journal of Cancer, 105:778-786, 2011; Wilhelm et al, Blood. 2003 Jul. 1; 102(1):200-6), indicating the need to isolate and test clinically new γδ T-cell populations.

The ability to selectively expand γδ T-cell subset populations having potent anti-tumor activity with improved purity and in clinically-relevant levels is highly desirable. Although antibodies and cytokine cocktails have been used to propagate a more diverse set of γδ T cells, activation of specific γδ T-cell subsets to sufficient purity and clinically-relevant levels, was not achieved (Dokouhaki et al, 2010; Kang et al, 2009; Lopez et al, 2000; Kress, 2006). Therefore, clinically-relevant methods of expanding specific γδ T cell subsets ex vivo, and the cells produced thereby, are greatly needed.

SEQUENCE LISTING

The instant application contains a Sequence Listing which has been submitted in ASCII format via EFS-Web and is hereby incorporated by reference in its entirety. Said ASCII copy, created on Jun. 21, 2017 is named ADC-0002-WO-_SL.txt and is 207,179 Kilobytes in size.

SUMMARY OF THE INVENTION

The present invention, in one aspect, provides ex vivo methods for producing enriched γδ T-cell populations. The enriched γδ T-cell populations can be produced from isolated mixed cell populations by a method comprising contacting the mixed cell population, or a purified fraction thereof, with one or more agents:
 i) which selectively expand δ1 T-cells by binding to an epitope specific of a δ1 TCR,
 ii) which selectively expand δ2 T-cells by binding to an epitope specific of a δ2 TCR,
 iii) which selectively expand δ1 and δ4 T-cells by binding to an epitope specific of a δ1 TCR and a δ4 TCR, or
 iv) which selectively expand δ1, δ3, δ4, and δ5 T-cells by binding to an epitope specific of a δ1 TCR, a δ3 TCR, a δ4 TCR, and a δ5 TCR, to provide an enriched γδ T cell population. In preferred embodiments, the enriched γδ T cell population comprises a clinically-relevant level of γδ T cells.

In another aspect, the invention provides ex vivo methods for producing an enriched γδ T-cell population from an isolated mixed cell population, comprising directly contacting the mixed cell population with one or more agents:
 i) which selectively expand δ1 T-cells by binding to an epitope specific of a δ1 TCR,
 ii) which selectively expand δ2 T-cells by binding to an epitope specific of a δ2 TCR,
 iii) which selectively expand δ1 and δ4 T-cells by binding to an epitope specific of a δ1 TCR and a δ4 TCR, or
 iv) which selectively expand δ1, δ3, δ4, and δ5 T-cells by binding to an epitope specific of a δ1 TCR, a δ3 TCR, a δ4 TCR, and a δ5 TCR, to provide a clinically-relevant level of an enriched γδ T cell population.

In certain embodiments, the clinically-relevant level comprises more than about, or at least about, $10^8$ γδ T cells, $10^9$ γδ T cells, $10^{10}$ γδ T cells, $10^{11}$ γδ T cells, or $10^{12}$ γδ T cells (e.g., from about $10^8$ to about $10^{12}$). In one embodiment, the isolated mixed cell population is derived from a single donor and the method provides a clinical relevant level of an enriched γδ T cell population expanded from a single donor, e.g., from a single sample from the single donor or 2 or more samples from the single donor. In other embodiments, the isolated mixed cell population is derived from more than one or multiple donors. In some embodiments, following the first enrichment step of the invention, the enriched γδ T-cell population comprises clinically-relevant levels of γδ T-cell subsets of $>10^8$. In other embodiments, following the second, third, fourth, fifth, etc. enrichment step of the invention, the enriched γδ T-cell population comprises clinically-relevant levels of γδ T-cell subsets of $>10^8$.

In certain embodiments, the agent which selectively expands δ1 T-cells is selected from an agent which binds to the same epitope as an antibody selected from TS-1 and TS8.2. In some embodiments, the agent which selectively expands δ1 T-cells is an agent that binds a different epitope than the epitope bound by TS-1 and/or TS8.2 antibody. In some embodiments, the agent which selectively expands δ1 T-cells is an agent that binds an epitope that does not overlap with the epitope bound by, or does not compete with, TS-1 or TS8.2 antibody. In some embodiments, the agent which selectively expands δ1 T-cells is selected from an agent which specifically binds to an epitope comprising a δ1 variable region. In other embodiments, the agent binds to a δ1 TCR variable region comprising an amino acid sequence of a consensus sequence of FIG. 24. In yet other embodiments, the agent binds to an epitope comprising residues Arg71 or Asp72 of the δ1 variable region, and/or Lys120 of a J1 or J2 region. In some embodiments, the agent has reduced binding to a mutant δ1 TCR polypeptide comprising a mutation at K120 of δ1 J1 or δ1 J2, e.g. K120A, K120G, K120P, K120V, K120E, K120D, or K120S.

In certain embodiments, the agent which selectively expands δ1 T-cells is selected from an agent which binds to the same epitope as antibody R9.12. In some embodiments, the agent which selectively expands δ1 T-cells is an agent that binds a different epitope than the epitope bound by antibody R9.12. In some embodiments, the agent which selectively expands δ1 T-cells is an agent that binds an epitope that does not overlap with the epitope bound by, or does not compete with, antibody R9.12.

In certain embodiments, the agent that selectively expands δ1 T-cells is an agent that selectively binds to and/or expands δ1 and δ4 T-cells, or δ1, δ3, δ4 and δ5 T cells. In certain embodiments, the agent that selectively expands δ1 T-cells is an agent that comprises the complementarity determining regions (CDRs) of an antibody selected from the group consisting of δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, and δ1-285. In certain embodiments, the agent that selectively expands δ1 T-cells is an agent that comprises the variable regions of an antibody selected from the group consisting of δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, and δ1-285. In certain embodiments, the agent that selectively expands δ1 T-cells is an agent that binds the same epitope, or essentially the same epitope, as, or competes with, an antibody selected from the group consisting of δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, and δ1-285. In certain embodiments, the agent that selectively expands δ1 T-cells is an antibody selected from the group consisting of δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-197, δ1-199, δ1-201, δ1-203, δ1-239, δ1-253, δ1-257, δ1-278, δ1-282, and δ1-285. In certain embodiments, the agent that selectively expands δ1 T-cells is an antibody that binds a Bin 1 δ1 epitope, a Bin 1b δ1 epitope, a Bin 2 δ1 epitope, a Bin 2b δ1 epitope, a Bin 2c δ1 epitope, a Bin 3 δ1 epitope, a Bin 4 δ1 epitope, a Bin 5 δ1 epitope, a Bin 6 δ1 epitope, a Bin 7 δ1 epitope, a Bin 8 δ1 epitope, or a Bin 9 δ1 epitope.

In some embodiments, the methods of the invention provide enriched γδ T-cell population(s) comprising greater than 60%, 70%, 80% or 90% δ1 cells from an isolated mixed cell population comprising T lymphocytes. In some embodiments, the methods of the invention provide enriched γδ T-cell population(s) comprising greater than 60%, 70%, 80% or 90% δ1 cells from an isolated, e.g., mixed, cell population comprising T lymphocytes, before a step of purifying an expanded γδ T-cell population, e.g., by positive selection of γδ T-cells (e.g., positive selection of δ1 T cells, δ1 and δ3 γδ T cells; δ1 and δ4 γδ T cells; or δ1, 63, 64, and δ5 T cells (e.g., γδ T cells of the indicated δ-subtype(s)); and/or positive selection of δ2 T cells) from the enriched γδ T-cell population(s), or by depletion of non-γδ T-cells (e.g., non-δ1 T cells such as αβ T cells) from the enriched γδ T-cell population(s).

In some embodiments, the methods of the present invention provide a γδ T-cell population comprising δ1 γδ T cells and δ2 γδ T cells, wherein the population is greater than 60%, 70%, 80% or 90% δ1 γδ T cells. In some embodiments, the methods of the present invention provide a γδ T-cell population comprising δ1 γδ T cells; δ2 γδ T cells; δ1 and δ4 γδ T cells; or δ1, 63, 64, and δ5 γδ T cells, wherein (i) the population is greater than 60%, 70%, 80% or 90% δ1 γδ T cells; (ii) the population is greater than 60%, 70%, 80% or 90% δ1 and δ3 γδ T cells; (iii) the population is greater than 60%, 70%, 80% or 90% δ1 and δ4 γδ T cells; or (iv) the population is greater than 60%, 70%, 80% or 90% δ1, δ3, δ4, and δ5 γδ T cells. In some embodiments, the methods of the present invention provide a composition comprising a population of γδ T cells (e.g., δ1 γδ T cells) that is free of, or contains less than about 2%, 1%, 0.5%, 0.4%, 0.1%, 0.05%, or 0.01%, αβ T cells.

In certain embodiments, the isolated mixed cell population from which the γδ T-cells are expanded in a method described herein comprises about or less than about 30%, 25%, 20%, 15%, 10%, 5%, 4%, 3%, 2%, 1.5%, 1.2%, 1%, 0.9%, 0.8%, 0.7%, 0.6%, 0.5%, 0.4% 0.3%, 0.2%, or 0.1% γδ T cells (e.g., δ1, δ2, δ1 and δ2, δ1 and δ3, or δ1 and δ4 γδ T cells, or a combination thereof). In certain embodiments, the isolated mixed cell population from which the γδ T-cells are expanded in a method described herein comprises from about 0.5% to about 5% γδ T cells (e.g., δ1, δ2, δ3, δ4, or δ8 γδ T cells, or a combination thereof).

In certain embodiments, the isolated mixed cell population is from a donor or multiple donors having a larger than median level of circulating or sample—(e.g., tumor- or epithelial sample-) infiltrating γδ T-cells. Thus, for example, in some embodiments, the isolated mixed cell population from which the γδ T-cells are expanded in a method described herein comprises from about 0.5% to about 10% γδ T cells (e.g., δ1, δ2, δ3, δ4, or δ8 γδ T cells, or a combination thereof). As another example, in some embodiments, the isolated mixed cell population from which the γδ T-cells are expanded in a method described herein comprises about from about 10% to about 30% γδ T cells (e.g., δ1, δ2, δ3, δ4, or δ8 γδ T cells, or a combination thereof). In some embodiments, the isolated mixed cell population from which the γδ T-cells are expanded in a method described herein comprises about or less than about 1.5% γδ T cells, preferably less than about 1.2% γδ T cells, more preferably less than about 1% γδ T cells, yet more preferably less than about 0.5% γδ T cells, e.g., from about 0.1% to about 0.4% γδ T cells.

In certain embodiments, the isolated mixed cell population from which the γδ T-cells are expanded in a method described herein comprises about 80%, 70%, 60%, 50%, 40%, 30%, or 20% T lymphocytes and less than about 30%, 25%, 20%, 15%, 10%, 5%, 4%, 3%, 2%, 1.5%, 1.2%, 1%, 0.9%, 0.8%, 0.7%, 0.6%, 0.5%, 0.4% 0.3%, 0.2%, or 0.1% γδ T cells (e.g., δ1, δ2, δ1 and δ3, δ1 and δ3, or δ1 and δ4 γδ T cells, or a combination thereof). In certain embodiments, the isolated mixed cell population from which the γδ T-cells are expanded in a method described herein comprises about 80%, 70%, 60%, 50%, 40%, 30%, or 20% T lymphocytes and from about 0.5% to about 5% γδ T cells (e.g., δ1, δ2, δ3, δ4, or δ8 γδ T cells, or a combination thereof).

In certain embodiments, the isolated mixed cell population is from a donor or multiple donors having a larger than median level of circulating or sample—(e.g., tumor- or epithelial sample-) infiltrating γδ T-cells. Thus, for example, in some embodiments, the isolated mixed cell population from which the γδ T-cells are expanded in a method described herein comprises about 80%, 70%, 60%, 50%, 40%, 30%, or 20% T lymphocytes and from about 0.5% to about 10% γδ T cells (e.g., δ1, δ2, δ3, δ4, or δ8 γδ T cells, or a combination thereof). As another example, in some embodiments, the isolated mixed cell population from which the γδ T-cells are expanded in a method described herein comprises about 80%, 70%, 60%, 50%, 40%, 30%, or 20% T lymphocytes and from about 10% to about 30% γδ T cells (e.g., δ1, δ2, δ3, δ4, or δ8 γδ T cells, or a combination thereof). In some embodiments, the isolated mixed cell population from which the γδ T-cells are expanded in a method described herein comprises about 80%, 70%, 60%, 50%, 40%, 30%, or 20% T lymphocytes and about or less than about 1.5% γδ T cells, preferably less than about 1.2% γδ T cells, more preferably less than about 1% γδ T cells, yet more preferably less than about 0.5% γδ T cells, e.g., from about 0.1% to about 0.4% γδ T cells.

In some embodiments, the isolated mixed cell population is selected from a peripheral blood sample (e.g., whole blood, PBMCs, or PBLs), a leukapheresis sample, a cord blood sample, a tumor sample, or a tissue sample (e.g., an epithelial sample). In some embodiments, the isolated mixed cell population is derived from a single donor. In other embodiments, the isolated mixed cell population is derived from more than one or multiple donors. In certain embodiments, the methods of the invention provide enriched γδ T-cell population(s) comprising polyclonal γδ TCR diversity.

In other embodiments, the agent which selectively expands δ2 T-cells is selected from an agent which binds to the same epitope as an antibody selected from B6 and 15D. In yet other embodiments, the agent which selectively expands δ2 T-cells is selected from an agent which binds to a different epitope than an antibody selected from B6 and 15D. In still other embodiments, the agent which selectively expands δ2 T-cells is selected from an agent which binds to an epitope that does not overlap with an epitope bound by, or compete with, a B6 or 15D antibody. In one embodiment, the agent which selectively expands δ2 T-cells is selected from an agent which specifically binds to an epitope comprising a δ2 variable region. In a specific embodiment, the agent has reduced binding to a mutant δ2 TCR polypeptide comprising a mutation at G35 of the δ2 variable region.

In certain embodiments, the agent that selectively expands δ2 T-cells is an agent that comprises the complementarity determining regions (CDRs) of an antibody selected from the group consisting of δ2-14, δ2-17, δ2-22, δ2-30, δ2-31, δ2-32, δ2-33, δ2-35, δ2-36, and δ2-37 (or δ2-14, δ2-17, δ2-30, δ2-31, δ2-32, δ2-33, δ2-35, δ2-36, and δ2-37). In certain embodiments, the agent that selectively expands δ2 T-cells is an agent that comprises the variable regions of an antibody selected from the group consisting of δ2-14, δ2-17, δ2-22, δ2-30, δ2-31, δ2-32, δ2-33, δ2-35, δ2-36, and δ2-37 (or δ2-14, δ2-17, δ2-30, δ2-31, δ2-32, δ2-33, δ2-35, δ2-36, and δ2-37).

In certain embodiments, the agent that selectively expands δ2 T-cells is an agent that binds the same, or essentially the same, epitope as, or competes with, an antibody selected from the group consisting of δ2-14, δ2-17, δ2-22, δ2-30, δ2-31, δ2-32, δ2-33, δ2-35, δ2-36, and δ2-37 (or δ2-14, δ2-17, δ2-30, δ2-31, δ2-32, δ2-33, δ2-35, δ2-36, and δ2-37). In certain embodiments, the agent that selectively expands δ2 T-cells is an antibody selected from the group consisting of δ2-14, δ2-17, δ2-22, δ2-30, δ2-31, δ2-32, δ2-33, δ2-35, δ2-36, and δ2-37 (or δ2-14, δ2-17, δ2-30, δ2-31, δ2-32, δ2-33, δ2-35, δ2-36, and δ2-37). In certain embodiments, the agent that selectively expands δ2 T-cells is an antibody that binds a Bin 1 δ2 epitope, a Bin 2 δ2 epitope, a Bin 3 δ2 epitope, or a Bin 4 δ2 epitope.

In some embodiments, the methods of the invention provide enriched γδ T-cell population(s) comprising greater than 60%, 70%, 80% or 90% δ2 cells from an isolated mixed cell population comprising T lymphocytes. In some embodiments, the methods of the invention provide enriched γδ T-cell population(s) comprising greater than 60%, 70%, 80% or 90% δ2 cells from an isolated, e.g., mixed, cell population comprising T lymphocytes, before a step of purifying an expanded γδ T-cell population, e.g., by positive selection of γδ T-cells (e.g., positive selection of δ2 T cells) from the enriched γδ T-cell population(s), or by depletion of non-γδ T-cells (e.g., depletion of non-δ2 T cells or depletion of αβ T cells) from the enriched γδ T-cell population(s). In some embodiments, the methods of the present invention provide a γδ T-cell population comprising δ2 γδ T cells and δ1 γδ T cells, wherein the population is greater than 60%, 70%, 80% or 90% δ2 γδ T cells. In some embodiments, the methods of the present invention provide a composition comprising a population of δ2 γδ T cells that is free of, or contains less than about 2%, 1%, 0.5%, 0.4%, 0.1%, 0.05%, or 0.01%, αβ T cells.

In certain embodiments, the isolated mixed cell population from which the γδ T-cells are expanded in a method described herein comprises about 80%, 70%, 60%, 50%, 40%, 30%, or 20% T lymphocytes and less than about 60%, 50%, 40%, 30%, 25%, 20%, 15%, 10%, 5%, 4%, 3%, 2%, 1%, 0.9%, 0.8%, 0.7%, 0.6%, 0.5%, 0.4% 0.3%, 0.2%, 0.1%, 0.05%, or 0.02% δ2 cells. In some embodiments, the isolated mixed cell population from which the γδ T-cells are expanded in a method described herein is selected from a peripheral blood sample (e.g., PBMC or PBL), a leukapheresis sample, a cord blood sample, a tumor, or a tissue. In certain embodiments, the methods of the invention provide an enriched γδ T-cell population(s) comprising polyclonal TCR diversity.

In certain embodiments, the enriched γδ T-cell population is not expanded by, or not expanded in the presence of, an antigen presenting cell (APC), an artificial antigen presenting cell (aAPC), an irradiated population of antigen presenting cells (e.g., irradiated PBMCs, an irradiated immortalized cell line, or irradiated aAPCs), an aminophosphonate, an aminophosphate, a bisphosphonate, or a combination thereof. In certain embodiments, the enriched γδ T-cell population is not expanded by, or not expanded in the presence of, irradiated PBMCs. In certain embodiments, the enriched γδ T-cell population is not expanded by, or not expanded in the presence of, irradiated aAPCs (e.g., engineered K562, RPMI8226, T2, or JVM-3). In certain embodiments, the enriched γδ T-cell population is not expanded by, or not expanded in the presence of, an irradiated population of cells of an immortalized cell line. In preferred embodiments, said one or more agents which selectively expand δ1 T-cells, δ2 T-cells, δ1 T-cells and δ4 T-cells, or δ1, δ3, δ4, and δ5 T cells (e.g., γδ T cells) are antibodies.

In some embodiments, said one or more agents which selectively expand δ1 T-cells, δ2 T-cells, δ1 T-cells and δ4 T-cells, or δ1, δ3, δ4, and δ5 T cells (e.g., γδ T cells of the indicated δ-subtype(s)) are immobilized on a surface. In some embodiments, said one or more agents which selectively expand δ1 T-cells, δ2 T-cells, δ1 T-cells and δ4 T-cells, or δ1, 63, 64, and δ5 T cells (e.g., γδ T cells of the indicated δ-subtype(s)) are immobilized on a surface of an antigen presenting cell (e.g., an aAPC) in a first and/or second or subsequent expansion. The agents immobilized on the surface of an antigen presenting cell can, e.g., be bound to an Fc receptor expressed on the surface of the APC or expressed on the surface of the APC.

In some embodiments, the methods of the present invention are performed using a culture medium supplemented with IL-2, IL-4, IL-7, IL-9, IL-12, IL-15, IL-18, IL-19, IL-21, IL-23, IL-33, IFNγ, granulocyte-macrophage colony stimulating factor (GM-CSF), granulocyte colony stimulating factor (G-CSF), a lectin (e.g., PHA-E, PHA-L, or ConA), or a combination of two or more, or all thereof. In some embodiments, the methods of the present invention are performed using a culture medium that is not supplemented with IL-21. In some embodiments, the methods of the present invention are performed with a first γδ T-cell expansion using a culture medium supplemented with IL-2, IL-4, IL-7, IL-9, IL-12, IL-15, IL-18, IL-19, IL-21, IL-23, IL-33, IFNγ, granulocyte-macrophage colony stimulating factor (GM-CSF), granulocyte colony stimulating factor (G-CSF), a lectin (e.g., PHA-E, PHA-L, or ConA), or a combination of two or more, or all thereof. In some embodiments, the methods of the present invention are performed with a first γδ T-cell expansion using a culture medium that is not supplemented with IL-21. In some embodiments, the methods of the present invention are performed with a second γδ T-cell expansion using a culture medium supplemented with IL-2, IL-4, IL-7, IL-9, IL-12, IL-15, IL-18, IL-19, IL-21, IL-23, IL-33, IFNγ, granulocyte-macrophage colony stimulating factor (GM-CSF), granulocyte colony stimulating factor (G-CSF), a lectin (e.g., PHA-E, PHA-L, or ConA), or a combination of two or more, or all thereof. In some embodiments, the methods of the present invention are performed with a second γδ T-cell expansion using a culture medium that is not supplemented with IL-21.

In some embodiments, the methods of the present invention are performed with a first γδ T-cell expansion comprising any of the γδ T-cell expansion methods or compositions described herein, and then a second γδ T-cell expansion using a culture medium that is free of the one or more agents which selectively expand δ1 T-cells; δ2 T-cells; δ1 T-cells and δ3 T-cells; δ1 T-cells and δ4 T-cells; or δ1, δ3, δ4, and δ5 T cells (e.g., γδ T cells of the indicated δ-subtype(s)). In some embodiments, the methods of the present invention are performed with a first γδ T-cell expansion comprising any of the γδ T-cell expansion methods or compositions (e.g., activation agents) described herein, which method includes contacting an engineered or non-engineered γδ T-cell, a population of engineered or non-engineered γδ T-cells, and/or an isolated mixed population of cells with an immobilized agent that selectively expands δ1 T-cells; δ2 T-cells; δ1 T-cells and δ4 T-cells; or δ1, δ3, δ4, and δ5 T cells (e.g., γδ T cells of the indicated δ-subtype(s)), and then a second γδ T-cell expansion using a culture medium that: i) is free of the one or more agents which selectively expand δ1 T-cells; δ2 T-cells; δ1 T-cells and δ4 T-cells; or δ1, δ3, δ4, and δ5 T cells; ii) contains an (e.g., immobilized) structurally different agent that selectively expands δ1 T-cells; δ2 T-cells; δ1 T-cells and δ4 T-cells; or δ1, δ3, δ4, and δ5 T cells; iii) contains a non-immobilized (soluble) agent that selectively expands δ1 T-cells; δ2 T-cells; δ1 T-cells and δ4 T-cells; or δ1, δ3, δ4, and δ5 T cells; or iv) contains an agent that expands T cells (e.g., expands αβ and γδ T cells) or selectively expands γδ T cells as compared to αβ T cells.

In some cases, the agent that expands T cells is an agent that binds CD3, such as an anti-CD3 antibody (e.g., OKT3). In some cases, the agent that selectively expands γδ T cells is an agent that binds a γ-chain constant region or a δ-chain constant region, or an agent that binds γδ TCR, such as an antibody that binds γδ TCR (e.g., IMMU510). In some cases, the γδ T-cell population is enriched by positive selection between the first cell expansion and the second cell expansion, and/or after the second cell expansion. In some cases, the γδ T-cell population is enriched by depletion of αβ T cells between the first cell expansion and the second cell expansion, and/or after the second cell expansion.

In certain embodiments of the methods of the present invention, an, e.g. enriched, γδ T-cell population is expanded in a first, second, or subsequent expansion in a culture medium containing an antigen presenting cell (APC). In some embodiments, the culture medium contains one or more agents that expand T cells, expand γδ T-cells, selectively expand γδ T-cells, or selectively expands δ1 T-cells, δ2 T-cells, δ1 T-cells and δ3 T-cells, or δ1 T-cells and δ4 T-cells (e.g., an antibody that binds a constant or variable region of a γδ TCR, an antibody that binds CD3, and/or an aminophosphonate). In certain embodiments, the enriched γδ T-cell population is expanded in a culture medium containing irradiated PBMCs. In certain embodiments, the enriched γδ T-cell population is expanded in a culture medium containing irradiated artificial APCs (aAPCs). In certain embodiments, the enriched γδ T-cell population is expanded in a culture medium containing irradiated population of cells of an immortalized cell line (e.g., K562 APCs). In some cases, the APCs do not express, or exhibit reduced expression of, HLA class I, HLA class II, HLA class II invariant chain, and/or HLA-DM. In some cases, the APCs express adhesion or co-stimulatory molecules such as intercellular adhesion molecule-1, CD11a, CD18, CD54, CD80, CD86, 4-1BBL, OX-40 L, CD70, or one or more γδ T cell activating agents anchored in the membrane, and/or leukocyte function-associated antigen-3. In some cases, the APCs express an Fc receptor, such as an Fc receptor that is specific for an isotype of an activation agent used in a γδ T-cell expansion method described herein. In some cases, the APCs express one or more Fc receptors selected from the group consisting of CD64, CD32A, CD32B, CD32C, CD16A, CD16B, FcRn, TRIM21, or CD307, or an engineered variant thereof having a higher affinity or altered specificity.

In some embodiments, the culture medium containing an antigen presenting cell (APC), an artificial antigen presenting cell (aAPC), or an irradiated population of antigen presenting cells (e.g., PBMCs, an immortalized cell line, or aAPCs) further contains one or more agents that selectively expand δ1 T-cells; δ2 T-cells; δ1 T-cells and δ3 T-cells; δ1 T-cells and δ4 T-cells; or δ1, δ3, δ4, and δ5 T cells. In certain embodiments, the, e.g., irradiated, PBMCs, APCs, aAPCs, or population of cells of an immortalized cell line express on their cell surface the one or more agents that selectively expand δ1 T-cells; δ2 T-cells; δ1 T-cells and δ4 T-cells; or δ1, δ3, δ4, and δ5 T cells. In some preferred embodiments, said one or more agents which selectively expand δ1 T-cells; δ2 T-cells; δ1 T-cells and δ4 T-cells; or δ1, δ3, δ4, and δ5 T cells are antibodies. In some embodiments, said one or more agents that selectively expand δ1 T-cells; δ2 T-cells; δ1 T-cells and δ4; or δ1, δ3, δ4, and δ5 T-cells are antibodies expressed on the surface of the APC or bound to an Fc-receptor (e.g., Fcγ receptor) expressed on the surface of the APC.

In some embodiments, the invention provides ex vivo methods for producing an enriched γ6 T-cell population from an isolated, e.g., mixed, cell population, comprising (i) directly contacting the, e.g., mixed, cell population with one or more agents which (a) expand γδ T-cells (e.g., by binding to a γδ TCR), or (b) selectively expand:
  δ1 T-cells by binding to an activating epitope specific of a δ1 TCR;
  δ2 T-cells by binding to an activating epitope specific of a δ2 TCR;
  δ1 T-cells and δ4 T-cells by binding to an activating epitope specific of a δ1 TCR and a δ4 TCR; or
  δ1, δ3, δ4, and δ5 T cells by binding to an activating epitope specific of a δ1, δ3, δ4, and δ5 TCR in a first γδ T-cell expansion, thereby producing a first enriched γδ T-cell population, and then (ii) directly contacting at least a portion of the first enriched γδ T-cell population with antigen presenting cells (APCs), optionally in the presence of one or more soluble or immobilized agents that (a) expand T cells, (b) expand γδ T-cells (e.g., by binding to a γδ TCR), or (c) selectively expands:
  δ1 T-cells by binding to an activating epitope specific of a δ1 TCR;
  δ2 T-cells by binding to an activating epitope specific of a δ2 TCR;
  δ1 T-cells and δ4 T-cells by binding to an activating epitope specific of a δ1 TCR and a δ4 TCR; or
  δ1, δ3, δ4, and δ5 T cells by binding to an activating epitope specific of a δ1, δ3, δ4, and δ5 TCR in a second γδ T-cell expansion, thereby producing a second enriched γδ T-cell population, wherein the second enriched γδ T-cell population comprises a clinically relevant number (e.g., >$10^8$) of δ1 T-cells; δ2 T-cells; δ1 T-cells and δ4 T-cells; or δ1, δ3, δ4, and δ5 T cells.

In some cases, the clinically relevant number (e.g., >$10^8$) of the γδ T-cells is obtained from a single donor, e.g., from a single sample or 2 or more samples from the donor. In some cases, the clinically relevant number (e.g., >$10^8$) of the γδ T-cells is obtained from a single donor, e.g., from a single sample or 2 or more samples from the donor, within less than 30 days of expansion, preferably less than 21 days of expansion, more preferably within 19 days of expansion.

In some cases, the γδ T-cell population is enriched by positive selection between (i) and (ii), or after (ii). In some cases, the γδ T-cell population is enriched by depletion of αβ T cells between (i) and (ii), or after (ii). In some cases, the agent that expands T cells is an agent that binds CD3, such as an anti-CD3 antibody. In some cases, the agent that selectively expands γδ T cells is an agent that binds a γ-chain constant region or a δ-chain constant region, or an agent that binds γδ TCR, such as an antibody that binds γδ TCR (e.g., IMMU510).

In certain embodiments of the methods of the present invention, an enriched γδ T-cell population is produced by (i) contacting an isolated, e.g., mixed, cell population with one or more first agents which (a) expand γδ T-cells (e.g., by binding to a γδ TCR) or (b) selectively expands:
  δ1 T-cells by binding to an activating epitope specific of a δ1 TCR;
  δ2 T-cells by binding to an activating epitope specific of a δ2 TCR;
  δ1 T-cells and δ4 T-cells by binding to an activating epitope specific of a δ1 TCR and a δ4 TCR; or
  δ1, δ3, δ4, and δ5 T cells by binding to an activating epitope specific of a δ1, δ3, δ4, and δ5 TCR to provide a first enriched γδ T cell population in a first γδ T-cell expansion; and then (ii) in a second γδ T-cell expansion, contacting the first enriched γδ T cell population, or a portion thereof, with one or more second agents that (a) expand T cells, (b) expand γδ T-cells (e.g., by binding to a γδ TCR), or (c) selectively expand:
  δ1 T-cells by binding to an activating epitope specific of a δ1 TCR;
  δ2 T-cells by binding to an activating epitope specific of a δ2 TCR;
  δ1 T-cells and δ4 T-cells by binding to an activating epitope specific of a δ1 TCR and a δ4 TCR; or
  δ1, δ3, δ4, and δ5 T cells by binding to an activating epitope specific of a δ1, δ3, δ4, and δ5 TCR, wherein the one or more second agents are structurally different from the one or more first agents, thereby providing a second enriched γδ T cell population. In some cases, the one or more second agents bind a different γδ TCR epitope as compared to the one or more first agents.

In some cases, the γδ T-cell population is enriched by positive selection between (i) and (ii), or after (ii). In some cases, the γδ T-cell population is enriched by depletion of αβ T cells between (i) and (ii), or after (ii). In some cases, the agent that expands T cells is an agent that binds CD3, such as an anti-CD3 antibody. In some cases, the agent that selectively expands γδ T cells is an agent that binds a γ-chain constant region or a δ-chain constant region, or an agent that binds γδ TCR, such as an antibody that binds γδ TCR (e.g., IMMU510).

In some cases, the first γδ T-cell expansion is performed in a culture medium that contains an antigen presenting cell (APC). In some cases, the second γδ T-cell expansion is performed in a culture medium that contains an antigen presenting cell (APC). In some cases, the first γδ T-cell expansion is performed in a culture medium that does not contain an antigen presenting cell (APC). In some cases, the first γδ T-cell expansion is performed in a culture medium that does not contain an antigen presenting cell (APC), and the second γδ T-cell expansion is performed in a culture medium that does contain an antigen presenting cell (APC). In some cases, the first and second γδ T-cell expansion is performed in a culture medium that does contain an antigen presenting cell (APC). In some cases, the first and second γδ T-cell expansion is performed in a culture medium that does contain an aminophosphate, an aminophosphonate, a bisphosphonate, or a combination thereof.

In another embodiment, the enriched γδ T-cell population(s) of the invention may be further formulated for administration to a subject. The enriched γδ T-cell population(s) of the invention includes a therapeutically effective amount of γδ T-cells. In certain embodiments, the γδ T-cell population(s) are engineered to stably express one or more structurally distinct tumor recognition moieties. In certain embodiments, the engineered γδ T-cell(s) are expanded and/or further expanded as described herein.

In some of the foregoing aspects, embodiments, cases, and examples the one or more agents stimulates an expansion of the γδ T-cell at a mean rate of 1 cell division in less than 30 hours, e.g., from greater than about 17 to less than about 30 hours. In some embodiments, said mean rate of division is for 0-4, 0-5, 0-7 contiguous days of γδ T-cell expansion, 0-13 contiguous days of γδ T-cell expansion, 0-19 contiguous days of γδ T-cell expansion, 0-21 contiguous days of γδ T-cell expansion, or for at least 3, 4, 5, 6, 7, 10, 13, 19, or 21 contiguous days of γδ T-cell expansion. In other embodiments, the one or more agents stimulates an expansion of the γδT-cell at a mean rate of 1 cell division in less than 24 hours, e.g., from greater than about 17 to less than about 24 hours. In other embodiments, the one or more agents stimulates an expansion of the γδT-cell at a mean rate of 1 cell division in less than 18 hours or about 18 hours.

It will be appreciated that one or more of the foregoing aspects, embodiments, cases, and examples can be readily adapted for γδ T-cell expansion (e.g., selective γδ T-cell expansion) from a substantially homogenous population of cells, such as after establishing a γδ T-cell engineered clone or cell line, population containing one or more (e.g., structurally different) engineered γδ T-cells, or after one or more steps of negative or positive selection of a population of cells containing γδ T-cells. Thus, one or more of the foregoing methods, or a combination thereof, can be used to expand engineered γδ T-cells by contacting an engineered γδ T-cell or population thereof with any one or more of the activation agents described herein, including one or more of the antibodies described herein in soluble or immobilized form (e.g., immobilized on the surface of an APC).

As such, in some embodiments, the isolated mixed cell population is substituted in a method or composition provided herein, with a γδ T-cell engineered clone or cell line, or a population containing one or more (e.g., structurally different) engineered γδ T-cells.

In other aspects, the invention provides selectively expanded γδ T-cell population(s), wherein greater than 60%, 70%, 80%, or 90% of the expanded γδ T-cells are δ1 T-cells; δ1 T-cells and δ4 T-cells; or δ1 T-cells, δ3 T-cells, δ4 T-cells, and δ5 T-cells. In certain embodiment, the selectively expanded γδ T-cell population(s) comprise δ1 T-cells and δ2 T-cells, wherein greater than 60%, 70%, 80%, or 90% of the expanded γδ T-cells are δ1 T-cells δ1 T-cells and δ4 T-cells; or δ1 T-cells, δ3 T-cells, δ4 T-cells, and δ5 T-cells. In certain embodiments, the selectively expanded γδ T-cell population(s) have not been purified by positive selection of γδ T-cells (e.g., positive selection of δ1 T cells, δ1 T-cells and δ3 T-cells, or δ1 T-cells and δ4 T-cells) from an enriched γδ T-cell population, or by depletion of non-γδ T-cells (e.g., depletion of non-δ1 T cells such as αβ T cells) from the enriched γδ T-cell population.

In certain embodiments, the selectively expanded γδ T-cell population(s) are expanded directly from an isolated mixed cell population comprising T lymphocytes. In certain embodiments, the isolated mixed cell population from which the γδ T-cells are expanded in a method described herein comprises about 80%, 70%, 60%, 50%, 40%, 30%, 20% T lymphocytes and less than about 30%, 25%, 20%, 15%, 10%, 5%, 4%, 3%, 2%, 1.5%, 1.2%, 1%, 0.9%, 0.8%, 0.7%, 0.6%, 0.5%, 0.4% 0.3%, 0.2%, or 0.1% δ1 cells. In certain embodiments, the isolated mixed cell population from which the γδ T-cells are expanded in a method described herein comprises less than about 30%, 25%, 20%, 15%, 10%, 5%, 4%, 3%, 2%, 1.5%, 1.2%, 1%, 0.9%, 0.8%, 0.7%, 0.6%, 0.5%, 0.4% 0.3%, 0.2%, or 0.1% δ1 cells. In some embodiments, the isolated mixed cell population is selected from a peripheral blood sample, a cord blood sample, a tumor, epithelial tissue, or a biopsy of skin, liver, or other tissue. In some embodiments, the isolated mixed cell population is derived from a single donor. In other embodiments, the isolated mixed cell population is derived from more than one or multiple donors. In one embodiment, the expanded γδ T-cell population(s) are derived from tumor infiltrating lymphocytes, which may be isolated, for example, from cancers of colon adenocarcinoma metastasis, liver, ovary, head and neck, or kidney.

In some embodiments, the selectively expanded γδ T-cell population(s) of the invention comprise greater than 60% or 70% the δ1 T-cells; δ1 T-cells and δ4 T-cells; or δ1 T-cells, δ3 T-cells, δ4 T-cells, and δ5 T-cells which express the naïve or T central memory (TCM) phenotype CD45RA+/CD27+ and/or CD45RA−/CD27+, respectively. In some embodiments, the expanded γδ T-cell population comprises polyclonal γδ TCR diversity.

In other aspects, the invention provides selectively expanded γδ T-cell population(s), wherein greater than 80% or 90% of the expanded γδ T-cells are δ2 T-cells. In certain embodiments, the selectively expanded γδ T-cell population(s) have not been purified by positive selection of γδ T-cells (e.g., positive selection of δ2 T cells) from an enriched γδ T-cell population, or by depletion of non-γδ T-cells (e.g., depletion of non-δ2 T cells such as depletion of αβ T cells) from the enriched γδ T-cell population. In certain embodiments, the selectively expanded γδ T-cell population(s) are expanded directly from an isolated mixed cell population comprising T lymphocytes. In certain embodiments, the isolated mixed cell population from which the γδ T-cell population(s) are expanded comprises about 80%, 70%, 60%, 50%, 40%, 30%, or 20% T lymphocytes and less than about 60%, 50%, 40%, 30%, 25%, 20%, 15%, 10%, 5%, 4%, 3%, 2%, 1.5%, 1.2%, 1%, 0.9%, 0.8%, 0.7%, 0.6%, 0.5%, 0.4% 0.3%, 0.2%, or 0.1% δ2 cells. In certain embodiments, the isolated mixed cell population from which the γδ T-cells are expanded in a method described herein comprises less than about 30%, 25%, 20%, 15%, 10%, 5%, 4%, 3%, 2%, 1.5%, 1.2%, 1%, 0.9%, 0.8%, 0.7%, 0.6%, 0.5%, 0.4% 0.3%, 0.2%, or 0.1% δ2 cells. In some embodiments, the isolated mixed cell population is selected from a peripheral blood sample, a cord blood sample or a tumor. In one embodiment, the expanded γδ T-cell population(s) are derived from tumor infiltrating lymphocytes, which may be isolated, for example, from cancers of colon adenocarcinoma metastasis, liver, ovary, head and neck, or kidney.

In other aspects, the invention provides selectively expanded γδ T-cell population(s), wherein 10-90% of the expanded γδ T-cells are δ1 T-cells and 90-10% of the expanded γδ T-cells are δ2 T-cells.

In certain embodiments, said populations are expanded together, e.g., by contacting a mixed cell population with an agent which selectively expands δ1 cells; δ1 T-cells and δ3 T-cells; δ1 T-cells and δ4 T-cells; or δ1 T-cells, δ3 T-cells, δ4 T-cells, and δ5 T-cells, and with an agent that selectively expands δ2 cells, either simultaneously or in separate contacting steps. In other embodiments, the populations are admixtures of δ1 and δ2 T-cell populations which have been separately and selectively expanded from an isolated mixed cell population. In all embodiments, the expanded γδ T-cell population(s) or admixtures thereof of the invention may further be formulated for administration to a subject.

In certain embodiments, a γδ T-cell or γδ T-cell population(s) of the invention are engineered to stably express one or more structurally distinct tumor recognition moieties encoded by expression cassettes. In one embodiment, the γδ T-cell is engineered to stably express two or more structurally distinct tumor recognition moieties encoded by expression cassettes. In some embodiments, the two or more structurally distinct tumor recognition moieties recognize different epitopes of the same antigen or different epitopes of different antigens. The tumor recognition moiety may be selected from the group consisting of αβ TCR, γδ TCR, a fragment of an αβ TCR or γδ TCR, a chimeric antigen receptor (CAR), whole antibody or their antigen-binding fragment, single-chain variable fragment (scFv), a heavy chain or a light chain single domain antibody (sdAb), a Fab, a F(ab)$_2$, or any combination thereof that binds to: (i) a cell surface tumor antigen or (ii) a peptide derived from a tumor antigen expressed on the cell surface as a complex with MHC (peptide-MHC complex). In certain embodiments, the tumor recognition moiety is a γδ TCR of a tumor infiltrating lymphocyte that recognizes a tumor-specific antigen in a non-MHC restricted manner.

In another aspect, the invention provides expanded γδ T-cell population(s) obtained according to the methods of the invention. In some embodiments, the γδ T-cell population is expanded ex vivo without antigen stimulation by an antigen presenting cell or an aminophosphonate. In certain embodiments, γδ T-cell population is activated ex vivo with a monoclonal antibody, antibody fragment, or a fusion protein. The γδ T-cell population(s) of the invention may also be formulated for administration to a subject without co-administration with IL-2. Alternatively, the γδ T-cell population(s) of the invention may also be formulated for administration to a subject with co-administration with IL-2.

In other aspects, the invention provides methods for treating a cancer in a subject in need thereof, comprising administering a therapeutically effective amount of an expanded γδ T-cell population according to the invention. In one embodiment, the expanded γδ T-cell population is allogeneic with respect to the MHC loci of the subject. In certain embodiments, the expanded γδ T-cell population is engineered to stably express one or more, or two or more, tumor recognition moieties encoded by one or more expression cassettes. In further embodiments, the expanded γδ T-cell population stably expresses at least two structurally different recognition moieties and each structurally different recognition moiety recognizes (i) different epitopes of the same antigen, or (ii) different epitopes of different antigens. The tumor recognition moiety may be selected from the group consisting of αβ TCR, γδ TCR, a chimeric antigen receptor (CAR), including whole antibody or their antigen-binding fragment, single-chain variable fragment (scFv), a heavy chain or a light chain single domain antibody (sdAb), a Fab, a F(ab)$_2$, or any combination thereof that binds to: (i) a cell surface tumor antigen or (ii) a peptide derived from a tumor antigen expressed on the cell surface as a complex with WIC (peptide-WIC complex).

In another aspect, the invention provides engineered γδ T-cells, wherein the engineered γδ T-cell is engineered to express a tumor recognition moiety, wherein the tumor recognition moiety recognizes a tumor antigen, and/or wherein the engineered γδ T-cell expands in vitro in the presence of (e.g., is in contact with in vitro) one or more agents which bind the same epitope as TS-1, TS8.2, B6, or 15D antibodies. In another aspect, the invention provides engineered γδ T-cells, wherein the engineered γδ T-cell is engineered to express a tumor recognition moiety, wherein the tumor recognition moiety recognizes a tumor antigen, and/or wherein the engineered γδ T-cell expands in vitro in the presence of (e.g., is in contact with in vitro) one or more agents which bind a different epitope than, or an epitope that does not overlap with, the epitope bound by TS-1, TS8.2, B6, or 15D antibodies. In some cases, the engineered γδ T-cell expands in vitro in the presence of (e.g., is in contact with in vitro) one or more agents that do not compete with binding of TS-1, TS8.2, B6, or 15D to a γδ T-cell. In one embodiment, the agent is any one or more of the soluble or immobilized activation agents described herein. In one embodiment, the engineered γδ T-cell is a δ1, δ2, δ3, or δ4 engineered T-cell.

In certain embodiments, the engineered γδ T-cell is further engineered to lack gene expression from at least one HLA loci. In one embodiment, the one or more agents stimulates an expansion of the engineered γδ T-cell at a mean rate of 1 cell division in less than 30 hours, e.g., from greater than about 17 to less than about 30 hours. In some embodiments, said mean rate of division is for 0-4, 0-5, 0-7 contiguous days of γδ T-cell expansion, 0-13 contiguous days of γδ T-cell expansion, 0-19 contiguous days of γδ T-cell expansion, 0-21 contiguous days of γδ T-cell expansion, or for at least 3, 4, 5, 6, 7, 10, 13, 19, or 21 contiguous days of γδ T-cell expansion. In other embodiments, the one or more agents stimulates an expansion of the engineered γδ T-cell at a mean rate of 1 cell division in less than 24 hours, e.g., from greater than about 17 to less than about 24 hours. In other embodiments, the one or more agents stimulates an expansion of the engineered γδT-cell at a mean rate of 1 cell division in less than 18 hours or about 18 hours. In certain embodiments, the tumor recognition moiety is derived from a tumor infiltrating lymphocyte.

In another aspect, the present invention provides an expanded population of γδ T-cells, wherein the γδ T-cell population comprises anti-tumor cytotoxicity. In some cases, the γδ T-cell population comprises anti-tumor cytotoxicity that is independent of NKp30 activity, NKp44 activity, and/or NKp46 activity. In some cases, the γδ T-cell population comprises anti-tumor cytotoxicity, wherein the anti-tumor cytotoxicity consists of, or consists essentially of, anti-tumor activity that is independent of NKp30 activity, NKp44 activity, and/or NKp46 activity. In some cases, the γδ T-cell population comprises anti-tumor cytotoxicity, wherein at least 50%, 60%, 75%, 80%, 90%, or 99% of the anti-tumor cytotoxicity is independent of NKp30 activity, NKp44 activity, and/or NKp46 activity.

In some cases, the γδ T-cell population is a population of engineered γδ T-cells. In some cases, the γδ T-cell population is a population of non-engineered γδ T-cells. In some cases, the γδ T-cell population does not comprise NKp30 activity-dependent anti-tumor cytotoxicity, NKp44 activity-dependent anti-tumor cytotoxicity, and/or NKp46 activity-dependent anti-tumor cytotoxicity. In some cases, the γδ T-cell population does not comprise NKp30 activity-dependent anti-tumor cytotoxicity. In some cases, the γδ T-cell population does not comprise NKp44 activity-dependent anti-tumor cytotoxicity. In some cases, the γδ T-cell population is an engineered population of γδ T-cells that comprise an anti-CD20 chimeric antigen receptor (CAR). In some cases, less than 90%, 80%, 75%, 70%, 60%, 50%, 40%, 30%, 20%, or 10% of the γδ T-cell cells in the population express a detectable level of NKp30, NKp44, and/or NKp46.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 14 depicts the human Vδ1 amino acid sequence (SEQ ID NO: 133). CDR1, CDR3, and CDR3 regions are underlined. FIG. 14 also discloses the nucleotide sequence as SEQ ID NO: 132.

FIG. 15 depicts the human Vδ2 amino acid sequence (SEQ ID NO: 135). CDR1, CDR3, and CDR3 regions are underlined. FIG. 15 discloses SEQ ID NOS 135, 134, 137, and 136, respectively, in order of appearance.

FIG. 24 depicts sequence alignment of human Vδ1J1, J2 and J3 regions and mutations made to the Vδ1J1 chain at the selected positions. BE-13 refers to δ1J region from a T cell leukemia cell line expressing δ1γ8 TCR (DSMZ accession #ACC 396). Replacement of a single amino acid residue at position Lys120 by Thr or Ala in the Vδ1J1 and Vδ1J2 region completely abolished binding of TS-1 and TS8.2 MAbs indicating that this amino acid in the Vδ1J1 and Vδ1J2 region is contributes to the binding of TS-1 and TS8.2. Replacement of a single amino acid residue at position Thr120 by Lys in the Vδ1J3 region resulted in a gain of binding of TS-1 and TS8.2 MAbs further indicating that this amino acid in the Vδ1J1 and Vδ1J2 region contributes to the binding of TS-1 and TS8.2. FIG. 24 discloses SEQ ID NOS 138-143, respectively, in order of appearance.

FIG. 26 depicts of human Vδ1 protein sequence (SEQ ID NO: 144) and the six mutated human Vδ1 sequences (SEQ ID NOS 145-150, respectively, in order of appearance) based on the differences between human Vδ1 and the bovine Vδ1 amino acid sequence (GenBank:AFP25182.1). Mutation are shown in bold.

Definitions

Figure 1:
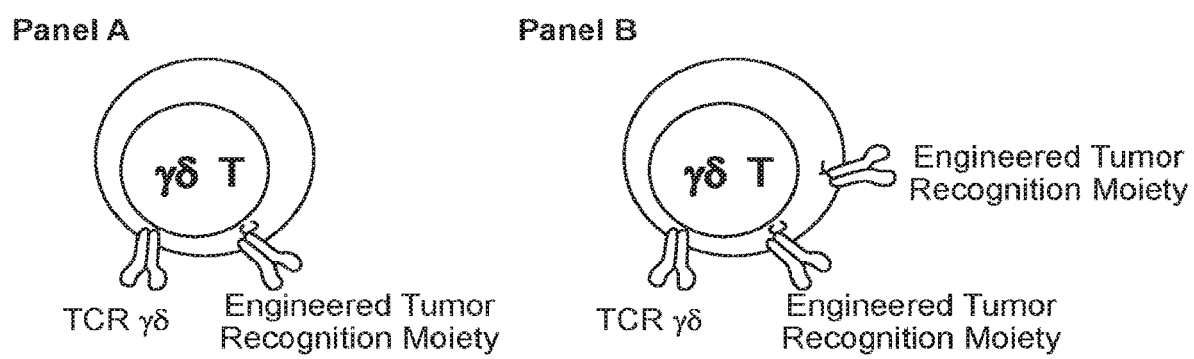
FIG. 1 schematically illustrates engineered γδ T-cells. Panel A illustrates an engineered γδ T-cell expressing one tumor recognition moiety. Panel B illustrates an engineered γδ T-cell expressing two structurally distinct tumor recognition moieties.

Unless defined otherwise, all technical and scientific terms used herein have the same meaning as commonly understood to one of ordinary skill in the art to which the inventions described herein belong. For purposes of interpreting this specification, the following definitions will apply and whenever appropriate, terms used in the singular will also include the plural and vice versa. In the event that any definition set forth conflicts with any document incorporated herein by reference, the definition set forth below shall control.

The term "γδ T-cells (gamma delta T-cells)" as used herein refers to a subset of T-cells that express a distinct T-cell receptor (TCR), γδTCR, on their surface, composed of one γ-chain and one δ-chain. The term "γδ T-cells" specifically includes all subsets of γδ T-cells, including, without limitation, Vδ1 and Vδ2, Vδ3 γδ T cells, as well as naïve, effector memory, central memory, and terminally differentiated γδ T-cells. As a further example, the term "γδ T-cells" includes Vδ4, Vδ5, Vδ7, and Vδ8 γδ T cells, as well as Vγ2, Vγ3, Vγ5, Vγ8, Vγ9, Vγ10, and Vγ11 γδ T cells.

As used herein, the term "T lymphocyte" or "T cell" refers to an immune cell expressing CD3 (CD3+) and a T Cell Receptor (TCR+). T cells play a central role in cell-mediated immunity.

As used herein, the term "TCR" or "T cell receptor" refers to a dimeric heterologous cell surface signaling protein forming an alpha-beta or gamma-delta receptor. αβTCR recognize an antigen presented by an MHC molecule, whereas γδTCR recognize an antigen independently of MHC presentation.

The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably.

As used herein, the term "peripheral blood lymphocyte(s)" or "PBL(s)" is used in the broadest sense and refers to white blood cell(s) comprising T cells and B cells of a range of differentiation and functional stages, plasma cells, monocytes, macrophages, natural killer cells, basocytes, eosinophils, etc. The range of T lymphocytes in peripheral blood is about 20-80%.

As used herein, the term "cell population" refers to a number of cells obtained by isolation directly from a suitable source, usually from a mammal. The isolated cell population may be subsequently cultured in vitro. Those of ordinary skill in the art will appreciate that various methods for isolating and culturing cell populations for use with the present invention and various numbers of cells in a cell population that are suitable for use in the present invention. A cell population may be, for example, a mixed heterogeneous cell population derived from a peripheral blood sample, a cord blood sample, a tumor, a stem cell precursor, a tumor biopsy, a tissue, a lymph, or from epithelial sites of a subject directly contacting the external milieu, or derived from stem precursor cells. Alternatively, the mixed cell population may be derived from in vitro cultures of mammalian cells, established from a peripheral blood sample, a cord blood sample, a tumor, a stem cell precursor, a tumor biopsy, a tissue, a lymph, or from epithelial sites of a subject directly contacting the external milieu, or derived from stem precursor cells.

An "enriched" cell population or preparation refers to a cell population derived from a starting mixed cell population that contains a greater percentage of a specific cell type than the percentage of that cell type in the starting population. For example, a starting mixed cell population can be enriched for a specific γδ T-cell population. In one embodiment, the enriched γδ T-cell population contains a greater percentage of δ1 cells than the percentage of that cell type in the starting population. As another example, an enriched γδ T-cell population can contain a greater percentage of both δ1 cells and a greater percentage of δ3 cells than the percentage of that cell type in the starting population. As yet another example, an enriched γδ T-cell population can contain a greater percentage of both δ1 cells and a greater percentage of δ4 cells than the percentage of that cell type in the starting population. As yet another example, an enriched γδ T-cell population can contain a greater percentage of δ1 T cells, δ3 T cells, δ4 T cells, and δ5 T cells than the percentage of that cell type in the starting population. In another embodiment, the enriched γδ T-cell population contains a greater percentage of δ2 cells than the percentage of that cell type in the starting population. In yet another embodiment, the enriched γδ T-cell population contains a greater percentage of both δ1 cells and δ2 cells than the percentage of that cell type in the starting population. In all embodiments, the enriched γδ T-cell population contains a lesser percentage of αβ T-cell populations.

By "expanded" as used herein is meant that the number of the desired or target cell type (e.g., δ1 and/or δ2 T-cells) in the enriched preparation is higher than the number in the initial or starting cell population. By "selectively expand" is meant that the target cell type (e.g., δ1 or δ2 T-cells) are preferentially expanded over other non-target cell types, e.g., αβ T-cells or NK cells. In certain embodiments, the activating agents of the invention selectively expand, e.g., engineered or non-engineered, δ1 T-cells without significant expansion of δ2 T-cells. In other embodiments, the activating agents of the invention selectively expand, e.g., engineered or non-engineered, δ2 T-cells without significant expansion of δ1 T-cells. In certain embodiments, the activating agents of the invention selectively expand, e.g., engineered or non-engineered, δ1 and δ3 T-cells without significant expansion of δ2 T-cells. In certain embodiments, the activating agents of the invention selectively expand, e.g., engineered or non-engineered, δ1 and δ4 T-cells without significant expansion of δ2 T-cells. In certain embodiments, the activating agents of the invention selectively expand, e.g., engineered or non-engineered, δ1, δ3, δ4 and δ5 T-cells without significant expansion of δ2 T-cells. In this context, the term "without significant expansion of" means that the preferentially expanded cell population are expanded at least 10-fold, preferably 100-fold, and more preferably 1,000-fold more than the reference cell population.

The term "admixture" as used herein refers to a combination of two or more isolated, enriched cell populations derived from a mixed, heterogeneous cell population. According to certain embodiments, the cell populations of the present invention are isolated γδ T cell populations.

The term "isolated," as applied to a cell population, refers to a cell population, isolated from the human or animal body, which is substantially free of one or more cell populations that are associated with said cell population in vivo or in vitro.

The term "contacting" in the context of a cell population, as used here refers to incubation of an isolated cell population with a reagent, such as, for example, an antibody, cytokine, ligand, mitogen, or co-stimulatory molecule that can be linked either to beads or to cells. The antibody or cytokine can be in a soluble form, or it can be immobilized. In one embodiment, the immobilized antibody or cytokine is tightly bound or covalently linked to a bead or plate. In one embodiment, the antibody is immobilized on Fc-coated wells. In desirable embodiments, the contact occurs ex vivo (e.g., in vitro), or in vivo.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "directed against" is meant that the antibody reacts with one or more antigenic determinants of the desired antigen and does not react with other polypeptides or binds at much lower affinity ($K_D>10^{-6}$ molar). Antibodies include, but are not limited to, polyclonal, monoclonal, chimeric, sdAb (heavy or light single domain antibody), single chain, $F_{ab}$, $F_{ab'}$ and $F_{(ab')2}$ fragments, scFvs, diabodies, minibodies, nanobodies, and $F_{ab}$ expression library.

The term "chimeric antigen receptors (CARs)," as used herein, may refer to artificial T-cell receptors, T-bodies, single-chain immunoreceptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain (allowing the T cell to activate upon engagement of targeting moiety with target cell, such as a target tumor cell), a transmembrane domain, and an extracellular domain that may vary in length and comprises a disease- or disorder-associated, e.g., a tumor-antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP 10/12, and/or OX40, ICOS, TLRs, etc. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "Fab" refers to an antibody fragment that consists of an entire L chain ($V_L$ and $C_L$) along with the variable region domain of the H chain ($V_H$), and the first constant domain of one heavy chain (CH1). Papain digestion of an intact antibody can be used to produce two Fab fragments, each of which contains a single antigen-binding site. Typically, the L chain and H chain fragment of the Fab produced by papain digestion are linked by an interchain disulfide bond.

The term "Fc" refers to an antibody fragment that comprises the carboxy-terminal portions of both H chains (CH2 and CH3) and a portion of the hinge region held together by disulfide bonds. The effector functions of antibodies are determined by sequences in the Fc region; this region is also the part recognized by Fc receptors (FcR) found on certain types of cells. One Fc fragment can be obtained by papain digestion of an intact antibody.

The term "F(ab')$_2$" refers to an antibody fragment produced by pepsin digestion of an intact antibody. F(ab')$_2$ fragments contain two Fab fragments and a portion of the hinge region held together by disulfide bonds. F(ab')$_2$ fragments have divalent antigen-binding activity and are capable of cross-linking antigen.

The term Fab' refers to an antibody fragment that is the product of reduction of an F(ab')$_2$ fragment. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group.

The term "Fv" refers to an antibody fragment that consists of a dimer of one heavy-chain variable region and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

The term "single-chain Fv" also abbreviated as "sFv" or "scFv" refer to antibody fragments that comprise the VH and VL antibody domains connected into a single polypeptide chain. Typically, the scFv polypeptide further comprises a polypeptide linker between the VH and VL domains, which enables the scFv to form the desired structure for antigen binding. For a review of scFv, see, e.g., Pluckthun, *The Pharmacology of Monoclonal Antibodies*, vol. 113, Rosenburg and Moore eds., Springer-Verlag, New York, pp. 269-315 (1994); and Malmborg et al., J. Immunol. Methods 183:7-13, 1995.

The expression "linear antibody" is used to refer to a polypeptide comprising a pair of tandem $V_H$-$C_H$1 segments ($V_H$-$C_H$1-$V_H$-$C_H$1) which form a pair of antigen binding regions. Linear antibodies can be bispecific or monospecific and are described, for example, by Zapata et al., *Protein Eng.* 8(10):1057-1062 (1995).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The term "hypervariable region," "HVR," or "HV," refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

"Framework regions" (FR) are those variable domain residues other than the CDR residues. Each variable domain typically has four FRs identified as FR1, FR2, FR3, and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In certain instances, for the VL, the subgroup is subgroup kappa I as in Kabat. In certain instances, for the VH, the subgroup is subgroup III as in Kabat.

As used herein, the "Kd" or "Kd value" refers to a dissociation constant measured by using surface plasmon resonance assays, for example, using a BIAcore™-2000 or a BIAcore™-3000 (BIAcore, Inc., Piscataway, N.J.) at 25° C. with CM5 chips immobilized with antigen or antibody at about 10 response units (RU). For divalent or other multivalent antibodies, typically the antibody is immobilized to avoid avidity-induced interference with measurement of the dissociation constant. For further details see, e.g., Chen et al., *J. Mol. Biol.* 293:865-881 (1999).

The term "epitope" includes any protein determinant, lipid or carbohydrate determinant capable of specific binding to an immunoglobulin or T-cell receptor. Epitopic determinants usually consist of active surface groupings of molecules such as amino acids, lipids or sugar side chains and usually have specific three dimensional structural characteristics, as well as specific charge characteristics. An antibody is said to specifically bind an antigen when the equilibrium dissociation constant ($K_D$) is range $10^{-6}$-$10^{-12}$M. An "activating epitope" is capable of activation of the specific γδ T-cell population upon binding.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in a number of different formats, using either labeled antigen or labeled antibody. In some embodiments, the antigen is immobilized on a 96-well plate, and the ability of unlabeled antibodies to block the binding of labeled antibodies is measured using radioactive or enzyme labels. Alternatively, the competition studies, using labelled and unlabeled antibodies, are performed using flow cytometry on antigen-expressing cells.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Epitope binning", as defined herein, is the process of grouping antibodies based on the epitopes they recognize. More particularly, epitope binning comprises methods and systems for discriminating the epitope recognition properties of different antibodies, combined with computational processes for clustering antibodies based on their epitope recognition properties and identifying antibodies having distinct binding specificities.

An "agent" or "compound" according to the present invention comprises small molecules, polypeptides, proteins, antibodies or antibody fragments. Small molecules, in the context of the present invention, mean in one embodiment chemicals with molecular weight smaller than 1000 Daltons, particularly smaller than 800 Daltons, more particularly smaller than 500 Daltons. The term "therapeutic agent" refers to an agent that has biological activity. The term "anti-cancer agent" refers to an agent that has biological activity against cancer cells.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including stem cells, blood cells, embryonic cord blood cells, tumor cells, transduced cells, etc.

The terms "treat" or "treatment" refer to both therapeutic treatment and prophylactic or preventative measures, wherein the object is to prevent or slow down (lessen) an undesired physiological change or disorder. Beneficial or desired clinical results include, but are not limited to, alleviation of symptoms, diminishment of extent of disease (e.g., decrease of tumor size, tumor burden, or tumor distribution), stabilized (i.e., not worsening) state of disease, delay or slowing of disease progression, amelioration or palliation of the disease state, and remission (whether partial or total), whether detectable or undetectable. "Treatment" can also mean prolonging survival, as compared to expected survival if not receiving treatment. Those in need of treatment include those already with the condition or disorder as well as those prone to have the condition or disorder or those in which the condition or disorder is to be prevented.

Administration "in combination with" one or more further therapeutic agents includes simultaneous (concurrent) and consecutive administration in any order.

The term "identical," as used herein, refers to two or more sequences or subsequences that are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75 to about 100 nucleic acids in length, over a region that is about 50 nucleic acids in length, or, where not specified, across the entire sequence of a polynucleotide sequence.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "subject," or "patient", as used herein, refers to a vertebrate. In certain embodiments, the vertebrate is a mammal. Mammals include, but are not limited to, humans, non-human primates, farm animals (such as cows), sport animals, and pets (such as cats, dogs, and horses). In certain embodiments, a mammal is a human.

The term "therapeutically effective amount," as used herein, refers to the amount of a composition containing the expanded cell populations and/or admixtures of the present invention administered to a subject, e.g., a human patient, already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

The term antigen presenting cell (APC) refers to a wild-type APC, or an engineered or artificial antigen presenting cell (aAPC). APCs can be provided as an irradiated population of APCs. APCs can be provided from a immortalized cell line (e.g., K562 or an engineered aAPC derived from an immortalized cell line) or as a fraction of cells from a donor (e.g., PBMCs).

As used herein, the terms "structurally different" and "structurally distinct," in reference to a protein or polypeptide fragment thereof, or an epitope, refer to a covalent (i.e., structural) difference between at least two different proteins, polypeptide fragments thereof, or epitopes. For example, two structurally different proteins (e.g., antibodies) can refer to two proteins that have different primary amino acid sequences. In some cases, structurally different activating agents bind structurally different epitopes, such as epitopes having a different primary amino acid sequence.

As used herein, the term "anti-tumor cytotoxicity" that is "independent of" a specified receptor activity (e.g., NKp30 activity, NKp44 activity, and/or NKp46 activity), refers to anti-tumor cytotoxicity that is exhibited whether or not the specified receptor or specified combination of receptors is expressed by the cell or functional. As such, a γδ T-cell that exhibits anti-tumor cytotoxicity that is independent of NKp30 activity, NKp44 activity, and/or NKp46 activity can also exhibit NKp30 activity-dependent anti-tumor cytotoxicity, NKp44 activity-dependent anti-tumor cytotoxicity, and/or NKp46 activity-dependent anti-tumor cytotoxicity.

As used herein, the terms "NKp30 activity-dependent anti-tumor cytotoxicity," "NKp44 activity-dependent anti-tumor cytotoxicity," and "NKp46 activity-dependent anti-tumor cytotoxicity" refer to anti-tumor cytotoxicity that requires functional expression of the specified receptor. The presence or absence of such receptor dependent anti-tumor cytotoxicity can be determined by performing standard in vitro cytotoxicity assays, such as performed in Example 48, in the presence or absence of an antagonist to the specified receptor. For example, presence or absence of NKp30 activity-dependent anti-tumor cytotoxicity can be determined by comparing the results of an in vitro cytotoxicity assays as described in Example 48 in the presence of an anti-NKp30 antagonist to the results obtained in the absence of an anti-NKp30 antagonist.

As used herein, a γδ T-cell population that comprises anti-tumor cytotoxicity, wherein at least a specified "%" of the anti-tumor cytotoxicity is "independent of" a specified receptor activity (e.g., NKp30 activity, NKp44 activity, and/or NKp46 activity), refers to a cell where blocking specified receptor reduces measured anti-tumor cytotoxicity by no more than the numerical % value. Thus, a γδ T-cell population that comprises anti-tumor cytotoxicity, wherein at least 50% of the anti-tumor cytotoxicity is independent of NKp30 activity would exhibit a reduction of 50% or less of in vitro anti-tumor cytotoxicity in the presence of an NKp30 antagonist as compared to in the absence of the NKp30 antagonist.

Overview

In humans, γδ T-cell(s) are a subset of T-cells that provide a link between the innate and adaptive immune responses. These cells undergo V-(D)-J segment rearrangement to generate antigen-specific γδ T-cell receptors (γδ TCRs), and γδ T-cell(s) and can be directly activated via the recognition of an antigen by either the γδ TCR or other, non-TCR proteins, acting independently or together to activate γδ T-cell effector functions. γδ T-cells represent a small fraction of the overall T-cell population in mammals, approximately 1-5% of the T-cells in peripheral blood and lymphoid organs, and they appear to reside primarily in epithelial cell-rich compartments like skin, liver, digestive, respiratory, and reproductive tracks. Unlike αβ TCRs, which recognize antigens bound to major histocompatibility complex molecules (WIC), γδ TCRs can directly recognize bacterial antigens, viral antigens, stress antigens expressed by diseased cells, and tumor antigens in the form of intact proteins or non-peptide compounds.

TS-1, TS8.2, B6, and 15D can activate γδ T cells. Without being bound by theory, different levels of activation and expansion of cultures originating from different donors may be due to the donor γδ variable TCR repertoire and the specificity of the antibody binding epitope. It has been discovered that not every agent which binds to specific γδ T-cell subsets is capable of activating the specific γδ T-cell and particularly activating the specific γδ T-cell population to clinically-relevant levels, i.e., >$10^8$ target γδ T cells in an enriched culture. Similarly, not every binding epitope of a γδ T-cell population is an activating epitope, i.e., capable of activation of the specific γδ T-cell population upon binding.

The inventors of the present invention have identified specific γδ variable TCR binding regions associated with potent activation of specific γδ T cell subtypes thus enabling the specific activation of γδ T cell subtypes which produces clinically relevant levels of highly enriched γδ T-cell populations with increased purity, and admixtures thereof, that can be administered to patients. Novel activating ligands, including antibodies, which specifically bind the activating epitopes capable of inducing enhanced activation and expansion of γδ T cell subtypes are also contemplated and further described herein.

In some cases, the production of clinically relevant levels (i.e., >$10^8$) of γδ T cells using the methods of the present invention can be obtained with relatively small volumes of culture medium. For example, in some embodiments, the clinically relevant levels of γδ T cells can be obtained from expansion of a population of cells (e.g., an isolated mixed population of cells), in a final culture volume of approximately 25 L; 20 L; 10 L; 5 L; 3 L; 2 L; 1,5000 mL; 1,000 mL; 500 mL; 200 mL; 150 mL; 100 mL, or less (e.g., from about 10 mL to about 100 mL, from about 100 mL to about 500 mL, from about 500 mL to about 5,000 mL, or from about 5 L to about 25 L). As another example, in some embodiments, the clinically relevant levels of γδ T cells can be obtained under conditions such that the total volume of culture media used in expanding an isolated mixed population of cells obtained from a donor, or multiple donors, is less than about 50 L, 25 L, 20 L, 10 L, 5 L, 1 L, or 750 mL (e.g., from about 750 mL to less than about 50 L, from about 100 mL to about 750 mL, from about 750 mL to about 5 L, from about 1 L to about 10 L, from about 10 L to about 50 L, or from about 10 L to about 25 L).

Described herein are methods for the selective activation and expansion of γδ T-cell subtypes directly from isolated mixed cell populations, e.g., without prior depletion of non-target cell types, providing clinically-relevant levels of enriched γδ T cell population(s) having cytotoxic properties. Activating γδ variable TCR epitopes of specific γδ cell population(s) are also described. The present invention also provides methods of treatment with compositions comprising the enriched γδ T-cell population(s) of the invention.

Described herein are methods of producing or providing clinically relevant levels (>$10^8$) of engineered or non-engineered γδ T-cells, including one or more specific subsets of γδ T-cells. Such methods can be used to produce such clinically relevant levels from a single donor, including from a single sample of a single donor. Moreover, such methods can be used to produce significantly greater than $10^8$ engineered or non-engineered γδ T-cells. For example, in some embodiments about, or at least about, $10^9$, $10^{10}$, $10^{11}$, or $10^{12}$ engineered or non-engineered γδ T-cells, including one or more specific subsets of γδ T-cells, can be produced in the methods described herein. In some cases, such population sizes can be achieved in as few as 19-30 days and/or with a total volume of culture media used of less than about 1 L.

Isolation of γδ T-Cells

In some aspects, the instant invention provides ex vivo methods for expansion of engineered or non-engineered γδ T-cells. In some cases, the method employ one or more (e.g., first and/or second) expansion steps that do not include a cytokine that favors expansion of a specific population of γδ T-cells, such as IL-4, IL-2, or IL-15, or a combination thereof. In some embodiments, the instant invention provides ex vivo methods for producing enriched γδ T-cell populations from isolated mixed cell populations, comprising contacting the mixed cell population with one or more agents which selectively expand δ1 T-cells; δ1 T-cells and δ3 T-cells; δ1 T-cells and δ4 T-cells; or δ1, δ3, δ4, and δ5 T cells by binding to an epitope specific of a δ1 TCR; a δ1 and δ4 TCR; or a δ1, δ3, δ4, and δ5 TCR respectively to provide an enriched γδ T cell population. In other aspects, the instant invention provides ex vivo methods for producing enriched γδ T-cell populations from isolated mixed cell populations, comprising contacting the mixed cell population with one or more agents which selectively expand δ2 T-cells by binding to an epitope specific of a δ2 TCR to provide an enriched γδ T cell population.

In other aspects, the present disclosure provides methods for the genetic engineering of γδ T-cells that have been isolated from a subject. Methods of enrichment, activation, expansion, or genetic engineering can be performed singly or in combination, in any order. In one embodiment, γδ T-cells can be isolated, genetically engineered, and then activated and expanded. In a preferred embodiment, γδ T-cells can be isolated, activated and expanded, and then optionally genetically engineered. In some embodiments, such activated and expanded and then genetically engineered γδ T-cells can be further activated and/or expanded.

An, e.g., non-engineered, γδ T-cell population can be expanded from a complex sample of a subject. A complex sample can be a peripheral blood sample (e.g., PBLs or PBMCs), a leukapheresis sample, a cord blood sample, a tumor, a stem cell precursor, a tumor biopsy, a tissue, a lymph, or from epithelial sites of a subject directly contacting the external milieu, or derived from stem precursor cells. In some cases, the present disclosure provides methods for selective expansion of Vδ1$^+$ cells, Vδ2$^+$ cells, Vδ1$^+$ cells and Vδ3$^+$, Vδ1$^+$ cells and Vδ4$^+$ cells, Vδ1$^+$ cells, Vδ3$^+$ cells, Vδ4$^+$ cells, and Vδ5$^+$ cells, or any combination thereof.

Peripheral blood mononuclear cells can be collected from a subject, for example, with an apheresis machine, including the Ficoll-Paque™ PLUS (GE Healthcare) system, or another suitable device/system. γδ T-cell(s), or a desired subpopulation of γδ T-cell(s), can be purified from the collected sample with, for example, flow cytometry techniques. Cord blood cells can also be obtained from cord blood during the birth of a subject. See WO 2016/081518, incorporated by reference herein in its entirety for all purposes including but not limited to methods and compositions for PBMC isolation, γδ T cell activation, and making and using γδ T cell activation agents.

A γδ T-cell may be expanded from an isolated complex sample or mixed cell population that is cultured in vitro by contacting the mixed cell population with one or more agents which expand γδ T-cell by specifically binding to an epitope of a γδ TCR to provide an enriched γδ T-cell population, e.g., in a first enrichment step. In some embodiments, γδ T cells comprised in a whole PBMC population, without prior depletion of one or more specific cell populations such as one or more or all of the following non-γδ T cell monocytes: αβ T-cells, B-cells, and NK cells, can be activated and expanded, resulting in an enriched γδ T-cell population. In some aspects, activation and expansion of γδ T-cell are performed without the presence of native or engineered APCs. In some aspects, isolation and expansion of γδ T cells from tumor specimens can be performed using immobilized γδ T cell mitogens, including antibodies specific to activating epitopes of a γδ TCR, and other activating agents, including lectins, which bind the activating epitopes of a γδ TCR provided herein.

In certain embodiments, the isolated mixed cell population is contacted with one or more agents which expand γδ T-cells for about, or at least about, 2 days, about 3 days, about 4 days, about 5 days, about 6 days, about 7 days, about 8 days, about 9 days, about 10 days, about 11 days, about 12 days, about 13 days, about 14 days, about 15 days, about 17 days, about 19 days, about 21 days, about 25 days, about 29 days, about 30 days, or any range therein. For example, the isolated mixed cell population is contacted with one or more agents which expand γδ T-cells for about 1 to about 4 days, about 2 to about 4 days, about 2 to about 5 days, about 3 to about 5 days, about 5 to about 21 days, about 5 to about 19 days, about 5 to about 15 days, about 5 to about 10 days, or about 5 to about 7 days, to provide a first enriched γδ T-cell population. As another example, the isolated mixed cell population is contacted with one or more agents which expand γδ T-cells for about 7 to about 21 days, about 7 to about 19 days, about 7 to about 23 days, or about 7 to about 15 days to provide a first enriched γδ T-cell population.

In some cases, a purification or isolation step is performed between the first and second expansion steps. In some cases, the isolation step includes removal of one or more activating agents. In some cases, the isolation step includes specific isolation of γδ T-cells, or a subtype thereof. In some cases, one or more (e.g., all) activating agents (e.g., all activating agents that are not common components of cell culture media such as serum components and/or IL-2)) are removed between first and second expansion steps, but γδ T-cells are not specifically isolated from other cell types (αβ T-cells).

In some embodiments, following the activation and expansion of γδ T cells using activating agents which bind to an activating epitope of a γδ TCR, in a first enrichment step, and optionally a second enrichment step, the, e.g., first, enriched γδ T cell population(s) of the invention may be further enriched or purified using techniques known in the art to obtain a second or further enriched γδ T cell population(s) in a second, third, fourth, fifth, etc. enrichment step. For example, the, e.g., first, enriched γδ T cell population(s) may be depleted of αβ T-cells, B-cells and NK cells. Positive and/or negative selection of cell surface markers expressed on the collected γδ T-cell(s) can be used to directly isolate a γδ T-cell, or a population of γδ T-cell(s) expressing similar cell surface markers from the, e.g., first, enriched γδ T-cell population(s). For instance, a γδ T-cell can be isolated from an enriched γδ T-cell population (e.g., after a first and/or second step of expansion) based on positive or negative expression of markers such as CD2, CD3, CD4, CD8, CD24, CD25, CD44, Kit, TCR α, TCR β, TCR γ (including one or more TCR γ sub-types), TCR δ (including one or more TCR δ sub-types), NKG2D, CD70, CD27, CD28, CD30, CD16, OX40, CD46, CD161, CCR7, CCR4, NKp30, NKp44, NKp46, DNAM-1, CD242, JAML, and other suitable cell surface markers.

In some embodiments, after a first step of expansion (e.g., after an isolation step performed subsequent to the first step of expansion), the expanded cells are, optionally diluted, and cultured in a second step of expansion. In preferred embodiments, the second step of expansion is performed under conditions in which culture media is replenished about every 1-2, 1-3, 1-4, 1-5, 2-5, 2-4, or 2-3 days in a second expansion step. In some embodiments, the second step of expansion is performed under conditions in which the cells are diluted or adjusted to a density that supports further γδ T-cell expansion 1, 2, 3, 4, 5, 6, or more times. In some cases, the cell density adjustment is performed contemporaneously with (i.e., on the same day as, or at the same time as) replenishment of culture media. For example, cell density can be adjusted every 1-2, 1-3, 1-4, 1-5, 2-5, 2-4, or 2-3 days in a second expansion step. Typical cell densities that support further γδ T-cell expansion include, but are not limited to, about $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$ cells/mL, $10\times10^6$ cells/mL, $15\times10^6$ cells/mL, $20\times10^6$ cells/mL, or $30\times10^6$ cells/mL of culture.

In some embodiments, cell density is adjusted to a density of from about $0.5\times10^6$ to about $1\times10^6$ cells/mL, from about 0.5×10⁶ to about 1.5×10⁶ cells/mL, from about 0.5×10⁶ to about 2×10⁶ cells/mL, from about 0.75×10⁶ to about 1×10⁶ cells/mL, from about 0.75×10⁶ to about 1.5×10⁶ cells/mL, from about 0.75×10⁶ to about 2×10⁶ cells/mL, from about 1×10⁶ to about 2×10⁶ cells/mL, or from about 1×10⁶ to about 1.5×10⁶ cells/mL, from about 1×10⁶ to about 2×10⁶ cells/mL, from about 1×10⁶ to about 3×10⁶ cells/mL, from about 1×10⁶ to about 4×10⁶ cells/mL, from about 1×10⁶ to about 5×10⁶ cells/mL, from about 1×10⁶ to about 10×10⁶ cells/mL, from about 1×10⁶ to about 15×10⁶ cells/mL, from about 1×10⁶ to about 20×10⁶ cells/mL, or from about 1×10⁶ to about 30×10⁶ cells/mL.

In some embodiments, the second step of expansion is performed under conditions in which the cells are monitored and maintained at a predetermined cell density (or density interval) and/or maintained in culture medium having a predetermined glucose content. For example, the cells can be maintained at a viable cell density of from about 0.5×10⁶ to about 1×10⁶ cells/mL, from about 0.5×10⁶ to about 1.5×10⁶ cells/mL, from about 0.5×10⁶ to about 2×10⁶ cells/mL, from about 0.75×10⁶ to about 1×10⁶ cells/mL, from about 0.75×10⁶ to about 1.5×10⁶ cells/mL, from about 0.75×10⁶ to about 2×10⁶ cells/mL, from about 1×10⁶ to about 1.5×10⁶ cells/mL, or from about 1×10⁶ to about 1.5×10⁶ cells/mL, from about 1×10⁶ to about 3×10⁶ cells/mL, from about 1×10⁶ to about 4×10⁶ cells/mL, from about 1×10⁶ to about 5×10⁶ cells/mL, from about 1×10⁶ to about 10×10⁶ cells/mL, from about 1×10⁶ to about 15×10⁶ cells/mL, from about 1×10⁶ to about 20×10⁶ cells/mL, from about 1×10⁶ to about 30×10⁶ cells/mL.

In some cases, the cells can be maintained at a higher concentration for at least a portion of the expansion. For example, for a first portion of a first or second expansion, cells viability may be enhanced at a higher cell concentration. As another example, for a final portion of a first or second expansion culture volume may be most efficiently utilized at a higher cell concentration. Thus, in some embodiments, cells can be maintained at a viable cell density of from about 1×10⁶ cells/mL to about 20×10⁶ cells/mL for at least a portion of a first or second expansion culture or all of a first or second expansion culture.

As another example, the cells can be maintained in culture medium having a glucose content of from about 0.5 g/L to about 1 g/L, from about 0.5 g/L to about 1.5 g/L, from about 0.5 g/L to about 2 g/L, from about 0.75 g/L to about 1 g/L, from about 0.75 g/L to about 1.5 g/L, from about 0.75 g/L to about 2 g/L, from about 1 g/L to about 1.5 g/L, from about 1 g/L to about 2 g/L, from 1 g/L to 3 g/L, or from 1 g/L to 4 g/L. In some embodiments, the cells can be maintained in culture medium having a glucose content of about 1.25 g/L. In some cases, such as where a high cell density culture is maintained, cells can be maintained in culture medium having a glucose content of about 1 g/L to about 5 g/L, from about 1 g/L to about 4 g/L, from about 2 g/L to about 5 g/L, or from about 2 g/L to about 4 g/L.

Typically glucose content is maintained by addition of fresh serum containing or serum free culture medium to the culture. In some embodiments, the cells can be maintained at a predetermined viable cell density interval and in a culture medium having a predetermined glucose content interval, e.g., by monitoring each parameter and adding fresh media to maintain the parameters within the predetermined limits. In some embodiments, glucose content is maintained by adding fresh serum containing or serum free culture medium in the culture while removing spent medium in a perfusion bioreactor while retaining the cells inside. In some embodiments, additional parameters including, without limitation, one or more of: pH, partial pressure of $O_2$, $O_2$ saturation, partial pressure of $CO_2$, $CO_2$ saturation, lactate, glutamine, glutamate, ammonium, sodium, potassium, and calcium, are monitored and/or maintained during a γδ T-cell expansion (e.g., selective γδ T-cell expansion) or during a first or second step of γδ T-cell expansion (e.g., selective γδ T-cell expansion) described herein.

A γδ T-cell subtype may be selectively expanded from an isolated complex sample or mixed cell population that is cultured in vitro by contacting the mixed cell population with one or more agents which:
  i) selectively expand δ1 T-cells by specifically binding to an epitope of a δ1 TCR,
  ii) selectively expand δ2 T-cells by specifically binding to an epitope of a δ2 TCR,
  iii) selectively expand δ1 and δ4 T cells by specifically binding to an epitope of a δ1 and a δ4 TCR; or
  iv) selectively expand δ1, δ3, δ4, and δ5 T cells by specifically binding to an epitope of a δ1, δ3, δ4, and a δ5 TCR,
  to provide an enriched γδ T-cell population, e.g., in a first enrichment step. In some cases, the one or more agents specifically bind to a δ1J1, δ1J2, or δ1J3 TCR, or two thereof, or all thereof. In some embodiments, γδ cells in a whole PBMC population, without prior depletion of specific cell populations such as monocytes, αβ T-cells, B-cells, and NK cells, can be activated and expanded, resulting in an enriched γδ T-cell population. In some aspects, activation and expansion of γδ T-cell are performed without the presence of native or engineered APCs. In some aspects, isolation and expansion of γδ T cells from tumor specimens can be performed using immobilized γδ T cell mitogens, including antibodies specific to activating epitopes specific of a δ1 TCR; a δ1, δ3, δ4, and δ5 TCR, a δ1 and δ4 TCR; or a δ2 TCR, and other activating agents, including lectins, which bind the activating epitopes specific of a δ1 TCR; a δ1, δ3, δ4 and δ5 TCR; a δ1 and δ4 TCR; or a δ2 TCR provided herein.

In certain embodiments, the isolated mixed cell population is contacted with one or more agents which selectively expand δ1, δ1 and δ4, δ2, or δ1 and δ2 T-cells for about 5 days, 6 days, about 7 days, about 8 days, about 9 days, about 10 days, about 11 days, about 12 days, about 13 days, about 14 days, about 15 days, or any range therein. For example, the isolated mixed cell population is contacted with one or more agents which selectively expand δ1 or δ2 T-cells for about 1 to about 3 days, about 1 to about 4 days, about 1 to about 5 days, about 2 to about 3 days, about 2 to about 4 days, about 2 to about 5 days, about 3 to about 4 days, about 3 to about 5 days, about 4 to about 5 days, about 5 to about 15 days, or about 5 to about 7 days, to provide a first enriched γδ T-cell population. In some embodiments selectively expanded δ1, δ1 and δ3, δ1 and δ4, δ2, or δ1 and T-cells are further expanded in a second step of expansion as described herein.

In certain embodiments, the starting isolated mixed cell population, e.g., peripheral blood sample, comprises T lymphocytes in the range of about 20-80%. In certain embodiments, the percent of residual αβ T cells and NK cells in enriched γδ T-cell population(s) of the invention is about, or less than about, 2.5% and 1%, respectively. In certain embodiments, the percent of residual αβ T cells or NK cells in enriched γδ T-cell population(s) of the invention is about, or less than about, 1%, 0.5%, 0.4%, 0.2%, 0.1%, or 0.01%. In certain embodiments, the percent of residual αβ T cells in enriched γδ T-cell population(s) of the invention is about, or less than about, 0.4%, 0.2%, 0.1%, or 0.01% (e.g., after a step of positive selection for γδ T-cells or a sub-type thereof or after depletion of αβ T cells). In some embodiments, αβ T cells are depleted, but NK cells are not depleted before or after a first and/or second γδ T-cell expansion. In certain aspects, the isolated mixed cell population is derived from a single donor. In other aspects, the isolated mixed cell population is derived from more than one donor or multiple donors (e.g., 2, 3, 4, 5, or from 2-5, 2-10, or 5-10 donors, or more).

As such, in some embodiments, the methods of the present invention can provide a clinically relevant number ($>10^8$, $>10^9$, $>10^{10}$, $>10^{11}$, or $>10^{12}$, or from about $10^8$ to about $10^{12}$) of expanded γδ T-cells from as few as one donor. In some cases, the methods of the present invention can provide a clinically relevant number ($>10^8$, $>10^9$, $>10^{10}$, $>10^{11}$, or $>10^{12}$, or from about $10^8$ to about $10^{12}$) of expanded γδ T-cells within less than 19 or 21 days from the time of obtaining a donor sample.

Following the specific activation and expansion of the specific γδ T cell subsets using activating agents which bind to an activating epitope specific of a δ1, a δ1 and δ3 TCR, a δ1 and δ4 TCR, or a δ2 TCR, in a first enrichment step, the first enriched γδ T cell population(s) of the invention may be further enriched or purified using techniques known in the art to obtain a second or further enriched γδ T cell population(s) in a second, third, fourth, fifth, etc. enrichment step. For example, the first enriched γδ T cell population(s) may be depleted of αβ T-cells, B-cells and NK cells. Positive and/or negative selection of cell surface markers expressed on the collected γδ T-cell(s) can be used to directly isolate a γδ T-cell, or a population of γδ T-cell(s) expressing similar cell surface markers from the first enriched γδ T-cell population(s). For instance, a γδ T-cell can be isolated from a first enriched γδ T-cell population based on positive or negative expression of markers such as CD2, CD3, CD4, CD8, CD24, CD25, CD44, Kit, TCR α, TCR β, TCR γ (or one or more subtypes thereof), TCR δ (or one or more subtypes thereof), NKG2D, CD70, CD27, CD28, CD30, CD16, OX40, CD46, CD161, CCR7, CCR4, DNAM-1, JAML, and other suitable cell surface markers.

In some embodiments, following the first γδ T-cell expansion, first enrichment step, second γδ T-cell expansion, and/or second enrichment step, of the invention, the enriched γδ T-cell population comprises clinically-relevant levels of γδ T-cell subsets of $>10^8$ cells, e.g., in a culture volume of less than 10 mL, 25 mL, 50 mL, 100 mL, 150 mL, 200 mL, 500 mL, 750 mL, 1 L, 2 L, 3 L, 4 L, 5 L, 10 L, 20 L, or 25 L. For example, the methods of the present invention can provide clinically-relevant levels of γδ T-cell subsets of $>10^8$ cells in a expansion culture having a volume of from 10-100 mL; from 25-100 mL; from 50-100 mL; from 75-100 mL; from 10-150 mL; from 25-150 mL; from 50-150 mL; from 75-150 mL; from 100-150 mL; from 10-200 mL; from 25-200 mL; from 50-200 mL; from 75-200 mL, from 100-200 mL; from 10-250 mL; from 25-250 mL; from 50-250 mL; from 75-250 mL, from 100-250 mL; from 150-250 mL; from 5-1,000 mL; from 10-1,000 mL, or from 100-1,000 mL; from 150-1,000 mL; from 200-1,000 mL; from 250-1,000 mL, 400 mL to 1 L, 1 L to 2 L, 2 L to 5 L, 2 L to 10 L, 4 L to 10 L, 4 L to 15 L, 4 L to 20 L, or 4 L to 25 L. In other embodiments, following the second, third, fourth, fifth, etc. enrichment step of the invention, the enriched γδ T-cell population comprises clinically-relevant levels of γδ T-cell subsets of $>10^8$.

In some embodiments, γδ T-cell(s) can rapidly expand in response to contact with one or more antigens. Some γδ T-cell(s), such as Vγ9Vδ2$^+$γδ T-cell(s) rapidly expand in vitro in response to contact with some antigens, like prenyl-pyrophosphates, alkyl amines, and metabolites or microbial extracts during tissue culture. In addition, some wild-type γδ T-cell(s), such as Vγ2Vδ2$^+$γδ T-cell(s) rapidly expand in vivo in humans in response to certain types of vaccination (s). Stimulated γδ T-cells can exhibit numerous antigen-presentation, co-stimulation, and adhesion molecules that can facilitate the isolation of a γδ T-cell(s) from a complex sample. A γδ T-cell(s) within a complex sample can be stimulated in vitro with at least one antigen for 1 day, 2 days, 3 days, 4 days, 5 days, 6 days, 7 days, about 5-15 days, 5-10 days, or 5-7 days, or another suitable period of time, e.g., in combination with, before, or after expansion with a selective γδ T-cell expansion agent described herein such as an antibody or an immobilized antibody. Stimulation of the γδ T-cell with a suitable antigen can expand the γδ T-cell population in vitro.

Non-limiting examples of antigens that may be used to stimulate the expansion of γδ T-cell(s) from a complex sample in vitro include, prenyl-pyrophosphates, such as isopentenyl pyrophosphate (IPP), alkyl-amines, metabolites of human microbial pathogens, metabolites of commensal bacteria, -methyl-3-butenyl-1-pyrophosphate (2M3B1PP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyro-phosphate (MEPP), 3-formyl-1-butyl-pyrophosphate (TU-BAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

Activation and expansion of γδ T-cells can be performed using activation and co-stimulatory agents described herein to trigger specific γδ T-cell proliferation and persistent populations. In some embodiments, activation and expansion of γδ T-cells from different cultures can achieve distinct clonal or mixed polyclonal population subsets. In some embodiments, different agonist agents can be used to identify agents that provide specific γδ activating signals. In one aspect, agents that provide specific γδ activating signals can be different monoclonal antibodies (MAbs) directed against the γδ TCRs.

In one aspect, the MAbs can bind to different epitopes on the constant or variable regions of γ TCR and/or δ TCR. In one aspect, the MAbs can include γδ TCR pan MAbs. In one aspect, the γδ TCR pan MAbs may recognize domains shared by different γ and δ TCRs on either the γ or δ chain or both, including δ1 and δ2 cell populations. In one aspect, the antibodies may be 5A6.E9 (Thermo scientific), B1 (Biolegend), IMMU510 and/or 11F2 (11F2) (Beckman Coulter). In one aspect, the MAbs can be directed to specific domains unique to the variable regions of the γ chain (7A5 Mab, directed to like Vγ9 TCR (Thermo Scientific #TCR1720)), or domains on Vδ1 variable region (Mab TS8.2 (Thermo scientific #TCR1730; MAb TS-1 (ThermoFisher #TCR 1055), MAb R9.12 (Beckman Coulter #IM1761)), or V02 chain (MAb 15D (Thermo Scientific #TCR1732 or Life technologies #TCR2732) B6 (Biolegend

Figure 35:
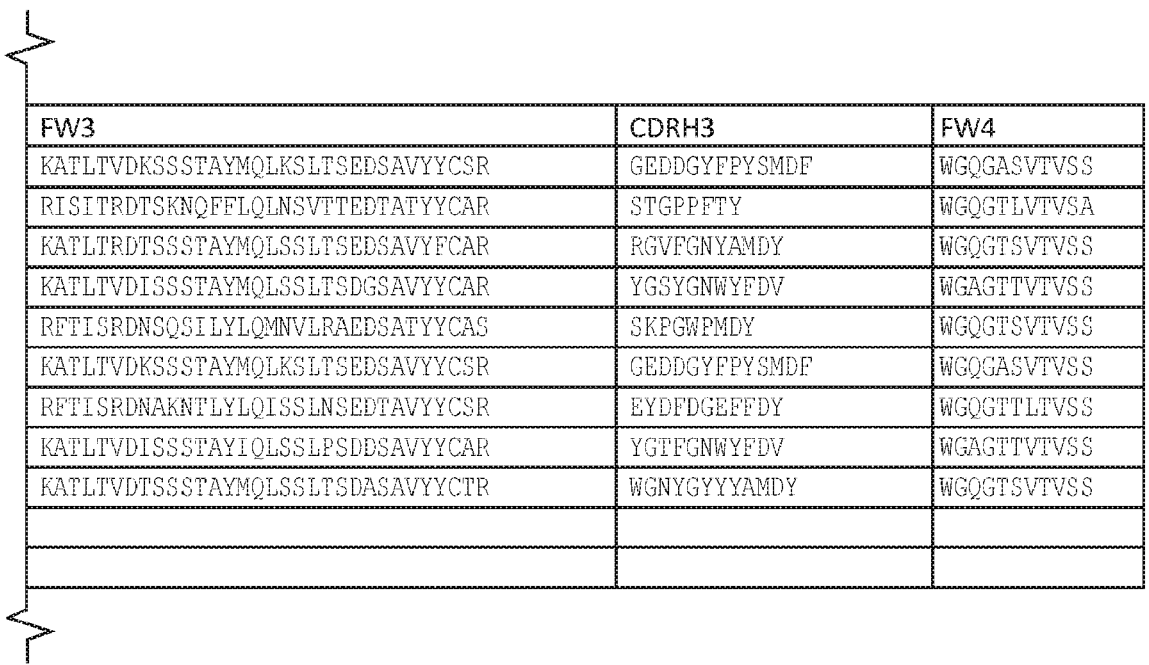

331402), one of the δ1-# antibodies described in FIGS. 33-34, or one of the δ2-# antibodies described in FIGS. 35-36.

In some embodiments, antibodies against different domains of the γδ TCR (pan antibodies and antibodies recognizing specific variable region epitopes on subset populations) can be combined to evaluate their ability to enhanced activation of γδ T cells. In some embodiments, γδ T-cells activators can include γδ TCR-binding agents such as MICA, an agonist antibody to NKG2D, an, e.g., Fc tag, fusion protein of MICA, ULBP1, or ULBP3 (R&D systems Minneapolis, MN) ULBP2, or ULBP6 (Sino Biological Beijing, China). In some embodiments, companion co-stimulatory agents to assist in triggering specific γδ T cell proliferation without induction of cell anergy and apoptosis can be identified. These co-stimulatory agents can include ligands to receptors expressed on γδ cells, such as ligand(s) to one or more of the following: NKG2D, CD161, CD70, JAML, DNAX, CD81 accessory molecule-1 (DNAM-1) ICOS, CD27, CD196, CD137, CD30, HVEM, SLAM, CD122, DAP, and CD28. In some aspects, co-stimulatory agents can be antibodies specific to unique epitopes on CD2 and CD3 molecules. CD2 and CD3 can have different conformation structures when expressed on αβ or γδ T-cells (s), and in some cases, specific antibodies to CD3 and CD2 can lead to selective activation of γδ T-cells.

A population of γδ T-cell(s) may be expanded ex vivo prior to engineering of the γδ T-cell(s). Non-limiting example of reagents that can be used to facilitate the expansion of a γδ T-cell population in vitro include anti-CD3 or anti-CD2, anti-CD27, anti-CD30, anti-CD70, anti-OX40 antibodies, IL-2, IL-4, IL-7, IL-9, IL-12, IL-15, IL-18, IL-19, IL-21, IL 23, IL-33, IFNγ, granulocyte-macrophage colony stimulating factor (GM-CSF), granulocyte colony stimulating factor (G-CSF), CD70 (CD27 ligand), concavalin A (ConA), pokeweed (PWM), protein peanut agglutinin (PNA), soybean agglutinin (SBA), Les *Culinaris* Agglutinin (LCA), *Pisum Sativum* Agglutinin (PSA), *Helix pomatia* agglutinin (HPA), *Vicia graminea* Lectin (VGA), *Phaseolus Vulgaris* Erythroagglutinin (PHA-E), *Phaseolus Vulgaris* Leucoagglutinin (PHA-L), *Sambucus Nigra* Lectin (SNA, EBL), *Maackia Amurensis*, Lectin II (MAL II), *Sophora Japonica* Agglutinin (SJA), *Dolichos Biflorus* Agglutinin (DBA), *Lens Culinaris* Agglutinin (LCA), *Wisteria Floribunda* Lectin (WFA, WFL) or another suitable mitogen capable of stimulating T-cell proliferation.

Genetic engineering of the γδ T-cell(s) may comprise stably integrating a construct expressing a tumor recognition moiety, such as an αβ TCR, a γδ TCR, a CAR encoding an antibody, an antigen binding fragment thereof, or a lymphocyte activation domain into the genome of the isolated γδ T-cell(s), a cytokine (e.g., IL-15, IL-12, IL-2, IL-7, IL-21, IL-18, IL-19, IL-33, IL-4, IL-9, IL-23, or IL1β) to enhance T-cell proliferation, survival, and function ex vivo and in vivo. Genetic engineering of the isolated γδ T-cell may also comprise deleting or disrupting gene expression from one or more endogenous genes in the genome the isolated γδ T-cell, such as the MHC locus (loci).

Ex-Vivo Expansion of γδ T-Cells

In other aspects, the present disclosure provides methods for the ex vivo expansion of a population of non-engineered and engineered γδ T-cells for adoptive transfer therapy. A non-engineered or engineered γδ T-cell of the disclosure may be expanded ex vivo. A non-engineered or engineered γδ T-cell of the disclosure can be expanded in vitro without activation by APCs, or without co-culture with APCs and/or aminophosphonates. Additionally, or alternatively, a non-engineered or engineered γδ T-cell of the disclosure can be expanded in vitro with at least one expansion step that includes activation by or co-culture with APCs and/or with one or more aminophosphonates.

In some embodiments, a non-engineered or engineered γδ T-cell of the disclosure can be expanded in vitro without activation by APC in a first γδ T-cell expansion, and then expanded in vitro with activation by APC in a second γδ T-cell expansion. In some cases, the first γδ T-cell expansion includes contacting the γδ T-cells with one or more agents which (a) expand γδ T-cells, or (b) selectively expand δ1 T-cells; δ2 T-cells; δ1 T-cells and δ3 T-cells; δ1 T-cells and δ4 T-cells; or δ1, δ3, δ4, and δ5 T-cells by binding to an activating epitope specific of a δ1 TCR; a δ2 TCR; a δ1 and δ4 TCR; or a δ1, δ3, δ4, and δ5 TCR respectively.

In some cases, the second γδ T-cell expansion is performed in a culture medium that is free of the one or more agents used in the first γδ T-cell expansion. In some cases, the second γδ T-cell expansion is performed in a culture medium that contains one or more second agents that (a) expand T cells, (b) expand γδ T-cells, or (c) selectively expand δ1 T-cells; δ2 T-cells; δ1 T-cells and δ3 T-cells; δ1 T-cells and δ4 T-cells; or δ1, δ3, δ4, and δ5 T-cells by binding to an activating epitope specific of a δ1 TCR; a δ2 TCR; a δ1 and δ4 TCR; or a δ1, δ3, δ4, and δ5 TCR respectively.

In some cases, the second agents are different (e.g., have a different primary amino acid sequence and/or bind a structurally different γδ TCR epitope) as compared to the agents used in the first γδ T-cell expansion. In some cases, the second agents bind an overlapping γδ TCR epitope, the same γδ TCR epitope, or can compete for binding to γδ TCR with the agents used in the first γδ T-cell expansion. In some cases, the second agents are expressed on the cell surface of an APC. In some cases, the second agents are bound to the surface of an APC, e.g., by a binding interaction between a constant region of the second agent and an Fc-receptor on the surface of the APC. In some cases, the second agents are soluble. In some cases, the second γδ T-cell expansion is performed in a culture medium containing soluble second agents and APCs, optionally wherein the APC express on their cell surface or bind to their cell surface an agent that expands or selectively expands a γδ T cell population.

In some cases, the first γδ T-cell expansion is performed without an APC, and the second γ6 T-cell expansion is performed with an APC. In some cases, the second γδ T-cell expansion is performed with an APC and one or more second agents that (a) expand T cells, (b) expand γδ T-cells, or (c) selectively expand δ1 T-cells; δ2 T-cells; δ1 T-cells and δ3 T-cells; δ1 T-cells and δ4 T-cells; or δ1, δ3, δ4, and δ5 T-cells by binding to an activating epitope specific of a δ1 TCR; a δ2 TCR; a δ1 and δ4 TCR; or a δ1, δ3, δ4, and δ5 TCR respectively.

One of skill in the art will appreciate that, in certain embodiments, the methods of the second expansion step described herein can be performed as a first expansion step and methods of the first step described herein can be performed as a second expansion step. As an example, and without limitation, in some embodiments, a mixed population of cells (e.g., PBMC) can be expanded by contacting with an APC in a first step, and then expanded in the absence of an APC, e.g., by contacting the expanded population from the first expansion step with an immobilized agent that selectively expands δ1 T-cells; δ2 T-cells; δ1 T-cells and δ3 T-cells; δ1 T-cells and δ4 T-cells; or δ1, δ3, δ4, and δ5

T-cells by binding to an activating epitope specific of a δ1 TCR; a δ2 TCR; a δ1 and δ4 TCR; or a δ1, δ3, δ4, and δ5 TCR respectively.

A method of the invention can expand various γδ T-cell(s) populations, such as a Vγ1+, a Vγ2+, or Vγ3+γδ T-cell population. In some cases, a method of the invention can expand a Vδ1+ T-cell population; a Vδ1+ and a Vδ3+ T-cell population; a Vδ1+ and a Vδ4+ T-cell population; a Vδ1+ and a Vδ2+ T-cell population; or a Vδ1+, Vδ3+, Vδ4+, and a Vδ5+ T-cell population.

In some instances, a γδ T-cell population can be expanded in vitro in fewer than 36 days, fewer than 35 days, fewer than 34 days, fewer than 33 days, fewer than 32 days, fewer than 31 days, fewer than 30 days, fewer than 29 days, fewer than 28 days, fewer than 27 days, fewer than 26 days, fewer than 25 days, fewer than 24 days, fewer than 23 days, fewer than 22 days, fewer than 21 days, fewer than 20 days, fewer than 19 days, fewer than 18 days, fewer than 17 days, fewer than 16 days, fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, or fewer than 3 days.

In some aspects, provided are methods for selectively expanding various γδ T-cells, including engineered and non-engineered γδ T-cells by contacting the γδ T-cells from the mixed cell population with an activation agent. In some cases, the activation or activating agent binds to a specific epitope on a cell-surface receptor of a γδ T-cell. The activation agent can be an antibody, such as a monoclonal antibody. The activation agent can specifically activate the growth of one or more types of γδ T-cells, such δ1, δ2, δ1 and δ3, or δ1 and δ4 cell populations. In some embodiments the activation agent specifically activates the growth of δ1 cell populations to provide an enriched δ1T-cell population. In other cases, the activation agent specifically activates the growth of δ2 cell populations to provide an enriched δ2 T-cell population.

An activation agent may stimulate the expansion of engineered and non-engineered γδ T-cells at a fast rate of growth. For instance, an agent that stimulates an expansion of the γδ T-cell population at a mean rate of 1 cell division in less than 30 hours, 1 cell division in less than 29 hours, 1 cell division in less than 28 hours, 1 cell division in less than 27 hours, 1 cell division in less than 26 hours, 1 cell division in less than 25 hours, 1 cell division in less than 24 hours, 1 cell division in less than 23 hours, 1 cell division in less than 22 hours, 1 cell division in less than 21 hours, 1 cell division in less than 20 hours, 1 cell division in less than 19 hours, 1 cell division in less than 18 hours, 1 cell division in less than 17 hours, 1 cell division in less than 16 hours, 1 cell division in less than 15 hours, 1 cell division in less than 14 hours, 1 cell division in less than 13 hours, 1 cell division in less than 12 hours, 1 cell division in less than 11 hours, 1 cell division in less than 10 hours, 1 cell division in less than 9 hours, 1 cell division in less than 8 hours, 1 cell division in less than 7 hours, 1 cell division in less than 6 hours, 1 cell division in less than 5 hours, 1 cell division in less than 4 hours, 1 cell division in less than 3 hours, 1 cell division in less than 2 hours.

In some cases, an activation agent may stimulate the expansion of engineered and non-engineered γδ T-cells at a mean rate of about 1 division per about 4 hours, a mean rate of about 1 division per about 5 hours, a mean rate of about 1 division per about 6 hours, a mean rate of about 1 division per about 7 hours, a mean rate of about 1 division per about 8 hours, a mean rate of about 1 division per about 9 hours, a mean rate of about 1 division per about 10 hours, a mean rate of about 1 division per about 11 hours, a mean rate of about 1 division per about 12 hours, a mean rate of about 1 division per about 13 hours, a mean rate of about 1 division per about 14 hours, a mean rate of about 1 division per about 15 hours, a mean rate of about 1 division per about 16 hours, a mean rate of about 1 division per about 17 hours, a mean rate of about 1 division per about 18 hours, a mean rate of about 1 division per about 19 hours, a mean rate of about 1 division per about 20 hours, a mean rate of about 1 division per about 21 hours, a rate of about 1 division per about 22 hours, a rate of about 1 division per about 23 hours, a mean rate of about 1 division per about 24 hours, a mean rate of about 1 division per about 25 hours, a mean rate of about 1 division per about 26 hours, a mean rate of about 1 division per about 27 hours, a rate of about 1 division per about 28 hours, a rate of about 1 division per about 29 hours, a mean rate of about 1 division per about 30 hours, a mean rate of about 1 division per about 31 hours, a mean rate of about 1 division per about 32 hours, a mean rate of about 1 division per about 33 hours, a rate of about 1 division per about 34 hours, a rate of about 1 division per about 35 hours, a mean rate of about 1 division per about 36 hours.

In some cases, an activation agent may stimulate the rapid expansion of engineered and/or non-engineered γδ T-cells in a γδ T-cell expansion culture, wherein the rapid expansion is at any one of the foregoing mean rates of cell division and is maintained for between about 1 contiguous day and about 19 contiguous days, between about 1 contiguous day and about 14 contiguous days, between about 1 contiguous day and about 7 contiguous days, between about 1 contiguous day and about 5 contiguous days, between about 2 contiguous days and about 19 contiguous days, between about 2 contiguous days and about 14 contiguous days, between about 2 contiguous days and about 7 contiguous days, between about 2 contiguous days and about 5 contiguous days, between about 4 contiguous days and about 19 contiguous days, between about 4 contiguous days and about 14 contiguous days, between about 4 contiguous days and about 7 contiguous days, or between about 4 contiguous days and about 5 contiguous days.

In some cases, an activation agent may stimulate the expansion of engineered and/or non-engineered γδ T-cells in a γδ T-cell expansion culture that has been maintained for between about 2 and about 7 contiguous days, or between about 2 and about 5 contiguous days, at a mean rate of about 1 division per about 12 hours (e.g., 10-12 hours), a mean rate of about 1 division per about 13 hours (e.g., 10-13 hours), a mean rate of about 1 division per about 14 hours (e.g., 10-14 hours), a mean rate of about 1 division per about 15 hours (e.g., 10-15 hours), a mean rate of about 1 division per about 16 hours (e.g., 10-16 hours), a mean rate of about 1 division per about 17 hours (e.g., 10-17 hours or 12-17 hours), a mean rate of about 1 division per about 18 hours (e.g., 10-18 hours or 12-18 hours), a mean rate of about 1 division per about 19 hours (e.g., 10-19 hours or 12-19 hours), a mean rate of about 1 division per about 20 hours (e.g., 12-20 hours, 16-20 hours or 18-20 hours), a mean rate of about 1 division per about 21 hours (e.g., 12-21 hours, 16-21 hours or 18-21 hours), a rate of about 1 division per about 22 hours (e.g., 12-22 hours, 16-22 hours or 18-22 hours), a rate of about 1 division per about 23 hours or less (e.g., 12-23 hours, 16-23 hours or 18-23 hours), a mean rate of about 1 division per about 24 hours (e.g., 12-24 hours, 16-24 hours or 18-24 hours).

In some cases, an activation agent may stimulate the expansion of engineered and/or non-engineered γδ T-cells in a γδ T-cell expansion culture that has been maintained for between about 2 and about 7 contiguous days, or between about 2 and about 5 contiguous days at a mean rate of about 1 division per about 25 hours (e.g., 12-25 hours, 16-25 hours 18-25 hours, or 20-25 hours), a mean rate of about 1 division per about 26 hours (e.g., 12-26 hours, 16-26 hours 18-26 hours, or 20-26 hours), a mean rate of about 1 division per about 27 hours (e.g., 12-27 hours, 16-27 hours 18-27 hours, or 20-27 hours), a rate of about 1 division per about 28 hours (e.g., 12-28 hours, 16-28 hours 18-28 hours, 20-28 hours, or 22-28 hours), a rate of about 1 division per about 29 hours (e.g., 16-29 hours 18-29 hours, 20-29 hours, or 22-29 hours), a mean rate of about 1 division per about 30 hours (e.g., 16-30 hours 18-30 hours, 20-30 hours, or 22-30 hours), a mean rate of about 1 division per about 31 hours (e.g., 16-31 hours 18-31 hours, 20-31 hours, 22-31 hours, or 24-31 hours), a mean rate of about 1 division per about 32 hours (e.g., 18-32 hours, 20-32 hours, 22-32 hours, or 24-32 hours), a mean rate of about 1 division per about 33 hours (e.g., 18-33 hours, 20-33 hours, 22-33 hours, or 24-33 hours), a rate of about 1 division per about 34 hours (e.g., 18-34 hours, 20-34 hours, 22-34 hours, or 24-34 hours), a rate of about 1 division per about 35 hours (e.g., 18-35 hours, 20-35 hours, 22-35 hours, or 24-35 hours), a mean rate of about 1 division per about 36 hours (e.g., 18-36 hours, 20-36 hours, 22-36 hours, or 24-36 hours).

In some cases, an activation agent may stimulate the expansion of engineered and/or non-engineered γδ T-cells in a γδ T-cell expansion culture that has been maintained for at least 14 contiguous days at a mean rate of about 1 division per about 12 hours (e.g., 10-12 hours), a mean rate of about 1 division per about 13 hours (e.g., 10-13 hours), a mean rate of about 1 division per about 14 hours (e.g., 10-14 hours), a mean rate of about 1 division per about 15 hours (e.g., 10-15 hours), a mean rate of about 1 division per about 16 hours (e.g., 10-16 hours), a mean rate of about 1 division per about 17 hours (e.g., 10-17 hours or 12-17 hours), a mean rate of about 1 division per about 18 hours (e.g., 10-18 hours or 12-18 hours), a mean rate of about 1 division per about 19 hours (e.g., 10-19 hours or 12-19 hours), a mean rate of about 1 division per about 20 hours (e.g., 12-20 hours, 16-20 hours or 18-20 hours), a mean rate of about 1 division per about 21 hours (e.g., 12-21 hours, 16-21 hours or 18-21 hours), a rate of about 1 division per about 22 hours (e.g., 12-22 hours, 16-22 hours or 18-22 hours), a rate of about 1 division per about 23 hours or less (e.g., 12-23 hours, 16-23 hours or 18-23 hours), a mean rate of about 1 division per about 24 hours (e.g., 12-24 hours, 16-24 hours or 18-24 hours).

In some cases, an activation agent may stimulate the expansion of engineered and/or non-engineered γδ T-cells in a γδ T-cell expansion culture that has been maintained for at least 14 contiguous days at a mean rate of about 1 division per about 25 hours (e.g., 12-25 hours, 16-25 hours 18-25 hours, or 20-25 hours), a mean rate of about 1 division per about 26 hours (e.g., 12-26 hours, 16-26 hours 18-26 hours, or 20-26 hours), a mean rate of about 1 division per about 27 hours (e.g., 12-27 hours, 16-27 hours 18-27 hours, or 20-27 hours), a rate of about 1 division per about 28 hours (e.g., 12-28 hours, 16-28 hours 18-28 hours, 20-28 hours, or 22-28 hours), a rate of about 1 division per about 29 hours (e.g., 16-29 hours 18-29 hours, 20-29 hours, or 22-29 hours), a mean rate of about 1 division per about 30 hours (e.g., 16-30 hours 18-30 hours, 20-30 hours, or 22-30 hours), a mean rate of about 1 division per about 31 hours (e.g., 16-31 hours 18-31 hours, 20-31 hours, 22-31 hours, or 24-31 hours), a mean rate of about 1 division per about 32 hours (e.g., 18-32 hours, 20-32 hours, 22-32 hours, or 24-32 hours), a mean rate of about 1 division per about 33 hours (e.g., 18-33 hours, 20-33 hours, 22-33 hours, or 24-33 hours), a rate of about 1 division per about 34 hours (e.g., 18-34 hours, 20-34 hours, 22-34 hours, or 24-34 hours), a rate of about 1 division per about 35 hours (e.g., 18-35 hours, 20-35 hours, 22-35 hours, or 24-35 hours), a mean rate of about 1 division per about 36 hours (e.g., 18-36 hours, 20-36 hours, 22-36 hours, or 24-36 hours).

In some cases, an activation agent may stimulate the expansion of engineered and/or non-engineered γδ T-cells in a γδ T-cell expansion culture that has been maintained for at least 19 contiguous days at a mean rate of about 1 division per about 12 hours (e.g., 10-12 hours), a mean rate of about 1 division per about 13 hours (e.g., 10-13 hours), a mean rate of about 1 division per about 14 hours (e.g., 10-14 hours), a mean rate of about 1 division per about 15 hours (e.g., 10-15 hours), a mean rate of about 1 division per about 16 hours (e.g., 10-16 hours), a mean rate of about 1 division per about 17 hours (e.g., 10-17 hours or 12-17 hours), a mean rate of about 1 division per about 18 hours (e.g., 10-18 hours or 12-18 hours), a mean rate of about 1 division per about 19 hours (e.g., 10-19 hours or 12-19 hours), a mean rate of about 1 division per about 20 hours (e.g., 12-20 hours, 16-20 hours or 18-20 hours), a mean rate of about 1 division per about 21 hours (e.g., 12-21 hours, 16-21 hours or 18-21 hours), a rate of about 1 division per about 22 hours (e.g., 12-22 hours, 16-22 hours or 18-22 hours), a rate of about 1 division per about 23 hours or less (e.g., 12-23 hours, 16-23 hours or 18-23 hours), a mean rate of about 1 division per about 24 hours (e.g., 12-24 hours, 16-24 hours or 18-24 hours).

In some cases, an activation agent may stimulate the expansion of engineered and/or non-engineered γδ T-cells in a γδ T-cell expansion culture that has been maintained for at least 19 contiguous days at a mean rate of about 1 division per about 25 hours (e.g., 12-25 hours, 16-25 hours 18-25 hours, or 20-25 hours), a mean rate of about 1 division per about 26 hours (e.g., 12-26 hours, 16-26 hours 18-26 hours, or 20-26 hours), a mean rate of about 1 division per about 27 hours (e.g., 12-27 hours, 16-27 hours 18-27 hours, or 20-27 hours), a rate of about 1 division per about 28 hours (e.g., 12-28 hours, 16-28 hours 18-28 hours, 20-28 hours, or 22-28 hours), a rate of about 1 division per about 29 hours (e.g., 16-29 hours 18-29 hours, 20-29 hours, or 22-29 hours), a mean rate of about 1 division per about 30 hours (e.g., 16-30 hours 18-30 hours, 20-30 hours, or 22-30 hours), a mean rate of about 1 division per about 31 hours (e.g., 16-31 hours 18-31 hours, 20-31 hours, 22-31 hours, or 24-31 hours), a mean rate of about 1 division per about 32 hours (e.g., 18-32 hours, 20-32 hours, 22-32 hours, or 24-32 hours), a mean rate of about 1 division per about 33 hours (e.g., 18-33 hours, 20-33 hours, 22-33 hours, or 24-33 hours), a rate of about 1 division per about 34 hours (e.g., 18-34 hours, 20-34 hours, 22-34 hours, or 24-34 hours), a rate of about 1 division per about 35 hours (e.g., 18-35 hours, 20-35 hours, 22-35 hours, or 24-35 hours), a mean rate of about 1 division per about 36 hours (e.g., 18-36 hours, 20-36 hours, 22-36 hours, or 24-36 hours).

An activation agent may stimulate the expansion of sub-populations of engineered or non-engineered γδ T-cells at different rates of growth. For instance, an agent may stimulate the growth of a δ1 cell population at a faster rate such that over a period of time from 1 day to 90 days of culture (e.g., about 1 day to about 19, 21, or 23 days of culture) the expansion results in greater than about 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 50,000-fold, 70,000-fold, 100,000-fold or 1,000,000-fold expansion over another γδ T-cell population, such as a δ2 or δ3 population; over a starting number of γδ T-cells before the expansion; over a starting number of γδ1 T-cells before the expansion; or over an αβ T cell population in the culture.

In other cases, the agent may stimulate the growth of a δ1 and δ4 population at faster rates such that over a period of time from 1 day to 90 days of culture (e.g., about 1 day to about 19, 21, or 23 days of culture) the expansion results in greater than 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 50,000-fold, 70,000-fold, 100,000-fold or 1,000,000-fold expansion over a δ2 T-cell population; over another γδ T-cell sub-population; over a starting number of γδ T-cells before the expansion; over a starting number of γδ1 T-cells before the expansion; over a starting number of γδ1 and γδ3 T-cells before the expansion; or over an αβ T cell population in the culture.

In other cases, the agent may stimulate the growth of a δ1 and δ4 population at faster rates such that over a period of time from 1 day to 90 days of culture (e.g., about 1 day to about 19, 21, or 23 days of culture) the expansion results in greater than 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 50,000-fold, 70,000-fold, 100,000-fold or 1,000,000-fold expansion over a δ2 T-cell population; over another γδ T-cell sub-population; over a starting number of γδ T-cells before the expansion; over a starting number of γδ1 T-cells before the expansion; over a starting number of γδ1 and γδ4 T-cells before the expansion; or over an αβ T cell population in the culture. In other cases, the agent may stimulate the growth of a δ1, δ3, δ4 and δ5 population at faster rates such that over a period of time from 1 day to 90 days of culture (e.g., about 1 day to about 19, 21, or 23 days of culture) the expansion results in greater than 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 50,000-fold, 70,000-fold, 100,000-fold or 1,000,000-fold expansion over a δ2 T-cell population; over another γδ T-cell sub-population; over a starting number of γδ T-cells before the expansion; over a starting number of γδ1 T-cells before the expansion; over a starting number of γδ1 and γδ3 T-cells before the expansion; over a starting number of γδ1, γδ3, γδ4, and γδ5 T-cells before the expansion; or over an αβ T cell population in the culture.

In other cases, the agent may stimulate the growth of a δ2 population at faster rates such that over a period of time from 1 day to 90 days of culture (e.g., about 1 day to about 19, 21, or 23 days of culture) the expansion results in greater than 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 50,000-fold, 70,000-fold, 100,000-fold or 1,000,000-fold expansion over a δ1 T-cell population; over a δ3 T-cell population; over another γδ T-cell sub-population; over a starting number of γδ T-cells before the expansion, over a starting number of γδ2 T-cells before the expansion, or over αβ T-cells.

In some aspects, the disclosure provides an engineered or non-engineered γδ T-cell population, in contact with an agent that stimulates an expansion of the γδ T-cell population at a rapid rate, such as of about 1 cell division per 30 hours or faster. In some cases, the agent selectively stimulates the proliferation of either δ1; δ2; δ1 and δ4; or δ1, δ3, δ4, and δ5 T-cells. A γδ T-cell population can comprise an amount of non-engineered γδ T-cells and an amount of engineered γδ T-cells. In some cases, the γδ T-cell population comprises different percentages of δ1, δ2, δ3, and δ4 T-cells. An engineered or non-engineered γδ T-cell population can comprise, for example, fewer than 90% δ1 T-cells, fewer than 80% δ1 T-cells, fewer than 70% δ1 T-cells, fewer than 60% δ1 T-cells, fewer than 50% δ1 T-cells, fewer than 40% δ1 T-cells, fewer than 30% δ1 T-cells, fewer than 20% δ1 T-cells, fewer than 10% δ1 T-cells, or fewer than 5% δ1 T-cells. Alternatively, an engineered or non-engineered γδ T-cell population can comprise greater than 5% δ1 T-cells, greater than 10% δ1 T-cells, greater than 20% δ1 T-cells, greater than 30% δ1 T-cells, greater than 40% δ1 T-cells, greater than 50% δ1 T-cells, greater than 60% δ1 T-cells, greater than 70% δ1 T-cells, greater than 80% δ1 T-cells, or greater than 90% δ1 T-cells. In some cases, the agent is one of the selective expansion agents described herein. In some cases, the agent is immobilized on a surface such as a cell culture surface, or a surface of an APC (e.g., expressed on the surface of the APC or bound to an Fc receptor expressed on the surface of the APC).

An engineered or non-engineered γδ T-cell population can comprise, for example, fewer than 90% δ2 T-cells, fewer than 80% δ2 T-cells, fewer than 70% δ2 T-cells, fewer than 60% δ2 T-cells, fewer than 50% δ2 T-cells, fewer than 40% δ2 T-cells, fewer than 30% δ2 T-cells, fewer than 20% δ2 T-cells, fewer than 10% δ2 T-cells, or fewer than 5% δ2 T-cells. Alternatively, an engineered or non-engineered γδ T-cell population can comprise greater than 5% δ2 T-cells, greater than 10% δ2 T-cells, greater than 20% δ2 T-cells, greater than 30% δ2 T-cells, greater than 40% δ2 T-cells, greater than 50% δ2 T-cells, greater than 60% δ2 T-cells, greater than 70% δ2 T-cells, greater than 80% δ2 T-cells, or greater than 90% δ2 T-cells.

An engineered or non-engineered γδ T-cell population can comprise, for example, fewer than 90% δ1 and δ4 T-cells, fewer than 80% δ1 and δ4 T-cells, fewer than 70% δ1 and δ4 T-cells, fewer than 60% δ1 and δ4 T-cells, fewer than 50% δ1 and δ4 T-cells, fewer than 40% δ1 and δ4 T-cells, fewer than 30% δ1 and δ4 T-cells, fewer than 20% δ1 and δ4 T-cells, fewer than 10% δ1 and δ4 T-cells, or fewer than 5% δ1 and δ4 T-cells. Alternatively, an engineered or non-engineered γδ T-cell population can comprise greater than 5% δ1 and δ4 T-cells, greater than 10% δ1 and δ4 T-cells, greater than 20% δ1 and δ4 T-cells, greater than 30% δ1 and δ4 T-cells, greater than 40% δ1 and δ4 T-cells, greater than 50% δ1 and δ4 T-cells, greater than 60% δ1 and δ4 T-cells, greater than 70% δ1 and δ4 T-cells, greater than 80% δ1 and δ4 T-cells, or greater than 90% δ1 and δ4 T-cells.

An engineered or non-engineered γδ T-cell population can comprise, for example, fewer than 90% δ4 T-cells, fewer than 80% δ4 T-cells, fewer than 70% δ4 T-cells, fewer than 60% δ4 T-cells, fewer than 50% δ4 T-cells, fewer than 40% δ4 T-cells, fewer than 30% δ4 T-cells, fewer than 20% δ4 T-cells, fewer than 10% δ4 T-cells, or fewer than 5% δ4 T-cells. Alternatively, an engineered or non-engineered γδ T-cell population can comprise greater than 5% δ1 and δ4 T-cells, greater than 10% δ1 and δ4 T-cells, greater than 20% δ1 and δ4 T-cells, greater than 30% δ1 and δ4 T-cells, greater than 40% δ1 and δ4 T-cells, greater than 50% δ1 and δ4 T-cells, greater than 60% δ1 and δ4 T-cells, greater than 70% δ1 and δ4 T-cells, greater than 80% δ1 and δ4 T-cells, or greater than 90% δ1 and δ4 T-cells. An engineered or non-engineered γδ T-cell population can comprise, for example, fewer than 90% δ1 and δ4 T-cells, fewer than 80% δ1 and δ4 T-cells, fewer than 70% δ1 and δ4 T-cells, fewer than 60% δ1 and δ4 T-cells, fewer than 50% δ1 and δ4

T-cells, fewer than 40% δ1 and δ4 T-cells, fewer than 30% δ1 and δ4 T-cells, fewer than 20% δ1 and δ4 T-cells, fewer than 10% δ1 and δ4 T-cells, or fewer than 5% δ1 and δ4 T-cells.

In certain embodiments, the present invention provides admixtures of expanded γδ T-cell populations comprising 10-90% δ1 T-cells and 90-10% δ2 T-cells. In certain embodiments, the present invention provides admixtures of expanded γδ T-cell populations comprising 10-90% δ1 and δ3 T-cells and 90-10% δ2 T-cells. In certain embodiments, the present invention provides admixtures of expanded γδ T-cell populations comprising 10-90% δ1 and δ4 T-cells and 90-10% δ2 T-cells. In certain embodiments, the present invention provides admixtures of expanded γδ T-cell populations comprising 10-90% δ1, δ3, δ4 and δ5 T-cells and 90-10% δ2 T-cells.

One or more activation agent can contact the γδ T-cells (for example an activator γδ T cell innate receptor) and thereafter a costimulatory molecule can contact the γδ T-cells to provide further stimulation and to expand the γδ T-cells. In some embodiments, the activation agent and/or costimulatory agent can be lectins of plant and non-plant origin, monoclonal antibodies that activate γδ T-cells, and other non-lectin/non-antibody agents. In other cases, the plant lectin can be concanavalin A (ConA) although other plant lectins such as may be used. Other examples of lectins include protein peanut agglutinin (PNA), soybean agglutinin (SBA), les culinaris agglutinin (LCA), Pisum sativum agglutinin (PSA), Helix pomatia agglutinin (HPA), Vicia graminea Lectin (VGA), Phaseolus Vulgaris Erythroagglutinin (PHA-E), Phaseolus Vulgaris Leucoagglutinin (PHA-L), Sambucus Nigra Lectin (SNA, EBL), Maackia Amurensis, Lectin II (MAL II), Sophora Japonica Agglutinin (SJA), Dolichos Biflorus Agglutinin (DBA), Lens Culinaris Agglutinin (LCA), Wisteria Floribunda Lectin (WFA, WFL).

Non-limiting examples of activating agents and costimulatory molecules include any one or more antibodies selective for a δ or γ-chain or subtypes thereof described herein, antibodies such as 5A6.E9, B1, TS8.2, 15D, B6, B3, TS-1, γ3.20, 7A5, IMMU510, R9.12, 11F2, or a combination thereof. Other examples of activating agents and costimulatory molecules include zoledronate, phorbol 12-myristate-13-acetate (TPA), mezerein, staphylococcal enterotoxin A (SEA), streptococcal protein A. or a combination thereof.

In other cases, the activation agent and/or costimulatory agent can be, antibodies or ligands to α TCR, β TCR, γ TCR, δ TCR, CD277, CD28, CD46, CD81, CTLA4, ICOS, PD-1, CD30, NKG2D, NKG2A, HVEM, 4-1 BB (CD137), OX40 (CD134), CD70, CD80, CD86, DAP, CD122, GITR, FcεRIγ, CD1, CD16, CD161, DNAX, accessory molecule-1 (DNAM-1), one or more NCRs (e.g., NKp30, NKp44, NKp46), SLAM, Coxsackie virus and adenovirus receptor or a combination thereof.

Engineered γδ T Cells

Engineered γδ T-cells (see, e.g., FIG. 1) may be generated with various methods known in the art. An engineered γδ T-cell may be designed to stably express a particular tumor recognition moiety. A polynucleotide encoding an expression cassette that comprises a tumor recognition, or another type of recognition moiety, can be stably introduced into the γδ T-cell by a transposon/transposase system or a viral-based gene transfer system, such as a lentiviral or a retroviral system, or another suitable method, such as transfection, electroporation, transduction, lipofection, calcium phosphate (CaPO$_4$), nanoengineered substances, such as Ormosil, viral delivery methods, including adenoviruses, retroviruses, lentiviruses, adeno-associated viruses, or another suitable method. An antigen specific TCR, either αβ or γδ, can be introduced into the engineered γδ T-cell by stably inserting a polynucleotide comprising a genetic code for the antigen specific TCR into the genome of the γδ T-cell. A polynucleotide encoding a CAR with a tumor recognition moiety may be introduced into the engineered γδ T-cell by stably inserting the polynucleotide into the genome of the γδ T-cell. In some cases, the engineered tumor recognition moiety is an engineered T-cell receptor, and the expression cassette incorporated into the genome of an engineered γδ T-cell comprises a polynucleotide encoding an engineered TCR α (TCR alpha) gene, an engineered TCR β (TCR beta) gene, an TCR δ (TCR delta) gene, or an engineered TCR γ (TCR gamma) gene. In some cases, the expression cassette incorporated into the genome of the engineered γδ T-cell comprises a polynucleotide encoding an antibody fragment or an antigen binding portion thereof. In some cases, the antibody fragment or antigen binding fragment thereof is a polynucleotide encoding a whole antibody, an antibody fragment, a single-chain variable fragment (scFv), a single domain antibody (sdAb), a Fab, F(ab)$_2$, an Fc, the light or heavy chains on an antibody, the variable or the constant region of an antibody, or any combination thereof that binds to a cell surface tumor antigen as part of the Chimeric Antigen Receptor (CAR) construct, or a bi-specific construct, comprising a CAR and a T-cell receptor (TCR), or CARs with antibodies directed to different antigens. In some cases, the polynucleotide is derived from a human or from another species. An antibody fragment or antigen binding fragment polynucleotide that is derived from a non-human species can be modified to increase their similarity to antibody variants produced naturally in humans, and an antibody fragment or antigen binding fragment can be partially or fully humanized. An antibody fragment or antigen binding fragment polynucleotide can also be chimeric, for example a mouse-human antibody chimera. An engineered γδ T-cell that expresses a CAR can also be engineered to express a ligand to the antigen recognized by the tumor recognition moiety.

Various techniques known in the art can be used to introduce a cloned, or synthetically engineered, nucleic acid comprising the genetic code for a tumor recognition moiety into a specific location within the genome of an engineered γδ T-cell. The RNA-guided Cas9 nuclease from the microbial clustered regularly interspaced short palindromic repeats (CRISPR) system, zinc finger nucleases (ZFNs), transcription activator-like effector nucleases (TALENs), and meganuclease technologies, as described, respectively by WO201409370, WO2003087341, WO2014134412, and WO2011090804, each of which is incorporated by reference herein in its entireties, can be used to provide efficient genome engineering in γδ T-cell(s). The technologies described herein can also be used to insert the expression cassette into a genomic location that simultaneously provides a knock-out of one gene and a knock-in of another gene. For example, a polynucleotide comprising an expression cassette of the disclosure can be inserted into a genomic region that encodes for an MEW gene. Such engineering can simultaneously provide the knock-in of one or more genes, e.g. the genes comprised in the expression cassette, and a knock-out of another gene, e.g. an MEW locus.

In one case, a Sleeping Beauty transposon that includes a nucleic acid coding for the tumor recognition moiety is introduced into the cell γδ T-cell that is being engineered. A mutant Sleeping Beauty transposase that provides for enhanced integration as compared to the wild-type Sleeping Beauty, such as the transposase described in U.S. Pat. No.

7,985,739, which is incorporated by reference herein in its entirety, may be used to introduce a polynucleotide in the engineered γδ T-cell.

In some cases, a viral method is used to introduce a polynucleotide comprising a tumor recognition moiety into the genome of an engineered γδ T-cell. A number of viral methods have been used for human gene therapy, such as the methods described in WO 1993020221, which is incorporated herein in its entirety. Non-limiting examples of viral methods that can be used to engineer a γδ T-cell include retroviral, adenoviral, lentiviral, herpes simplex virus, vaccinia virus, pox virus, or adeno-virus associated viral methods.

A polynucleotide containing the genetic code for a tumor recognition moiety may comprise mutations or other transgenes that affect the growth, proliferation, activation status of the engineered γδ T-cell or an antigen specific to tumor cells such as testis-specific cancer antigens. A γδ T-cell of the disclosure may be engineered to express a polynucleotide comprising an activation domain that is linked to the antigen recognition moiety, such as a molecule in TCR-CD3 complex or a co-stimulatory factor. An engineered γδ T-cell can express an intracellular signaling domain that is a T-lymphocyte activation domain. The γδ T-cell may be engineered to express an intracellular activation domain gene or an intracellular signaling domain. The intracellular signaling domain gene, may be, for example CD3ζ, CD28, CD2, ICOS, JAML, CD27, CD30, OX40, NKG2D, CD4, OX40/CD134, 4-1BB/CD137, FcεRIγ, IL-2RB/CD 122, IL-2RG/CD132, DAP molecules, CD70, cytokine receptor, CD40, or any combination thereof. In some cases, the engineered γδ T-cell is also engineered to express a cytokine, an antigen, a cellular receptor, or other immunomodulatory molecule.

The appropriate tumor recognition moiety to be expressed by the engineered γδ T-cell can be selected based on the disease to be treated. For example, in some cases a tumor recognition moiety is a TCR. In some cases, a tumor recognition moiety is a receptor to a ligand that is expressed on a cancer cell. Non-limiting examples of suitable receptors include NKG2D, NKG2A, NKG2C, NKG2F, LLT1, AICL, CD26, NKRP1, CD244 (2B4), DNAM-1, NKp30, NKp44, NKp46, and NKp80. In some cases, a tumor recognition moiety can include a ligand, e.g. IL-13 ligand, or a ligand mimetic to the tumor antigen, such as the IL-13 mimetic to IL13R.

A γδ T-cell may be engineered to express a chimeric tumor recognition moiety comprising a ligand binding domain derived from NKG2D, NKG2A, NKG2C, NKG2F, LLT1, AICL, CD26, NKRP1, CD244 (2B4), DNAM-1, or an anti-tumor antibody such as anti-Her2neu or anti-EGFR and a signaling domain obtained from CD3-ζ, Dap 10, Dap 12, CD28, 41BB, and CD40 L. In some examples, the chimeric receptor binds MICA, MICB, Her2neu, EGFR, EGFRvIII, mesothelin, CD38, CD20, CD19, BCMA, PSA, RON, CD30, CD22, CD37, CD38, CD56, CD33, CD138, CD123, CD79b, CD70, CD75, CA6, GD2, alphafetoprotein (AFP), CS1, carcinoembryonic antigen (CEA), CEACAM5, CA-125, MUC-16, 5T4, NaPi2b, ROR1, ROR2, PLIF, Her2/Neu, EGFRvIII, GPMNB, LIV-1, glycolipidF77, fibroblast activation protein (FAP), PSMA, STEAP-1, STEAP-2, c-Met, CSPG4, CD44v6, PVRL-4, VEGFR2, C4.4a, PSCA, folate binding protein/receptor, SLC44A4, Cripto, CTAG1B, AXL, IL-13Rα2, IL-3R, EPHA3, SLTRK6, gp100, MART1, Tyrosinase, SSX2, SSX4, NYESO-1, epithelial tumor antigen (ETA), MAGEA family genes (such as MAGEA3. MAGEA4), KKLC1, mutated ras (H, N, K), BRaf, p53, β-catenin, EGFRT790, MHC class I chain-related molecule A (MICA), or MHC class I chain-related molecule B (MICB), or one or more antigens of HPV, CMV, or EBV.

In some cases, the tumor recognition moiety targets an MHC class I molecule (HLA-A, HLA-B, or HLA-C) in complex with a tumor-associated peptide. Methods and compositions for generating and using tumor recognition moieties that target a tumor-associated peptide in complex with a MEW class I molecule include those described in Weidanz et al., Int. Rev. Immunol. 30:328-40, 2011; Scheinberg et al, Oncotarget. 4(5):δ47-8, 2013; Cheever et al, Clin. Cancer Res. 15(17):5323-37, 2009; Dohan & Reiter Expert Rev Mol Med. 14:eδ, 2012; Dao et al., Sci Transl Med. 2013 Mar. 13; 5(176):176ra33; U.S. Pat. No. 9,540,448; and WO 2017/011804. In some embodiments, the targeted tumor-associated peptide of the peptide MHC complex is a peptide of Wilms' tumor protein 1 (WT1), human telomerase reverse transcriptase (hTERT), survivin, mouse double minute 2 homolog (MDM2), cytochrome P450 (CYP1B), KRAS, or BRAF.

Two or more tumor recognition moieties may be expressed in the γδ T-cell from genetically different, substantially different, or substantially identical, αβ TCR polynucleotides stably expressed from the engineered γδ T-cell or from genetically distinct αβ TCR polynucleotides stably incorporated in the engineered γδ T-cell. In the case of genetically distinct αβ TCR(s), αβ TCR(s) recognizing different antigens associated with the same condition may be utilized. In one preferred embodiment, a γδ T-cell is engineered to express different TCRs, from human or mouse origin, from one or more expression cassettes that recognize the same antigen in the context of different MHC haplotypes. In another preferred embodiment, a γδ T-cell is engineered to express one TCR and two or more antibodies directed to the same or different peptides from a given antigen complexed with different MHC haplotypes. In some cases, expression of a single TCR by an engineered γδ T-cell facilitates proper TCR pairing. An engineered γδ T-cell that expresses different TCRs can provide a universal allogeneic engineered γδ T-cell. In a second preferred embodiment, a γδ T-cell is engineered to express one or more different antibodies directed to peptide-MHC complexes, each directed to the same or different peptide complexed with the same or different MHC haplotypes. In some cases, a tumor recognition moiety can be an antibody that binds to peptide-MHC complexes.

A γδ T-cell can be engineered to express TCRs from one or more expression cassettes that recognize the same antigen in the context of different MHC haplotypes. In some cases, an engineered γδ T-cell is designed to express a single TCR, or a TCR in combination with a CAR to minimize the likelihood of TCR mispairing within the engineered cell. The tumor recognition moieties expressed from two or more expression cassettes preferably have different polynucleotide sequences, and encode tumor recognition moieties that recognize different epitopes of the same target, e.g., in the context of different HLA haplotypes. An engineered γδ T-cell that expresses such different TCRs or CARs can provide a universal allogeneic engineered γδ T-cell.

In some cases, a γδ T-cell is engineered to express one or more tumor recognition moieties. Two or more tumor recognition moieties may be expressed from genetically identical, or substantially identical, antigen-specific chimeric (CAR) polynucleotides engineered in the γδ T-cell. Two or more tumor recognition moieties may be expressed from genetically distinct CAR polynucleotides engineered in the γδ T-cell. The genetically distinct CAR(s) may be designed to recognize different antigens associated with the same condition.

A γδ T-cell may alternatively be bi-specific. A bi-specific engineered γδ T-cell can express two or more tumor recognition moieties. A bi-specific engineered γδ T-cell can express both TCR and CAR tumor recognition moieties. A bi-specific engineered γδ T-cell can be designed to recognize different antigens associated with the same condition. An engineered γδ T-cell can express two or more CAR/TCR(s) bi-specific polynucleotides that recognize an identical or substantially identical antigen. An engineered γδ T-cell can express two or more CAR/TCR(s) bi-specific constructs that recognize distinct antigens. In some cases, a bi-specific construct of the disclosure binds to an activating and an inactivating domain of a target cell, thereby providing increased target specificity. The γδ T-cell may be engineered to express at least 1 tumor recognition moiety, at least 2 tumor recognition moieties, at least 3 tumor recognition moieties, at least 4 tumor recognition moieties, at least 5 tumor recognition moieties, at least 6 tumor recognition moieties, at least 7 tumor recognition moieties, at least 8 tumor recognition moieties, at least 9 tumor recognition moieties, at least 10 tumor recognition moieties, at least 11 tumor recognition moieties, at least 12 tumor recognition moieties, or another suitable number of tumor recognition moieties.

Proper TCR function may be enhanced by two functioning ζ (zeta) proteins comprising ITAM motifs. Proper TCR function may also be enhanced by expression of αβ or γδ activation domains, such as CD3ζ, CD28, CD2, CTLA4, ICOS, JAML, PD-1, CD27, CD30, 41-BB, OX40, NKG2D, HVEM, CD46, CD4, FcεRIγ, IL-2RB/CD122, IL-2RG/CD132, DAP molecules, and CD70. The expressed polynucleotide may include the genetic code for a tumor recognition moiety, a linker moiety, and an activation domain. Translation of the polynucleotide by the engineered γδ T-cell may provide a tumor recognition moiety and an activation domain linked by a protein linker. Often, the linker comprises amino acids that do not obstruct the folding of the tumor recognition moiety and the activation domain. A linker molecule can be at least about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 amino acids in length. In some cases, at least 50%, at least 70% or at least 90% of the amino acids in the linker are serine or glycine.

In some cases, an activation domain can comprise one or more mutations. Suitable mutations may be, for example, mutations that render an activation domain constitutively active. Altering the identity of one or more nucleic acids changes the amino acid sequence of the translated amino acid. A nucleic acid mutation can be made such that the encoded amino acid is modified to a polar, non-polar, basic or acidic amino acid. A nucleic acid mutation can be made such that the tumor recognition moiety is optimized to recognize an epitope from a tumor. The engineered tumor recognition moiety, an engineered activation domain, or another engineered component of a γδ T-cell may include more than 1 amino acid mutation, 2 amino acid mutations, 3 amino acid mutations, 4 amino acid mutations, 5 amino acid mutations, 6 amino acid mutations, 7 amino acid mutations, 8 amino acid mutations, 9 amino acid mutations, 10 amino acid mutations, 11 amino acid mutations, 12 amino acid mutations, 13 amino acid mutations, 14 amino acid mutations, 15 amino acid mutations, 16 amino acid mutations, 17 amino acid mutations, 18 amino acid mutations, 19 amino acid mutations, 20 amino acid mutations, 21 amino acid mutations, 22 amino acid mutations, 23 amino acid mutations, 24 amino acid mutations, 25 amino acid mutations, 26 amino acid mutations, 27 amino acid mutations, 28 amino acid mutations, 29 amino acid mutations, 30 amino acid mutations, 31 amino acid mutations, 32 amino acid mutations, 33 amino acid mutations, 34 amino acid mutations, 35 amino acid mutations, 36 amino acid mutations, 37 amino acid mutations, 38 amino acid mutations, 39 amino acid mutations, 40 amino acid mutations, 41 amino acid mutations, 42 amino acid mutations, 43 amino acid mutations, 44 amino acid mutations, 45 amino acid mutations, 46 amino acid mutations, 47 amino acid mutations, 48 amino acid mutations, 49 amino acid mutations, or 50 amino acid mutations.

In some cases, a γδ T-cell of the disclosure does not express one or more MHC molecules. Deletion of one or more MHC loci in an engineered γδ T-cell can decrease the likelihood that the engineered γδ T-cell will be recognized by the host immune system. The human Major Histocompatibility Complex (MHC) loci, known as the human leukocyte antigen (HLA) system, comprises a large gene family that is expressed in antigen presenting cells, including γδ T-cells. The HLA-A, HLA-B, and HLA-C molecules function to present intracellular peptides as antigens to antigen presenting cells. The HLA-DP, HLA-DM, HLA-DOA, HLA-DOB, HLA-DQ, and HLA-DR molecules function to present extracellular peptides as antigens to antigen presenting cells. Some alleles of the HLA genes have been associated with GVHD, autoimmune disorders, and cancer. An engineered γδ T-cell described herein can be further engineered to lack, or to disrupt gene expression of one or more HLA genes. An engineered γδ T-cell described herein can be further engineered to lack, or to disrupt gene expression of one or more components of the MEW complex, such as complete deletion of one or more of the MEW genes, deletion of specific exons, or deletion of the $\beta_2$ microglobulin (B2m). Genetic excision or genetic disruption of at least one HLA gene can provides a clinically therapeutic γδ T-cell that can be administered to a subject with any HLA haplotype without causing host-versus-graft disease. An engineered γδ T-cell as described herein can be a universal donor for a human subject with any HLA haplotype.

A γδ T-cell can be engineered to lack one or various HLA locus (loci). An engineered γδ T-cell can be engineered to lack an HLA-A allele, an HLA-B allele, an HLA-C allele, an HLA-DR allele, an HLA-DQ allele, or an HLA-DP allele. In some cases, an HLA allele is associated with a human condition, such as an auto-immune condition. For instance, the HLA-B27 allele has been associated with arthritis and uveitis, the HLA-DR2 allele has been associated with systemic lupus erythematosus, and multiple sclerosis, the HLA-DR3 allele has been associated with 21-hydroxylase deficiency, the HLA-DR4 has been associated with rheumatoid arthritis and type 1 diabetes. An engineered γδ T-cell that lacks, for example, the HLA-B27 allele can be administered to a subject afflicted with arthritis without being readily recognized the immune system of the subject. In some cases, deletion of one or more HLA loci provides an engineered γδ T-cell that is a universal donor for any subject with any HLA haplotype.

In some cases, engineering a γδ T-cell requires the deletion of a portion of the γδ T-cell genome. In some cases, the deleted portion of the genome comprises a portion of the MHC locus (loci). In some instances, the engineered γδ T-cell is derived from a wild-type human γδ T-cell, and the MHC locus is an HLA locus. In some cases, the deleted a portion of the genome comprises a portion of a gene corresponding to a protein in the MHC complex. In some cases, the deleted portion of the genome comprises the β2 microglobulin gene. In some instances, the deleted portion of the genome comprises an immune checkpoint gene, such as PD-1, CTLA-4, LAG3, ICOS, BTLA, KIR, TIM3, A2aR, B7-H3, B7-H4, and CECAM-1. In some cases, an engineered γδ T-cell can be designed to express an activation domain that enhances T-cell activation and cytotoxicity. Non-limiting examples of activation domains that can be expressed by an engineered γδ T-cell include: CD2, ICOS, 4-1 BB (CD137), OX40 (CD134), CD27, CD70, CD80, CD86, DAP molecules, CD122, GITR, FcεRIγ.

Any portion of the genome of an engineered γδ T-cell can be deleted to disrupt the expression of an endogenous γδ T-cell gene. Non-limiting examples of genomic regions that can be deleted or disrupted in the genome of an γδ T-cell include a promoter, an activator, an enhancer, an exon, an intron, a non-coding RNA, a micro-RNA, a small-nuclear RNA, variable number tandem repeats (VNTRs), short tandem repeat (STRs), SNP patterns, hypervariable regions, minisatellites, dinucleotide repeats, trinucleotide repeats, tetranucleotide repeats, or simple sequence repeats. In some cases, the deleted a portion of the genome ranges between 1 nucleic acid to about 10 nucleic acids, 1 nucleic acid to about 100 nucleic acids, 1 nucleic acid to about 1,000 nucleic acids, 1 nucleic acid to about 10,000 nucleic acids, 1 nucleic acid to about 100,000 nucleic acids, 1 nucleic acid to about 1,000,000 nucleic acids, or other suitable range.

HLA gene expression in an engineered γδ T-cell can also be disrupted with various techniques known in the art. In some cases, large loci gene editing technologies are used to excise a gene from the engineered γδ T-cell genome, or to disrupt gene expression of at least one HLA locus in the engineered γδ T-cell. Non-limiting examples of gene editing technologies that can be used to edit a desired locus on a genome of an engineered γδ T-cell include Clustered Regularly Interspaced Short Palindromic Repeats (CRISPR)-Cas, zinc finger nucleases (ZFNs), Transcription activator-like effector nucleases (TALENs), and meganuclease technologies, as described, respectively by WO201409370, WO2003087341, WO2014134412, and WO 2011090804, and each of which is incorporated by reference herein in its entireties.

A γδ T-cell may be engineered from an isolated non-engineered γδ T-cell that already expresses a tumor recognition moiety. The engineered γδ T-cell can retain a tumor cell recognition moiety that is endogenously expressed by the isolated wild-type γδ T-cell, e.g., isolated from tumor infiltrating lymphocytes of a tumor sample. In some cases, the engineered γδ T-cell tumor cell recognition moiety replaces the wild-type γδ TCR.

A γδ T-cell can be engineered to express one or more homing molecules, such as a lymphocyte homing molecule. Homing molecules can be, for instance, lymphocyte homing receptors or cell adhesion molecules. A homing molecule can help an engineered γδ T-cell to migrate and infiltrate a solid tumor, including a targeted solid tumor upon administration of the engineered γδ T-cell to the subject. Non-limiting examples of homing receptors include members of the CCR family, e.g: CCR2, CCR4, CCR7, CCR8, CCR9, CCR10, CLA, CD44, CD103, CD62 L, E-selectin, P-selectin, L-selectin, integrins, such as VLA-4 and LFA-1. Non-limiting examples of cell adhesion molecules include ICAM, N-CAM, VCAM, PE-CAM, L1-CAM, Nectins (PVRL1, PVRL2, PVRL3), LFA-1, integrin alphaXbeta2, alphavbeta7, macrophage-1 antigen, CLA-4, glycoprotein IIb/IIIa. Additional examples of cell adhesion molecules include calcium dependent molecules, such as T-cadherin, and antibodies to matrix metaloproteinases (MMPs) such as MMP9 or MMP2.

The steps involved in T-cell maturation, activation, proliferation, and function may be regulated through co-stimulatory and inhibitory signals through immune checkpoint proteins. Immune checkpoints are co-stimulatory and inhibitory elements intrinsic to the immune system. Immune checkpoints aid in maintaining self-tolerance and modulating the duration and amplitude of physiological immune responses to prevent injury to tissues when the immune system responds to disease conditions, such as cell transformation or infection. The equilibrium between the co-stimulatory and inhibitory signals used to control the immune response from either γδ and αβ T-cells can be modulated by immune checkpoint proteins. Immune checkpoint proteins, such as PD1 and CTLA4 are present on the surface of T-cells and can be used to turn an immune response "on" or "off." Tumors can dysregulate checkpoint protein function as an immune-resistance mechanism, particularly against T-cells that are specific for tumor antigens. An engineered γδ T-cell of the disclosure can be further engineered to lack one or more immune checkpoint locus (loci), such as PD-1, CTLA-4, LAG3, ICOS, BTLA, KIR, TIM3, A2aR, CEACAM1, B7-H3, and B7-H4. Alternatively, the expression of an endogenous immune check point gene in an engineered γδ T-cell of the disclosure can be disrupted with gene editing technologies.

Immunological checkpoints can be molecules that regulate inhibitory signaling pathways (exemplified by CTLA4, PD1, and LAG3) or molecules that regulate stimulatory signaling pathways (exemplified by ICOS) in an engineered γδ T-cell of the disclosure. Several proteins in the extended immunoglobulin superfamily can be ligands for immunological checkpoints. Non-limiting examples of immune checkpoint ligand proteins include B7-H4, ICOSL, PD-L1, PD-L2, MegaCD40 L, MegaOX40 L, and CD137 L. In some cases, immune checkpoint ligand proteins are antigens expressed by a tumor. In some cases, the immune checkpoint gene is a CTLA-4 gene. In some cases, the immune checkpoint gene is a PD-1 gene.

PD1 is an inhibitory receptor belonging to the CD28/CTLA4 family and is expressed on activated T lymphocytes, B cells, monocytes, DCs, and T-regs. There are two known ligands for PD1, PD-L1 and PD-L2, which are expressed on T cells, APCs, and malignant cells function to suppress self-reactive lymphocytes and to inhibit the effector function of TAA-specific cytotoxic T lymphocytes (CTLs). Accordingly, an engineered γδ T-cell that lacks PD1 can retain its cytotoxic activity regardless of expression of PD-L1 and PD-L2 by tumor cells. In some cases, an engineered γδ T-cell of the disclosure lacks the gene locus for the PD-1 gene. In some cases, expression of the PD-1 gene in an engineered γδ T-cell is disrupted by gene editing technologies.

CTLA4 (cytotoxic T-lymphocyte antigen 4) is also known as CD152 (Cluster of differentiation 152). CTLA4 shares sequence homology and ligands (CD80/B7-1 and CD86/B7-2) with the costimulatory molecule CD28, but differs by delivering inhibitory signals to T-cells expressing CTLA4 as a receptor. CTLA4 has a much higher overall affinity for both ligands and can out-compete CD28 for binding when ligand densities are limiting. CTLA4 is often expressed on the surface of $CD8^+$ effector T-cells, and plays a functional role in the initial activation stages of both naive and memory T-cells. CTLA4 counteracts the activity of CD28 via increased affinity for CD80 and CD86 during the early stages of T-cell activation. The major functions of CTLA4 include down-modulation of helper T-cells and enhancement of regulatory T-cell immunosuppressive activity. In some instances, an engineered γδ T-cell of the disclosure lacks the CTLA4 gene. In some cases, expression of the CTLA4 gene in an engineered γδ T-cell is disrupted by gene editing technologies.

LAG3 (Lymphocyte-activation gene 3) is expressed on activated antigen-specific cytotoxic T-cells, and can enhance the function of regulatory T-cells and independently inhibit CD8+ effector T-cell activity. LAG3 is a CD-4-like negative regulatory protein with a high affinity binding to MHC Class II proteins, which are upregulated on some epithelial cancers, leading to tolerance of T cell proliferation and homeostasis. Reduction of the LAG-3/Class II interaction using a LAG-3-IG fusion protein may enhance antitumor immune responses. In some cases, an engineered γδ T-cell of the disclosure lacks the gene locus for the LAG3gene. In some instances, expression of the LAG3gene in an engineered γδ T-cell is disrupted by gene editing technologies.

Phenotype of Non-Engineered and Engineered γδ T-Cells

An engineered γδ T-cell may home to a specific physical location in a subject's body. Migration and homing of engineered γδ T cells, can be dependent on the combined expression and actions of specific chemokines and/or adhesion molecules. Homing of engineered γδ T cells can be controlled by the interactions between chemokines and their receptors. For example, cytokines including but not limited to CXCR3 (whose ligands are represented by IP-10/CXCL10 and 6Ckine/SLC/CCL21) CCR4+ CXCR5+ (receptor for RANTES, MIP-1α, MIP-1β), CCR6+ and CCR7 may affect homing of engineered γδ T cells. In some cases, an engineered γδ T-cell may home to sites of inflammation and injury, and to diseased cells to perform repair functions. In some cases, an engineered γδ T-cell can home to a cancer. In some cases, an engineered γδ T-cell may home to a thymus, a bone marrow, a skin, a larynx, a trachea, pleurae, a lung, an esophagus, an abdomen, a stomach, a small intestine, a large intestine, a liver, a pancreas, a kidney, a urethra, a bladder, a testis, a prostate, a ductus deferens, am ovary, an uretus, a mamary gland, a parathyroid gland, a spleen or another site in a subject's body. An engineered γδ T-cell can express one or more homing moieties, such as particular TCR allele and/or a lymphocyte homing molecule.

An engineered γδ T-cell may have a particular phenotype and a phenotype can be described in terms of cell-surface marker expression. Various types of γδ T-cells can be engineered as described herein. In preferred embodiments, the engineered γδ T-cell is derived from a human, but the engineered γδ T-cell may also be derived from a different source, such as a mammal or a synthetic cell.

The immunophenotype of the expanded cell populations may be determined using markers including but not limited to CD27, CD45RA, CD45RO, CCR7 and CD62 L (Klebanoff et al., Immunol Rev. 211: 214 2006). CD45RA is expressed on naïve T lymphocytes, replaced by CD45RO upon antigen encounter, but re-expressed in late effector cells (Michie et al., Nature 360, 264-265 (1992); CD62 L is a cell adhesion molecule that acts as a homing molecule to enter secondary lymphoid tissues and is lost after T-cell activation, when T-cells acquire effector functions (Sallusto et al., Nature. 401:708 (1999). CD27 is costimulation markers that are lost during T-cell differentiations (Appay et al., Nat Med. 8:379 (2002); Klebanoff et al., Immunol Rev. 211: 214 2006).

Antigens

The invention disclosed herein provides an engineered γδ T-cell that expresses an antigen recognition moiety, wherein the antigen recognition moiety recognizes a disease-specific epitope. An antigen may be a molecule that provokes an immune response. This immune response may involve either antibody production, the activation of specific immunologically-competent cells, or both. An antigen may be, for example, a peptide, a protein, a hapten, a lipid, a carbohydrate, bacteria, a pathogen, or a virus. An antigen may be a tumor antigen. A tumor epitope may be presented by the MHC I or MHC II complexes on the surface of tumor cells. An epitope can be the portion of the antigen that is expressed on the cell surface and recognized by the tumor recognition moiety.

Non-limiting examples of antigens recognized by an engineered γδ T-cell include CD19, CD20, CD30, CD22, CD37, CD38, CD56, CD33, CD138, CD123, CD79b, CD70, CD75, CA6, GD2, alphafetoprotein (AFP), carcinoembryonic antigen (CEA), RON, CEACAM5, CA-125, MUC-16, 5T4, NaPi2b, ROR1, ROR2, PLIF, Her2/Neu, EGFRvIII, GPMNB, LIV-1, glycolipidF77, fibroblast activation protein (FAP), PSMA, STEAP-1, STEAP-2, mesothelin, c-Met, CSPG4, PVRL-4, VEGFR2, PSCA, CLEC12a, L1CAM, GPC2, GPC3, folate binding protein/receptor, SLC44A4, Cripto, CTAG1B, AXL, IL-13R, IL-3Rα2, SLTRK6, gp100, MART1, Tyrosinase, SSX2, SSX4, NYESO-1, WT-1, PRAME, epithelial tumor antigen (ETA), MAGEA family genes (such as MAGEA3. MAGEA4), KKLC1, mutated ras, □□af, p53, MHC class I chain-related molecule A (MICA), or MHC class I chain-related molecule B (MICB), or one or more antigens of HPV, CMV, or EBV.

An antigen can be expressed in the intracellular or the extracellular compartment of a cell and an engineered γδ T-cell can recognize an intracellular or an extracellular tumor antigen. In some cases, an αβ TCR in the engineered γδ T-cell recognizes a peptide derived from either an intracellular or an extracellular tumor antigen. For example, an antigen may be a protein intracellularly or extracellularly produced by a cell infected with a virus, such as an HIV, an EBV, a CMV, or an HPV protein. An antigen may also be a protein intracellularly or extracellularly expressed by a cancerous cell.

An antigen recognition moiety may recognize an antigen from a cell in distress, such as a cancerous cell or a cell that has been infected with a virus. For instance, the human MHC class I chain-related genes (MICA and MICB) are located within the HLA class I region of chromosome 6. MICA and MICB proteins are considered to be markers of "stress" in the human epithelia, and act as ligands for cells expressing a common natural killer-cell receptor (NKG2D). As stress markers, MICA and MICB can be highly expressed from cancerous cells. An engineered γδ T-cell can recognize a MICA or a MICB tumor epitope.

A tumor recognition moiety may be engineered to recognize an antigen with certain avidity. For instance, a tumor recognition moiety encoded by a TCR or CAR construct may recognize an antigen with a dissociation constant of at least at least 10 fM, at least 100 fM, at least 1 picomolar (pM), at least 10 pM, at least 20 pM, at least 30 pM, at least 40 pM, at least 50 pM, at least δ0 pM, at least 7 pM, at least 80 pM, at least 90 pM, at least 100 pM, at least 200 pM, at least 300 pM, at least 400 pM, at least 500 pM, at least δ00 pM, at least 700 pM, at least 800 pM, at least 900 pM, at least 1 nanomolar (nM), at least 2 nM, at least 3 nM, at least 4 nM, at least 5 nM, at least 6 nM, at least 7 nM, at least 8 nM, at least 9 nM, at least 10 nM, at least 20 nM, at least 30 nM, at least 40 nM, at least 50 nm, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, at least 1 µM, at least 2 µM, at least 3 µM, at least 4 µM, at least 5 µM, at least 6 µM, at least 7 µM, at least 8 µM, at least 9 µM, at least 10 µM, at least 20 µM, at least 30 µM, at least 40 µM, at least 50 µM, at least 60 µM, at least 70 µM, at least 80 µM, at least 90 µM, or at least 100 µM.

In some instances, a tumor recognition moiety may be engineered to recognize an antigen with a dissociation constant of at most 10 fM, at most 100 fM, at most 1 picomolar (pM), at most 10 pM, at most 20 pM, at most 30 pM, at most 40 pM, at most 50 pM, at most 60 pM, at most 7 pM, at most 80 pM, at most 90 pM, at most 100 pM, at most 200 pM, at most 300 pM, at most 400 pM, at most 500 pM, at most 600 pM, at most 700 pM, at most 800 pM, at most 900 pM, at most 1 nanomolar (nM), at most 2 nM, at most 3 nM, at most 4 nM, at most 5 nM, at most 6 nM, at most 7 nM, at most 8 nM, at most 9 nM, at most 10 nM, at most 20 nM, at most 30 nM, at most 40 nM, at most 50 nm, at most 60 nM, at most 70 nM, at most 80 nM, at most 90 nM, at most 100 nM, at most 200 nM, at most 300 nM, at most 400 nM, at most 500 nM, at most 600 nM, at most 700 nM, at most 800 nM, at most 900 nM, at most 1 µM, at most 2 µM, at most 3 µM, at most 4 µM, at most 5 µM, at most 6 µM, at most 7 µM, at most 8 µM, at most 9 µM, at most 10 µM, at most 20 µM, at most 30 µM, at most 40 µM, at most 50 µM, at most 60 µM, at most 70 µM, at most 80 µM, at most 90 µM, or at most 100 µM.

Novel Activating Agents

The inventors of the present invention have identified activation agents that bind specific subtypes of γδ TCRs and thereby activate specific populations of γδ T cells. In one aspect, the invention provides novel activating agents which bind the novel activating epitopes identified and described herein in Examples 14, and 39, and FIGS. 23-30, and 33-36. Activation agents include, but are not limited to MAbs TS8.2, TS-1, 15D, B6, R9.12, δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, δ1-285, δ2-14, δ2-17, δ2-22, δ2-30, δ2-31, δ2-32, δ2-33, δ2-35, δ2-36, and δ2-37.

These activation agents further include, but are not limited to activation agents that bind the same epitope or compete with one or more MAbs selected from the group consisting of TS8.2, TS-1, 15D, B6, R9.12, δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, 61-253, δ1-257, δ1-278, δ1-282, δ1-285, δ2-14, δ2-17, δ2-22, δ2-30, δ2-31, δ2-32, δ2-33, δ2-35, δ2-36, and δ2-37.

These activation agents further include, but are not limited to activation agents that contain the complementarity determining regions (CDRs) and/or variable regions of a MAb selected from the group consisting of TS8.2, TS-1, 15D, B6, R9.12, δ1-05, δ1-08, δ1-18, δ1-22, δ1-23, δ1-26, 61-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, δ1-285, δ2-14, δ2-17, δ2-22, δ2-30, δ2-31, δ2-32, δ2-33, δ2-35, δ2-36, and δ2-37.

The present invention also provides a nucleic acid encoding an activation agent that: (i) contains the complementarity determining regions (CDRs) and/or variable regions of; (ii) binds the same epitope as or competes with; or (iii) is a MAb selected from the group consisting of TS8.2, TS-1, 15D, B6, R9.12, δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, δ1-285, δ2-14, δ2-17, δ2-22, δ2-30, δ2-31, δ2-32, δ2-33, δ2-35, δ2-36, and δ2-37. In some cases, the nucleic acid is in a host cell (e.g., a heterologous host cell). In some cases, the nucleic acid is operably linked to a heterologous promoter or operably linked to a nucleic acid encoding a heterologous polypeptide. As used herein, the term "heterologous" refers to two components that do not naturally exist together in nature.

In certain embodiments the activating agent (e.g., antibody) expands or activates one or more γδ T-cell populations (e.g., δ1 T-cells or δ2 T-cells). In certain embodiments, the activating agent selectively activates δ1 and δ3 T-cells. In certain embodiments, the activating agent selectively activates δ1 and δ4 T-cells. In certain embodiments, the activating agent selectively activates δ1 T-cells. In certain embodiments, the activating agent selectively activates δ1, δ3, δ5, and δ5 T-cells. In certain embodiments, the activating agent selectively activates δ2 T-cells.

The present invention also provides methods of producing one or more of the foregoing activation agents. For example, a host cell containing a nucleic acid encoding an activation agent can be cultured to produce one or more of the foregoing activation agents.

APCs

Also described herein are APCs for expansion of engineered or non-engineered γδ T-cells, such as one or more subpopulations of γδ T-cells. In some embodiments, described herein is an APC that contains a heterologous nucleic acid encoding one or more of the foregoing activation agents. In some embodiments, described herein is an APC that expresses one or more of the foregoing activation agents on a cell surface. In some embodiments, described herein is an APC that expresses one or more Fc receptors on its cell surface, wherein the Fc receptor(s) are in contact with and/or bound to one or more of the foregoing activation agents.

In some cases, the APCs (e.g., APCs having one or more of the foregoing activation agents expressed, on or bound to an Fc receptor expressed on, the cell surface) do not express, or exhibit reduced expression of, HLA class I, HLA class I, invariant chain, and/or HLA-DM. In some cases, the APCs express adhesion molecules such as intercellular adhesion molecule-1, CD11a, CD18, CD54, and/or leukocyte function-associated antigen-3. In some cases, the APCs express an Fc receptor, such as an Fc receptor that is specific for an isotype of an activation agent used in a γδ T-cell expansion method described herein. In some cases, the APCs express one or more Fc receptors selected from the group consisting of CD64, CD32A, CD32B, CD32C, CD16A, CD16B, FcRn, TRIM21, or CD307, or an engineered variant thereof having a higher affinity or altered specificity.

Also described herein cultures comprising one or more of the foregoing APCs. The culture can further contain expanded or unexpanded, engineered or non-engineered, γδ T-cells. The culture can additionally or alternatively contain a selective or non-selective γδ T-cell activation agent including any one of the γδ T-cell activation agents described herein. In some cases, the culture does not contain IL-21. In some cases, the culture does not contain IL-4, IL-2, or IL-15, or a combination thereof. In some cases, the culture does not contain a cytokine that selectively expands a sub-population of γδ T cells.

Epitope Identification

The inventors of the present invention have identified binding regions within the epitope of γδ TCR activating MAbs TS8.2, TS-1, 15D, B6, R9.12, δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, δ1-285, δ2-14, δ2-17, δ2-22, δ2-30, δ2-31, δ2-32, δ2-33, δ2-35, δ2-36, and δ2-37. Exemplary epitopes include, but are not limited to, the epitopes of γδ TCR activating MAbs TS8.2, TS-1, 15D, B6, R9.12, δ1-05, δ1-08, δ1-18, δ1-22, δ1-23, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-239, δ1-253, δ1-257, δ1-278, δ1-282, δ1-285, δ2-14, δ2-17, δ2-22, δ2-30, δ2-31, δ2-32, δ2-33, δ2-35, δ2-36, and δ2-37. In some embodiments, the epitope is an epitope specifically bound by one or more of γδ TCR activating MAbs TS8.2, TS-1, 15D, B6, R9.12, δ1-05, δ1-08, δ1-22, δ1-26, δ1-35, δ1-37, δ1-39, δ1-113, δ1-143, δ1-149, δ1-155, δ1-182, δ1-183, δ1-191, δ1-192, δ1-195, δ1-197, δ1-199, δ1-201, δ1-203, δ1-253, δ1-257, δ1-278, δ1-282, δ1-285, δ2-14, δ2-17, δ2-30, δ2-31, δ2-32, δ2-33, δ2-35, δ2-36, and δ2-37.

In one aspect, the disclosure provides a method for identifying the epitope of an agent that stimulates the expansion of engineered and non-engineered γδ T-cells at a fast rate of growth. An epitope can include at least 3, 4, 5, 6, 7, 8, 9, 10, 11, 12, 13, 14, 15, 16, 17, 18, 19, or 20 amino acids in a unique spatial conformation. Epitopes can be formed both from contiguous amino acids or noncontiguous amino acids juxtaposed by tertiary folding of a protein. Epitopes formed from contiguous amino acids can be typically retained on exposure to denaturing solvents whereas epitopes formed by tertiary folding can be typically lost on treatment with denaturing solvents.

Epitope mapping can be performed to identify the linear or non-linear, discontinuous amino acid sequence(s), i.e. the epitope, that is (e.g., specifically) recognized by an activating agent of interest, such as the TS8.2, 15D, B6, TS-1, and R9.12, antibodies. A general approach for epitope mapping can require the expression of the full-length polypeptide sequence that is recognized by an antibody or ligand of interest, as well as various fragments, i.e., truncated forms of the polypeptide sequence, generally in a heterologous expression system. These various recombinant polypeptide sequences or fragments thereof (e.g., fused with an N-terminal protein (e.g., GFP)) can then be used to determine if the antibody or ligand of interest is capable of binding to one or more of the truncated forms of the polypeptide sequence.

In some embodiments, the recombinant polypeptide sequences are chimeras containing joined fragments of two or more homologous parental polypeptides, wherein at least one parental polypeptide binds to the activating agent of interest and at least one parental polypeptide does not bind to the activating agent of interest. For example, segments of a human δ1 chain can gene be joined with segments of a homologous dolphin δ chain gene, and tested for the ability to generate a chimeric TCR in a recombinant expression system. Chimeric TCR genes that form a TCR, as e.g., indicated by detection with a pan-γδ-TCR antibody on a cell surface, can then be tested for binding to the activation agent of interest. As another example, segments of a human δ2 chain can gene be joined with segments of a homologous macaque δ chain gene, and tested for the ability to generate a chimeric TCR in a recombinant expression system. Chimeric TCR genes that form a TCR, as e.g., indicated by detection with a pan-γδ-TCR antibody on a cell surface, can then be tested for binding to the activation agent of interest.

Through the use of reiterative truncation and the generation of recombinant polypeptide sequences with overlapping amino acid regions, it is possible to identify the region of the polypeptide sequence that is recognized by the antibody of interest (see, e.g., Epitope Mapping Protocols in Methods in Molecular Biology, Vol. 66, Glenn E. Morris, Ed (1996)). The methods rely on the ability of an agent such as an antibody of interest to bind to sequences that have been recreated from epitope libraries, such as epitope libraries derived from, synthetic peptide arrays on membrane supports, combinatorial phage display peptide libraries. The epitope libraries then provide a range of possibilities that are screened against an antibody. Additionally, site specific mutagenesis, or random Ala scan, targeting one or more residues of an epitope can be pursued to confirm the identity of an epitope.

A library of epitopes can be created by synthetically designing various possible recombinations of a γδ T-cell receptor (γδ TCR) as cDNA constructs and expressing them in a suitable system. For instance, a plurality of Vδ1 gene segments differing in their Jδ region can be synthetically designed, including Jδ1, Jβ2 and Jβ3 gene segments. Alternatively, Vβ2Jβ1 and Vδ3Jδ1 chains can also be ordered as synthetic genes and cloned into suitable vectors. A plurality of synthetically cloned δ TCR chains, such as Vδ1Jδ1, Vδ1Jδ2, Vδ1Jδ3, Vδ1Jδ4, Vδ2 and Vδ3, chains can be co-transfected into a host system with synthetically cloned γ TCR chains such as Vγ2, Vγ3, Vγ4, Vγ5, Vγ8, Vγ9 and Vγ10 synthetically designed gene segments. In other cases, δ TCR chains, such as Vδ1Jδ1, Vδ1Jδ2, Vδ1Jδ3, Vδ1Jδ4, Vδ2 and Vδ3, chains can be amplified out of Total RNA extracted from human PBMCs or γδ T-cells isolated from human normal and malignant tissue.

The host system can be any suitable expression system such as 293 cells, insect cells, or a suitable in-vitro translation system. The plurality of various possible recombinations of synthetically designed γδ T-cell segments transfected into a host system can provide, for instance, more than 25, 30, 35, 40, 45, 50, 55, 60, 65, 70, 75, 80, 85, or 90 possible pairing combinations of γδ TCRs. The binding of an agent to one of the epitopes in the previously described library can be detected by contacting a labeled antibody, such as TS8.2, 15D, B6, TS-1, and R9.12, with an epitope of the library and detecting a signal from the label.

For epitope mapping, computational algorithms have also been developed which have been shown to map conformational discontinuous epitopes. Conformational epitopes can be identified by determining spatial conformation of amino acids with methods that include, e.g., x-ray crystallography and 2-dimensional nuclear magnetic resonance. Some epitope mapping methods, such as, x-ray analyses of crystals of antigen:antibody complexes can provide atomic resolution of the epitope. In other cases, computational combinatorial methods for epitope mapping can be employed to model a potential epitope based on the sequence of the antibody, such as TS-1 antibody or TS8.2 antibody. In such cases, the antigen binding portion of the antibody is sequenced, and computation models are used to reconstruct and predict a potential binding site of the antibody.

In some cases the disclosure provides a method of determining an epitope of a γδ T-cell receptor, comprising: (a) preparing a library of epitopes from the γδ T-cell receptor;

(b) contacting the library of epitopes with an antibody; and (b) identifying the amino acid sequence of at least one epitope in the library of epitopes that is bound by the antibody. In some cases, the antibody is selected from the group consisting of, TS8.2, 15D, B6, TS-1, and R9.12, antibodies. In one instance, the antibody is attached to a solid support. The library of epitopes can comprise sequences that correspond to continuous and discontinuous epitopes of a T-cell receptor, such as a γ TCR or a δ TCR. In some cases, the library of epitopes comprises fragments from a γδ T-cell receptor ranging from about 10 amino acids to about 30 amino acids in length, from about 10 amino acids to about 20 amino acids in length, or from about 5 amino acids to about 12 amino acids in length. In some cases, the antibody is labeled and the label is a radioactive molecule, a luminescent molecule, a fluorescent molecule, an enzyme, or biotin.

δ1 Epitope Bins

In some embodiments, the epitope, that is (e.g., specifically) recognized by an activating agent of interest is an epitope comprised of amino acids 47-70 of human Vδ1 (SKEMIFLIRQ GSDEQNA) (SEQ ID NO: 17) and J1 (TDKLIFGKGTRVTVEP) (SEQ ID NO: 18) or J2 (LTAQLFFGKGTQLIVEP) (SEQ ID NO: 19), wherein the activating agent does not bind an epitope containing a K120T mutation in J1 or J2. This epitope is referred to herein as a Bin 1 δ1 epitope. Exemplary activating agents that bind a Bin 1 δ1 epitope include but are not limited to TS-1; and δ1-18. A human Vδ1 J region can vary due to (D)(J) recombination, an exemplary Vδ1 J region of a δ1 chain of a γδ TCR having the Bin 1 δ1 epitope is SKEMIFLIRQGSDEQNAKSGRYSVNFKKAAKSVALTISALQLEDSAKYFCALGTGVRGLQDTDKLIFGKGTRVTVEP (SEQ ID NO: 20); and another exemplary Vδ1 J region Bin 1 δ1 epitope of a δ1 chain of a γδ TCR is (SEQ ID NO: 21)
SKEMIFLIRQGSDEQNAKSGRYSVNFKKAAKSVALTISALQLEDSAKYFC

ALGEAPSAWGKHLTAQLFFGKGTQLIVEP.

In some cases, activating agents that bind a Bin 1 δ1 epitope bind a δ1 chain of a γδ TCR having the sequence of: AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 22); but do not bind a δ1 chain of a γδ TCR having the sequence of:

(SEQ ID NO: 23)
AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGTGVRGL

QDSWDTRQMFFGTGIKLFVEP.

The activating agents that bind a Bin 1 δ1 epitope can also bind a δ1 chain of a γδ TCR having the sequence of:

(SEQ ID NO: 24)
AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGEAPSAW

GKHLTAQLFFGKGTQLIVEP.

In some embodiments, the epitope, that is (e.g., specifically) recognized by an activating agent of interest is an epitope comprised of amino acids 47-70 of human Vδ1 (SKEMIFLIRQ GSDEQNA) (SEQ ID NO: 17) and J1 (TDKLIFGKGTRVTVEP) (SEQ ID NO:18), wherein the activating agent does not bind an epitope containing a K120T mutation in J1. This epitope is referred to herein as a Bin 1b δ1 epitope. Exemplary activating agents that bind a Bin 1b δ1 epitope include but are not limited to δ1-37. An exemplary Vδ1 J region of a δ1 chain of a γδ TCR having the Bin 1b δ1 epitope is (SEQ ID NO: 20)
SKEMIFLIRQGSDEQNAKSGRYSVNFKKAAKSVALTISALQLEDSAKYFC

ALGTGVRGLQDTDKLIFGKGTRVTVEP.

In some cases, activating agents that bind a Bin 1b δ1 epitope bind a δ1 chain of a γδ TCR having the sequence of: AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 22); but do not bind a δ1 chain of a γδ TCR having the sequence of:

(SEQ ID NO: 23)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGTGVR

GLQDSWDTRQMFFGTGIKLFVEP.

The activating agents that bind a Bin 1b δ1 epitope also do not bind a δ1 chain of a γδ TCR having the sequence of:

(SEQ ID NO: 24)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGEAPS

AWGKHLTAQLFFGKGTQLIVEP.

In some embodiments, the epitope that is (e.g., specifically) recognized by an activating agent of interest is an epitope comprised of amino acids 11-21 of human Vδ1 (VSMPVRKAVTL) (SEQ ID NO: 26). This epitope is referred to herein as a Bin 2 δ1 epitope. Exemplary activating agents that bind a Bin 2 δ1 epitope include but are not limited to and δ1-285.

In some cases, activating agents that bind a Bin 2 δ1 epitope bind a δ1 chain of a γδ TCR having the sequence of: AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 22); but do not bind a δ1 chain of a γδ TCR having the sequence of:

(SEQ ID NO: 25)
AQKVTQVQRAMSSQLGEAVTLNCLYETSWWSYYIFWYKQLPSKEMIFLI

RQGSDEQNAKSGRYSVNFKKAAKSVALTISALQLEDSAKYFCALGTGVR

GLQDTDKLIFGKGTRVTVEPRSQPHTKPSVFVMKNGTNVACLVKEF.

In some embodiments, the epitope that is (e.g., specifically) recognized by an activating agent of interest is an epitope comprised of amino acids 11-21 of human Vδ1

(VSMPVRKAVTL) (SEQ ID NO: 26), wherein the activating agent that binds this epitope does not bind an epitope containing a mutation of R16 in Vδ1, such as an R16N mutation. This epitope is referred to herein as a Bin 2b δ1 epitope. Exemplary activating agents that bind a Bin 2b δ1 epitope include but are not limited to R9.12.

In some cases, activating agents that bind a Bin 2b δ1 epitope bind a δ1 chain of a γδ TCR having the sequence of:

AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 22); but do not bind a δ1 chain of a γδ TCR having the sequence of:

AQKVTQAQSSVSMPVNKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 27); and/or do not bind a δ1 chain of a γδ TCR having the sequence of:

```
                                           (SEQ ID NO: 25)
AQKVTQVQRAMSSQLGEAVTLNCLYETSWWSYYIFWYKQLPSKEMIFLI

RQGSDEQNAKSGRYSVNFKKAAKSVALTISALQLEDSAKYFCALGTGVR

GLQDTDKLIFGKGTRVTVEPRSQPHTKPSVFVMKNGTNVACLVKEF.
```

In some embodiments, the epitope that is (e.g., specifically) recognized by an activating agent of interest is an epitope comprised of amino acids 11-21 of human Vδ1 (VSMPVRKAVTL) (SEQ ID NO: 26), wherein the activating agent that binds this epitope also binds (cross-reacts) with δ3, δ4, and δ5 γδ TCRs. This epitope is referred to herein as a Bin 2c δ1 epitope. Exemplary activating agents that bind a Bin 2c δ1 epitope include but are not limited to δ1-39.

In some cases, activating agents that bind a Bin 2c δ1 epitope bind a δ1 chain of a γδ TCR having the sequence of:

AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 22); but do not bind a δ1 chain of a γδ TCR having the sequence of:

```
                                           (SEQ ID NO: 25)
AQKVTQVQRAMSSQLGEAVTLNCLYETSWWSYYIFWYKQLPSKEMIFLI

RQGSDEQNAKSGRYSVNFKKAAKSVALTISALQLEDSAKYFCALGTGVR

GLQDTDKLIFGKGTRVTVEPRSQPHTKPSVFVMKNGTNVACLVKEF.
```

In some embodiments, the epitope that is (e.g., specifically) recognized by an activating agent of interest is an epitope comprised of amino acids 80-95 of human Vδ1 (FKKAAKSVALTISALQ) (SEQ ID NO: 28) or 70 to 95 of human Vδ1 (AKSGRYSVNFKKAAKSVALTISALQ) (SEQ ID NO: 29). This epitope is referred to herein as a Bin 3 δ1 epitope. Exemplary activating agents that bind a Bin 3 δ1 epitope include but are not limited to δ1-08; and δ1-23.

In some cases, activating agents that bind a Bin 3 δ1 epitope bind a δ1 chain of a γδ TCR having the sequence of:

```
                                           (SEQ ID NO: 22)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGTGVR

GLQDTDKLIFGKGTRVTVEP
``` but do not bind a δ1 chain of a γδ TCR having the sequence of:

```
                                           (SEQ ID NO: 30)
AQKVTQVQRAMSSQLGEAVTLSCQYETSLSWYDIFWYKQLPSGEMTFLIH

QISSDQNAKNGRYSVNFQERHKFISLTISALQLEDSAKYFCALGTGVRGL

QDTDKLIFGKGTRVTVEPRSQPHTKPSVFVMKNGTNVACLVKEFYPKD.
```

In some embodiments, the epitope that is (e.g., specifically) recognized by an activating agent of interest is an epitope comprised of amino acids 1-11 of human Vδ1 (AQKVTQAQSSV) (SEQ ID NO: 227) and J1 or J2. This epitope is referred to herein as a Bin 4 δ1 epitope. In some cases, the Bin 4 δ1 epitope binding activating agent does not bind an epitope containing a K120T mutation in J1 or J2. Exemplary activating agents that bind a Bin 4 δ1 epitope include but are not limited to δ1-35; and δ1-203.

In some cases, activating agents that bind a Bin 4 δ1 epitope bind a δ1 chain of a γδ TCR having the sequence of:

AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGTGVRGLQDTDKLIFGKGTRVTVE P (SEQ ID NO: 22); but do not bind a δ1 chain of a γδ TCR having the sequence of:

```
                                           (SEQ ID NO: 23)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGTGVR

GLQDSWDTRQMFFGTGIKLFVEP.
```

In some cases, activating agents that bind a Bin 4 δ1 epitope bind a δ1 chain of a γδ TCR having the sequence of:

```
                                           (SEQ ID NO: 24)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGEAPS

AWGKHLTAQLFFGKGTQLIVEP.
```

In some embodiments, the epitope that is (e.g., specifically) recognized by an activating agent of interest is an epitope comprised of amino acids 28-47 of human Vδ1 (SWWSYYIFWYKQLPS) (SEQ ID NO: 31) and J1. This epitope is referred to herein as a Bin 5 δ1 epitope. Exemplary activating agents that bind a Bin 5 δ1 epitope include but are not limited to δ1-113; δ1-155; δ1-183; δ1-191; δ1-278; and δ1-282. An exemplary Vδ1 J1 region of a δ1 chain of a γδ TCR having the Bin 5 δ1 epitope is (SEQ ID NO: 32)
SWWSYYIFWYKQLPSKEMIFLIRQGSDEQNAKSGRYSVNFKKAAKSVAL

TISALQLEDSAKYFCALGTGVRGLQDTDKLIFGKGTRVTVEP.

In some cases, activating agents that bind a Bin 5 δ1 epitope bind a δ1 chain of a γδ TCR having the sequence of:
AQKVTQAQSSVSMPVRKAVTLNCLY-
ETSWWSYYIFWYKQLPSKEMIFLIRQGSDEQ NAKS-
GRYSVNFKKAAKSVALTISALQLEDSAKYFCAL-
GTGVRGLQDTDKLIFGKGTRVTVE P (SEQ ID NO: 22);
but do not bind a δ1 chain of a γδ TCR having the sequence of:

(SEQ ID NO: 24)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGEAPS

AWGKHLTAQLFFGKGTQLIVEP.

In some embodiments, the epitope that is (e.g., specifically) recognized by an activating agent of interest is an epitope comprised of amino acids 21-28 of human Vδ1 (LNCLYETS) (SEQ ID NO: 33) and J1. This epitope is referred to herein as a Bin 6 δ1 epitope. Exemplary activating agents that bind a Bin 6 δ1 epitope include but are not limited to TS 8.2 and δ1-143. An exemplary Vδ1 J1 region of a δ1 chain of a γδ TCR having the Bin 6 δ1 epitope is (SEQ ID NO: 34)
LNCLYETSWWSYYIFWYKQLPSKEMIFLIRQGSDEQNAKSGRYSVNFKKA

AKSVALTISALQLEDSAKYFCALGTGVRGLQDTDKLIFGKGTRVTVEP.

In some cases, activating agents that bind a Bin 6 δ1 epitope bind a δ1 chain of a γδ TCR having the sequence of:

AQKVTQAQSSVSMPVRKAVTLNCLY-ETSWWSYYIFWYKQLPSKEMIFLIRQGSDEQ NAKS-GRYSVNFKKAAKSVALTISALQLEDSAKYFCAL-GTGVRGLQDTDKLIFGKGTRVTVE P (SEQ ID NO: 22); but do not bind a δ1 chain of a γδ TCR having the sequence of:

(SEQ ID NO: 23)
AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGTGVRGL

QDSWDTRQMFFGTGIKLFVEP.

In some embodiments, the epitope that is (e.g., specifically) recognized by an activating agent of interest is an epitope comprised of amino acids 47-70 of human Vδ1 (SKEMIFLIRQGSDEQNA) (SEQ ID NO: 17) and J1 or J2. This epitope is referred to herein as a Bin 7 δ1 epitope. Exemplary activating agents that bind a Bin 7 δ1 epitope include but are not limited to δ1-149; δ1-253, and δ1-257. An exemplary Vδ1 J region of a δ1 chain of a γδ TCR having the Bin 7 δ1 epitope is SKEMIFLIRQGSDEQNAKS-GRYSVNFKKAAKSVALTISALQLEDSAKYFCAL-GTGVRGLQD TDKLIFGKGTRVTVEP (SEQ ID NO: 20); and another exemplary Vδ1 J region Bin 7 δ1 epitope of a δ1 chain of a γδ TCR is (SEQ ID NO: 21)
SKEMIFLIRQGSDEQNAKSGRYSVNFKKAAKSVALTISALQLEDSAKYFC

ALGEAPSAWGKHLTAQLFFGKGTQLIVEP.

In some cases, activating agents that bind a Bin 7 δ1 epitope bind a δ1 chain of a γδ TCR having the sequence of:

AQKVTQAQSSVSMPVRKAVTLNCLY-ETSWWSYYIFWYKQLPSKEMIFLIRQGSDEQ NAKS-GRYSVNFKKAAKSVALTISALQLEDSAKYFCAL-GTGVRGLQDTDKLIFGKGTRVTVE P (SEQ ID NO: 22); but do not bind a δ1 chain of a γδ TCR having the sequence of:

(SEQ ID NO: 23)
AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGTGVRGL

QDSWDTRQMFFGTGIKLFVEP.

In some embodiments, the epitope that is (e.g., specifically) recognized by an activating agent of interest is an epitope comprised of amino acids 70-80 of human Vδ1 (AKSGRYSVNF) (SEQ ID NO: 35) and J1 or J2. This epitope is referred to herein as a Bin 8 δ1 epitope. Exemplary activating agents that bind a Bin 8 δ1 epitope include but are not limited to δ1-192. An exemplary Vδ1 J region of a δ1 chain of a γδ TCR having the Bin 8 δ1 epitope is AKSGRYSVNFKKAAKSVALTISALQLEDSAKYFCAL-GTGVRGLQDTDKLIFGKGTRVTVEP (SEQ ID NO: 36); and another exemplary Vδ1 J region Bin 8 δ1 epitope of a δ1 chain of a γδ TCR is AKSGRYSVNFKKAAKSVALTI-SALQLEDSAKYFCALGEAPSAWGKHL-TAQLFFGKGTQLIV EP (SEQ ID NO: 37).

In some cases, activating agents that bind a Bin 8 δ1 epitope bind a δ1 chain of a γδ TCR having the sequence of:

AQKVTQAQSSVSMPVRKAVTLNCLY-ETSWWSYYIFWYKQLPSKEMIFLIRQGSDEQ NAKS-GRYSVNFKKAAKSVALTISALQLEDSAKYFCAL-GTGVRGLQDTDKLIFGKGTRVTVE P (SEQ ID NO: 22); but do not bind a δ1 chain of a γδ TCR having the sequence of:

(SEQ ID NO: 23)
AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGTGVRGL

QDSWDTRQMFFGTGIKLFVEP.

In some embodiments, the epitope that is (e.g., specifically) recognized by an activating agent of interest is an epitope comprised of amino acids 80-95 of human Vδ1 (FKKAAKSVALTISALQ) (SEQ ID NO: 28). This epitope is referred to herein as a Bin 9 δ1 epitope. Exemplary activating agents that bind a Bin 9 δ1 epitope include but are not limited to δ1-201.

In some cases, activating agents that bind a Bin 9 δ1 epitope bind a δ1 chain of a γδ TCR having the sequence of:

AQKVTQAQSSVSMPVRKAVTLNCLY-ETSWWSYYIFWYKQLPSKEMIFLIRQGSDEQ NAKS-GRYSVNFKKAAKSVALTISALQLEDSAKYFCAL-GTGVRGLQDTDKLIFGKGTRVTVE P (SEQ ID NO: 22); but do not bind a δ1 chain of a γδ TCR having the sequence of (SEQ ID NO: 38)
AQKVTQVQRAMSSQLGEAVTLSCQYETSLSWYDIFWYKQLPSGEMTFLIH

QISSDQNAKNGRYSVNFQERHKFISLTISALQLEDSAKYFCALGTGVRGL

QDTDKLIFGKGTRVTVEP.

The δ1-specific antibodies described herein selectively bind δ1-containing γδ-TCRs over δ2-containing γδ-TCRs. As such, the foregoing δ1-specific antibodies do not bind, e.g., the sequence of and/or a γδ-TCR comprising the sequence of:

(SEQ ID NO: 39)
AIELVPEHQTVPVSIGVPATLRCSMKGEAIGNYYINWYRKTQGNTMTFIY

REKDIYGPGFKDNFQGDIDIAKNLAVLKILAPSERDEGSYYCACDPLGGP

PDKLIFGKGTRVTVEP.

δ2 Epitope Bins

In some embodiments, the epitope, that is (e.g., specifically) recognized by an activating agent of interest is an epitope comprised of amino acids 83-94 of human Vδ2 (AKNLAVLKILAP) (SEQ ID NO: 40). This epitope is referred to herein as a Bin 1 δ2 epitope. In some cases, the activating agent that binds the Bin 1 δ2 epitope does not bind an epitope containing a mutation of K90 in Vδ2, such as an K90N mutation. Exemplary activating agents that bind a Bin 1 δ2 epitope include but are not limited to δ2-17, and Bδ.

In some cases, activating agents that bind a Bin 1 δ2 epitope bind a δ2 chain of a γδ TCR having the sequence of
AIELVPEHQTVPVSIGVPATLRCSMKGEAIGNYY-INWYRKTQGNTMTFIYREKDIYGP GFKDNFQGDIDI-AKNLAVLKILAPSERDEGSYY-CACDPLGGPPDKLIFGKGTRVTVEP (SEQ ID NO: 39); but do not bind a δ2 chain of a γδ TCR having the sequence of:

(SEQ ID NO: 41)
AIELVPEHQTVPVSIGVPATLRCSMKGEAIGNYYINWYRKTQGNTMTFIY

REKDIYGPGFKDNFQGDIDFLNNQAVLNILEASERDEGSYYCACDPLGGP

PDKLIFGKGTRVTVEP.

In some embodiments, the epitope, that is (e.g., specifically) recognized by an activating agent of interest is an epitope comprised of amino acids 28-38 of human Vδ2 (EAIGNYY) (SEQ ID NO: 42). This epitope is referred to herein as a Bin 2 δ2 epitope. In some cases, the activating agent that binds the Bin 2 δ2 epitope does not bind an epitope containing a mutation of G35 in Vδ2, such as an G35S mutation. Exemplary activating agents that bind a Bin 2 δ2 epitope include but are not limited to 15D.

In some cases, activating agents that bind a Bin 2 δ2 epitope bind a δ2 chain of a γδ TCR having the sequence of:
AIELVPEHQTVPVSIGVPATLRCSMKGEAIGNYY-INWYRKTQGNTMTFIYREKDIYGP GFK.DNFQGDIDI-AKNLAVLKILAPSERDEGSYY-CACDPLGGPPDKLIFGKGTRVTVEP (SEQ ID NO: 39); but do not bind a δ2 chain of a γδ TCR having the sequence of:

(SEQ ID NO: 43)
AIELVPEHQTVPVSIGVPATLRCSMKGDSISNYYTFWYRRTPGNTMTLIY

REGGTYGPGFEDNLQGEIDFLNNQAVLNILEASERDEGSYYCACDPLGGP

PDKLIFGKGTRVTVEP.

In some embodiments, the epitope, that is (e.g., specifically) recognized by an activating agent of interest is an epitope comprised of amino acids 72-83 of human Vδ2 (KDNFQGDIDIA) (SEQ ID NO: 44). This epitope is referred to herein as a Bin 3 δ2 epitope. Exemplary activating agents that bind a Bin 3 δ2 epitope include but are not limited to δ2-32.

In some cases, activating agents that bind a Bin 3 δ2 epitope bind a δ2 chain of a γδ TCR having the sequence of:
AIELVPEHQTVPVSIGVPATLRCSMKGEAIGNYY-INWYRKTQGNTMTFIYREKDIYGP GFK.DNFQGDIDI-AKNLAVLKILAPSERDEGSYY-CACDPLGGPPDKLIFGKGTRVTVEP (SEQ ID NO: 39); but do not bind a δ2 chain of a γδ TCR having the sequence of:

(SEQ ID NO: 45)
AIELVPEHQTVPVSIGVPATLRCSMKGEAIGNYYINWYRKTQGNTMTFIY

REKDIYGPGFEDNLQGEIDFLNNQAVLNILEASERDEGSYYCACDPLGGP

PDKLIFGKGTRVTVEP.

In some embodiments, the epitope, that is (e.g., specifically) recognized by an activating agent of interest is an epitope comprised of amino acids 1-27 of human Vδ2 (AIELVPEHQTVPVSIGVPATLRCSMKG) (SEQ ID NO: 46). This epitope is referred to herein as a Bin 4 δ2 epitope. Exemplary activating agents that bind a Bin 4 δ2 epitope include but are not limited to δ2-14; δ2-22; δ2-30; δ2-31; δ2-36; and δ2-37.

In some cases, activating agents that bind a Bin 4 δ2 epitope bind a δ2 chain of a γδ TCR having the sequence of:
AIELVPEHQTVPVSIGVPATLRCSMKGEAIGNYY-INWYRKTQGNTMTFIYREKDIYGP GFKDNFQGDIDI-AKNLAVLKILAPSERDEGSYY-CACDPLGGPPDKLIFGKGTRVTVEP (SEQ ID NO: 39); but do not bind a δ2 chain of a γδ TCR having the sequence of:

(SEQ ID NO: 47)
AVTLVPQNQARSVSVGESVTLRCSMKGDSISNYYTFWYRRTPGNTMTLIY

REGGTYGPGFEDNLQGEIDFLNNQAVLNILEASERDEGSYYCACDPLGGP

PDKLIFGKGTRVTVEP.

The δ2-specific antibodies described herein selectively bind δ2-containing γδ-TCRs over δ1-containing γδ-TCRs. As such, the foregoing δ2-specific antibodies do not bind, e.g., the sequence of and/or a γδ-TCR comprising the sequence of:

(SEQ ID NO: 22)
AQKVTQAQSSVSMPVRKAVTLNCLYETSWWSYYIFWYKQLPSKEMIFLIR

QGSDEQNAKSGRYSVNFKKAAKSVALTISALQLEDSAKYFCALGTGVRGL

QDTDKLIFGKGTRVTVEP.

Generally, the δ1- and δ2-specific antibodies described herein recognize a conformational epitope in the context of a γδ-TCR. In some cases, the δ1- and δ2-specific antibodies described herein are specific for one or more pairs of γδ1- or γδ2-TCRs respectively. For example, in some cases, the δ1-specific antibodies described herein are specific for a γ8δ1-TCR. In some cases, the δ1-specific antibodies described herein bind γ8δ1-TCR but not γ9δ1-TCR.

Methods of Treatment

Pharmaceutical compositions containing a non-engineered, enriched γδ T-cell population, an engineered, enriched γδ T-cell population, and/or admixtures thereof, as described herein may be administered for prophylactic and/or therapeutic treatments. In therapeutic applications, the compositions can be administered to a subject already suffering from a disease or condition in an amount sufficient to cure or at least partially arrest the symptoms of the disease or condition. A non-engineered, enriched γδ T-cell population, an engineered, enriched γδ T-cell population, and/or admixtures thereof, can also be administered to lessen a likelihood of developing, contracting, or worsening a condition. Effective amounts of a population of a non-engineered, enriched γδ T-cell population, an engineered, enriched γδ T-cell population, and/or admixtures thereof, for therapeutic use can vary based on the severity and course of the disease or condition, previous therapy, the subject's health status, weight, and/or response to the drugs, and/or the judgment of the treating physician.

A non-engineered, enriched γδ T-cell population, an engineered, enriched γδ T-cell population, and/or admixtures thereof, of the disclosure can be used to treat a subject in need of treatment for a condition. Examples of conditions include cancer, infectious disease, autoimmune disorder and sepsis. Subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants.

Figure 2:
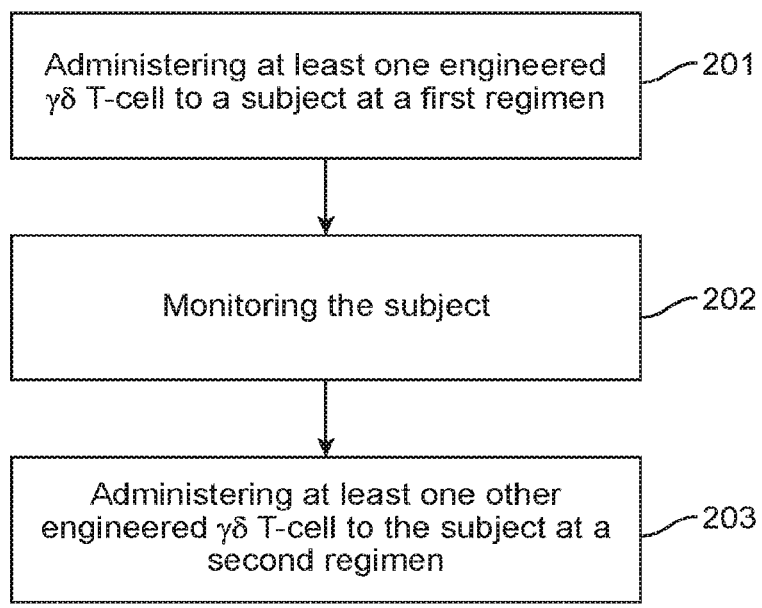
FIG. 2 schematically illustrates a method for treating a subject.

A method of treating a condition (e.g., ailment) in a subject with an enriched γδ T-cell population of the instant invention may comprise administering to the subject a therapeutically-effective amount of a non-engineered, enriched γδ T-cell population, an engineered, enriched γδ T-cell population, and/or admixtures thereof. An enriched γδ T-cell population, and/or admixtures thereof, of the disclosure may be administered at various regimens (e.g., timing, concentration, dosage, spacing between treatment, and/or formulation). A subject can also be preconditioned with, for example, chemotherapy, radiation, or a combination of both, prior to receiving a an enriched γδ T-cell population and/or admixtures thereof, of the disclosure. As part of a treatment, a non-engineered, enriched γδ T-cell population, an engineered, enriched γδ T-cell population, and/or admixtures thereof, may be administered to a subject at a first regimen and the subject may be monitored to determine whether the treatment at the first regimen meets a given level of therapeutic efficacy. In some cases, the engineered γδ T-cell or another engineered γδ T-cell may be administered to the subject at a second regimen. FIG. 2 schematically illustrates a method for treating a subject. In a first operation 201, at least one engineered γδ T-cell is administered to a subject that has or is suspected of having a given condition (e.g., cancer). The engineered γδ T-cell may be administered at a first regimen. In a second operation 202, the subject may be monitored, for example by a healthcare provider (e.g., treating physician or nurse). In some examples, the subject is monitored to determine or gauge an efficacy of the engineered γδ T-cell in treating the condition of the subject. In some situations, the subject may also be monitored to determine the in vivo expansion of a γδ T-cell population in the subject. Next, in a third operation 203, at least one other engineered γδ T-cell is administered to the subject at a second regimen. The second regimen may be the same as the first regimen or different than the first regimen. In some situations, the third operation 203 is not performed, for example, if the administration of the engineered γδ T-cell in the first operation 201 is found to be effective (e.g., a single round of administration may be sufficient to treat the condition). Due to their allogeneic and universal donor characteristics, a population of engineered γδ T-cells may be administrated to various subjects, with different MHC haplotypes. An engineered γδ T-cell may be frozen or cryopreserved prior to being administered to a subject.

Figure 3:
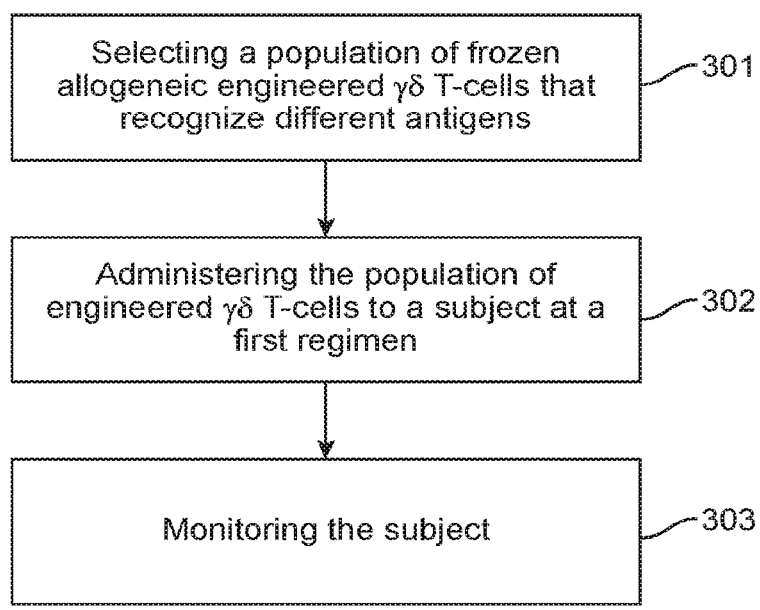
FIG. 3 schematically illustrates a method for administrating a population of engineered γδ T-cells to a subject.

A enriched population of γδ T-cells (i.e., engineered or non-engineered) and/or admixtures thereof, may also be frozen or cryopreserved prior to being administered to a subject. In certain embodiments, a population of engineered, enriched γδ T-cells can comprise two or more cells that express identical, different, or a combination of identical and different tumor recognition moieties. For instance, a population of engineered, enriched γδ T-cells can comprises several distinct engineered γδ T-cells that are designed to recognize different antigens, or different epitopes of the same antigen. For example, human cells afflicted with melanoma can express the NY-ESO-1 oncogene. Infected cells within the human can process the NY-ESO-1 oncoprotein into smaller fragments and present various portions of the NY-ESO-1 protein for antigen recognition. A population of engineered, enriched γδ T-cells can comprise various engineered γδ T-cells that express different tumor recognition moieties designed to recognize different portions of the NY-ESO-1 protein. FIG. 3 schematically illustrates a method for treating a subject with a population of engineered γδ T-cells that recognizes different epitopes of the melanoma antigen NY-ESO-1. In a first operation 301, a population of engineered γδ T-cells that recognize different epitopes of the same antigen is selected. For example, the population of engineered γδ T-cells may comprise two or more cells that expressing different tumor recognition moieties that recognize different portions of the NY-ESO-1 protein. In a second operation 302, The population of engineered γδ T-cells may be administered at a first regimen. In a second operation 303, the subject may be monitored, for example by a healthcare provider (e.g., treating physician or nurse).

An enriched γδ T-cell population, i.e., non-engineered or engineered, and/or admixtures thereof, of the disclosure may be used to treat various conditions. In some cases, a non-engineered, enriched γδ T-cell population, an engineered, enriched γδ T-cell population, and/or admixtures thereof, of the disclosure may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some cases, a non-engineered, enriched γδ T-cell population, an engineered, enriched γδ T-cell population, and/or admixtures thereof, of the disclosure may be used to treat an infectious disease. An infectious disease may be caused, for example, by a pathogenic bacterium or by a virus. Various pathogenic proteins, nucleic acids, lipids, or fragments thereof can be expressed by a diseased cell. An antigen presenting cell can internalize such pathogenic molecules, for instance with phagocytosis or by receptor-mediated endocytosis, and display a fragment of the antigen bound to an appropriate MHC molecule. For instance, various 9 mer fragments of a pathogenic protein may be displayed by an APC. Engineered, enriched γδ T-cell populations of the disclosure may be designed to recognize various antigens and antigen fragments of a pathogenic bacterium or a virus. Non-limiting examples of pathogenic bacteria can be found in the: a) *Bordetella* genus, such as *Bordetella pertussis* species; b) *Borrelia* genus, such *Borrelia burgdorferi* species; c) *Brucella* genus, such as *Brucella* abortus, *Brucella canis, Brucella meliterisis*, and/or *Brucella suis* species; d) *Campylobacter* genus, such as *Campylobacter jejuni* species; e) *Chlamydia* and *Chlamydophila* genuses, such as *Chlamydia* pneumonia, *Chlamydia trachomatis*, and/or *Chlamydophila psittaci* species; f) *Clostridium* genus, such as *Clostridium botulinum, Clostridium difficile, Clostridium perfringens, Clostridium tetani* species; g) *Corynebacterium* genus, such as *Corynebacterium diphtheria* species; h) *Enterococcus* genus, such as *Enterococcus faecalis*, and/or *Enterococcus faecium* species; i) *Escherichia* genus, such as *Escherichia coli* species; j) *Francisella* genus, such as *Francisella tularensis* species; k) *Haemophilus* genus, such as *Haemophilus influenza* species; 1) *Helicobacter* genus, such as *Helicobacter pylori* species; m) *Legionella* genus, such as *Legionella pneumophila* species; n) *Leptospira* genus, such as *Leptospira interrogans* species; o) *Listeria* genus, such as *Listeria monocytogenes* species; p) *Mycobacterium* genus, such as *Mycobacterium leprae, Mycobacterium tuberculosis*, and/or *mycobacterium ulcerans* species; q) *Mycoplasma* genus, such as *Mycoplasma pneumonia* species; r) *Neisseria* genus, such as *Neisseria gonorrhoeae* and/or *Neisseria meningitidia* species; s) *Pseudomonas* genus, such as *Pseudomonas aeruginosa* species; t) *Rickettsia* genus, such as *Rickettsia rickettsii* species; u) *Salmonella* genus, such as *Salmonella typhi* and/or *Salmonella typhimurium* species; v) *Shigella* genus, such as *Shigella sonnei* species; w) *Staphylococcus* genus, such as *Staphylococcus aureus, Staphylococcus epidermidis*, and/or *Staphylococcus saprophyticus* species; x) *Streptococcus* genus, such as *Streptococcus* agalactiae, *Streptococcus pneumonia*, and/or *Streptococcus pyogenes* species; y) *Treponema* genus, such as *Treponema pallidum* species; z) *Vibrio* genus, such as *Vibrio cholera*; and/or aa) *Yersinia* genus, such as *Yersinia pestis* species.

In some cases, a non-engineered, enriched γδ T-cell population, an engineered, enriched γδ T-cell population, and/or admixtures thereof, of the disclosure may be used to treat an infectious disease, an infectious disease may be caused a virus. Non-limiting examples of viruses can be found in the following families of viruses and are illustrated with exemplary species: a) Adenoviridae family, such as Adenovirus species; b) Herpesviridae family, such as Herpes simplex type 1, Herpes simplex type 2, Varicella-zoster virus, Epstein-barr virus, Human cytomegalovirus, Human herpesvirus type 8 species; c) Papillomaviridae family, such as Human papillomavirus species; d) Polyomaviridae family, such as BK virus, JC virus species; e) Poxviridae family, such as Smallpox species; f) Hepadnaviridae family, such as Hepatitis B virus species; g) Parvoviridae family, such as Human bocavirus, Parvovirus B19 species; h) Astroviridae family, such as Human astrovirus species; i) Caliciviridae family, such as Norwalk virus species; j) Flaviviridae family, such as Hepatitis C virus (HCV), yellow fever virus, dengue virus, West Nile virus species; k) Togaviridae family, such as *Rubella* virus species; l) Hepeviridae family, such as Hepatitis E virus species; m) Retroviridae family, such as Human immunodeficiency virus (HIV) species; n) Orthomyxoviridaw family, such as Influenza virus species; o) Arenaviridae family, such as Guanarito virus, Junin virus, Lassa virus, Machupo virus, and/or Sabia virus species; p) Bunyaviridae family, such as Crimean-Congo hemorrhagic fever virus species; q) Filoviridae family, such as Ebola virus and/or Marburg virus species; Paramyxoviridae family, such as Measles virus, Mumps virus, Parainfluenza virus, Respiratory syncytial virus, Human metapneumovirus, Hendra virus and/or Nipah virus species; r) Rhabdoviridae genus, such as Rabies virus species; s) Reoviridae family, such as Rotavirus, Orbivirus, Coltivirus and/or Banna virus species. In some examples, a virus is unassigned to a viral family, such as Hepatitis D.

In some cases, a non-engineered, enriched γδ T-cell population, an engineered, enriched γδ T-cell population, and/or admixtures thereof, of the disclosure may be used to treat an immune disease, such as an autoimmune disease. Inflammatory diseases, including autoimmune diseases are also a class of diseases associated with B-cell disorders. Examples of immune diseases or conditions, including autoimmune conditions, include: rheumatoid arthritis, rheumatic fever, multiple sclerosis, experimental autoimmune encephalomyelitis, psoriasis, uveitis, diabetes mellitus, systemic lupus erythematosus (SLE), lupus nephritis, eczema, scleroderma, polymyositis/scleroderma, polymyositis/dermatomyositis, unceratіve protitis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, HIV, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis, acute idiopathic thrombocytopenic purpura, chronic idiopathic thrombocytopenia purpura, dermatomyositis, Sydenham'a chorea, myasthenia gravis, polyglandular syndromes, bullous pemphigoid, Henoch-Schonlein purpura, poststreptococcalnephritis, erythema nodosum, erythema multiforme, gA nephropathy, Takayasu's arteritis, Addison's disease, sarcoidosis, ulcerative colitis, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, chronic active hepatitis, polychondritis, pamphigus vulgaris, Wegener's granulomatosis, membranous nephropathy, amyotrophic lateral sclerosis, tabes *dorsalis*, giant cell arteritis,/polymyalgia, peraiciousanemia, rapidly progressive glomerulonephritis, psoriasis, fibrosing alveolitis, and cancer.

Treatment with a γδ T-cell population, and/or admixtures thereof, of the disclosure may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can comprise administering to a subject a pharmaceutical composition comprising a non-engineered, enriched γδ T-cell population, an engineered, enriched γδ T-cell population, and/or admixture thereof, of the disclosure.

In some cases, administration of a non-engineered, enriched γδ T-cell population, an engineered, enriched γδ T-cell population, and/or admixture thereof, of the disclosure to a subject modulates the activity of endogenous lymphocytes in a subject's body. In some cases, administration of the non-engineered, enriched γδ T-cell population, an engineered, enriched γδ T-cell population, and/or admixtures thereof, to a subject provides an antigen to an endogenous T-cell and may boost an immune response. In some cases, the memory T-cell is a CD4+ T-cell. In some cases, the memory T-cell is a CD8+ T-cell. In some cases, administration of the non-engineered, enriched γδ T-cell population, an engineered, enriched γδ T-cell population, and/or admixtures thereof, to a subject activates the cytotoxicity of another immune cell. In some cases, the other immune cell is a CD8+ T-cell. In some cases, the other immune cell is a Natural Killer T-cell. In some cases, administration of the non-engineered, enriched γδ T-cell population, an engineered, enriched γδ T-cell population, and/or admixtures thereof, to a subject suppress a regulatory T-cell. In some cases, the regulatory T-cell is a Fox3+ Treg cell. In some cases, the regulatory T-cell is a Fox3-Treg cell. Non-limiting examples of cells whose activity can be modulated by a non-engineered, enriched γδ T-cell population, an engineered, enriched γδ T-cell population, and/or admixtures thereof, of the disclosure include: hematopioietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells.

During most bone marrow transplants, a combination of cyclophosphamide with total body irradiation is conventionally employed to prevent rejection of the hematopietic stem cells (HSC) in the transplant by the subject's immune system. In some cases, incubation of donor bone marrow with interleukin-2 (IL-2) ex vivo is performed to enhance the generation of killer lymphocytes in the donor marrow. Interleukin-2 (IL-2) is a cytokine that is necessary for the growth, proliferation, and differentiation of wild-type lymphocytes. Current studies of the adoptive transfer of γδ T-cells into humans may require the co-administration of γδ T-cells and interleukin-2. However, both low- and high-dosages of IL-2 can have highly toxic side effects. IL-2 toxicity can manifest in multiple organs/systems, most significantly the heart, lungs, kidneys, and central nervous system. In some cases, the disclosure provides a method for administrating a non-engineered, enriched γδ T-cell population, an engineered, enriched γδ T-cell population, and/or admixtures thereof, to a subject without the co-administration of a cytokine, such as IL-2, IL-15, IL-12, or IL-21. In some cases, a non-engineered, enriched γδ T-cell population, an engineered, enriched γδ T-cell population, and/or admixtures thereof, can be administered to a subject without co-administration with IL-2. In some cases, a non-engineered, enriched γδ T-cell population, an engineered, enriched γδ T-cell population, and/or admixtures thereof, is administered to a subject during a procedure, such as a bone marrow transplant without the co-administration of IL-2.

Methods of Administration

One or multiple non-engineered, enriched γδ T-cell population, engineered, enriched γδ T-cell population, and/or admixtures thereof, of the invention can be administered to a subject in any order or simultaneously. If simultaneously, the multiple non-engineered, enriched γδ T-cell population, engineered, enriched γδ T-cell population, and/or admixtures thereof, of the invention can be provided in a single, unified form, such as an intravenous injection, or in multiple forms, for example, as multiple intravenous infusions, s.c, injections or pills. The non-engineered, enriched γδ T-cell population, engineered, enriched γδ T-cell population, and/or admixtures thereof, of the invention can be packed together or separately, in a single package or in a plurality of packages. One or all of the non-engineered, enriched γδ T-cell population, engineered, enriched γδ T-cell population, and/or admixtures thereof, of the invention can be given in multiple doses. If not simultaneous, the timing between the multiple doses may vary to as much as about a week, a month, two months, three months, four months, five months, six months, or about a year. In some cases, a non-engineered, enriched γδ T-cell population, an engineered, enriched γδ T-cell population, and/or admixtures thereof, of the invention can expand within a subject's body, in vivo, after administration to a subject. Non-engineered, enriched γδ T-cell population, engineered, enriched γδ T-cell population, and/or admixtures thereof, can be frozen to provide cells for multiple treatments with the same cell preparation. Non-engineered, enriched γδ T-cell population, engineered, enriched γδ T-cell population, and/or admixtures thereof, of the disclosure, and pharmaceutical compositions comprising the same, can be packaged as a kit. A kit may include instructions (e.g., written instructions) on the use of the non-engineered, enriched γδ T-cell population, the engineered, enriched γδ T-cell population, and/or admixtures thereof, and compositions comprising the same.

In some cases, a method of treating a cancer comprises administering to a subject a therapeutically-effective amount of a non-engineered, enriched γδ T-cell population, an engineered, enriched γδ T-cell population, and/or admixtures thereof, wherein the administration treats the cancer. In some embodiments the therapeutically-effective amount of the non-engineered, enriched γδ T-cell population, the engineered, enriched γδ T-cell population, and/or admixtures thereof, is administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In some embodiments the therapeutically-effective amount of the non-engineered, enriched γδ T-cell population, the engineered, enriched γδ T-cell population, and/or admixtures thereof, is administered for at least one week. In some embodiments the therapeutically-effective amount of the non-engineered, enriched γδ T-cell population, the engineered, enriched γδ T-cell population, and/or admixtures thereof, is administered for at least two weeks.

A non-engineered, enriched γδ T-cell population, an engineered, enriched γδ T-cell population, and/or admixtures thereof, described herein can be administered before, during, or after the occurrence of a disease or condition, and the timing of administering a pharmaceutical composition containing a non-engineered, enriched γδ T-cell population, an engineered, enriched γδ T-cell population, and/or admixtures thereof, can vary. For example, the non-engineered, enriched γδ T-cell population, the engineered, enriched γδ T-cell population, and/or admixtures thereof, can be used as a prophylactic and can be administered continuously to subjects with a propensity to conditions or diseases in order to lessen a likelihood of the occurrence of the disease or condition. The non-engineered, enriched γδ T-cell population, the engineered, enriched γδ T-cell population, and/or admixtures thereof, can be administered to a subject during or as soon as possible after the onset of the symptoms. The administration of the non-engineered, enriched γδ T-cell population, the engineered, enriched γδ T-cell population, and/or admixtures thereof, can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In some examples, the administration of a non-engineered, enriched γδ T-cell population, an engineered, enriched γδ T-cell population, and/or admixtures thereof, of the disclosure is an intravenous administration. One or multiple dosages of a non-engineered, enriched γδ T-cell population, an engineered, enriched γδ T-cell population, and/or admixtures thereof, can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of a non-engineered, enriched γδ T-cell population, an engineered, enriched γδ T-cell population, and/or admixtures thereof, can be administered years after onset of the cancer and before or after other treatments. In some examples, a non-engineered, enriched γδ T-cell population, an engineered, enriched γδ T-cell population, and/or admixtures thereof, can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject.

Dosages

A non-engineered, enriched γδ T-cell population, an engineered, enriched γδ T-cell population, and/or admixtures thereof, as disclosed herein may be formulated in unit dosage forms suitable for single administration of precise dosages. In some cases, the unit dosage forms comprise additional lymphocytes. In unit dosage form, the formulation is divided into unit doses containing appropriate quantities of one or more compounds. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Multiple-dose reclosable containers can be used, for example, in combination with a preservative or without a preservative. In some examples, the pharmaceutical composition does not comprise a preservative. Formulations for parenteral injection can be presented in unit dosage form, for example, in ampoules, or in multi-dose containers with a preservative.

A non-engineered, enriched γδ T-cell population, an engineered, enriched γδ T-cell population, and/or admixtures thereof, as described herein may be present in a composition in an amount of at least 5 cells, at least 10 cells, at least 20 cells, at least 30 cells, at least 40 cells, at least 50 cells, at least 60 cells, at least 70 cells, at least 80 cells, at least 90 cells, at least 100 cells, at least 200 cells, at least 300 cells, at least 400 cells, at least 500 cells, at least 600 cells, at least 700 cells, at least 800 cells, at least 900 cells, at least $1 \times 10^3$ cells, at least $2 \times 10^3$ cells, at least $3 \times 10^3$ cells, at least $4 \times 10^3$ cells, at least $5 \times 10^3$ cells, at least $6 \times 10^3$ cells, at least $7 \times 10^3$ cells, at least $8 \times 10^3$ cells, at least $9 \times 10^3$ cells, at least $1 \times 10^4$ cells, at least $2 \times 10^4$ cells, at least $3 \times 10^4$ cells, at least $4 \times 10^4$ cells, at least $5 \times 10^4$ cells, at least $6 \times 10^4$ cells, at least $7 \times 10^4$ cells, at least $8 \times 10^4$ cells, at least $9 \times 10^4$ cells, at least $1 \times 10^5$ cells, at least $2 \times 10^5$ cells, at least $3 \times 10^5$ cells, at least $4 \times 10^5$ cells, at least $5 \times 10^5$ cells, at least $6 \times 10^5$ cells, at least $7 \times 10^5$ cells, at least $8 \times 10^5$ cells, at least $9 \times 10^5$ cells, at least $1 \times 10^6$ cells, at least $2 \times 10^6$ cells, at least $3 \times 10^6$ cells, at least $4 \times 10^6$ cells, at least $5 \times 10^6$ cells, at least $6 \times 10^6$ cells, at least $7 \times 10^6$ cells, at least $8 \times 10^6$ cells, at least $9 \times 10^6$ cells, at least $1 \times 10^7$ cells, at least $2 \times 10^7$ cells, at least $3 \times 10^7$ cells, at least $4 \times 10^7$ cells, at least $5 \times 10^7$ cells, at least $6 \times 10^7$ cells, at least $7 \times 10^7$ cells, at least $8 \times 10^7$ cells, at least $9 \times 10^7$ cells, at least $1 \times 10^8$ cells, at least $2 \times 10^8$ cells, at least $3 \times 10^8$ cells, at least $4 \times 10^8$ cells, at least $5\times10^8$ cells, at least $6\times10^8$ cells, at least $7\times10^8$ cells, at least $8\times10^8$ cells, at least $9\times10^8$ cells, at least $1\times10^9$ cells, or more.

The therapeutically effective dose of a non-engineered, enriched γδ T-cell population, an engineered, enriched γδ T-cell population, and/or admixtures thereof, of the invention can be from about 1 cell to about 10 cells, from about 1 cell to about 100 cells, from about 1 cell to about 10 cells, from about 1 cell to about 20 cells, from about 1 cell to about 30 cells, from about 1 cell to about 40 cells, from about 1 cell to about 50 cells, from about 1 cell to about 60 cells, from about 1 cell about 70 cells, from about 1 cell to about 80 cells, from about 1 cell to about 90 cells, from about 1 cell to about 100 cells, from about 1 cell to about $1\times10^3$ cells, from about 1 cell to about $2\times10^3$ cells, from about 1 cell to about $3\times10^3$ cells, from about 1 cell to about $4\times10^3$ cells, from about 1 cell to about $5\times10^3$ cells, from about 1 cell to about $6\times10^3$ cells, from about 1 cell to about $7\times10^3$ cells, from about 1 cell to about $8\times10^3$ cells, from about 1 cell to about $9\times10^3$ cells, from about 1 cell to about $1\times10^4$ cells, from about 1 cell to about $2\times10^4$ cells, from about 1 cell to about $3\times10^4$ cells, from about 1 cell to about $4\times10^4$ cells, from about 1 cell to about $5\times10^4$ cells, from about 1 cell to about $6\times10^4$ cells, from about 1 cell to about $7\times10^4$ cells, from about 1 cell to about $8\times10^4$ cells, from about 1 cell to about $9\times10^4$ cells, from about 1 cell to about $1\times10^5$ cells, from about 1 cell to about $2\times10^5$ cells, from about 1 cell to about $3\times10^5$ cells, from about 1 cell to about $4\times10^5$ cells, from about 1 cell to about $5\times10^5$ cells, from about 1 cell to about $6\times10^5$ cells, from about 1 cell to about $7\times10^5$ cells, from about 1 cell to about $8\times10^5$ cells, from about 1 cell to about $9\times10^5$ cells, from about 1 cell to about $1\times10^6$ cells, from about 1 cell to about $2\times10^6$ cells, from about 1 cell to about $3\times10^6$ cells, from about 1 cell to about $4\times10^6$ cells, from about 1 cell to about $5\times10^6$ cells, from about 1 cell to about $6\times10^6$ cells, from about 1 cell to about $7\times10^6$ cells, from about 1 cell to about $8\times10^6$ cells, from about 1 cell to about $9\times10^6$ cells, from about 1 cell to about $1\times10^7$ cells, from about 1 cell to about $2\times10^7$ cells, from about 1 cell to about $3\times10^7$ cells, from about 1 cell to about $4\times10^7$ cells, from about 1 cell to about $5\times10^7$ cells, from about 1 cell to about $6\times10^7$ cells, from about 1 cell to about $7\times10^7$ cells, from about 1 cell to about $8\times10^7$ cells, from about 1 cell to about $9\times10^7$ cells, from about 1 cell to about $1\times10^8$ cells, from about 1 cell to about $2\times10^8$ cells, from about 1 cell to about $3\times10^8$ cells, from about 1 cell to about $4\times10^8$ cells, from about 1 cell to about $5\times10^8$ cells, from about 1 cell to about $6\times10^8$ cells, from about 1 cell to about $7\times10^8$ cells, from about 1 cell to about $8\times10^8$ cells, from about 1 cell to about $9\times10^8$ cells, or from about 1 cell to about $1\times10^9$ cells.

In some cases, the therapeutically effective dose of a non-engineered, enriched γδ T-cell population, an engineered, enriched γδ T-cell population, and/or admixtures thereof, of the invention can be from about $1\times10^3$ cells to about $2\times10^3$ cells, from about $1\times10^3$ cells to about $3\times10^3$ cells, from about $1\times10^3$ cells to about $4\times10^3$ cells, from about $1\times10^3$ cells to about $5\times10^3$ cells, from about $1\times10^3$ cells to about $6\times10^3$ cells, from about $1\times10^3$ cells to about $7\times10^3$ cells, from about $1\times10^3$ cells to about $8\times10^3$ cells, from about $1\times10^3$ cells to about $9\times10^3$ cells, from about $1\times10^3$ cells to about $1\times10^4$ cells, from about $1\times10^3$ cells to about $2\times10^4$ cells, from about $1\times10^3$ cells to about $3\times10^4$ cells, from about $1\times10^3$ cells to about $4\times10^4$ cells, from about $1\times10^3$ cells to about $5\times10^4$ cells, from about $1\times10^3$ cells to about $6\times10^4$ cells, from about $1\times10^3$ cells to about $7\times10^4$ cells, from about $1\times10^3$ cells to about $8\times10^4$ cells, from about $1\times10^3$ cells to about $9\times10^4$ cells, from about $1\times10^3$ cells to about $1\times10^5$ cells, from about $1\times10^3$ cells to about $2\times10^5$ cells, from about $1\times10^3$ cells to about $3\times10^5$ cells, from about $1\times10^3$ cells to about $4\times10^5$ cells, from about $1\times10^3$ cells to about $5\times10^5$ cells, from about $1\times10^3$ cells to about $6\times10^5$ cells, from about $1\times10^3$ cells to about $7\times10^5$ cells, from about $1\times10^3$ cells to about $8\times10^5$ cells, from about $1\times10^3$ cells to about $9\times10^5$ cells, from about $1\times10^3$ cells to about $1\times10^6$ cells, from about $1\times10^3$ cells to about $2\times10^6$ cells, from about $1\times10^3$ cells to about $3\times10^6$ cells, from about $1\times10^3$ cells to about $4\times10^6$ cells, from about $1\times10^3$ cells to about $5\times10^6$ cells, from about $1\times10^3$ cells to about $6\times10^6$ cells, from about $1\times10^3$ cells to about $7\times10^6$ cells, from about $1\times10^3$ cells to about $8\times10^6$ cells, from about $1\times10^3$ cells to about $9\times10^6$ cells, from about $1\times10^3$ cells to about $1\times10^7$ cells, from about $1\times10^3$ cells to about $2\times10^7$ cells, from about $1\times10^3$ cells to about $3\times10^7$ cells, from about $1\times10^3$ cells to about $4\times10^7$ cells, from about $1\times10^3$ cells to about $5\times10^7$ cells, from about $1\times10^3$ cells to about $6\times10^7$ cells, from about $1\times10^3$ cells to about $7\times10^7$ cells, from about $1\times10^3$ cells to about $8\times10^7$ cells, from about $1\times10^3$ cells to about $9\times10^7$ cells, from about $1\times10^3$ cells to about $1\times10^8$ cells, from about $1\times10^3$ cells to about $2\times10^8$ cells, from about $1\times10^3$ cells to about $3\times10^8$ cells, from about $1\times10^3$ cells to about $4\times10^8$ cells, from about $1\times10^3$ cells to about $5\times10^8$ cells, from about $1\times10^3$ cells to about $6\times10^8$ cells, from about $1\times10^3$ cells to about $7\times10^8$ cells, from about $1\times10^3$ cells to about $8\times10^8$ cells, from about $1\times10^3$ cells to about $9\times10^8$ cells, or from about $1\times10^3$ cells to about $1\times10^9$ cells.

In some cases, the therapeutically effective dose of a non-engineered, enriched γδ T-cell population, an engineered, enriched γδ T-cell population, and/or admixtures thereof, of the invention can be from about $1\times10^6$ cells to about $2\times10^6$ cells, from about $1\times10^6$ cells to about $3\times10^6$ cells, from about $1\times10^6$ cells to about $4\times10^6$ cells, from about $1\times10^6$ cells to about $5\times10^6$ cells, from about $1\times10^6$ cells to about $6\times10^6$ cells, from about $1\times10^6$ cells to about $7\times10^6$ cells, from about $1\times10^6$ cells to about $8\times10^6$ cells, from about $1\times10^6$ cells to about $9\times10^6$ cells, from about $1\times10^6$ cells to about $1\times10^7$ cells, from about $1\times10^6$ cells to about $2\times10^7$ cells, from about $1\times10^6$ cells to about $3\times10^7$ cells, from about $1\times10^6$ cells to about $4\times10^7$ cells, from about $1\times10^6$ cells to about $5\times10^7$ cells, from about $1\times10^6$ cells to about $6\times10^7$ cells, from about $1\times10^6$ cells to about $7\times10^7$ cells, from about $1\times10^6$ cells to about $8\times10^7$ cells, from about $1\times10^6$ cells to about $9\times10^7$ cells, from about $1\times10^6$ cells to about $1\times10^8$ cells, from about $1\times10^6$ cells to about $2\times10^8$ cells, from about $1\times10^6$ cells to about $3\times10^8$ cells, from about $1\times10^6$ cells to about $4\times10^8$ cells, from about $1\times10^6$ cells to about $5\times10^8$ cells, from about $1\times10^6$ cells to about $6\times10^8$ cells, from about $1\times10^6$ cells to about $7\times10^8$ cells, from about $1\times10^6$ cells to about $8\times10^8$ cells, from about $1\times10^6$ cells to about $9\times10^8$ cells, from about $1\times10^6$ cells to about $1\times10^9$ cells, from about $1\times10^6$ cells to about $2\times10^9$ cells, from about $1\times10^6$ cells to about $3\times10^9$ cells, from about $1\times10^6$ cells to about $4\times10^9$ cells, from about $1\times10^6$ cells to about $5\times10^9$ cells, from about $1\times10^6$ cells to about $6\times10^9$ cells, from about $1\times10^6$ cells to about $7\times10^9$ cells, from about $1\times10^6$ cells to about $8\times10^9$ cells, from about $1\times10^6$ cells to about $9\times10^9$ cells, from about $1\times10^7$ cells to about $1\times10^9$ cells, from about $1\times10^7$ cells to about $2\times10^9$ cells, from about $1\times10^7$ cells to about $3\times10^9$ cells, from about $1\times10^7$ cells to about $4\times10^9$ cells, from about $1\times10^7$ cells to about $5\times10^9$ cells, from about $1\times10^7$ cells to about $6\times10^9$ cells, from about $1\times10^7$ cells to about $7\times10^9$ cells, from about $1\times10^7$ cells to about $8\times10^9$ cells, from about $1\times10^7$ cells to about $9\times10^9$ cells, from about 1×10⁸ cells to about 1×10⁹ cells, from about 1×10⁸ cells to about 2×10⁹ cells, from about 1×10⁸ cells to about 3×10⁹ cells, from about 1×10⁸ cells to about 4×10⁹ cells, from about 1×10⁸ cells to about 5×10⁹ cells, from about 1×10⁸ cells to about 6×10⁹ cells, from about 1×10⁸ cells to about 7×10⁹ cells, from about 1×10⁸ cells to about 8×10⁹ cells, from about 1×10⁸ cells to about 9×10⁹ cells, or from about 1×10⁹ cells to about 1×10¹⁰ cells.

Preservation

In some embodiments, enriched γδ T-cell populations, and/or admixtures thereof, may be formulated in freezing media and placed in cryogenic storage units such as liquid nitrogen freezers (−195C) or ultra-low temperature freezers (−85C, −80C or −120C) for long-term storage of at least about 1 month, 2 months, 3 months, 4 months, 5 months, 6 months, 1 year, 2 years, 3 years, or at least 5 years. The freeze media can contain dimethyl sulfoxide (DMSO), and/or sodium chloride (NaCl), and/or dextrose, and/or dextran sulfate and/or hydrohyethyl starch (HES) with physiological pH buffering agents to maintain pH between about 6.0 to about 6.5, about 6.5 to about 7.0, about 7.0 to about 7.5, about 7.5 to about 8.0 or about 6.5 to about 7.5. The cryopreserved γδ T-cells can be thawed and further processed by stimulation with antibodies, proteins, peptides, and/or cytokines as described herein. The cryopreserved γδ T-cells can be thawed and genetically modified with viral vectors (including retroviral and lentiviral vectors) or non-viral means (including RNA, DNA, and proteins) as described herein. Alternatively, non-engineered γδ T-cells can be expanded by the methods described herein, genetically modified, and cryopreserved.

Thus, genetically engineered and/or non-engineered γδ T-cells can be further cryopreserved to generate cell banks in quantities of at least about 1, 5, 10, 100, 150, 200, 500 vials at about at least 10¹, 10², 10³, 10⁴, 10⁵, 10⁶, 10⁷, 10⁸, 10⁹, or at least about 10¹⁰ cells per mL in freeze media. The cryopreserved cell banks may retain their functionality and can be thawed and further stimulated and expanded. In some aspects, thawed cells can be stimulated and expanded in suitable closed vessels such as cell culture bags and/or bioreactors to generate quantities of cells as allogeneic cell product. Cryopreserved γδ T-cells can maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In some aspects, no preservatives are used in the formulation. The cryopreserved γδ T-cells can be thawed and infused into multiple patients as allogeneic off-the-shelf cell product.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

The present invention is explained in more detail by the following non-limiting examples.

EXAMPLES

Example 1. Primary Cell Isolation, Digestion and Culture

Primary human peripheral blood mononuclear cells (PBMCs) are collected from healthy donors using an apheresis machine. The PBMCs are purified with the Ficolll-Paque™ PLUS (GE Healthcare Bio-Sciences AB, Uppsala, Sweden) system or similar systems. The cells are then re-suspended in an appropriate growth medium.

Alternatively, primary human cells are collected from peripheral blood, cord blood, bone marrow, healthy tissues, or tissues afflicted with a disease, such as cancerous tissues.

Tissue from Healthy Donors

Fresh tissues from healthy donors are received from The Cooperative Human Tissue Network (CHTN) and are transported to the laboratory in RPMI-1640 media. Tissues are sliced into 1-3 mm³ fragments with a scalpel. 2-5 fragments/well placed in a 24-well plate (Costar) in 2 mL RPMI-1640 supplemented with GlutaMAX, 25 mM HEPES pH 7.2, 100 U/ml penicillin, 100 U/ml streptomycin and 10% Human AB Serum and 100 IU/ml of rhIL-2 or digested as described below. The plates are incubated in a humidified incubator at 37° C., with 5% $CO_2$ in air. Cultures are inspected every other day to monitor proliferation of lymphocytes. Half of the medium is replaced in all wells every 7 days after culture initiation. Lymphocytes are collected when a dense lymphocytic carpet covers the surrounding the fragments or lymphocyte population derived from digested tissues reached the proper concentration, as described below.

Tissue Enzymatic Digestion

Fresh tissue samples from healthy donors were received from The Cooperative Human Tissue Network (CHTN) and were transported to the laboratory in RPMI-1640 media. Lymphocytes were isolated by enzymatic digestion using two enzyme blend Liberase™ DL Research Grade (Sigma Aldrich Co., St. Louis, MO), or Liberase™ TM Research Grade (Sigma Aldrich Co., St. Louis, MO) or the Miltenyi tumor dissociation kit (130-095-929) with the gentleMACS Dissociator.

The tissues were cut into 2-3 mm³ fragments and digested for 1 hour at 37° C. and 5% CO2. The digested cell suspension was passed through a 40-micron filter, spun down and washed with RPMI-1640 medium. Cells were counted and re-suspended in RPMI medium (GIBCO BRL), supplemented with 10% Human AB serum (Corning) and 100 IU/ml of rhIL-2. The collected cell population was seeded at 0.5 to 1×10⁶ cells/ml in 24-well tissue culture plates. Cells were split into RPMI-IL2 containing medium when cells exceeded concentration of 1.5×10⁶ cells/ml.

Culture of Tumor Specimens

Fresh tumor specimens from patients with primary and metastatic cancers, including those of the colon, breast, ovary, kidney, head and neck, oral cavity, pancreas and liver, were received from The Cooperative Human Tissue Network (CHTN) and were transported to the laboratory in RPMI media. Tumor specimens were sliced into 1-3 mm³ fragments with a scalpel. 2-5 fragments/well were placed in a 24-well plate (Costar) in 2 ml RPMI-1640 supplemented with GlutaMAX, 25 mM HEPES pH 7.2, 100 U/ml penicillin, 100 U/ml streptomycin and 10% Human AB serum and 100 IU/ml of rhIL-2. The plates were incubated in a humidified incubator at 37° C., with 5% $CO_2$ in air. Cultures were inspected every other day to monitor proliferation of lymphocytes. Half of the medium was replaced in all wells every 7 days after culture initiation. Lymphocytes were collected when a dense lymphocytic carpet covers the surrounding the fragments.

Fresh Tumor Specimens Enzymatic Digestion

Fresh tumor specimens from patients with primary and metastatic cancers, including those of the colon, breast, ovary, kidney, head and neck, oral cavity, pancreas and liver, were received from The Cooperative Human Tissue Network (CHTN) and were transported to the laboratory in RPMI media. Lymphocytes were isolated by enzymatic digestion using enzyme blend Liberase™ DL Research Grade (Sigma Aldrich Co., St. Louis, MO), Liberase™ TM Research Grade (Sigma Aldrich Co., St. Louis, MO), or the Miltenyi tumor dissociation kit (130-095-929) with the gentleMACS Dissociator. The tissues were cut into 2-3 mm³ fragments and digested for 1 hour at 37° C. with 5% $CO_2$ in air. The digested cell suspension was passed through a 40-micron filter, spun down and washed with RPMI-1640 medium. Cells were counted and re-suspended in RPMI medium (GIBCO BRL), supplemented with 10% Human AB Serum (Corning) and 100 IU/ml of rhIL-2. The collected cell population was seeded at 0.5 to $1 \times 10^6$ cells/ml in 24-well tissue culture plates. Cells were split into RPMI-IL2 containing medium when cells exceeded concentration of $1.5 \times 10^6$ cell s/ml.

Culture of Primary Cells in Exemplary Serum Supplemented Media

PBMC populations were generated by separation from buffy coats derived from healthy donors, using Ficoll-Paque™ PLUS (GE Healthcare Bio-Sciences PA, USA). PBMCs were cultured at $1 \times 10^6$ cells/mL in 24-well tissue culture plate in RPMI-1640 (Corning CellGro) supplemented with 10% fetal Bovine serum (Gibco), 2 mmol/L L-glutamine, 100 U/mL penicillin, 100 U/mL streptomycin, and 100 IU rhIL-2/ml.

Similar culture conditions can be used to grow primary human cells collected from peripheral blood, cord blood, bone marrow, healthy tissues, or tissues afflicted with a disease, such as the cancerous tissues previously described.

Culture of Primary Cells in Exemplary Serum-Free Media

PBMC populations were generated by separation from buffy coats derived from healthy donors, using Ficoll-Paque™ PLUS (GE Healthcare Bio-Sciences PA, USA). PBMCs were cultured at $1 \times 10^6$ cells/mL in 24-well tissue culture plate in CTS serum-free media with CTS-OpTmizer supplement.

Similar culture conditions can be used to grow primary human cells collected from peripheral blood, cord blood, bone marrow, healthy tissues, or tissues afflicted with a disease, such as the cancerous tissues previously described.

Example 2: Depletion of Adherent Monocytes and Macrophages and CD4+ and CD8+ αβ T Cells PMBCs are collected with apheresis methods as previously described and red blood cells are removed by hypotonic treatment or density separation using Ficoll gradient centrifugation. The red blood cell-free PBMCs are incubated in large-scale tissue culture vessels such as 10-stack or 40-stack Cell Factory (Nunc), roller bottles (Nunc). Adherent populations, comprising macrophages and monocytes, typically remain bound to the surface of the cell culture vessels. The cell population grown in suspension population is enriched in γδ T-cells. Approximately $10^8$, $10^9$ or $10^{10}$ PBMC are incubated with anti-human CD4 and anti-human CD8 coated iron-containing microbeads (e.g. Miltenyi Biotech Microbeads). The incubated cell population flows pass a magnetic field in which the $CD4^+$ and $CD8^+$ T-cells are retained. The "flow-through" cell population is enriched for γδ T-Cells.

Example 3: Depletion of Monocytes and Macrophages

PMBCs are collected with apheresis methods as previously described and red blood cells are removed by hypotonic treatment or density separation using Ficoll gradient centrifugation. The red blood cell-free PBMCs are incubated in large-scale tissue culture vessels such as 10-stack or 40-stack Cell Factory (Nunc), roller bottles (Nunc). Monocytes and macrophages are removed by flowing the red blood cell-removed PBMC over a packed glass wool column. The "flow-through" cell population is enriched in γδ T-cells for further processing.

Example 4: Enrichment of γδ T-Cells

PMBCs are collected with apheresis methods as previously described and red blood cells are removed by hypotonic treatment or density separation using Ficoll gradient centrifugation. The red blood cell-free PBMCs are incubated in large-scale tissue culture vessels such as 10-stack or 40-stack Cell Factory (Nunc), roller bottles (Nunc). Monocytes and macrophages are depleted either with the methods described in Example 2 or in Example 3. Approximately $10^8$, $10^9$ or $10^{10}$ PBMC are incubated with CD4 and CD8 coated iron-containing microbeads (e.g. Miltenyi Biotech Microbeads). The incubated cell population flows pass a magnetic field in which the anti human $CD4^+$ and anti human $CD8^+$ T-cells are retained. The "flow-through" cell population is enriched for γδ T-cells. Undesired cells, such as NK, γδ T-cells, B cells, monocytes and macrophages are removed by immunomagnetic beads separation (e.g. Miltenyi Biotech AutoMACS system) using a cocktail of antibodies directed against the undesired cell types.

Alternatively, undesired cell types are removed by using mouse anti human αβ TCR (IP26, BW242/412) antibody, one or more other antibody directed against surface receptors on NK, αβT cells, B cells, monocytes or macrophages and attached to Anti-Mouse IgG MicroBeads (Miltenyi 130-048-401), or one or more tetrameric antibody complex or bi-specific antibody directed against surface receptors on NK, αβ T cells, B cells, monocytes or macrophages, or combinations thereof Isolation of γδ T-Cells from Primary Cells with Antibodies In one example, native γδ T-cells are isolated from primary cultures with flow cytometry sorting, based on the positive (i.e. γδ TCR) or negative (i.e. αβ TCR, CD4, CD8, CD56), expression of cell surface markers.

Example 5. Isolation of γδ T-Cells from Primary Tumors

γδ T-cells were isolated according to the methods detailed in Example 1. Briefly, freshly harvested tumor specimens were obtained from NCI Cooperative Human Tissue Network (CHTN). Colon adenocarcinoma metastasis to liver (TIL 1) and renal tumor (TIL 2) were shipped in RPMI-1640 media. The tumor tissues were minced into small pieces of 2 mm³ in size using a flat blade followed by digestion with 2 mL Liberase enzyme cocktail (Sigma Chemical Co., St. Louis, MO) in RPMI and 3000 units of DNase as described. After digestion tumors were filtered through sterile gauze 40-micron nylon mesh, and washed twice in RPMI-1640. Cells were counted and plated in 24 well plate at 1×106/ml in RPMI-1640 containing 10% human AB serum supplemented with L-glutamine, and 100 U/mL of rhIL-2. Tumor infiltrating lymphocytes were collected after 6 days in culture. The presence of γδ T lymphocytes was analyzed by flow cytometry anti-δ1 TCR (FITC conjugated anti Vδ1TS8.2, (Thermo Fisher) and anti –Vδ2 B6 (Biolegend). Data was analyzed with FlowJo software.

Figure 4:
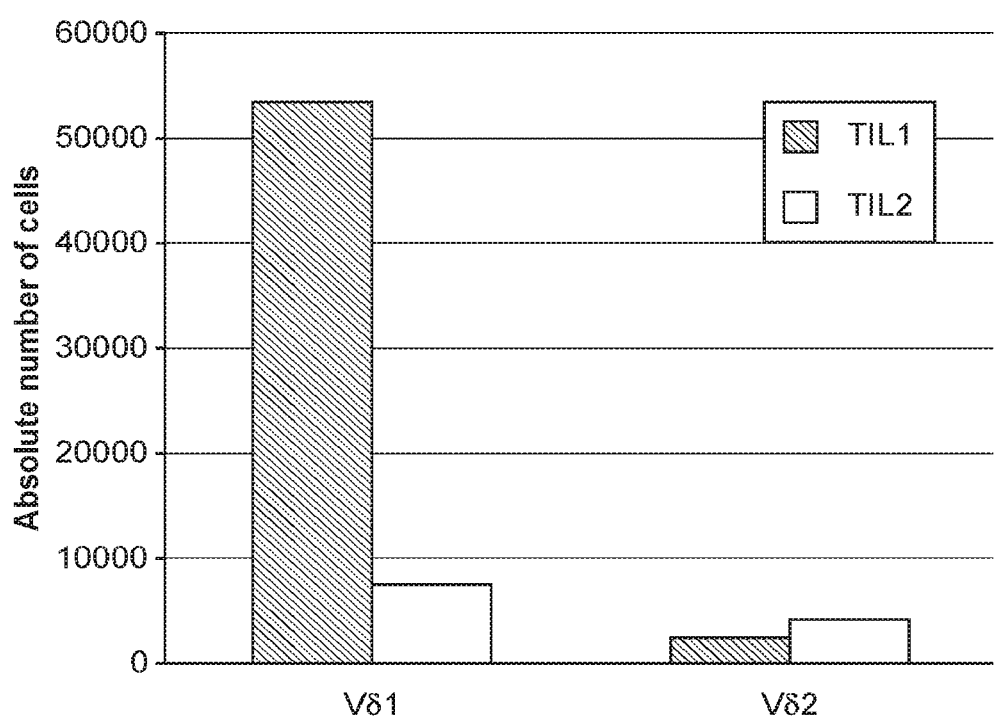
FIG. 4 depicts a graph illustrating growth of γδ1 and γδ2 lymphocytes isolated from colon adenocarcinoma metastasis to liver (TIL 1) and renal tumors (TIL 2) and have been shown to express CCR4 and CCR7.

FIG. 4 depicts a graph illustrating growth of γδ1 and γδ2 lymphocytes isolated from colon adenocarcinoma metastasis to liver (TIL 1) and renal tumors (TIL 2). These lymphocytes have been shown to express CCR4 and CCR7 (data not shown). As illustrated by FIG. 4, the Vδ1 subset was the predominant population isolated from both types of tumors.

Example 6. Stimulation and Expansion of γδ T-Cells

γδ T-Cells are stimulated and expanded in serum-free media such as Ex-Vivo 10 (Lonza 04-380Q), Ex-Vivo 15 (Lonza 04-744Q), Ex-Vivo 20 (Lonza 04-448Q), AIMV media (ThermoFisher Scientific 12055091), Optimizer CTS (ThermoFisher Scientific A1048501), containing cytokines (IL-2, IL-4, IL-7, IL-15, IL-12, IL-21, IL-23 or IL-33), growth factors (insulin and transferrin, insulin-like growth factors), albumin, lipids (cholesterol, lipid solutions, lipid pre-cursors), vitamins, copper, iron, selenium, protein hydrolysate, essential amino acids, non-essential amino acids, and shear protectant (Pluronic F-δ8).

The serum-free media described in the examples herein can also be supplemented with additives to support high cell density γδ T-cell growth between $10^5$ to $2 \times 10^7$ cells/mL in suspension culture (e.g. WAVE bioreactor) while maintaining biological functionality of the γδ T-cell.

Additional additives that provided robust γδ T-cell growth include, for example, Calcium Chloride, Anhydrous, Calcium Nitrate, Cupric Sulfate, Pentahydrate, Ferric Citrate, Ferric Nitrate, Ferrous Sulfate, Zinc Sulfate, and/or Putrescine.

Trace metals were provided in the serum free media to provide low levels of elemental components to replace serum, including Ammonium Paramolybdate, Vanadium, Manganese, Nickel, Sodium Selenite, Sodium Metasilicate, Nonahydrate, Stannous Chloride, Aluminum Chloride, Barium Acetate, Cadmium Chloride, Chromic Chloride, Cobalt, Germanium Dioxide, Potassium Bromide, Potassium Iodide, Rubidium Chloride, Silver Nitrate, Sodium Fluoride, and/or Zirconyl Chloride.

Other components added to cell culture media that support robust growth of γδ T-cells are, for example, Adenosine, Guanosine, Cytidine, Uridine, Betaine, Taurine, Folinic acid, Ethanolamine, Linoleic Acid, Oleic Acid Hydrocortisone, pyruvate, plant hydrolysates, yeast hydrolysates, and/or beta-mercaptoethanol.

Vitamins added to promote robust γδ T cell growth include: Biotin (B7), D-Calcium Pantothenate (B5), Choline Chloride, Cyanocobalamin (B12), Folic Acid (B9), i-Inositol (myo-Inositol), Niacinamide (B3), Pyridoxal, Monohydrochloride, Pyridoxine, Monohydrochloride (B6), Riboflavin (B2), Thiamine, and/or Monohydrochloride (B1).

Example 7: Characterization of Expanded γδ T-Cells: Immunophenotype

Expanded T-cell populations may be characterized, for example, by FACS staining for cell surface markers that distinguish between the different populations. The cells were washed once in HEPES buffered saline solution (HBSS) containing 2% fetal bovine serum, incubated with appropriate amounts of MAbs at 4° C. for 30 minutes and rewashed in HBSS. Briefly, $1 \times 10^6$ cells are stained in 100 µl volume of FACS staining medium (FSM; HBSS containing 2% fetal bovine serum) containing fluoroisothiocyanate (FITC) or phycoerythrin (PE) conjugated MAbs directed against CD2, CD3 (BioLegend, clone OKT3), CD4 (BioLegend clone OKT4), CD7, CD8 (BioLegend, clone RPAT8), CD11a, CD16, CD18, CD19, CD27, CD28, CD38, CD45RA, CD56, CD57, CD69, CD71, CD95, CD107, ICAM-1, MICA/B, NKG2D DR5, CCR1, CCR2, CCR3, CCR4, CCR5 CCR6, CCR7, CCR10, CXCR1, CXCR2, CXCR3, CXCR5, CXCR5, CXCR6, CXCR7, IL-2R, IL-7R, Ki67, L-selectin, VLA-4, JAML, PD1, PDL1, CTLA-4, Ox40, TCR Vδ1 (ThermoFisher Scientific, clone TS8.2), or TCR Vδ2 (BioLegend, clone B6).

In addition to surface markers, cytokine secretion, intracellular cytokines and/or membrane associated cytokines including, for example, TNF-α IFN-γ, GM-CSF, IL-1, IL-2, IL-4, IL-6, IL-7, IL-10, IL-17, or IL-21 may be characterized according to methods known in the art.

In certain examples herein, live cells were determined by absence or low incorporation of zombie violet (BioLegend) amine dye. Fluorescence Minus One (FMO) controls are used to define positive and negative gate boundaries of the surface expression of each antigen. Stained cells are collected on a Sony SH800 cytometer and data analyzed using FlowJo v10.1. Flow cytometry data are visualized as dot plots.

Example 8. δ2 T-Cell Expansion in Serum-Containing and Serum-Free Media

Figure 5:
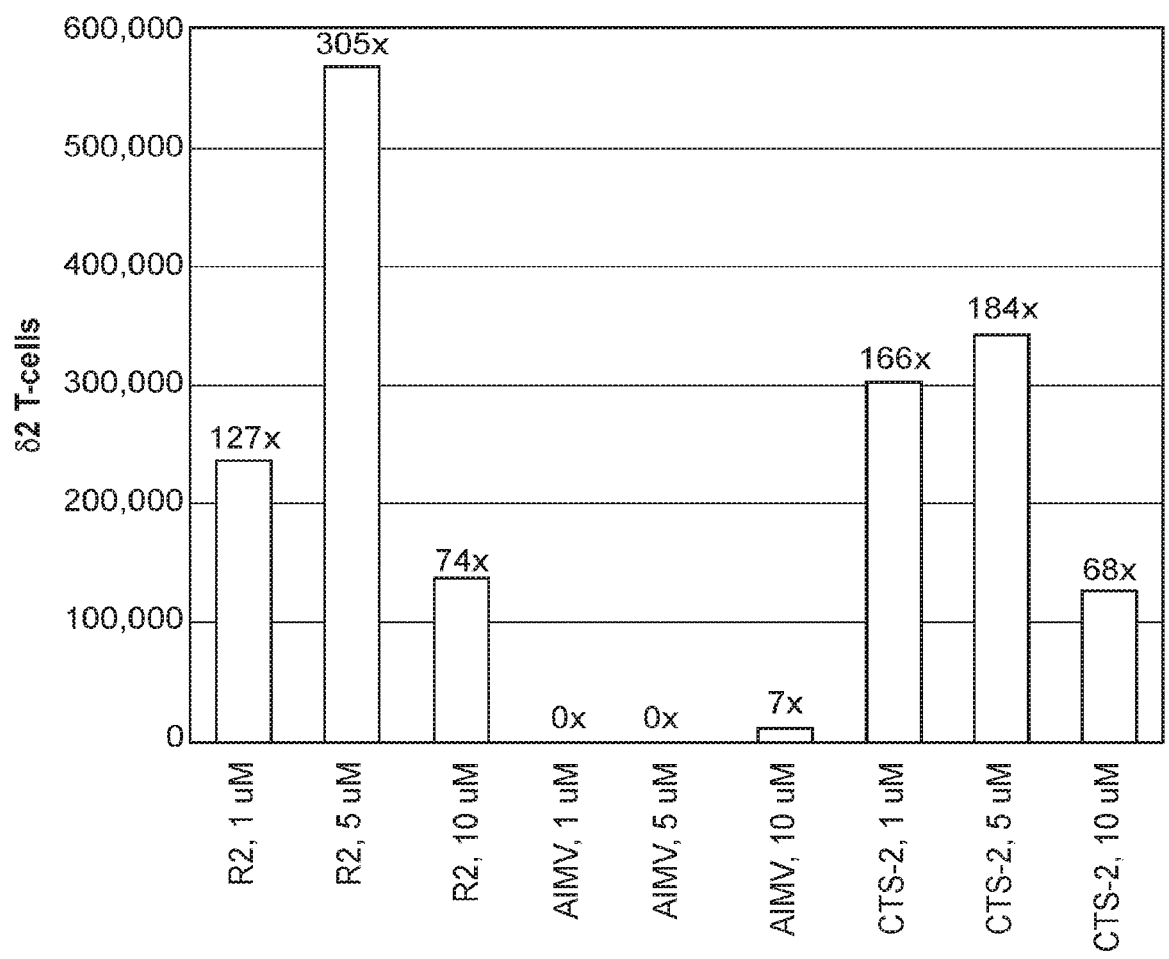
FIG. 5 depicts a graph illustrating γδ T-cells growth in serum-containing and serum-free media.

The growth and rate of expansion of different δ2 T-cells was evaluated in serum-containing media (R2:RPMI+10% FBS), and serum-free media (AIMV+bovine albumin; CTS serum-free Supplement). FIG. 5 depicts a graph illustrating the growth of δ2 T-cells. All media used in the current experiment contained 100 IU/mL IL-2, 2 mM glutamine and 1×penicillin/streptomycin. In addition, cells were stimulated with Zoledronic acid at 1, 5, and 20 µM on day 0. Media was replenished every 2-3 days without further addition of Zoledronic acid. The total number δ2 T-cells expanded from $10^6$ PBMC and the fold expansion of each treatment after a time period of 13 days are shown in FIG. 5. These results indicate that δ2 T-cells can be expanded in serum-free media.

Example 9. Anti-γδ TCR Antibody Blocking and Competition Assays

Figure 6:
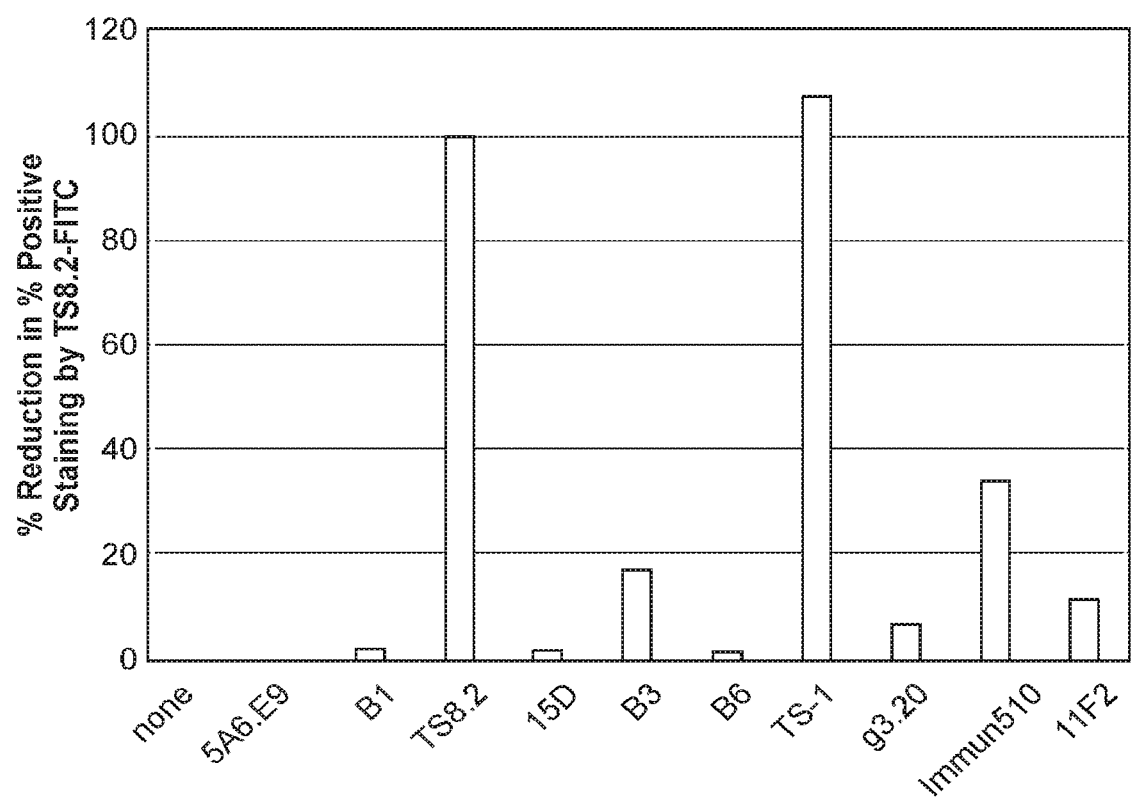
FIG. 6 depicts a graph illustrating anti-γδ TCR antibody blocking experiments with 5A6.E9, B1, TS8.2, 15D, B3, B6, TS-1, γ3.20, IMMU510, or 11F2.
Figure 7:
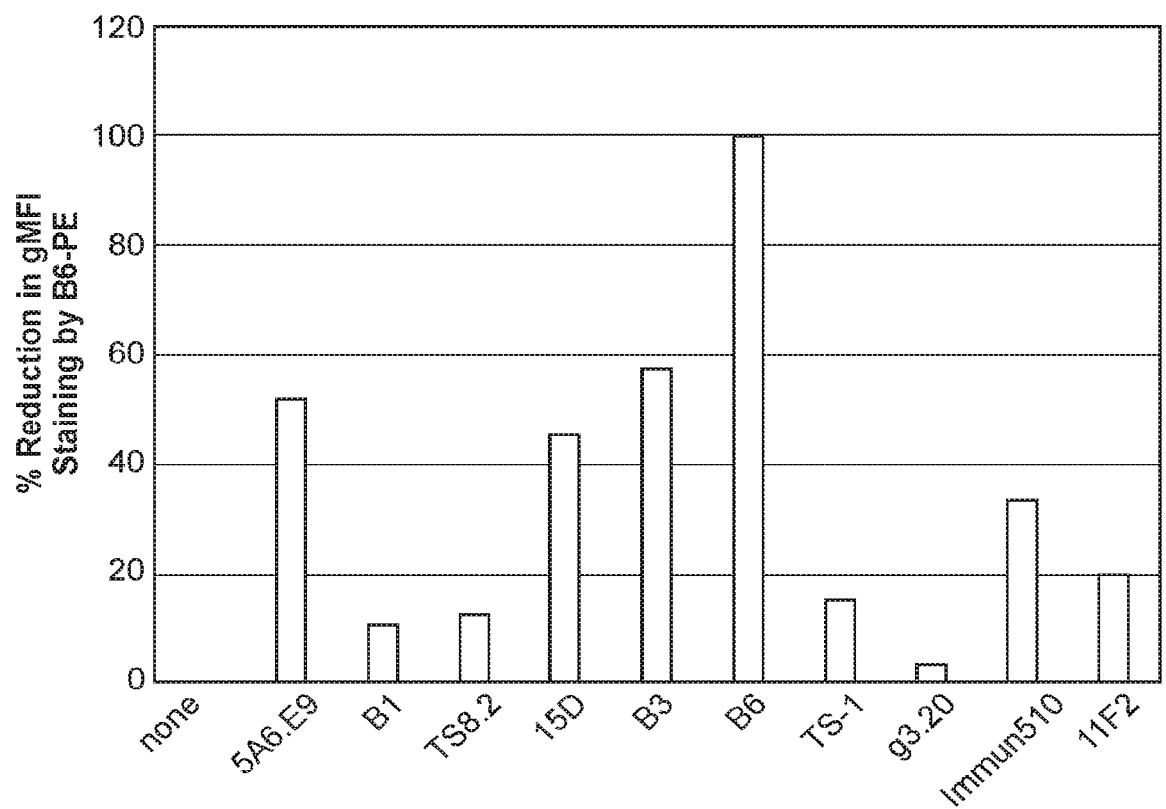
FIG. 7 depicts a graph illustrating anti-γδ TCR antibody blocking experiments with 5A6.E9, B1, TS8.2, 15D, B3, B6, TS-1, γ3.20, IMMU510, or 11F2.
Figure 8:
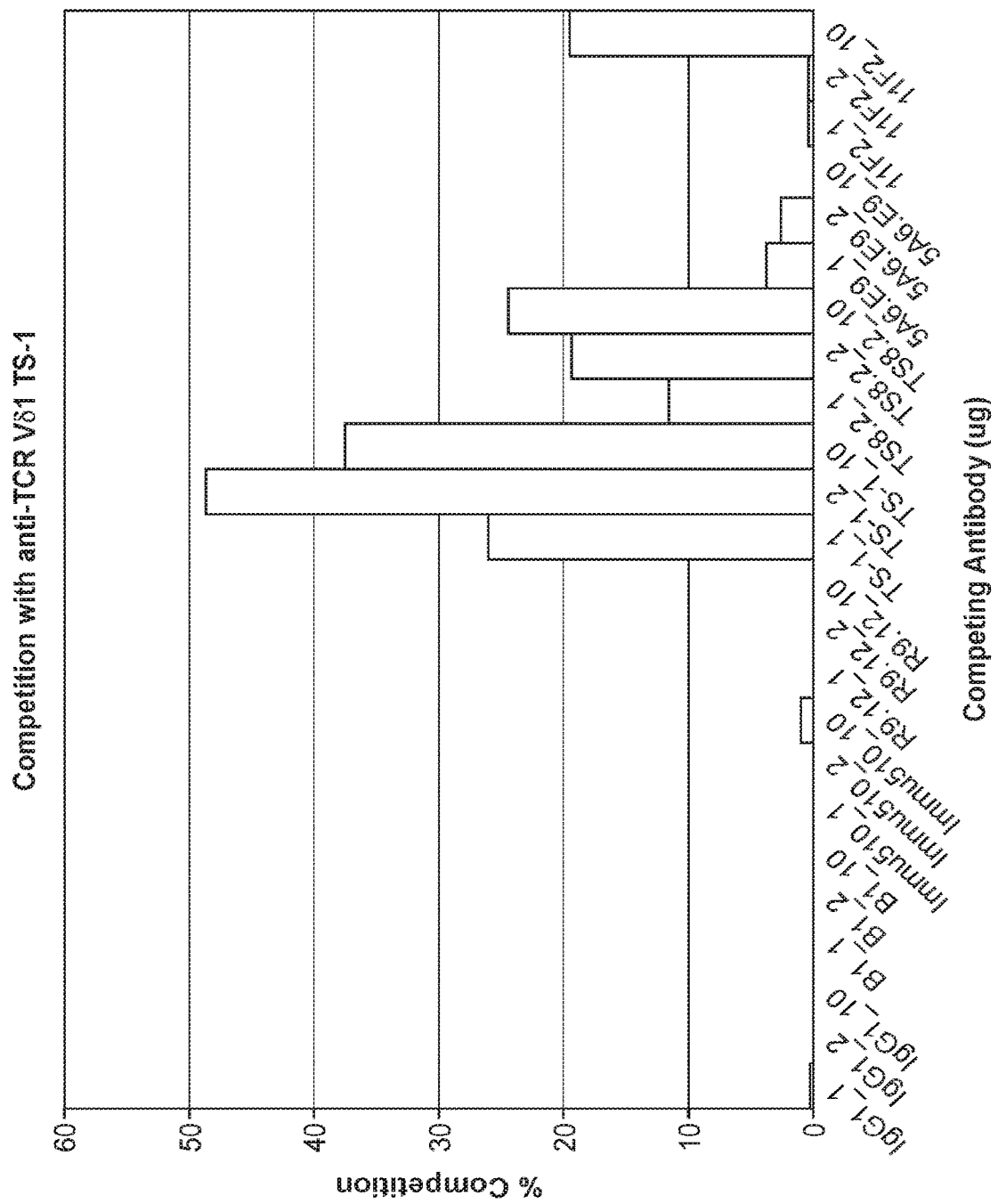
FIG. 8 depicts a competition experiment with anti-TCR Vδ1 TS-1 antibody.
Figure 9:
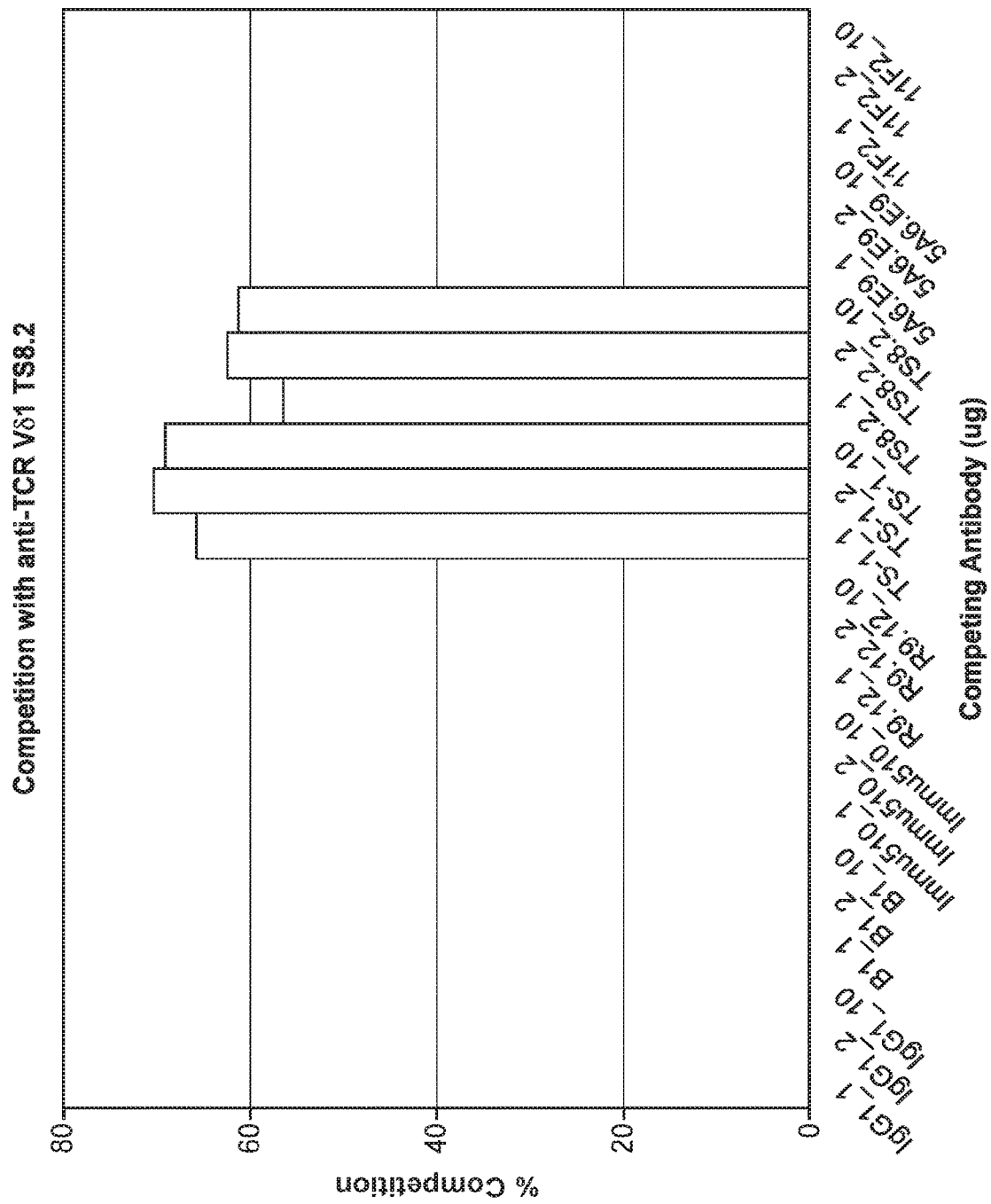
FIG. 9 depicts a competition experiment with anti-TCR Vδ1 TS8.2 antibody.

FIG. 6 and FIG. 7 depict graphs illustrating anti-γδ TCR antibody blocking experiments and FIG. 8 and FIG. 9 depict antibody competition assays. FIG. 6 and FIG. 7 illustrate the results of blocking experiments where PBMCs were pre-incubated with various antibodies, namely, 5A6.E9, B1, TS8.2, 15D, B3, B6, TS-1, γ3.20, IMMU510, or 11F2. The cells were subsequently washed and stained with the secondary TS8.2-FITC (δ1-specific) or B6-PE (δ2-specific) antibodies. PBMCs samples were analyzed by flow cytometry. Reduction in geometric mean fluoresce intensity (gMFI) was used to assess degree of blocking. The level of inhibition is illustrated against TS8.2-FITC (FIG. 6) and against B6-PE (FIG. 7).

Competition studies between MAbs TS-1 and TS8.2 and antibodies 5A6.E9, B1, IMMU510, R9.12-2, or 11F2 for binding on γδ1TCR-expressing cell line BE13 were performed by incubating $1 \times 10^5$ cells with 1, 2 or 10 µg of unlabeled competing antibodies (IgG1, 5A6.E9, B1, TS8.2, TS-1, R9.12, IMMU510, or 11F2) and 0.2 µg of FITC conjugated anti-Vδ1 TCR clone TS8.2 (FIG. 8) or anti-Vδ1 TCR clone TS-1 (FIG. 9) simultaneously on ice for 30 minutes. % Competition is calculated by change in geometric mean fluorescence divided by the maximum change in geometric mean fluorescence. As depicted in FIG. 9, TS-1 antibody competed with TS8.2 binding to the cells as effectively as the TS8.2 antibody itself. None of the other antibodies tested were able to compete with TS8.2 binding. TS8.2 antibody competed with TS-1 binding to the cells but not as effectively as the TS-1 itself. Some level of competition with TS-1 binding was also observed with 11F2 antibody. These results indicate that both TS-1 and TS8.2 antibodies bind to γδ1 but likely not at the same epitope.

Example 10. Enzymatic Digestion of Tumor Specimens and γδ T-Cell Expansion with Antibodies to Specific γδ Epitopes 24 well plates were coated with 0.5-1 µg anti-γδ TCR antibodies. Cells isolated from digested tumor tissues as described in example 4 were counted and seeded on antibody coated wells at $0.5-1 \times 10^6$ cell/ml 1 in RPMI 1640 medium supplemented with 10% human AB serum and rhIL-2 (100 IU/mL). The cultures were incubated at 37° C., 5% $CO_2$ for 7-21 days.

Example 11. Enzymatic Digestion of Tumor Specimens and γδ T-Cell Expansion with Antibodies to Specific γδ Epitopes Cells isolated from digested tumor tissues as described in example 1 in section "Fresh Tumor Specimens Enzymatic Digestion" were counted and seeded on antibody coated wells of a 3D cell culture plate (Corning® Costar® Ultra-Low attachment multi well plates) at $0.5-1 \times 10^6$ cell/ml in RPMI 1640 medium supplemented with 10% human AB serum and rhIL-2 (100 IU/mL). The cultures were incubated at 37° C., 5% $CO_2$ for 7-21 days.

Example 12. Activation and Expansion of γδ T-Cells from PBMC

Activating agents were tested either as soluble agents, or agents immobilized on the culture wells. Soluble antigens and antibodies were added at a final concentration of 0.1-5 µg/ml to human PBMCs cultured in 24 well plate at a cell density of $1 \times 10^6$ cell/ml. Alternatively, the same anti γδ TCR antibodies were immobilized by coating wells of 24-well culture plates. Anti γδ TCR antibodies were added at 0.1-10 µg/ml concentration. Wells were washed twice with PBS, then PBMCs were transferred to the plates and cultured in either RPMI-1640, AIM-V or CTS-OpTmizer media as described above. Cultured media was supplemented with 100 IU/mL of rhIL-2.

Figure 10:
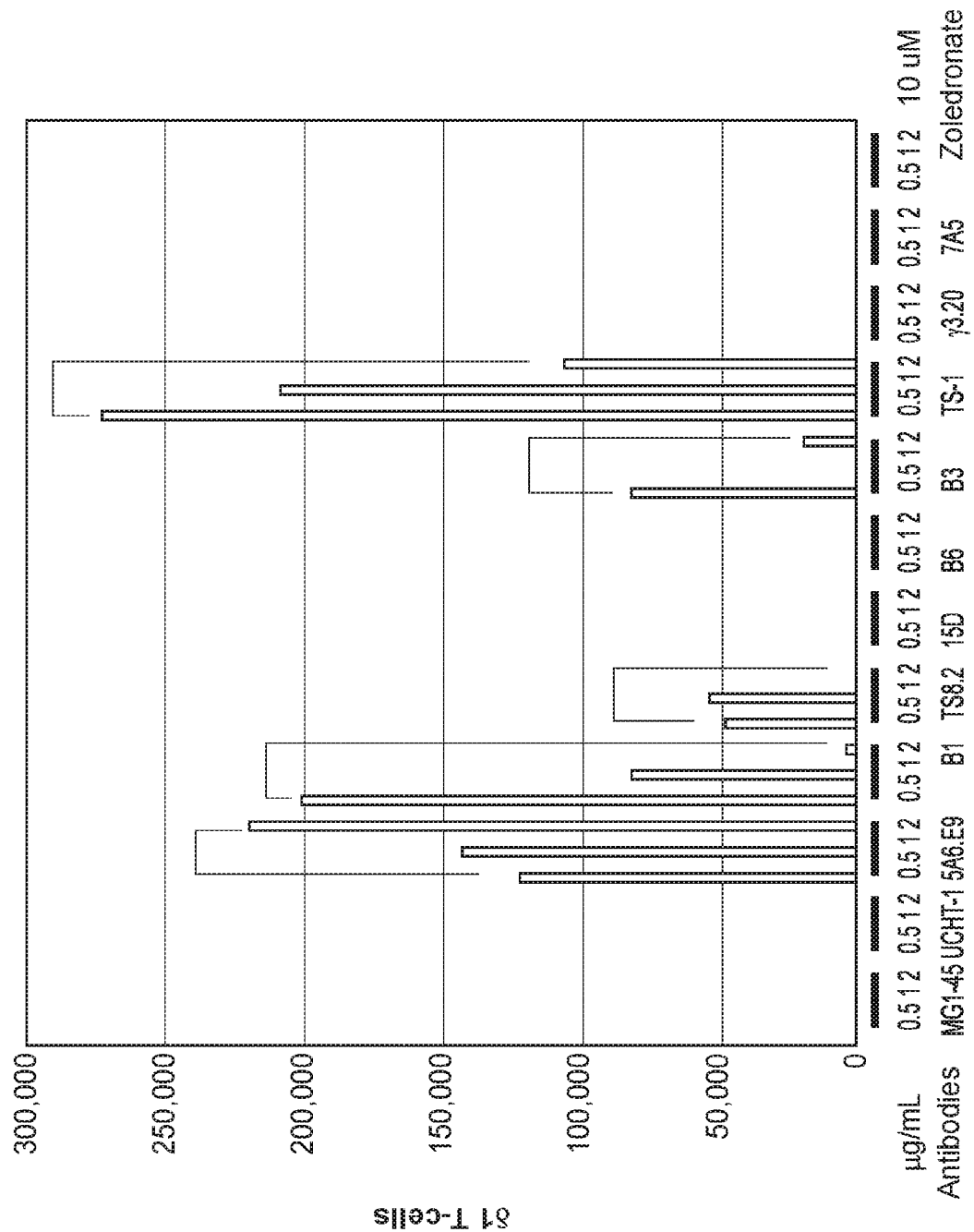
FIG. 10 depicts a graph illustrating activation and expansion of δ1 T-cells from PBMC.
Figure 11:
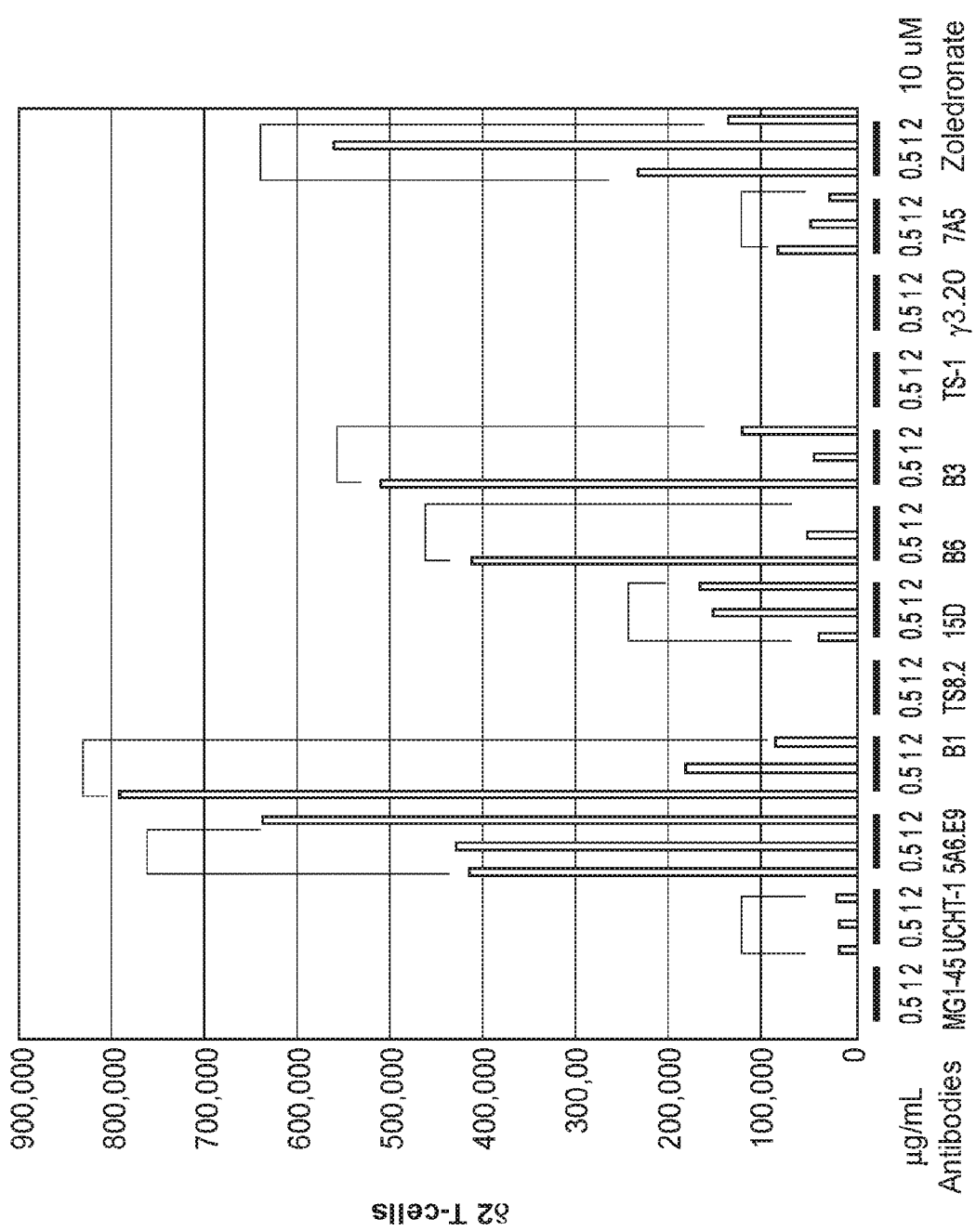
FIG. 11 depicts a graph illustrating activation and expansion of δ2 T-cells from PBMC.

In a specific example, one million PBMCs/ml from donor B3 were stimulated on Day-0 with various antibodies immobilized at 0.5, 1, and 2 µg per well in 24-well plates. The antibodies tested were Mouse IgG1 Isotype control clone MG1-45 (Bio Legend), UCHT-1, 5A6.E9, B1, TS8.2, 15D, B6, B3, TS-1, γ3.20, 7A5, and Zoledronate. FIG. 10 and FIG. 11 depict graphs illustrating activation and expansion of δ1 and δ2 T-cells respectively from PBMC. Cells were activated and expanded in media containing RPMI with 10% FBS, 100 IU/mL rhIL-2, glutamine and 1× penicillin streptomycin. On Day-7 after the initial stimulation, cells were passaged in fresh media and placed in a newly coated 24-well plate with the same antibodies at the same concentrations. Media in the re-stimulated cultures were replenished every 2-3 days until Day 13 and analyzed by flow cytometry.

Figure 12:
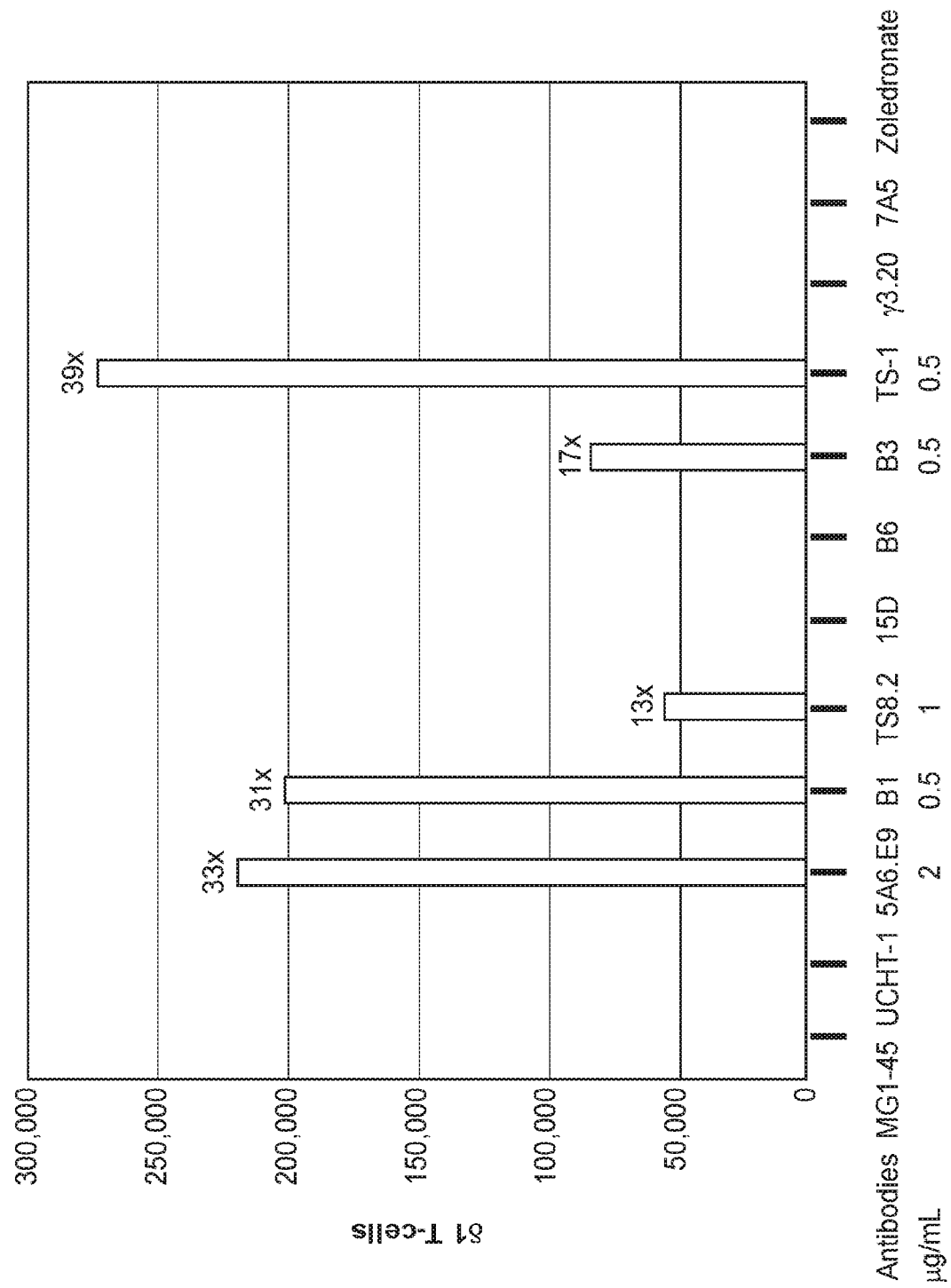
FIG. 12 depicts a graph illustrating fold expansion of δ1 T-cells from PBMC.
Figure 13:
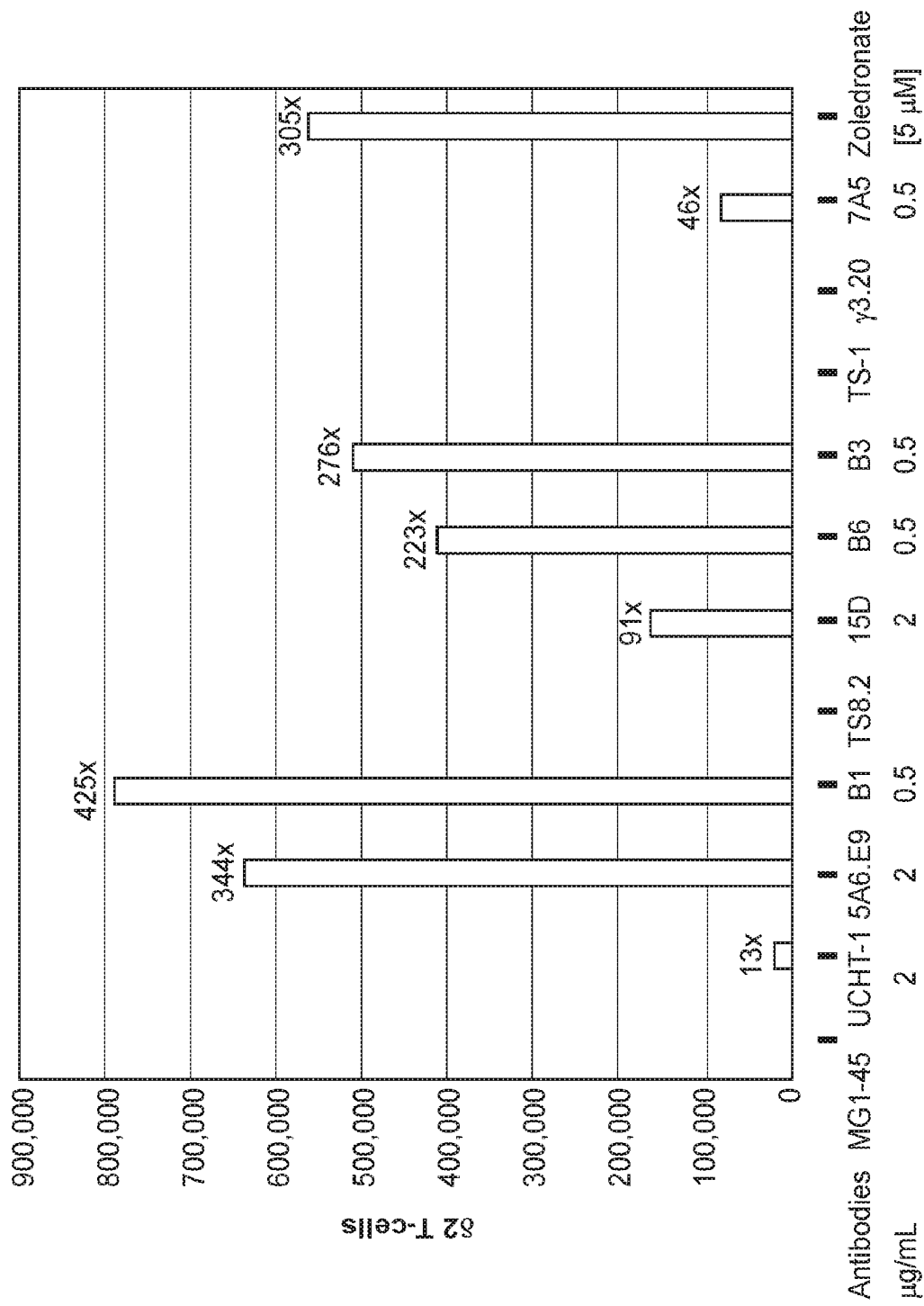
FIG. 13 depicts a graph illustrating fold expansion of δ2 T-cells from PBMC.
Figure 16A:
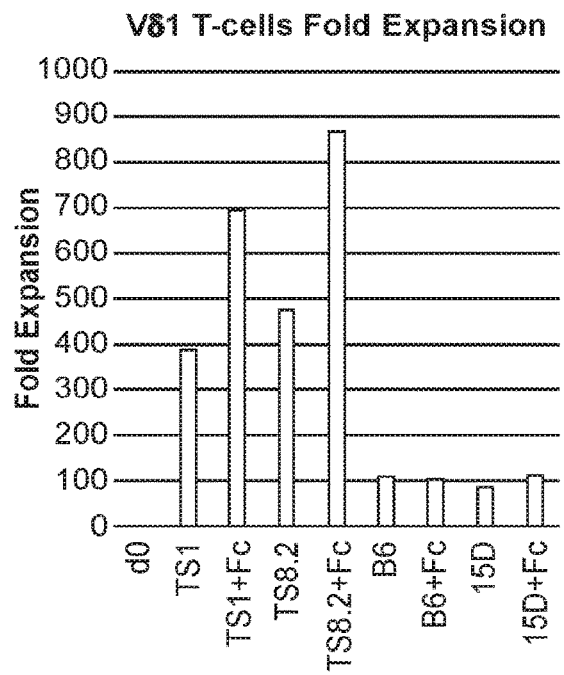
FIGS. 16A-D depict activation of PBMCs with TS-1 or TS8.2 antibodies resulting in significant and specific expansion of Vδ1$^+$ T cells. (A) MAbs were directly coated (1 μg/mL) (TS1, TS8.2, B6, and 15D) or captured (0.1 μg/mL) with goat-anti-mouse Fc (5 μg/mL) (TS1Fc, TS8.2Fc, B6Fc and 15DFc) in 24-well plates. PBMCs were plated at $10^6$ cells/mL in RPMI with 10% FBS and 100 IU/mL IL-2. On day 7, cells were transferred to new plates without antibodies and further expanded until day 14. Culture media was replenished every 2-3 days. Data depicts expansion of Vδ1$^+$ cells over 14 days; (B) Same culture as A, showing percentage of Vδ1$^+$ cells on day 14 and day 0 (d0); (C) Vδ1$^+$ cells were expanded from isolated PBMCs from a different donor as follows. MAbs were directly coated (1 μg/mL) (TS1, TS8.2, B6 and 15D) or captured (0.1 μg/mL) with goat-anti-mouse Fc (5 μg/mL) (TS1Fc, TS8.2Fc, B6Fc and 15DFc) in 24-well plates. PBMCs f were plated at $10^6$ cells/mL in RPMI with 10% FBS and 100 IU/mL IL-2. Cells were transferred to new plate without antibodies on day 7, adjusted to $10^6$ cells/mL with fresh media. Culture media was replenished every 2-3 days and adjusted to $10^6$ cells/mL. Data depicts Vδ1+ cells expansion over 14 days. (D) PBMCs were plated at $10^6$ cells/mL in RPMI with 10% FBS and 100 IU/mL IL-2. On day 7, cells were transferred to a new plate without antibodies, adjusted to $10^6$ cells/mL and further expanded until day 23. Culture media was replenished every 2-3 days.
Figure 16B:
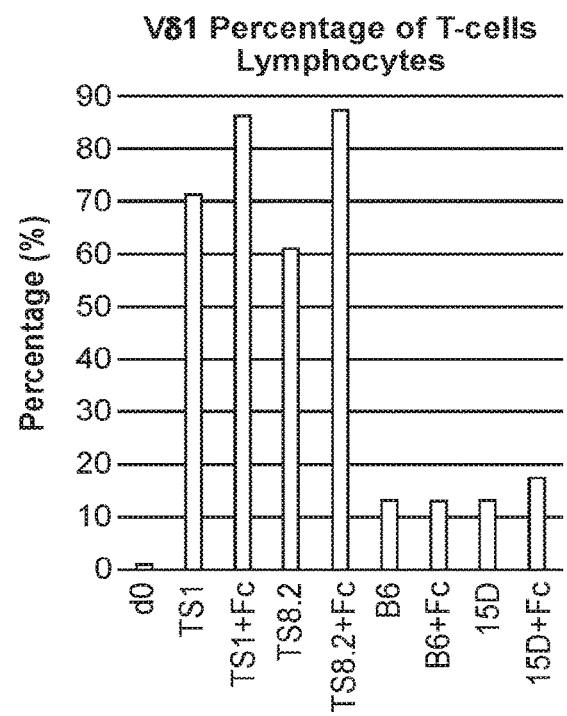
Figure 16C:
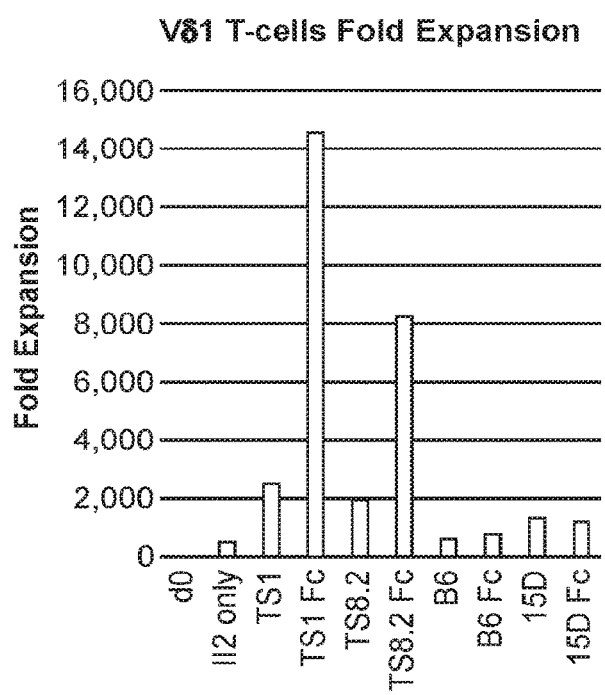
Figure 16D:
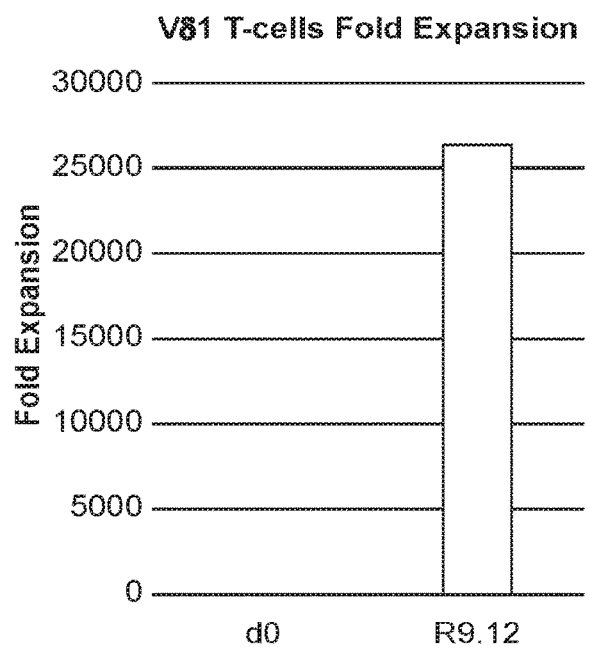

FIG. 12 illustrates the total number of δ1 T-cells, and FIG. 13 illustrates the total number of δ2 T-cells after 13 days of growth and expansion. The total number of γδ T-cells was calculated by multiplying the percentage δ1 and δ2 T-cells (as determined by flow cytometry using TS8.2-FITC and B6-PE, respectively) by the total viable cell number and subtracting the negative control values from δ1 and δ2 T-cell cells activated by the non-specific mouse IgG MG1-45 (BioLegend 401403).

Activation for cell expansion was obtained only when the antibodies were immobilized on the culture plates, with no detected expansion when these antibodies were added to the culture in soluble form, including in whole PBMC cell population (data not shown). Pan γδ TCR MAbs 5A6.E9 and B1 and activated the growth of both δ1 and δ2 cell populations. MAbs 15D and B6 induced selective growth of δ2 cell population. MAbs TS8.2 and TS-1 induced selective growth of δ1 cell population. Of interest is that although MAbs TS-1 and TS8.2 compete with each other in binding to cell surface TCR, TS-1 induced proliferation was 3-fold higher. Similarly, different extent of δ2 cell population proliferation induction was detected between antibodies B1, 5A6.E9, 15D, B6, and B3. This data indicates that unique epitopes are required to trigger a specific and robust expansion of γδ cell populations.

Example 13: Activation and Expansion of Specific γδ T Cell Populations from PBMCs Activation and Expansion of Vol T-Cells from PBMCs Activating antibodies (TS1, TS8.2, R9.12, B6 and 15D) were immobilized directly to plastic 24-well plates at 0.25 or 1 µg/mL (data shown for 0.25 µg/mL) or captured at 0.05 or 0.1 mg/mL (data shown for 0.05 µg/mL) by plate-bound goat anti-mouse IgGFc (5 µg/mL) in 24-well plates. Human PBMCs were activated at $1 \times 10^6$ cell/ml in media containing RPMI with 10% FBS, 100 IU/mL rhIL-2. Media in the cultures were replenished every 2-3 days. On day-7 cells were transferred into new plates without activating antibodies and further expanded by replenishing fresh media every 2-3 days for a total of 14 or 23 days. Cell count and flow cytometry analysis were conducted on day 0, 7, 14 and 23 to determine percentage and number of Vδ1 and Vδ2 T-cells. Fold expansion is defined as the number of the γδ T-cells divided by the number the same γδ T-cell type in the starting PBMCs plated in each well. FIG. 16 depicts graphs illustrating activation and expansion of Vδ1 T-cells from PBMC from different donors. MAbs TS-1. R9.12 and TS8.2 induced significant selective growth and enrichment of Vδ1 T-cell population. Vδ1 T-cells were expanded from 400 to 14,500 fold (FIG. 16A, C) and enriched from 1.2% up to 87.0% of the T lymphocytes population, which comprised about 95% of the total cell population (FIG. 16B) in 14 days. Vδ1 T-cells were expanded by 26,330 fold (FIG. 16D) in 23 days.

Activation and Expansion of V52 T-Cells from PBMCs

Figure 17A:
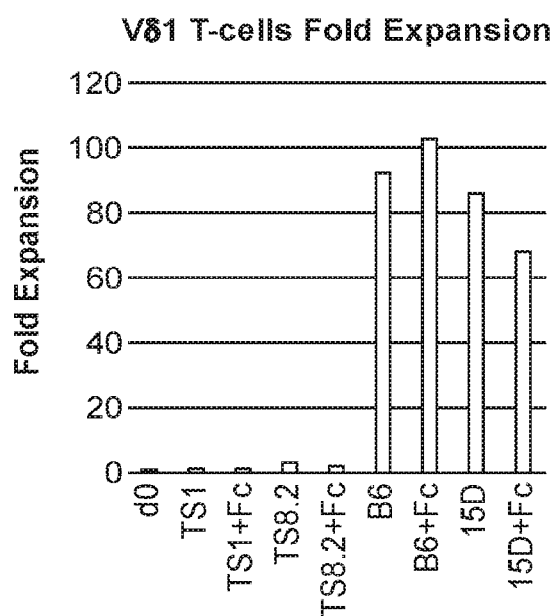
FIGS. 17A-D depict activation of PBMCs with B6 and 15D antibodies result in significant specific activation and expansion of Vδ2+ T cells. (A) MAbs were directly coated (1 μg/mL) (TS1, TS8.2, B6, and 15D) or captured (0.1 μg/mL) with goat-anti-mouse Fc (5 μg/mL) (TS1Fc, TS8.2Fc, B6Fc and 15DFc) in 24-well plates. PBMCs were plated at $10^6$ cells/mL in RPMI with 10% FBS and 100 IU/mL IL-2. On day 7, cells were transferred to new plates without antibodies and further expanded until day 14. Culture media was replenished every 2-3 days. Data depicts Vδ2$^+$ T-cells expansion over 14 days; (B) Same culture as A, showing percentage of Vδ2$^+$ cells on day 14 and day 0 (d0); (C) MAbs were directly coated (1 μg/mL) (15D and pan-γδ TCR Mab Immu510) in 24-well plates. PBMCs from a different donor were plated at $10^6$ cells/mL in RPMI with 10% FBS and 100 IU/mL IL-2. Cells were transferred to new plates without antibodies on day 7. Culture was replenished every 2-3 days and adjusted to $10^6$ cells/mL with fresh media. Data depicts Vδ2$^+$ T-cells expansion over 14 days; (D) Same culture as C, showing percentage of Vδ2$^+$ T-cells on day 14 and day 0 (d0). (E) MAbs were directly coated (1 μg/mL) (TS1, TS8.2, B6, and 15D) or captured (0.1 μg/mL) with goat-anti-mouse Fc (5 μg/mL) (TS1Fc, TS8.2Fc, B6Fc and 15DFc) in 24-well plates. PBMCs from another donor were plated at $10^6$ cells/mL in RPMI with 10% FBS and 100 IU/mL IL-2. Cells were transferred to new plates without antibodies on day 7, adjusted to $10^6$ cells/mL with fresh media. Culture media was replenished every 2-3 days and adjusted to $10^6$ cells/mL. Data depicts Vδ2+ T-cells expansion over 14 days.
Figure 17B:
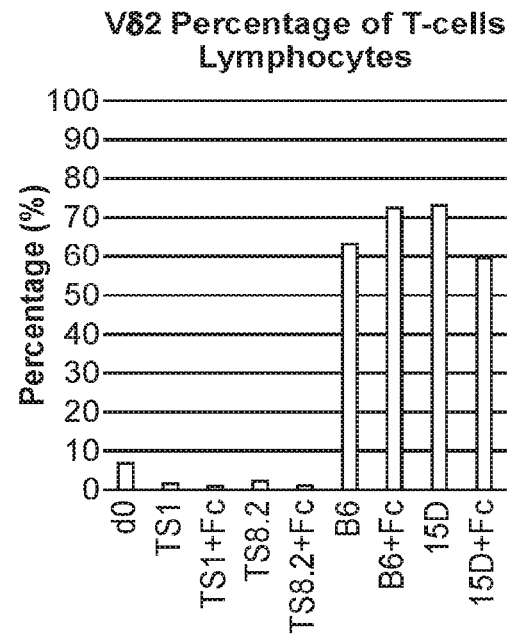
Figure 17C:
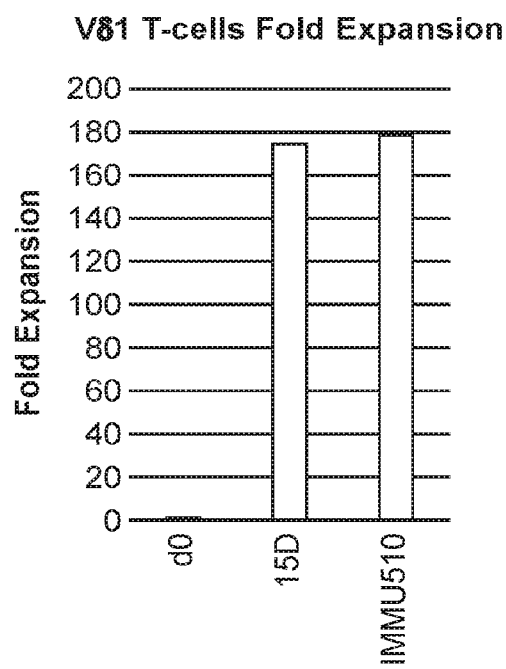
Figure 17D:
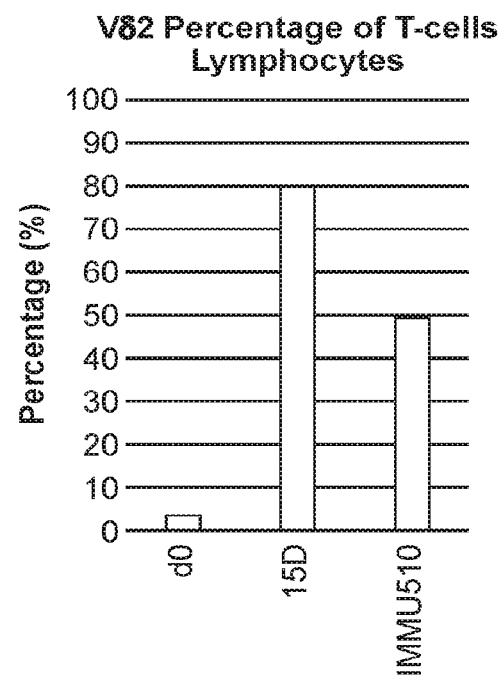
Figure 17E:
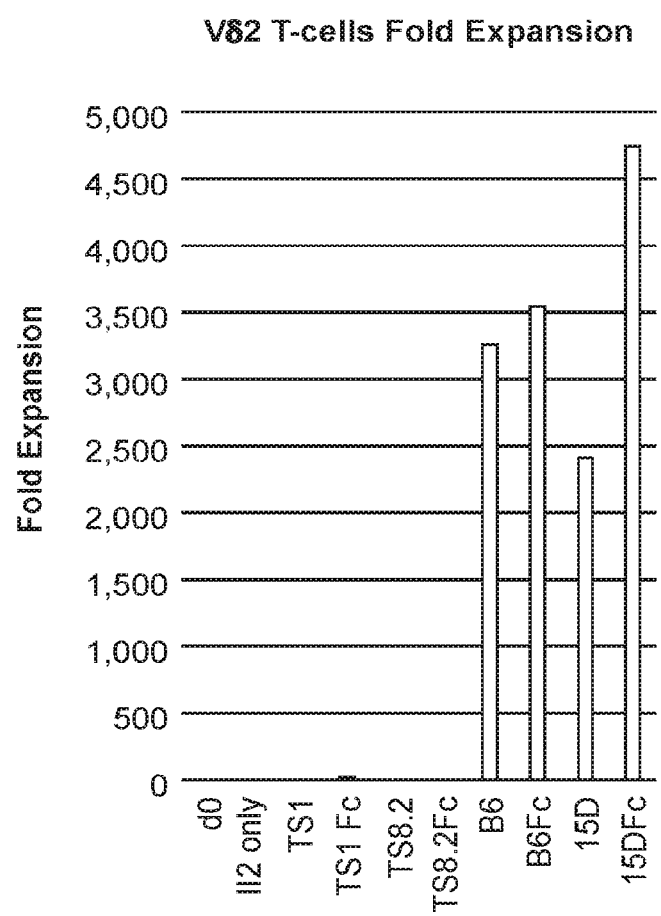

Activating antibodies (TS1, TS8.2, R9.12, B6 and 15D) were immobilized directly to plastic 24-well plates at 0.25 or 1 µg/mL (data shown for 0.25 µg/mL) or captured at 0.05 or 0.1 µg/mL (data shown for 0.05 µg/mL) by plate-bound goat anti-mouse IgGFc (5 µg/mL). Human PBMCs were activated at $1 \times 10^6$ cell/ml in media containing RPMI with 10% FBS, 100 IU/mL rhIL-2. Media in the cultures were replenished every 2-3 days. On day-7 cells were transferred into new plates without activating antibodies and further expanded by replenishing fresh media every 2-3 days for a total of 14 days. FIG. 17 illustrate the fold expansion and percentage of Vδ2 T-cells after 14 days from different donors. MAbs B6 and 15D induced selective expansion of Vδ2 T-cell population from 70 fold to 4,740 fold (FIGS. 17A, 17C and 17E) over 14-days and enriched δ2 populations up to 80% of the T lymphocytes population, which comprised about 95% of the total cell population (FIGS. 17B and 17D).

Reduction in the Percentage of αβ T-Cells In γδ TCR Activated PBMC

Figure 18A:
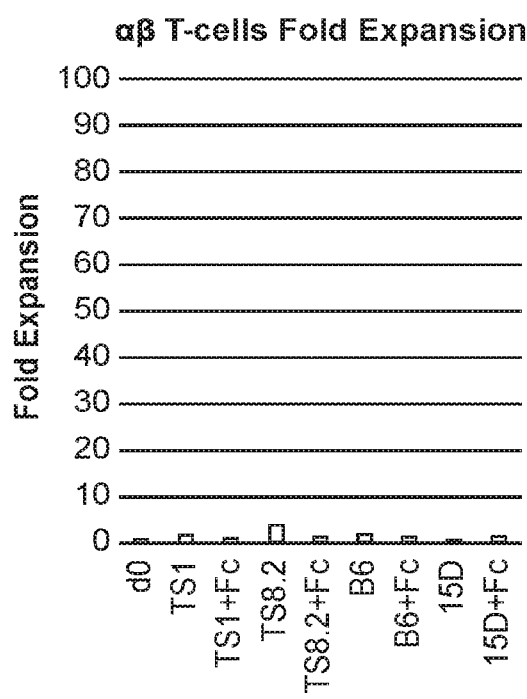
FIGS. 18A-B depict significant reduction in percentage of 4 T cells in PBMC cultured with γδ-specific antibodies TS1, TS8.2, B6, and 15D. (A) MAbs were directly coated (1 μg/mL) (TS1, TS8.2 B6 and 15D) or captured (0.1 μg/mL) with goat-anti-mouse Fc (5 μg/mL) (TS1Fc, TS8.2Fc, B6Fc and 15DFc) in 24-well plates. PBMCs were plated at $10^6$ cells/mL in RPMI with 10% FBS and 100 IU/mL IL-2. On day 7, cells were transferred to new plates without antibodies and further expanded until day 14. Culture media was replenished every 2-3 days. Data depicts 4 T-cells expansion over 14 days; (B) Same culture as A, showing percentage of 4 T-cells on day 14 and day 0 (d0).
Figure 18B:
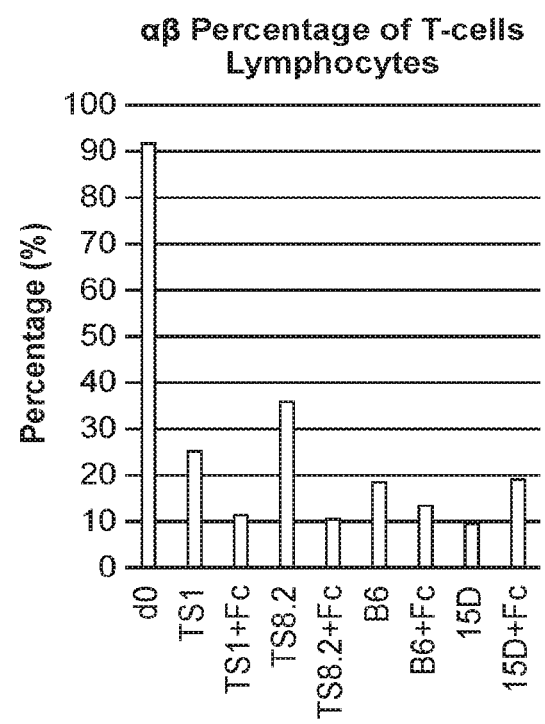

Immobilized activating agents were tested in cell culture wells. MAbs (TS1, TS8.2, B6 and 15D) were directly coated (1 μg/mL) or captured (0.1 μg/mL) with goat-anti-mouse Fc (5 μg/mL) in 24-well plates. Human PBMC were activated at $1 \times 10^6$ cell/ml in media containing RPMI with 10% FBS, 100 IU/mL rhIL-2. Media in the cultures were replenished every 2-3 days. On day-7, cells were transferred into new plates without antibodies and further expanded by replenishing media every 2-3 days until day 14 and analyzed by flow cytometry. FIG. 18 illustrates the fold expansion and percentage of αβ T-cells after 14 days. PBMCs cultured with MAbs TS1, TS8.2, B6 and 15D led to significant reduction in αβ T-cells from 92% to as low as 9% over the 14-day culture period.

Figures 19A, 19B, 19C:
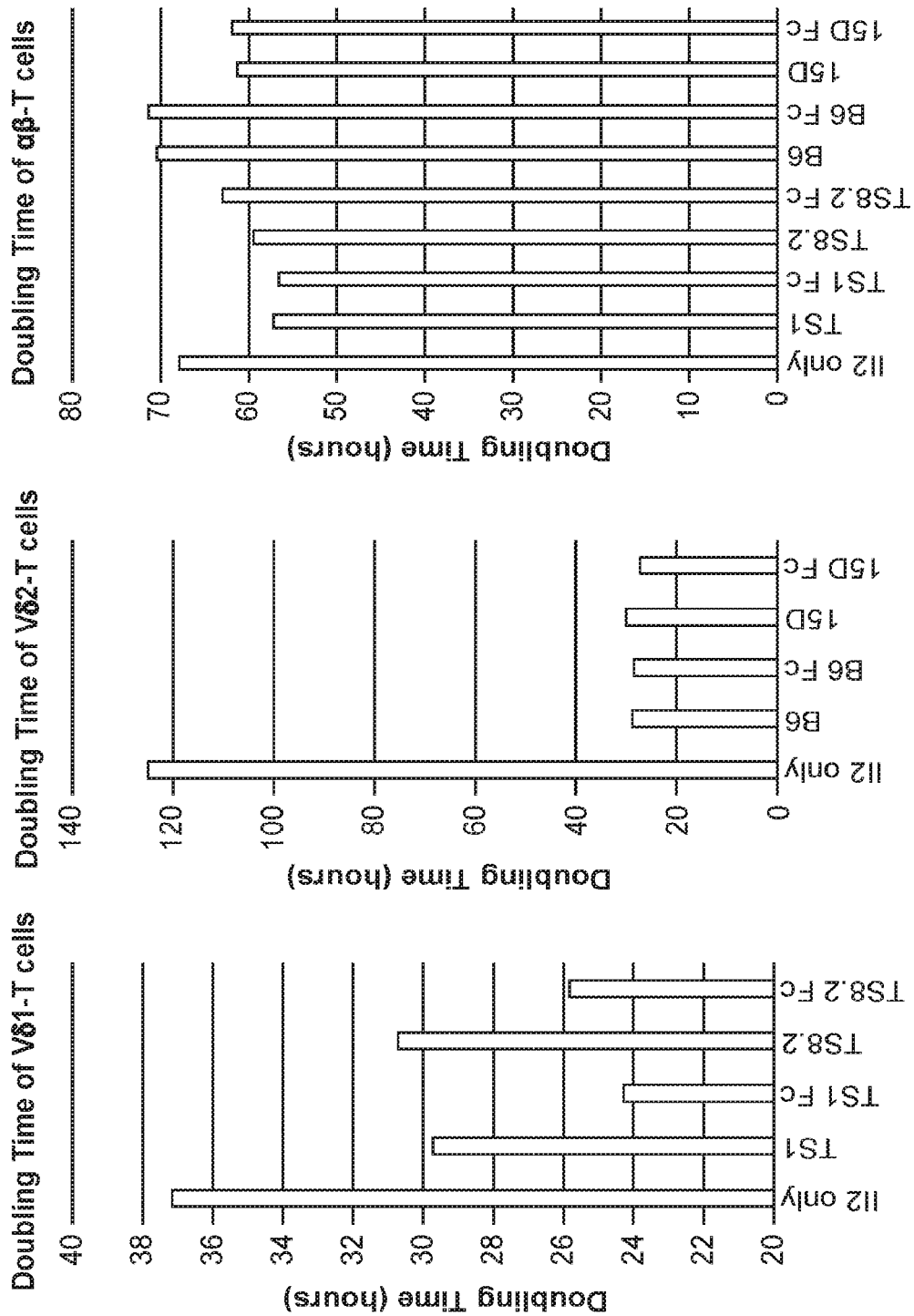
FIGS. 19A-C depict activation of γδ TCR results in reduction of γδ T-cell doubling time MAbs were directly coated (1 μg/mL) (TS1, TS8.2, B6 and 15D) or captured (0.1 μg/mL) with goat-anti-mouse Fc (5 μg/mL) (TS1Fc, TS8.2Fc, B6Fc and 15DFc) in 24-well plates. PBMCs were plated at $10^6$ cells/mL in RPMI with 10% FBS and 100 IU/mL IL-2. Cells were transferred to new plate without antibodies on day 7, adjusted to $10^6$ cells/mL with fresh media. Culture was replenished every 2-3 days and adjusted to $10^6$ cells/mL with fresh media. Doubling times for Vδ1, Vδ2 and 4 T-cells are shown in (A), (B) and (C), respectively.

Activation with δ1 and δ2 Specific Antibodies Reduces the Population Doubling Time for δ1 and δ2 T-Cells MAbs were directly coated (1 μg/mL) or captured (0.1 μg/mL) with goat-anti-mouse Fc (5 μg/mL) in 24-well plates. PBMCs were plated at $10^6$ cells/mL in RPMI with 10% FBS and 100 IU/mL IL-2. Cells were transferred to new plate without antibodies on day 7, adjusted to $10^6$ cells/mL with fresh media. Culture was transferred to a new plate without antibodies and adjusted to $10^6$ cells/mL on day 7 and replenished with fresh media every 2-3 days. The results are depicted in FIG. 19. Vδ1 T-cells population doubling time was reduced from 37 hours in the absence of activating antibody to 24 hours in the presence of immobilized TS1 antibody. Vδ2 T-cells population doubling time was reduced from 125 hours in the absence of activating antibody to 27.5 hours when activated with immobilized 15D antibody. Alpha beta T-cells population doubling time was not affected significantly by γδ TCR antibody activation.

Figure 20:
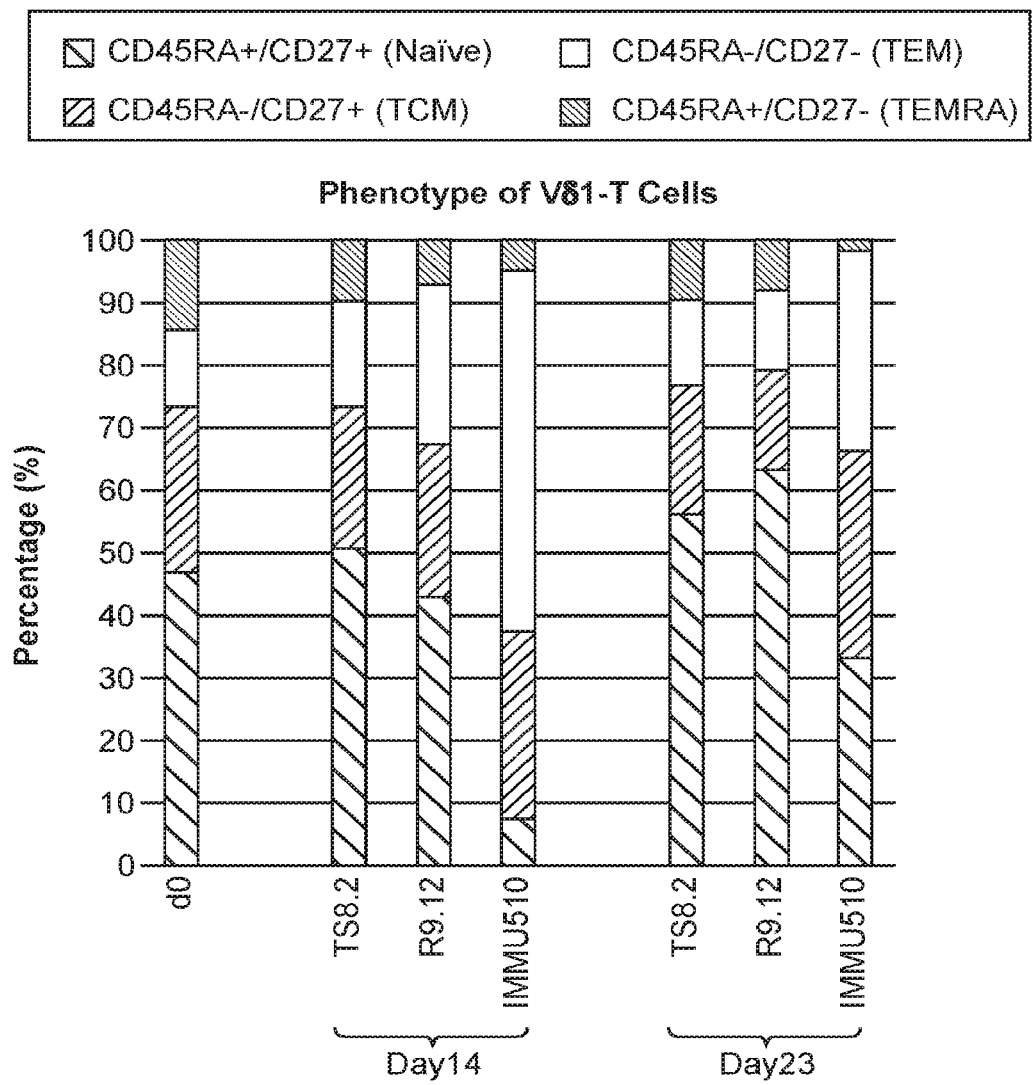
FIG. 20 depicts activation of Vδ1 by antibodies TS8.2 and TS1 results in predominantly naïve and central memory phenotypes. Antibodies were directly coated at 1 μg/mL in 24 well plates (TS8.2, R9.12 and pan-γδ Immu510). PBMCs were plated at $10^6$/mL in RPMI with 10% FBS and 100 IU/mL IL-2. Media was replenished every 2-3 days until day 23, except on day 15 when cultures were diluted 1:2 in fresh media. Cells phenotypes on days 14 and 23 are determined by CD45RA and CD27 expression using flow cytometry analysis.

Activation Using TS8.2 and TS1 Antibodies Results in Predominately Naïve and Central Memory Phenotypes Antibodies TSB, R9.12 and Immuno510 were immobilized directly to plastic wells at a concentration of 1.0 μg/mL. Human PBMCs were activated at $1 \times 10^6$ cell/ml and cultured in media containing RPMI with 10% FBS, 100 IU/mL rhIL-2. Media in the cultures were replenished every 2-3 days until Day 23 and analyzed by flow cytometry on days 0, 14 and 23. FIG. 20 depicts phenotype of Vδ1 T-cells on days 14 and 23 as determined by CD45RA and CD27 expression analysis by flow cytometry. Phenotypes of the γδ cells were defined as naïve (CD45RA+/CD27+), central memory (TCM, CD45RA-/CD27+), effector memory (TEM, CD45RA-/CD27-) and effector memory expressing (TEMRA, CD45RA+/CD27-). Activation with TS8.2 and R9.12 maintained the Vδ1 T-cell phenotype over the 23-day expansion period with 43% to 63% naïve populations and 23% to 27% central memory populations. In contrast, activation with pan-γδ antibody Immuno510 resulted in the reduction in the naïve Vδ1-T cells from 47% to between 8% and 33%.

Specific Enhanced Expansion of Vδ1 T-Cell Population by MICA-Fc

Figure 21A:
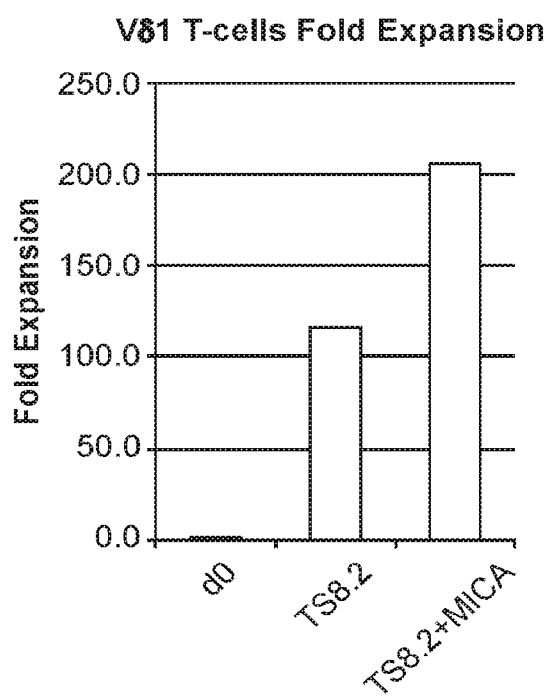
FIGS. 21A-B depict activation of PBMC by TS8.2 and MICA results in enhanced expansion of Vδ1 T-cells but not αβ T-cells. Antibody TS8.2 (1 μg/mL) or TS8.2 with MICA-Fc (1 and 5 μg/mL) were directly coated in 24 well plates. PBMCs were plated at $10^6$/mL in RPMI with 10% FBS and 100 IU/mL IL-2. Media is replenished every 2-3 days. (A) Vδ1 T-cells expansion; (B) αβT-cells expansion.
Figure 21B:
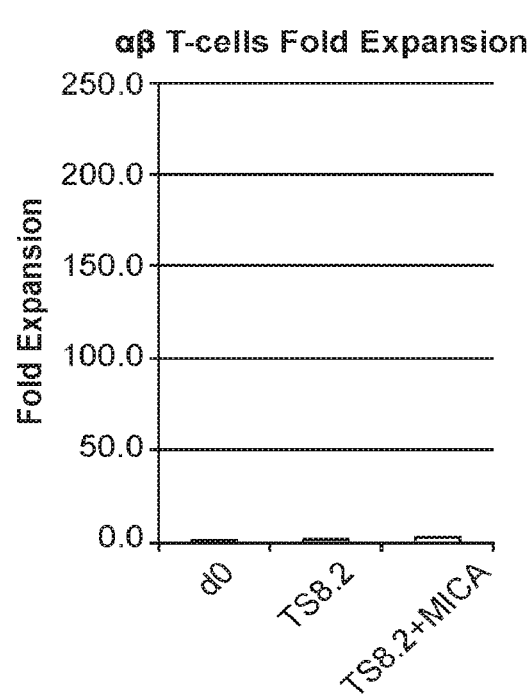

Human PBMCs were activated with plate-bound TS8.2 antibody (1 μg/mL) or plate-bound TS8.2 and MICA-Fc fusion protein (1 and 5 μg/mL, respectively). Cultures were expanded in RPMI media containing 10% FBS, 100 IU/mL rhIL-2. FIG. 21 depicts cell expansion after 10 days. Combination of TS8.2 with MICA-Fc enhanced the expansion of Vδ1 T-cell population by 2 fold over TS8.2-only control (A) with no effect on αβ T-cell population (B).

Figure 22A:
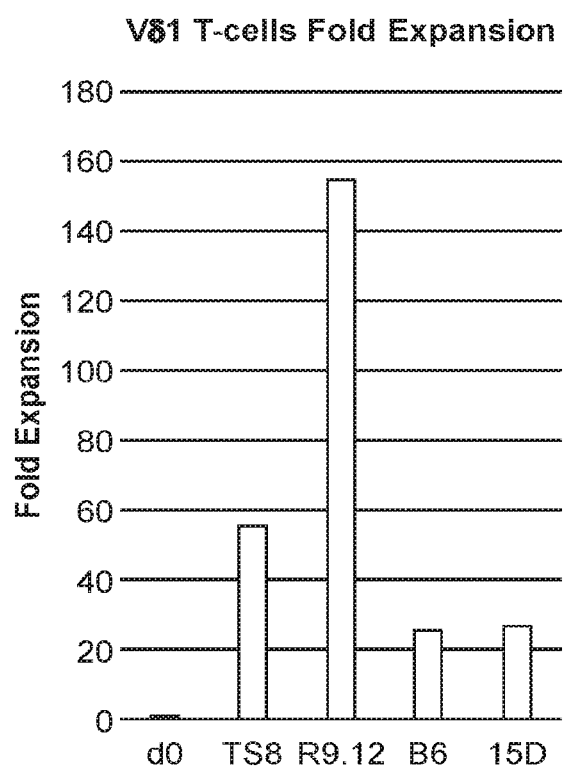
FIGS. 22A-B depict activation of umbilical cord blood mononuclear cells with δ1 and δ2 specific antibodies result in significant and specific expansion of $Vδ1^+$ and $Vδ2^+$ T-cells. MAbs TS8.2, R9.12, B6 and 15D were directly coated at 1 μg/mL in 24 well plates. Umbilical cord blood mononuclear cells were activated at $10^6$/mL in RPMI with 10% FBS and 100 IU/mL IL-2. Vδ1 and Vδ2 T-cells expansion are shown in (A) and (B), respectively.
Figure 22B:
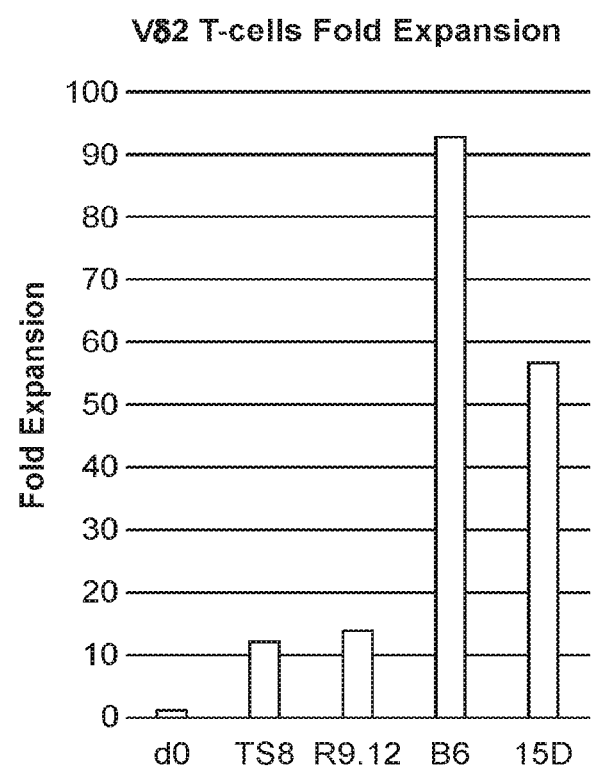

Specific and Significant Activation of δ1 and δ2 T-Cells from Umbilical Cord Blood Mononuclear cells from human umbilical cord blood were isolated by density gradient centrifugation using Ficol and activated with antibodies TS8.2, R9.12, B6 and 15D in media containing RPMI, 10% FBS, 100 IU/mL rhIL-2. FIG. 22 shows that Vδ1 T-cells were expanded by up to 152 fold using δ1-specific antibodies and Vδ2 T-cells were expanded by up to 93 fold using δ2-specific antibodies over 7 days.

Example 14. Epitope Mapping of Activating γδ TCR MAbs

Epitope binding domains of γδ TCR activating antibodies were determined. The binding epitope of γδ TCR δ1 specific activating MAbs TS8.2, TS1 and the δ2 specific activating MAbs 15D and B6 was determined in ELISA binding assays using different combinations of wild type and mutated γδ TCR paired chains. TS1, TS8.2 and R9.12 are δ1 specific MAbs that bind the surface of human T-leukemia cell line BE13 expressing δ1 TCR as detected by flow cytometry (data not shown). The BE13 TCR chains δ1J1 and γ8J2 were cloned and used for epitope mapping of δ1 specific MAbs.

Soluble TCR constructs containing the extracellular V, diversity (D), joining (J), and C regions domains of δ and γ chains were cloned and fused to the hinge region, CH2 and CH3 domains of human IgG1 heavy chain Fusion γδTCR-FC proteins expressed by transient transfection of 293 cells.

For the mapping of δ1 specific MAbs, different δ1 chains were expressed to include Vδ1J1, Vδ1J2 and Vδ1J3. Additional Vδ1J1 chains mutated at the V and J regions were generated. All of the different δ1 chains were paired with the γ8 TCR chain cloned out the BE13 cell line, the binding of δ1 specific MAbs were not affected by the pairing with γ chains.

The different γδ TCRs were co-transfected into 293 cells and were able to assemble correctly and to form disulfide-linked, heterodimers secreted as correctly paired receptor chains. The correct folding of the TCR γδ-FC heterodimers was confirmed by an ELISA binding assay using the anti-TCR pan γδ antibodies including B1.1 (Biolegend #331202), 5E6.E9 (ThermoFisher Scientific #TCR1061), 11F2 (Beckman Coulter #340884) and IMMU510 (Beckman Coulter #IM1349) antibodies which recognize all γδ T cell receptors.

In all cases binding of all γδ TCR MAbs was restricted to the γδ TCR heterodimers indicating that the pairs of the δ1 and δ2 chains with γ chain is necessary for the proper binding structure.

Transient Transfection of 293 Cells and Production of Chimeric Proteins. 239 cells were grown in Dulbecco's modified Eagle medium (DMEM) supplemented with 10% fetal calf serum. Adherent 293 cell were plated on 24 well plates the day before transfection, at $1 \times 10^5$ cells/well, and incubated at 37° C. (5% CO2) overnight. One μg of each TCR γ-Fc and TCR δ-FC plasmids were combined. Plasmid DNA and fectin293 transfection reagent (ThermoFisher Scientific #12347019) were diluted in serum-free Opti-MEM media for 5 minutes, before complexing at room temperature for 20-30 minutes. The entire volume of transfection mixture was added drop wise to prepared cells. Transfected 293 cells were incubated for 48-72 hours, at 37° C. (5% CO2). Cell supernatants were collected at 48 hours post transfection and tested for binding to selected anti human γδ TCR monoclonal antibodies by ELISA assay.

Sandwich ELISA Assay. Cell culture supernatants were tested by enzyme-linked immunosorbent assay (ELISA). Assay plates (Greiner Bio-One high binding microplates) were incubated overnight at 4° C. with 100 µl of 1 µg/ml Goat Anti-Human IgG, Fcγ fragment specific antibody (Jackson ImmunoResearch #109-005-008). Plates were blocked for 1 h at room temperature with 200 µl/well of blocking buffer (PBS containing 3% BSA). Supernatants containing soluble γδTCR were added in PBS-Tween (Tween at 0.5 ml/L in PBS) and incubated at room temperature for 1 h, followed by washing and incubation with selected mouse anti human γδ TCR specific mabs. Binding of γδTCR mAbs to the set of soluble TCRs was detected using HRP conjugated Goat anti mouse FC specific (Jackson ImmunoResearch Laboratories; Peroxidase-AffiniPure Goat Anti-Mouse IgG, Fcγ Fragment Specific #115-035-008) diluted to 1:10,000 in blocking buffer for one hour. The plate was then washed and developed with TMB reagent. Color changes on the plates were measured on a Victor X3 plate reader (Perkin Elmer) at wavelength 450 nm.

Figure 23:
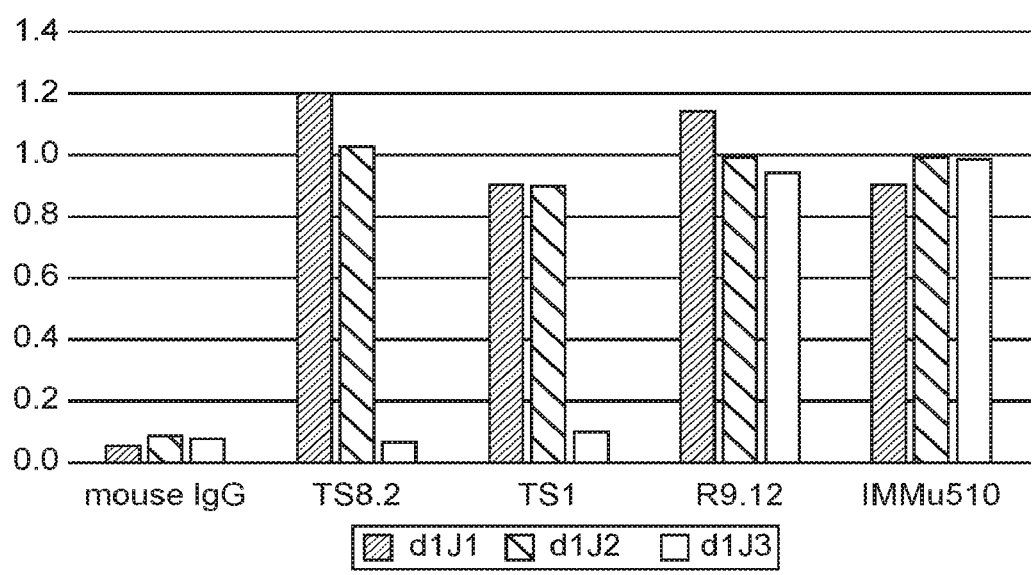
FIG. 23 depicts binding to soluble TCR generated from pairing of Vδ1J1, Vδ1J2 and Vδ1J3 chain with γ8 chain. Data show that TS1 and TS8.2 recognize the soluble TCR generated from Vδ1J1 and Vδ1J2 chains but failed to bind to the Vδ1J3 chain, indicating that the J1 and J2 gene segments are critical for TS1 and TS8.2 binding. R9.12 that bind to Vδ1, and the pan antibody Immuno510, which binds to δ constant region, are not affected by the specific J region.

As shown in FIG. 23, binding of TS1 and TS8.2 to soluble TCRs was detected when the δ1 chain include Vδ1J1 and Vδ1J2 sequences but not to the Vδ1J3 chain, indicating that the binding of TS1 and TS8.2 involved critical residues in the delta J1 and delta J2 region, that are missing in the delta J3. Data indicates that TS1 and TS8.2 bind δ1J1 and δ1J2 TCR, and R9.12 binds δ1J1 δ1J2 and δ1J3 TCR, and that J1 and J2 segments contain sequences that are critical for TS1 and TS8.2 binding.

Figure 25:
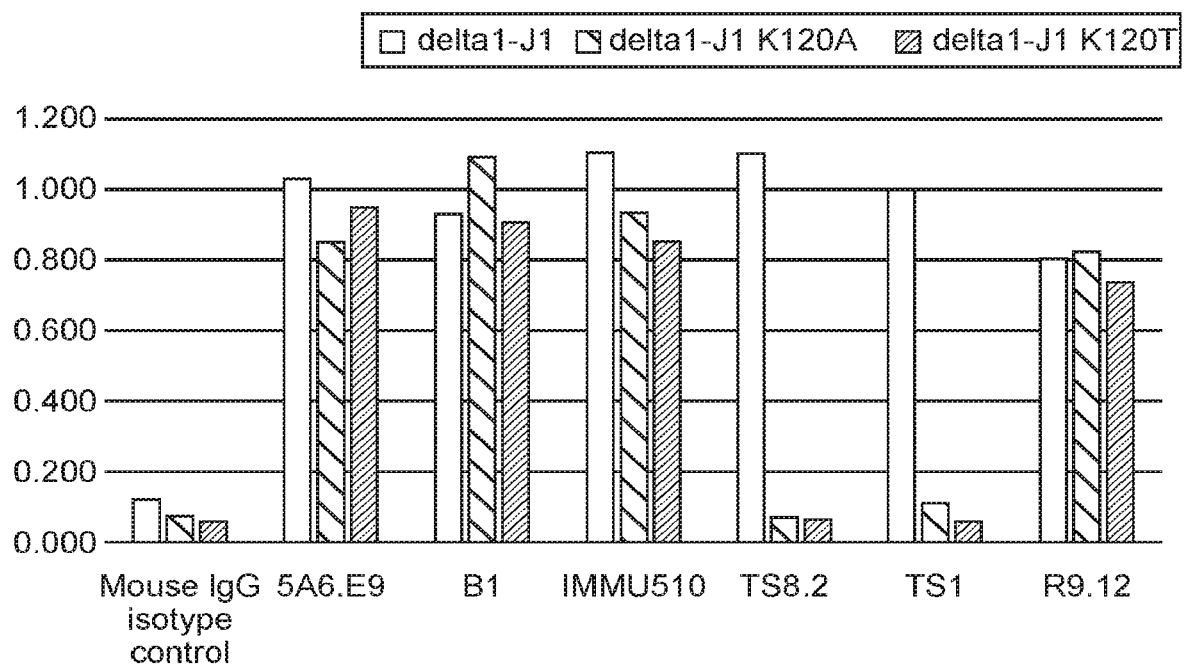
FIG. 25 depicts that point mutation in Vδ1J1 from Lys120 to Thr or Ala resulted in the loss of binding by TS-1 and TS8.2 MAbs.

To identify the critical amino acid(s) in the J1/J2 regions necessary for the TS8.2 and TS1 binding, sequence alignment of human delta J region pointed to 4 possible residues 9 J1/J2 residues Leu116, Lys120 and Thr122 that are shared between J1 and J2 but different in the J3 sequence. The δJ1 sequence was modified according to the J3 sequence at the selected positions; Leu116 was modified to Met, Lys 120 was modified to Thr and Ala, and Thr122 was replaced by Ile. Change of Lys120 by Thr abolished the binding of both TS8.2 and TS1 but not binding of R9.12. As shown in FIGS. 24 and 25, the Lysine residue at position 120 at the delta J1 and delta J2 is critical for TS-1 and TS8.2 antibody binding.

To further identify Vδ1 sequences important for TS8.2 and TS1 binding, additional mutated Vδ1 TCR constructs were made. As shown in FIG. 26, six mutated Vδ1 chains were constructed. The mutations were designed based on the differences in amino acid sequences between the highly homologous bovine Vδ1S1 and the human Vδ1 (δ8% identity). Mutated Vδ1 chains were generated using synthetic genes (Integrated DNA Technologies). Soluble TCRS were expressed as Vδ1 chains paired with human γ8 TCR Fc chain.

Figure 27:
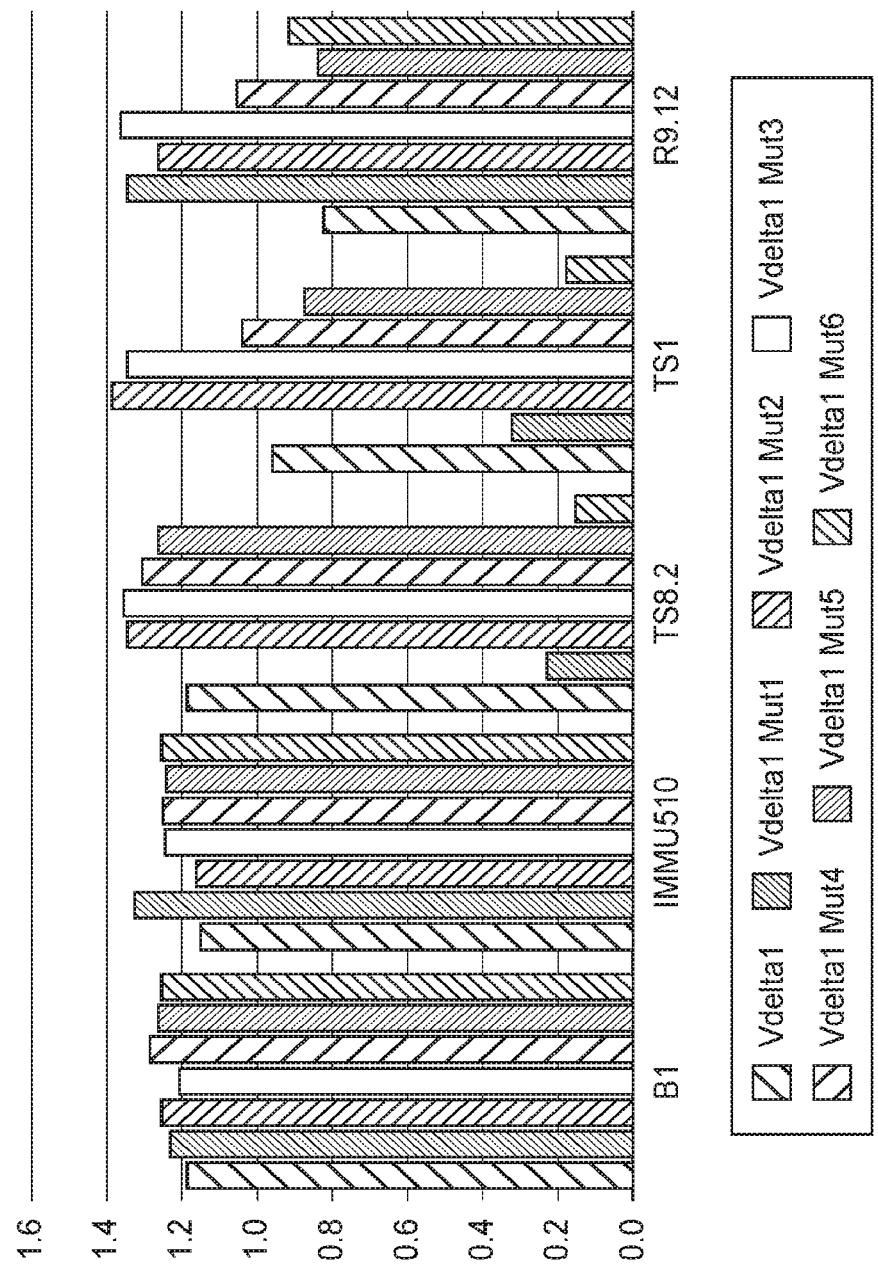
FIG. 27 depicts loss of binding of TS-1 and TS8.2 antibodies to the human Vδ1 m of example only. Numerous variations, changes, and substitutions may occur to those skilled in the art without departing from the invention. It should be understood that various alternatives to the embodiments of the invention described herein may be employed.

As shown in FIG. 27, TS-1 and TS8.2 antibodies failed to bind to the two of the mutated Vδ1 chains, Vδ1Mut1 and Vδ1Mut6. The Vδ1Mut1 displays 9 residue changes in the stretch of residues between the region of Gly57 to Ala88 of the variable region of human δ1 chain, and Vδ1Mut6 displays a change in two residues at position 71 and 72 (numbering as shown in FIG. 14). The binding of Vδ1 MAb R9.12 and pan δ chain constant MAb Immuno510 were not affected by any of the changes to the Vδ1. Therefore, the Vδ1 residues at position Arg71 and Asp72 together with Lys120 at The J1/J2 region are critical for binding of both Ts-1 and TS8.2 MAbs.

Taken together, the data indicate that the critical binding and activating epitope of both TS-1 and TS8.2 is located within the V and J1/J2 regions of the δ1 chain.

Epitope Mapping of Vδ2 Specific Activating MAbs 15D and B6

Specific binding of Mabs B6 and 15D to the δ2 T cell population activated by zoledronic acid was detected by flow cytometry, while no binding was detected to the BE13 cell line expressing δ1TCR (data not shown). Competition binding assay data also showed that B6 and 15D do not compete with each other and recognize different epitopes.

γδ TCR chain combinations. To identify the binding epitope for 15D and B6 MAbs, different γδ2 TCR constructs were generated. Vδ2 chain was co-transfected with γ3, γ4, γ8, γ9J1 and γ9JP FC fusion chains. The correct folding of the secreted δ2 TCR heterodimer was confirmed by an ELISA binding assay using the anti-TCR PAN γδ antibody IMMU510 (Backman Coulter #IM1349) and with the γ9 specific MAb the 7A5 (ThermoFisher Scientific #TCR1720).

Figure 28:
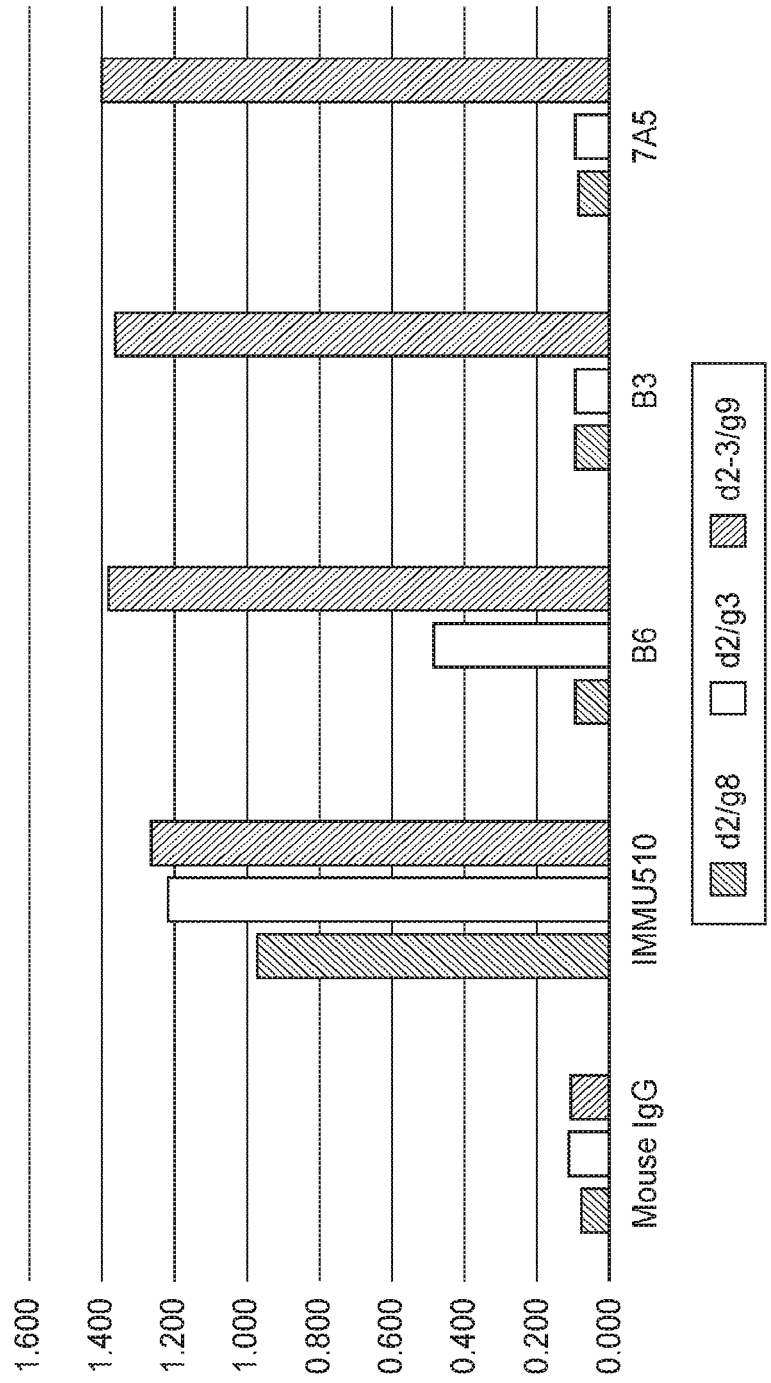

Binding of B6 was affected by the γ chain selected for paring with the δ2 chain. Binding of B6 was detected when the δ2 chain was paired with the γ9 chain regardless of the γ9 J sequence. The binding to the γ3δ2 TCR pair was greatly reduced, and the binding to the δ2 chain paired with γ8 was undetectable. As shown in FIG. 28, the most stabilized binding of the B6 MAb is to the δ2γ9 TCR. Both γ3 and γ8 belong to gamma family 1 and share high sequence homology (75%) with each other, γ9 a member of the gamma 2 family and shares low sequence homology with γ3 and γ8 (~20%). High binding affinity of B6 involves residues on both δ2 and γ9 chains. Positive control MAbs were IMMU510 a pan γδTCR that binds the constant region of the δ chain and recognize all γδTCRs, and 7A5 MAb a γ9 specific MAb. Binding of the B6 MAb was detected to the δ2γ9 TCR. B3 is a Vγ9 antibody.

Figure 30:
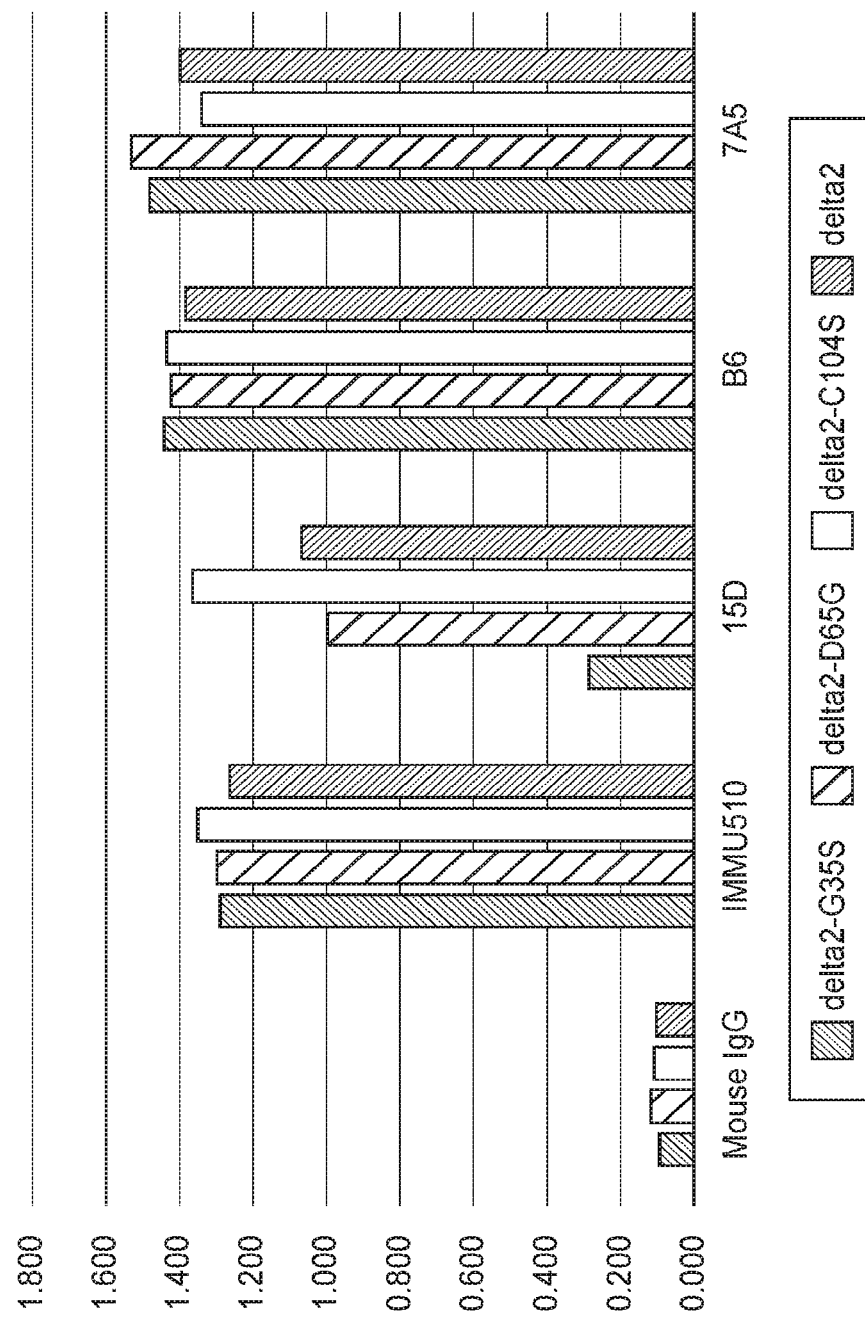

Recently, it was shown that human and Rhesus γδ2 T cells show a high degree of germline sequence homology of the TCR gene segments and the diversity of the CDR3 regions (Daubenberger C A, et al., J Immunol 2001; 167:6421-30). To identify critical sequences that are required for the binding of 15D, specific point mutations were introduced into the CDRs domain of human Vδ2 chain, and were replaced by the rhesus monkey sequence at positions Gly35 (Vδ2 CDR1) Aspδ5 (Vδ2 CDR2) and Cys104 (Vδ2 CDR3), by site directed mutagenesis. FIG. 29 shows the protein sequence alignment of human (IMGT Human TRDV2) and Rhesus monkey (GenBank: AY190028.1) Vδ2 variable regions. The changes were made in CDR1 (G35S), CDR2 (D65G) and the CDR3 C104S (numbering as shown in FIG. 15). The replacement of a single residue at the CDR1 of human Vδ2 from Gly to Ser led to complete loss of binding activity by 15D. As shown in FIG. 30, Gly35 was identified as a critical residue for the binding of 15D. Changes in CDR1, CDR2 and CDR3 of Vδ2 did not affect the binding of B6, IMMU510 a γδTCR pan MAb and 7A5 a γ9 specific Mab.

Example 15. Epitope Mapping of Novel Modulators of γδ T-Cell Activation and Expansion CD2 Epitopes:

The CD2 molecule consists of two extracellular immunoglobulin superfamily domains Ig-like V-type domain and Ig-like C-type domain, on which three major immunogenic regions have been described (Davis et al., Immunol Today 1996; 17: 177-187). Regions 1 and 2 are located in the first domain and region 3 is located in the second domain. MAbs that recognize region 1 bind both resting and activated T-cells and can strongly inhibit the binding of CD58 to CD2. Monoclonal antibodies that recognize region 2 have similar binding properties but are not effective at blocking CD58 binding. Monoclonal antibodies that recognize region 3 recognize CD2 only on activated T-cells and do not block CD58 binding.

Mapping of the binding epitope of CD2 agonist MAbs is done by competition assays against CD58, the natural ligand of CD2 and activation assays. In addition, site directed mutagenesis of critical CD2 binding residues is that leads to loss of binding of CD58, is tested for MAbs binding. Examples of mutations include mutagenesis of the CD2 sequence at position δ7 (K to R), 70 (Q to K), 110 (Y to D) and at position 111 (D to H). To design constructs for the mapping of the binding epitope of CD2 a sequence alignment of human and mouse CD2 using VectorNTI (Thermo Fisher) are performed. The alignments show a 50% sequence homology between human and mouse CD2. MAbs that bind the extracellular domain of human CD2 are not expected to cross react with the mouse CD2. To identify the binding epitopes, we generate domain swapping of mouse/human chimeric CD2 constructs. In such constructs, the human N-terminal Ig-like V-type domain (residues 25-128) is replaced with mouse residues (23-121) in expression vector expressing the extra cellular domain of CD2. Chimeric cDNA species are transiently transfected into CHO or 293 cells. Human wildtype CD2 and human mouse chimeric constructs are expressed on the surface of CHO cells. Chimeric CD2 Cell-surface expression is analyzed by FACScanto. Binding or loss of binding to chimeric molecule is detected by flow cytometry and validated by activation assays.

NKG2D Epitopes:

Epitope mapping of activating MAbs against NKG2D is tested by the ability of anti-hNKG2D antibody to reduce or block NKG2D interactions with one or more of its ligands, (MICA/MICB) or by competition with an antibody known to block hNKG2D ligand interaction. Agonist MAb is identified by its ability to reduce NKG2D-mediated activation of NK or T-cells. This can be evaluated by typical cytotoxicity assays, addition of ligand-blocking antibodies, or by blocking γδ T-cells mediated killing of MICA-expressing tumor cells in a dose-dependent fashion.

CD27 Epitopes:

Epitope mapping of agonist antibodies against CD27 is done by functional assay and their ability to block the interaction between human CD27 and its natural ligand human CD70. CD27 expressing cells are incubated for 30 min with 5 μg of MAbs at 4° C., after which 1 μg of biotinylated CD70 is added to the tube. The mixture is incubated for another 15 min at 4° C. before washing. Next, cells are incubated for 30 min with a mixture of streptavidin-PE (for detection of CD70 ligand binding) followed by several washing steps and analysis using FACS. Blockage of CD70 binding indicates that the MAb and CD70 share the same epitope.

Example 16: Characterization of TCR Vδ Repertoire of a Population of Expanded γδ T-Cells Clonal diversity of expanded γδT-cells from individual donors is assessed with polymerase chain reaction (PCR). The clonal diversity of freshly isolated PBMC from healthy donors is compared to the clonal diversity of cultures that are stimulated for 7 and 13 days with different activation agents described herein, including anti-TCR specific antibodies, ligand, and lectins.

RNA from the aforementioned γδT-cells is extracted, reverse transcribed into cDNA, and amplified by PCR using Vδ1, Vδ2, and Vδ3-specific primer pairs. Vol forward primer (5'ATGCTGTTCTCCAGCCTGCTGTGTGTATTT 3'; SEQ ID NO: 1) Vδ2 forward primer (5'ATGCAGAGGATCTCCTCCCTCATCCATCT 3'; SEQ ID NO: 2) and Vδ3 forward primer (5'ATGATTCTTACTGTGGGCTTTAGCTTTTTG 3'; SEQ ID NO: 3) were used in combination with A Cδ reverse primer (5'CTTGGGGTAGAATTCCTTCACCAGACAAGC3'; SEQ ID NO. 4) to amplify 500 bp DNA fragments.

The γ chain was amplified in separated RT-PCR reaction using Vγ specific primers to amplify Vγ2, Vγ3, Vγ4, and Vγ5 (5' GGTGCTTCTAGCTTTCCTGTCTCCTGC3' (SEQ ID NO: 10)), Vγ8 (5'ATGCTGTTGGCTCT AGCTCTGCTTCTA3' (SEQ ID NO: 11)) and Vγ9 (5'ATGCTGTCACTGCTCCACACATCAACG3' (SEQ ID NO: 12)) Vγ primers are paired with the Cγ reverse primer (5'GGAAGAAAAATAGTGGGCTTGGGGGAA3' (SEQ ID NO: 13)). The γ reverse primer based on consensus sequence of the Cγ1 and Cγ2. PCR fragments are cloned and the nucleotide sequence of 80 independent Vγ inserts are obtained. The Vδ, Dδ and Jδ junctional sequences are analyzed, together with CDR3 sequence alignment.

Example 17: MAbs and Related Targeting Constructs for Engineering of γδ T-Cells The human CD20 gene is obtained from a cDNA clone (Origene Technologies, Inc., 6 Taft Court, Suite 100, Rockville, Md. 20850). The CD20 gene is amplified using the forward primer (5' ATGACAACACCCAGAAATTCAGTAAATGG3' (SEQ ID NO: 14)) and the reverse primer (5' TCAAGGAGAGCTGTCATTTTCTATTGGTG3' (SEQ ID NO: 15)) the amplified CD20 cDNA is incorporated into pCDNA3.4 (Thermo Fisher Scientific) as a high expression vector for mammalian cells, and transfected into CHO cells as the host cells. Recombinant CHO cells (CD20/CHO cells) expressing CD20 molecules at a high level on their cell surfaces are identified by FACS analysis.

The CD20/CHO cells are used to immunize BALB/C mice or transgenic mice engineered to produce fully human antibodies as described in Jakobovits and Bornstein (Jakobovits Curr. Opin. Biotechnol. 1995 6:5δ1-6; Bornstein et al., Invest New Drugs. 2010 28:5δ1-74.). Antibodies with high affinity and specificity towards human CD20 are screened by FACS assays. Mouse antibodies are humanized by CDR grafting (Kim and Hong Methods Mol Biol. 2012; 907:237-45. Human single domain CD20 antibodies are also generated from mice or rats engineered to produce human heavy chain single domain antibodies (Janssens et al., PNAS 2006 vol. 103:15130).

The gene coding for the high affinity/specificity CD20 antibody described above is cloned into the MSGV1 retroviral vector backbone or the pCAG lentiviral vector. VH and VL domains are cloned either from the mouse hybridoma expressing the selected MAb, or from humanized antibody chains. γδ T-Cells are engineered with the CD20 MAbs described herein.

Example 18: TCR Constructs for Engineering of γδ T-Cells

Constructs expressing TCRs comprising sequences of highly reactive αβ TCR chains are isolated from T-lymphocytes expressing NY-ESO-1-MHC specific peptide complexes. The NY-ESO-1-MHC specific peptide complexes induce potent in vitro and in vivo anti-tumor activity against various NYESO-1-expressing tumors.

The highly reactive αβ TCR chains are isolated from melanoma, sarcoma patients or from mice bearing patient-derived xenografts derived from human melanoma or sarcoma tumors. Alternatively, the TCR is derived from mice altered to have a humanized immune system that expresses NY-ESO-1 peptides or NYESO-1-peptide complexes (See Gonzales et al., Immunol Res. 2013 57: 326-334; Boucherma etal., J Immuno. 2013. 191; 583-593; Liang-PingL. Et al., Nature Med. 2010, 16:1029-1035). T-cells that recognize epitopes of the NY-ESO-1-in the context of the dominant class I alleles HLA-A*02 (for example, peptide SLLMWITQC Residues 157-167 (SEQ ID NO: 16)) and dominant HLA-A*01-associated peptide are identified.

Sequences of TCRα and TCRβ transcripts are generated by reverse transcription-polymerase chain reaction (RT-PCR) using the One step RT-PCR kit (Qiagen Hilden Germany) according to the manufacturer's suggestions. First strand cDNA is generated from RNA isolated from the reactive T-cell. Total RNA is extracted with TRIzol Total RNA Isolation Reagent (Invitrogen Life Technologies) from CTL clones. Amplification of TCR α and β chains is done by a set of degenerate primers that can bind to highly conserved region of the TCR α and β chain V regions centered around the tryptophan-tyrosine residues at amino acid positions 34 and 35 (Kabat numbering) are used in combination with the α and β constant region reverse primers (Moonka and Loh Journal of Immunological Methods 169 (1994) 41-51). Amplified PCR fragments are gel purified and directly sequenced. Sequence information is used to design PCR primers suitable for cloning of the individual full-length cDNAs.

TCRs genes are cloned and inserted into MSGV-based retroviral vectors and full-length cDNAs amplified from selected T cells. Retroviral vectors encoding both α and β chains of wild-type NY-ESO-1-reactive human TCR are constructed using a MSGV1 backbone. Linking of the TCRα and TCRβ chains is done via an internal ribosome entry site (IRES) element in one construct, or by separation using a cleavable picorovirus peptide sequence.

Retroviral supernatants are generated by co-transfecting 293 cells that stably expressed MMLV gag and pol proteins with each MSGV1 TCR vector and a vector encoding the endogenous virus retroviral envelope protein using Lipofectamine 2000 (Invitrogen) as described previously or by electroporation using the Nucleofector (Lonza). Supernatants are collected at day 2 and 3 post-transfection and were diluted 1:1 with fresh DMEM containing 10% FCS. Engineered γδ T-cells are capable of properly express the genes encoding the TCR α and β chains without any further manipulation.

Example 19. Engineering γδ T-Cells with an αβ TCR Construct

A polynucleotide comprising an αβ TCR (tumor recognition moiety) is cloned from T-cells selected to be specific to the desired antigen using standard techniques. Isolated endogenous wild-type γδ T-cells are grown with methods described in previous examples to at least 6×10$^6$ cells prior to infection with the retrovirus or a lentivirus comprising an expression cassette encoding the tumor recognition moiety. A standard protocol for viral infection can be used to introduce the vector system into the wild-type γδ T-cell. Expression of the selection marker is used to select cells that have been successfully transfected.

The expression of the engineered αβ TCR can be evaluated by flow cytometry and/or by quantitative QRT-PCR and by functional assays with target cells for cytotoxicity and cytokine secretion. The expression of the engineered activation domain can also be evaluated by flow cytometry and/or by quantitative qRT-PCR. The number of engineered γδ T-cells expressing a cell surface marker of interest is determined by flow cytometry. The engineered γδ T-cell is further engineered with a suitable methodology described herein, such as the CRISPR-Cas, talen, meganucleases, zinc finger, or sleeping beauty transposon technologies to delete an exon associated with an HLA gene or a β2M gene.

Example 20: Engineering γδ T-Cells with CAR and TCR Constructs

γδ T-cells are transduced with retro- or lenti-viral based vectors to express targeting moieties that can direct the engineered γδ T-cells to specifically recognize tumor cells and get activated to kill it. The transduced targeting moieties include MAbs directed against tumor-specific surface proteins or tumor-specific intracellular peptides. γδ T-cells are also engineered with high affinity TCRs directed to peptide-MHC complexes.

Alternatively, cells can be engineered via transduction with non-viral vectors.

Example 21: Engineering of Isolated γδ T-Cells with Targeting Moieties

CAR construct design comprises of different main functional domains, a target moiety that recognizes a protein or a MHC associated peptide of interest displayed on a tumor cell, a short spacer that connects the extracellular receptor targeting element to the transmembrane domain, which transverses the cell membrane and connects to the intracellular activation signaling domain.

The target moiety receptor expressed on the surface of a γδ T-cell will be designed to specifically bind to a target protein that is expressed on a cancer cell. Tumor recognition moieties will be designed against targets including CD19, CD20, CD22, CD37, CD38, CD56, CD33, CD30, CD138, CD123, CD79b, CD70, CD75, CA6, GD2, alphafetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activation protein (FAP), PSMA, STEAP-1, STEAP-2, mesothelin, c-Met, CSPG4, PVRL-4, VEGFR2, PSCA, folate binding protein/receptor, SLC44A4, Cripto, CTAG1B, AXL, IL-13Rα2, IL-3R, and SLTRKδ.

The target moiety receptor can be derived from a portion of an antibody specific to tumor glycoprotein expressed on the surface of tumor cells, or alternatively the engineered receptor can be derived from a TCR receptor with a known specificity or an antibody recognizing a specific peptide sequence derived from intracellular tumor specific antigen presented on the on the surface in association with WIC complex including gp100, MART1, Tyrosinase, SSX2, SSX4, NYESO-1, epithelial tumor antigen (ETA), MAGEA family genes (such as MAGEA3. MAGEA4), KKLC1, mutated N, and K and H ras, BRaf, p53, WIC class I chain-related molecule A (MICA), WIC class I chain-related molecule B (MICB), or one or more antigens of HPV, EBV, or CMV. Such high affinity T-cell receptor like tumor recognition moieties will recognize peptide-WIC complex with a high degree of specificity.

Example 22: Targeting Moiety Constructs with a Spacer and a Transmembrane Domain Different spacers will be engineered into a tumor recognition moiety construct in order to optimize the potency of an engineered T-cell towards a cancer cell. The size of each spacer will vary according to the size of the target protein, the epitope recognized by the receptor, the size of the engineered tumor recognition moiety and the affinity of the receptor. Spacers that can accommodate conformational changes including sequences of human IgG, CD8a and CD4 hinge region.

Spacers that are tested consist of Gly, Ser, and Thr amino acids used at different lengths (from 19 to 9 residues) in order to provide chimeric receptor with improved binding affinity properties. The hinge and transmembrane portions of each construct is derived from the CD8a sequence (residues 117 to 178 of human CD8a) or alternatively the human IgG1 hinge-Fc cDNA with CD28 transmembrane domain (residues 153-179).

Example 23: Targeting Moiety Constructs with Co-Stimulatory Domains

Different co-stimulatory domains will be engineered into a construct comprising a tumor recognition moiety. A co-stimulatory domain comprising a CD28, 4-1BB, CD2, CD27, NKG2D, DAP10, DAP12, CD161, CD30, JAML, TLRs, CD244 or CD100 costimulatory signaling domain is engineered into a γδ T-cell to mimic a "second signal" that amplifies the activation through the chimeric receptor, leading to a more robust signal to multiply and kill the cancer cell.

The cytoplasmic region is derived from the endodomains of αβ and/or γδ T-cell co-stimulatory molecules including: CD28 (residues 180-220), CD137 (residues 214-255), ICOS (residues 165-199) CD27 (residues 213-260) NKG2D (Residues 1-51), JAML (residues 297-394) CD2 (residues 236-351), CD30 (residues 408-595) OX40 (Residues 1-23), HVEM (residues 224-283), or CD46 molecules. The optimal constructs are selected based on the degree of activation of the engineered γδ T-cell populations for induced cell cytotoxicity and based on the degree of cytokine secretion in-vitro and in-vivo.

Example 24: Targeting Moieties Comprising CD3ζ Activating Domain

The intracellular CD3ζ (residues 52-164) containing three ITAM domains (ITAM1: APAYQQGQNQLYNELNLGR-REEYDVLDKR, (SEQ ID NO: 5); ITAM 2: PQRRKNPQEGLYNELQKDKMAEAYSEIGM, (SEQ ID NO: 6); and ITAM3: ERRRGKGHDGLYQGLSTATKDTY-DALHMQ, (SEQ ID NO: 7) was cloned.

The intracellular domain of TCRζ was amplified using primers 5' AGAGTGAAGTTCAGCAGGAGCGCA-3' (SEQ ID NO: 8) and the reverse primer 5' CTCGAGTGGCTGTTAGCCAGA-3' (SEQ ID NO: 9).

The CAR constructs are generated by multistep overlap extension PCR. The products were fused in a separate PCR reaction driven by primers tailed with the Platinum Taq DNA Polymerase High Fidelity kit (Invitrogen), using the Overlap extension polymerase chain reaction protocol, The DNA encoding the full-length construct was ligated into MSGV1 Retroviral Vector. The construct provides a CAR targeting moiety comprising a CD3ζ activating domain.

Example 25: Engineering γδ T-Cells with More than One Recognition Moiety

γδ T-cells are transduced with more than one construct comprising a tumor recognition moiety, including a TCR and a MAb directed to the same intracellular tumor-specific protein. Each construct is selected to recognize a specific peptide in the context of different MHC haplotypes, such as A2 and A1, antibodies directed to different targets expressed on the same tumor cells or antibodies directed to different epitopes on the same target.

Example 26. In Vitro Expansion of Engineered γδ T-Cells

Engineered γδ T-cells are grown and expanded with an appropriate tissue culture media, such as the tissue culture media described in previous examples. The Engineered γδ T-cells are grown exponentially to about $1 \times 10^6$ in a 5% $CO_2$ incubator at 37° C. with or without stimulation by an external antigen and without co-culture with APCs or aminophosphates.

Example 27: Functional Characterization of Cytokines Released by Activated Engineered and Non-Engineered γδ T-Cells The expression of IFN-γ, TNF-α (R&D Systems), IL-1β, IL-2, (Biosource International), IL-12 (Diaclone Research), IL-6, and IL-18 will be measured using commercial enzyme-linked immunosorbent assay (ELISA) kits. The enzyme-linked immunosorbent assays will be performed according to the manufacturers' instructions. The amount of cytokine will be measured at different time points (from 24 to 72 hours) in a polystyrene 96-well plate (Maxisorb, Nunc) coated with a monoclonal mouse IgG1 against the human cytokine, at a concentration of 1 μg/ml in 0.05 M sodium bicarbonate buffer overnight at 4° C. After washing with PBS containing 0.05% Tween 20 the plate will be blocked with 3% bovine serum albumin (BSA, wt/vol, Sigma) in PBST for 1 h at 37° C. A standard (recombinant human Cytokine from R&D) and supernatant from γδ cultures samples will be added and the plate will be incubated at RT for 2 h. Detection is performed with a matched antibody pairs in relation to recombinant human cytokine standards.

Example 28. Identifying Co-Stimulatory Agents

The ability of different co-stimulatory agents to support activation, expansion and viability of engineered and non-engineered γδ T-cells is tested by adding co-stimulatory agents to whole PBMCs or enriched engineered and non-engineered γδ T-cell populations. Co-stimulatory agents are added in a soluble or immobilized form to different activating agents, including anti γδ TCR specific MAbs. Human PBMCs purified from buffy coats of healthy donors as described in previous examples or lymphocytes isolated from tissues are plated at $2 \times 10^6$ in 1 mL of complete RPMI-1640 media supplemented with 100 IU/mL rhIl-2 in 24-well flat-bottom tissue with 2-10 μg of anti γδTCR antibody in the presence or absence of soluble or immobilized agonistic antibodies to CD2, CD27, CD28, CD30, CD137, ICOS, CD161, CD122, CD244, and NKG2D, or stimulating ligands including, CD70-FC (ligand to CD27)

MICA, MICB and ULBP (ligands to NKG2D), 4-1BB (ligand to CD137), and Pilar 9 (ligand to CD161).

Example 29. Cytokine Support Activation

The ability of different cytokines to support activation, expansion and viability of engineered and non-engineered γδ T-cells is tested by adding cytokines to whole PBMCs or enriched engineered and non-engineered γδ T-cell populations. To test cytokine activation support, various cytokines are individually added to separate cell cultures every 3 days at 100 IU/mL. The cytokines that are tested include IL-2, IL-7, IL-12, IL-15, IL-33, IL-21, IL-18, IL-19, IL-4, IL-9, IL-23, IFN-γ, and IL1β. After the end of a select time period, a sample of cells is harvested and the composition of the cell population, i.e., percentages of γδ T-cells, αβ T-cells, B-cells, and NK cells is determined by flow cytometry.

Cells are kept in culture and expansion of select populations is tested at day 14 and day 21.

Example 30: Activation-Derived Vδ1+, Vδ2+ T Cell Populations are Cytotoxic to Tumor Cells To determine the cytotoxicity of selectively activated, enriched δ1 and δ2 T-cell populations of the invention, PBMCs were isolated from buffy coat obtained from normal donors using Ficoll paque PLUS (GE Healthcare #17-1440-02) density gradient centrifugation and plated in 24-well plates at 1×106 cells/mL in R2 medium (10% fetal bovine serum in RPMI1640 supplemented with penicillin/streptomycin, L-glutamine and 100 IU/mL of human recombinant IL2).

Figure 31:
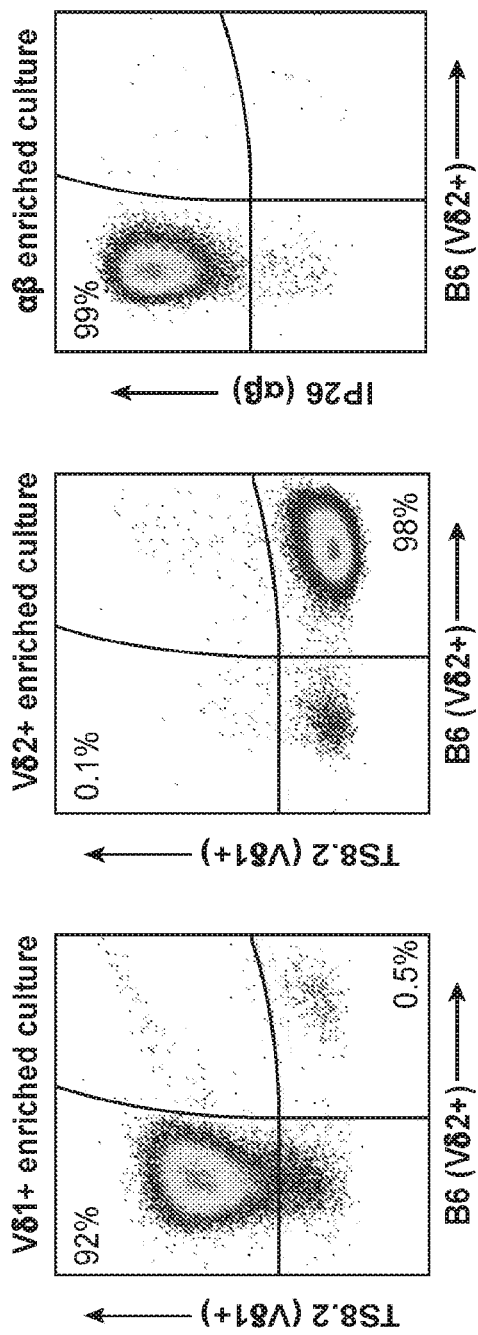

On Day 0, cells were plated on wells coated with either 1 μg/ml of δ1 specific MAbs (TS1, TS8.2) or δ2 specific MAbs (15D, B6) to activate γδ cells within the PBMC population. 50% medium exchange was performed on day 3 and 5. On Day 7, activated cells were moved to 6-well culture dishes without any MAb coating, expanded and maintained at ~1×10$^6$ cells/mL until day 14. To further the Vδ1+ and Vδ2+ activated T cell cultures, αβ T cells were positively selected and depleted from δ1 and δ2 activated cultures using IP26 monoclonal antibody (Biolegend #306702) bound to anti-Mouse IgG MicroBeads (Miltenyi #130-048-401). This led to highly enriched Vδ1+ and Vδ2+ T cell populations, as shown in FIG. 31. Positively selected αβ T cells were also collected (αβ enriched). These enriched Vδ1+, Vδ2+ and αβ T cell cultures were maintained in R2 medium until Day 22.

On day 22, γδ and αβ T cell composition of enriched cultures was determined by flow cytometry surface TCR staining using TS8.2, B6 and IP26 antibodies for δ1, δ2 and αβ, respectively. The highly enriched cultures contained 92%, 98% and 99% of Vδ1+(TS8.2+), Vδ2+(B6+) and (IP26+) T cells respectively.

In Vitro Cytotoxicity Assay with Vδ1+, Vδ2+ and αβ T Cell Populations

To assess cytotoxicity of the Vδ1+, Vδ2+ and αβ T cell cultures, effector cells were incubated at a 10:1 ratio with target cell lines for 6 hours. Target cell lines tested in this assay included solid tumor cell lines BxPc3 (ATCC® CRL-1687™) pancreatic adenocarcinoma and SK-MEL-5 (ATCC® HTB-70™) human melanoma as well as hematological B tumor cell line RPMI 8226 (ATCC® CCL-155™). Cell death was measured using CytoTox Glo reagent (Promega Cat #). % Specific lysis was calculated using the following formula:

$$\% \text{ Specific Lysis} = \left( \frac{(T_{Exp}) - (Tspon + Espon)}{T_{100\%} - Tspon} \right) * 100$$

Figure 32B:
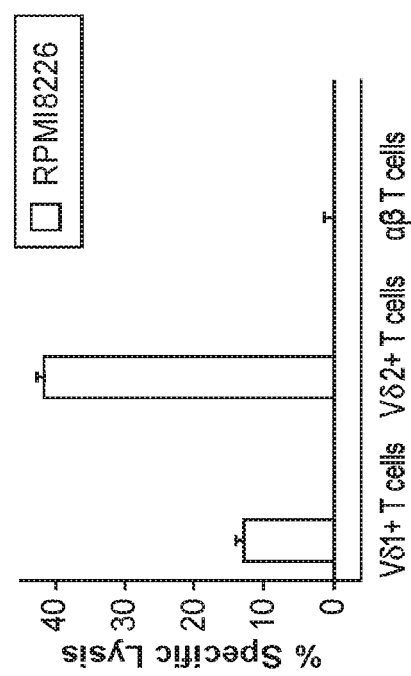
Figure 32A:
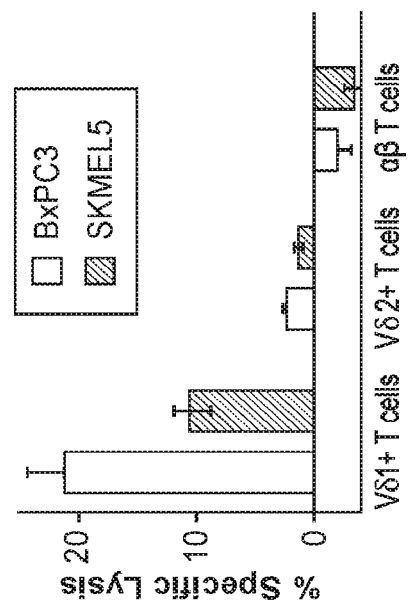

Highly enriched Vδ1+, Vδ2+ and αβ T cell cultures were tested for killing of BxPC3, SKMEL5 and RPMI8226 cell lines. As shown in FIG. 32, Vδ1+ T cells show killing of the epithelial tumor cell lines BxPC3 and SKMEL5 as well as the plasmacytoma cell line RPMI8226. (FIG. 32A) while Vδ2+ T cells show potency mostly towards RPMI8226 and were less effective against the solid tumor cell lines. T cells do not show any cytotoxic activity.

Example 31: Anti-Tumor Activity of Expanded γδ T-Cells In-Vitro

The cytotoxic activity against various tumor cell lines and primary tumor cells are tested at effector to target ratio between 1:1 to 40:1. Lysis of tumor cell lines and primary tumor cells are measured by detecting the release of intracellular enzymes lactate dehydrogenase. The percentage of γδ T-cells expressing engineered tumor recognition moieties in the culture is measured by flow cytometry, ELISA and/or ELISPOT assays.

Example 32: In Vivo Anti-Tumor Activity

Cohorts of immune-deficient mice engrafted with human tumor xenografts, or huPBMC-NOG (Taconic) mice, or mice with humanized immune system as described above, are injected subcutaneously or orthotopically with cells derived from patient-derived tumor or tumor cell lines, including cancers of the colon, breast, ovary, kidney, head and neck, prostate, bladder, oral cavity, pancreas and liver, and allowed to reach an average size of 50-100 mm$^3$. Enriched or isolated γδ-T cells, either naïve or engineered, are injected intravenously into mice or directly into the tumor at a range of doses. Tumor regression is defined as a reduction in tumor volume after γδ-T cell dosing, and compared to untreated and standard of care for the specific indication. In some experiments naïve or engineered γδ T-cells are labeled with GFP or luciferase and injected to tumor-bearing mice to follow their persistence and homing. At the end of the study, tumors are harvested and GFP positive cells were analyzed by flow cytometry and immunohistochemistry.

Example 33. Polyclonal TCR Diversity of Vδ1 and Vδ2 Populations Derived from Antibody Specific Activation TCR chains were amplified and cloned out of TS8.2 and B6 activated populations. PBMCs cultures were harvested after 14 days of specific activation with δ1 specific activating mAbs TS8.2 and the δ2 specific MAb B6. PBMCs cultures were lysed in 350 μl RLT buffer (Qiagen,), Total RNA was purified from 5×10$^5$ cell using the Qiagen RNeasy Mini Kit (Qiagen, catalog number 74106), following the manufacturer's instructions. In brief, 350 μl of 70% Ethanol was added to the cell lysate to provide ideal binding conditions. The lysate was then loaded onto the RNeasy silica membrane spin column. Contaminants were washed away. Concentrated RNA was eluted in 50 μl water.

One step RT PCR: Full length delta chains were amplified using the 5' δ1 (5' GCCCAGAAGGTTACTCAAGCCCAGTC3') (SEQ ID NO: 48) and 5' δ2 (5' GCCATTGAGTTGGTGCCTGAACACC 3') (SEQ ID NO: 49) primers, in combination with 3' human C6 (5' TTACAAGAAAAATAACTTGGCAGTCAAGAGAAA 3') (SEQ ID NO: 50) primer. A 800 bp PCR fragments of the full length delta chain were cloned into the pCI expression vector (Promega catalog number E1841). Similarly, full length gamma chains were amplified using the 5' primers γ2, γ3, γ4 (5' TCTTCCAACTTGGAAGGGAGAACGAAGTC 3') (SEQ ID NO: 51) γ5 (5' TCTTCCAACTTGGAAGGGGGAACGA 3') (SEQ ID NO: 52), γ8 (5' TCTTCCAACTTGGAAGGGAGAACAAAGTC 3') (SEQ ID NO: 53) γ9 (5' GCAGGTCACCTAGAGCAACCTCAAATTTCC 3') (SEQ ID NO: 54) in combination with a single 3' Cgamma primer (5' GGAAGAAAAATAGTGGGCTTGGGGGAA 3') (SEQ ID NO: 13)

The delta and gamma transcripts were amplified from 100 ng total RNA using reverse transcriptase polymerase chain reaction (RT-PCR). A total of five RT-PCR reactions were run for each sample activated with the TS8.2 MAb (δ1, γ2-γ4, γ5, γ8 and γ9) and two RT-PCR reactions were run for each sample activated with the B6 MAb (δ2, and γ9). The QIAGEN One Step RT-PCR kit was used for amplification, (Qiagen, Inc.). This kit provides a blend of Sensiscript and Omniscript Reverse Transcriptases, HotStarTaq DNA Polymerase, dNTP mix, buffer and Q-Solution, a novel additive that enables efficient amplification of "difficult" (e.g., GC-rich) templates. Reaction mixtures were prepared that included 5 μl of RNA, 0.5 of 100 μM of either delta or gamma chains primers (custom synthesized by IDT), 5 μl of 5×RT-PCR buffer, 1 μl dNTPs, 1 μl of enzyme mix containing reverse transcriptase and DNA polymerase, and 0.4 μl of ribonuclease inhibitor RNasin (1 unit). The reaction mixture contains all of the reagents required for both reverse transcription and PCR. The thermal cycler program was RT step 50° C. for 30 minutes 95° C. for 15 minutes followed by 30 cycles of (95° C. for 30 seconds, 48° C. for 30 seconds, 72° C. for 1.0 minutes). There was then a final incubation at 72° C. for 10 minutes. The extracted PCR products were directly cloned into pCI expression vector. Nucleotide sequences were analyzed using IMGT to identify germline V, D and J gene members with the highest sequence homology.

Examples of Sequences of Vδ1 Chains Activated by TS8.2 CDR3 (Junctional Diversity is Indicated by Bold Text)

```
TS8.2 activated clone 1 Vδ1, J1
                                                        (SEQ ID NO: 55)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALGPVVIPKGKLSFGKGTRVTVEP

TS8.2 activated clone 2 Vδ1, D3, J1
                                                        (SEQ ID NO: 56)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALGELCLGDTYTDKLIFGKGTRVTVEP

TS8.82 activated clone 3 Vδ1, D2 + D3, J1
                                                        (SEQ ID NO: 57)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALGDPKVYWGCTDKLIFGKGTRVTVEP

TS8.2 activated clone 4 Vδ1, D3, J1
                                                        (SEQ ID NO: 58)
AQKVTQAQSSVSMPVRKAVTLNCLYETSWWSYYIFWYKQLPSKEMIFLIRQGSDEQDAKS

GRYSVNFKKAAKSVALTISALQLEDSAKYFCALGTGVRGLQDADKLIFGKGTRVTVEP

TS8.2 activated clone 5 Vδ1 D1 + D3, J1
                                                        (SEQ ID NO: 59)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALLLGDTSFYTDKLIFGKGTRVTVEP

TS8.2 activated clone 6 Vδ1 D1 + D3, J1
                                                        (SEQ ID NO: 60)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCAALLPFLPSDWGIPVTDKLIFGKGTRVTVE
P

TS8.2 activated clone 7 Vδ1, D2 and D3, J1
                                                        (SEQ ID NO: 61)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALGTGVRGLQDTDKLIFGTGTRVTVEP
```

-continued

TS8.2 activated clone 8 Vδ1, D2 and D3, J1
(SEQ ID NO: 62)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALGGLSSLDLGDTDNHYTDKLIFGKGTRV

TVEP

TS8.2 activated clone 9 Vδ1, D2 and D3, J1
(SEQ ID NO: 63)
AQKVTQAQSSVSMPVRKAVTLNCLYETSWWSYYIFWYKQLPSKEMIFLIRQGSDEQNAKS

GRYSVNFKKAAKSVALTISALQLEDSAKYFCALGHPRSLMGVYTDKLIFGKGTRVTVEP

Examples of Gamma chains activated by TS8.2 Mab:
B8 TS8.82 activated Clone-1 γ4, J1/J2
(SEQ ID NO: 64)
SSNLEGRTKSVIRQTGSSAEITCDLAEGSTGYIHWYLHQEGKAPQRLLYYDSYTSSVVLESGI

SPGKYDTYGSTRKNLRIILRNLIENDSGVYYCATWDDGKKLFGSGTTLVVT

B8 TS8.82 activated Clone-2 γ9, JP1
(SEQ ID NO: 65)
AGHLEQPQISSTKTLSKTARLECVVSGITISATSVYWYRERPGEVIQFLVSISYDGTVRKESGI

PSGKFEVDRIPETSTSTLTIHNVEKQDIATYYCALWDDTRLGKKIKVFAPGTKLIIT

TS8.2 activated Clone-3 γ4, J1
(SEQ ID NO: 66)
SSNLEGRTKSVIRQTGSSAEITCDLAEGSTGYIHWYLHQEGKAPQRLLYYDSYTSSVVLESGI

SPGKYDTYGSTRKNLRMILRNLIENDSGVYYCATWSDKKLFGSGTTLVVT

TS8.2 activated Clone-4 γ9, J1/J2
(SEQ ID NO: 67)
AGHLEQPQISSTKTLSKTARLECVVSGITISATSVYWYRERPGEVIQFLVSISYDGTVRKESGI

PSGKFEVDRIPETSTSTLTIHNVEKQDIATYYCALWIHKKLFGSGTTLVVT

TS8.2 activated Clone 5 γ2, J1
(SEQ ID NO: 68)
SSNLEGRTKSVIRQTGSSAENTCDLAEGSNGYIHWYLHQEGKTPQRLQYYDSYNSKVVLES

GVSPGKYYTYASTRNNLRLILRNLIENDSGVYYCATWDCHYKKLFGSGTTLVVT

TS8.2 activated Clone 6 γ3, JP2
(SEQ ID NO: 69)
SSNLEGRTKSVTRQTGSSAEITCDLTVTNTFYIHWYLHQEGKAPQRLLYYDVSTARDVLESG

LSPGKYYTHTPRRWSWILRLQNLIENDSGVYYCATWDRRWIKTFAKGTKLIVTSP

TS8.2 activated Clone 7 γ2, JP1
(SEQ ID NO: 70)
SSNLEGRTKSVIRQTGSSAEITCDLAEGSNGYIHWYLHQEGKAPQRLQYYDSYNSKVVLES

GVSPGKYYTYASTRNNLRLILRNLIENDSGVYYCATWDGLDATCGVDTTGWFKIFAEGT

KLIVTSP

TS8.2 activated Clone 8 γ4, J1/J2
(SEQ ID NO: 71)
SSNLEGRTKSVTRPTGSSAVITCDLPVENAVYTHWYLHQEGKAPRRLLYYDSYTSSVVLES

GISPGKYDTYGSTRKNLRMILRNLIENDSGVYYCATKKLFGSGTTLVVT

TS8.2 activated Clone 9 γ9, JP1
(SEQ ID NO: 72)
AGHLEQPQISSTKTLSKTARLECVVSGITISATSVYWYRERPGEVIQFLVSISYDGTVRKESGI

PSGKFEVDRIPETSTSTLTIHNVEKQDIATYYCALWEIASQLGKKIKVFGPGTKLIIT

TS8.2 activated Clone 10 γ3, J1
(SEQ ID NO: 73)
SSNLGGRTKSVTRQTGSSAEITCDLTVTNTFYIHWYLHQEGKAPQRLLYYDVSTARDVLES

GLSPGKYYTHTPRRWSWILRLQNLIENDSGVYYCATWDRYYYKKLFGSGTTLVVT

```
TS8.2 activated Clone 11 γ3, JP2
                                                           (SEQ ID NO: 74)
SSNLEGRTKSVTRQTGSSAEITCDLTVTNTFYIHWYLHQEGKAPQRLLYYDVSTARDVLESG

LSPGKYYTHTPRRWSWILRLQNLIENDSGVYYPNSSDWIKTFAKGTKLIVTSP

TS8.2 activated Clone 12 γ4, J2
                                                           (SEQ ID NO: 75)
SSNLEGGTKSVTRPTRSSAEITCDLAERNTFYIHWYLHQEGKAPQRLQYYDSYTSSVVLESG

ISPGKYDTYGSTRKNLRMILRNLIENDSGVYYCATRDVPNYYKKLFGSGTTLVVT

TS8.2 activated Clone 13 γ2, JP1
                                                           (SEQ ID NO: 76)
SSNLEGRTKSVIRQTGSSAEITCDLAEGSNGYIHWYLHQEGKAPQRLQYYDSYNSKVVLES

GVSPGKYYTYASTRNNLRLILRNLIENDSGVYYCATWDGRVSYTTGWFKIFAEGTKLIVTS

P

TS8.2 activated Clone 14 γ4, J1/J2
                                                           (SEQ ID NO: 77)
SSNLEGRTKSVIRQTGSSAEITCDLAEGSTGYIHWYLHQEGKAPQRLLYYDSYTSSVVLESGI

SPGKYDTYGSTRKNLRMILRNLIENDSGVYYCATWDKGRKLFGSGTTLVVT

TS8.2 activated Clone 15 γ9, J1
                                                           (SEQ ID NO: 78)
AGHLEQPQISSTKTLSKTARLECVVSGITISATSVYWYRERPGEVIQFLVSISYDGTVRKESGI

PSGKFEVDRIPETSTSTLTIHNVEKQDIATYYCALWETHYKKLFGSGTTLVVT

TS8.2 activated Clone 16 γ2, J1
                                                           (SEQ ID NO: 79)
SSNLEGRTKSVIRQTGSSAEITCDLAEGSNGYIHWYLHQEGKAPQRLQYYDSYNSKVVLES

GVSPGKYYTYASTRNNLRLILRNLIENDSGVYYCATWDGRYKKLFGSGTTLVVT

TS8.2 activated Clone 17 γ4, JP1
                                                           (SEQ ID NO: 80)
SSNLEGRTKSVIRQTGSSAEITCDLAEGSTGYIHWYLHQEGKAPQRLLYYDSYTSSVVLESGI

SPGKYDTYGSTRKNLRMILRNLIENDSGVYYCATWGTTGWFKIFAEGTKLIVTSP

B8(Buffy coat 8)- B6 activated clones:
B6 activated Clone δ2, D3. J1
                                                           (SEQ ID NO: 81)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDKVLGVPTASYTDNKLIFGKGTRVTVEP

B6 activated Clone δ2 ,D3, J1
                                                           (SEQ ID NO: 82)
AIELVPEHQTVPVSIGVPATLRCSMKGEAIGNYYINWYRKTQGNTMSFIYREKDIYGPGFKD

NFQGDIDIAKNLAVLKILAPSERDEGSYYCACDTVGILPYDKLIFGKGTRVTVEP

B6 activated Clone δ2, D2 + D3, J1
                                                           (SEQ ID NO: 83)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDILTVLGDNRTDKLIFGKGTRVTVEP

B6 activated Clone δ2, D3, J1
                                                           (SEQ ID NO: 84)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDVVGEGGADKLIFGKGTRVTVEP

B6 activated Clone δ2, D3, J1
                                                           (SEQ ID NO: 85)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDTVGGGEYTDKLIFGKGTRVTVEP

B6 activated Clone δ2, D3, J1
                                                           (SEQ ID NO: 86)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDTVGTGDIRTYTDKLIFGKGTRVTVEP
```

-continued

B6 activated Clone δ2, D2 + D3, J1
(SEQ ID NO: 87)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDSLTGGSGLTDKLIFGKGTRVTVEP

B6 activated Clone δ2, D3, J3
(SEQ ID NO: 88)
AIELVPEHQTVPVSIGVPATLRCSMKGEAIGNYYINWYRKTQGNTMTFIYREKDIYGPGFKD

NFQGDIDIAKNLAVLKILPPSERDEGSYYCACDTGGYSSWDTRQMFFGTGIKLFVEP

B6 activated Clone δ2, D2 + D3, J1
(SEQ ID NO: 89)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDPLKTLGTYTDKLIFGKGTRVTVEP

B6 activated Clone δ2, D1 + D3, J1
(SEQ ID NO: 90)
AIELVPEHQTVPVSIGVPATLRCSMKGEAIGNYYINWYRKTQGNTMTFIYREKDIYGPGFKD

NFQGDIDIAKNLAVLKILAPSERDEGSYYCACDAVIAGGSFTDKLIFGKGTRVTVEP

B6 activated Gamma chains:
B6 activated clone γ9, JP1
(SEQ ID NO: 91)
AGHLEQPQISSTKTLSKTARLECVVSGITISATSVYWYRERPGEVIQFLVSISYDGTVRKESGI

PSGKFEVDRIPETSTSTLTIHNVEKQDIATYYCALWEDQELGKKIKVFGPGTKLIIT

B6 activated clone γ9, JP1
(SEQ ID NO: 92)
AGHLEQPQISSTKTLSKTARLECVVSGITISATSVYWYRERPGEVIQFLVSISYDGTVRKESGI

PSGKFEVDRIPETSTSTLTIHNVEKQDIATYYCALWAYPPELGKKIKVFGPGTKLIIT

B6 activated clone γ9, JP1
(SEQ ID NO: 93)
AGHLEQPQISSTKTLSKTARLECAVSGITISATSVYWYRERPGEVIQFLVSISYDGTVRKESGI

PSGKFEVDRIPETSTSTLTIHNVEKQDIATYYCALWEVQELGKKIKVFGPGTKLIIT

B6 activated clone γ9, JP1
(SEQ ID NO: 94)
AGHLEQPQISSTKTLSKTARLECVVSGITISATSVCWYRERPGEVIQFLVSISYDGTVRKESGI

PSGKFEVDRIPETSTSTLTIHNVEKQDIATYYCALWEVLQELGKKIKVFGPGTKLIIT

B6 activated clone γ9, JP1
(SEQ ID NO: 95)
AGHLEQPQISSTKTLSKTARLECVVSGITISATSVYWYRERPGEVIQFLVSISYDGTVRKESGI

PSGKFEVDRIPETSTSTLTIHNVKKQDIATYYCALWEVRELGKKIKVFGPGTKLIIT

B6 activated clone γ9, JP1
(SEQ ID NO: 96)
AGHLEQPQISSTKTLSKTARLECVVSGITISATSVYWYRERPGEVIQFLVSISYDGTVRKE

SGIPSGKFEVDRIPETSTSTLTIHNVEKQDIATYYCALWRELGKKIKVFGPGTKLIIT

B6 activated clone γ9, JP1
(SEQ ID NO: 97)
AGHLEQPQISSTKTLSKTARLECVVSGITISATSVYWYRERPGEVIQFLVSISYDGTVRKE

SGIPSGKFEVDRIPETSTSTLTIHNVEKQDIATYYCALWEAQELGKKIKVFGPGTKLIIT

B6 activated clone γ9, JP1
(SEQ ID NO: 98)
AGHLEQPQISSTKTLSKTARLECVVSGITISATSVYWYRERPGEVIQFLVSISYDGTVRKE

SGIPSGKFEVDRIPETSTSTLTIHNVEKQDIATYYCALWETELGKKIKVFGPGTKLIIT

B6 activated clone γ9, JP1
(SEQ ID NO: 99)
AGHLEQPQISSTKTLSKTARLECVVSGITISATSVYWYRERPGEVIQFLVSISYDGTVRKE

SGIPSGKFEVDRIPETSTSTLTIHNVEKQDIATYYCALWEEVELGKKIKVFGPGTKLIIT

-continued

B6 activated clone γ9, JP1

(SEQ ID NO: 100)

AGHLEQPQISSTKTLSKTARLECVVSGITISATSVYWYRERPGEVIQFPVSISYDGTVRKESGI

PSGKFEVDRIPETSTSTLTIHNVEKQDIATYYCALWEPPQSLGKKIKVFGPGTKLIIT

Example 34. Cryopreservation of γδ T-Cells in Freeze Media to Generate Cell Banks for Further Processing Non-modified γδ T-Cells will be formulated in freezing media and placed in cryogenic storage units such as liquid nitrogen freezers (−195° C.) or ultra-low temperature freezers (−δ5° C., −80° C. or −120° C.) for long-term storage. The freeze media will contain dimethyl sulfoxide (DMSO), sodium chloride (NaCl), dextrose, dextran sulfate or hydroxyethyl starch (HES) with physiological pH buffering agents ranging between 6.5 and 7.5.

The cryopreserved γδ T-cells will be thawed and further processed by stimulation with antibodies, proteins, peptides, and cytokines. The cryopreserved γδ T-Cells will be thawed and genetically modified as previously described in this application. The engineered γδ T-cells will be further cryopreserved to generate cell banks in quantities of 10, 100, 200 vials at $10^6$ to $10^8$ cells per mL in freeze media. The non-engineered and/or engineered γδ T-cells will be further cryopreserved to generate cell banks in quantities of 10, 100, 200, 500, and 1,000 vials or bags at $10^6$ to $10^8$ cells per mL in freeze media.

Example 35. Alternative Cryopreservation of γδ T-Cells in Freeze Media to Generate Cell Banks for Further Processing Other cryoprotectants are added to the cryopreservation support described in the previous example to provide nutritional support and biophysical cell protection against lysis during the freezing and thawing process. These include D-glucose, mannitol, sucrose, adenine, guanosine, recombinant human albumin, citrate, anti-coagulant, Benzonase, DNase, propylene glycol, ethylene glycol, 2-methyl-2,4-pentanediol. Additional additives designed to provide buffering capacity for high cell density frozen product include inorganic phosphate, sodium bicarbonate and HEPES.

Example 36. Cryopreservation of γδ T-Cells in Freeze Media to Generate Cell Banks for Further Processing Initial freezing of γδ T-cells are performed in a temperature controlled ramp designed to achieve a freezing rate of between −0.1° C. to −5° C. per minute using a controlled rate freezer (e.g. CryoMed Controlled Rate Freezer) or a mechanical −70° C. freezer with appropriately insulated racking system to deliver the desired freeze rate. The frozen cells are placed in −70° C. freezers for short-term storage of up to 30 to 60 days. The frozen cells are placed in liquid $N_2$ storage tanks for longer-term storage of up to 12, 24, 36 and 48 months while maintaining γδ T-cell number and cell functions without deterioration as measured by methods described in earlier sections.

The cryopreserved cells described in this example will be thawed and further stimulated and expanded in suitable closed vessels such as cell culture bags and/or bioreactors to generate suitable quantities of engineered γδ T-cells for administration to a subject.

Example 37. Formulation of γδ T-Cells for Direct Infusion into Patients

Engineered γδ T-cells are concentrated by centrifugation and/or membrane dia-filtration to between $5 \times 10^6$ cells/mL and $10^8$ cells/mL in physiological buffer containing cryoprotective excipients and placed in cryogenic storage units such as liquid nitrogen, or ultra-low temperature freezers for long-term storage.

Example 38. Treatment of a Human Subject Afflicted with Cancer

Fresh or frozen engineered and/or non-engineered γδ T-cells are thawed at bedside and intravenously infused into human subjects. About 1 cell per kilogram to about $1 \times 10^{10}$ cells per kilogram engineered and/or non-engineered γδ T-cells are infused into the human subject over a 30-δ0 minute period of time. The engineered γδ T-cells are administered with or without the aid of the co-stimulatory cytokine IL-2 or other cytokines. Optionally, the procedure is repeated. In vivo expansion of the γδ T-cells in the subject is measured by flow cytometry.

Example 39. Generation of Specific γδ T Cell Activators

γδ T cell activators in the form of murine antibodies were produced by immunization of recombinant soluble human γδ TCR. δ1-specific activators were generated by immunization using γ8δ1-TCR-FC, and δ2-specific activators were generated by immunization using γ9δ2—TCR-FC, both constructs comprising the mature ECD of the γδTCR chains fused to human IgG1FC. Three strains of mice (Balb/c, CD-1 and FVB) were inoculated with human recombinant γδTCR to provide hybridomas that secrete high affinity, murine monoclonal antibody activators.

The hγδTCR-Fc fusion constructs were generated by PCR amplification. γ8δ1 TCR chains were amplified from RNA isolated from the BE13 (DSMZ #ACC 396), a T cell leukemia cell line expressing γ8δ1 TCR. γ9δ2 TCR chains were amplified from RNA isolated from Zoledronic acid activated human PBMCs. Soluble δ1TCR-FC and δ2TCR-FC were purified from the supernatant of transiently transfected HEK 293 cells. 10 μg of soluble TCR was emulsified with an equal volume of TITERMAX® Gold (Sigma Aldrich) or Imject Alum Adjuvant (Thermo Fisher) and used for the immunization of each mouse. The resulting emulsions were then injected into six mice (2 each: Balb/c, CD-1 and FVB) via the footpad route.

Solid-phase ELISA assays were used to screen mouse sera for mouse IgG antibodies specific for human γδTCR. Briefly, 96 well plates (VWR International, Cat. #δ10744) were coated with recombinant γδTCR- at 1 μg/ml in ELISA coating buffer overnight. After washing with PBS containing 0.02% (v/v) Tween 20, the wells were blocked with 3% (w/v) BSA in PBS, 200 μL/well for 1 hour at room temperature (RT). Mouse serum was titrated (1:100, 1:200, 1:400, and 1:800) and added to the γδTCR coated plates at 50 µL/well and incubated at RT for 1 hour. The plates are washed and then incubated with 50 µL/well HRP-labeled goat anti-mouse IgG diluted 1:10,000 in 3% BSA-PBS or 2% FCS in PBS for 1 hour at RT. Again the plates were washed and 40 µL/well of a TMB substrate solution (Thermo Scientific 34028) was added for 15 minutes at RT. After developing, an equal volume of 2N H2SO4 was added to stop substrate development and the plates were analyzed by spectrophotometer at OD 450.

Sera-positive immunized mice were sacrificed and draining lymph nodes (popliteal and inguinal) were dissected out and used as a source for antibody producing cells. A single cell suspension of B cells (766×10⁶ cells) was fused with non-secreting P3×63Ag8.653 myeloma cells (ATCC #CRL-1580) at a ratio of 1:1 by electrofusion. Electrofusion was performed using the BTX Hybrimmune™ System, (BTX Harvard Apparatus) as per the manufacturer's directions. After the fusion, the cells were resuspended in hybridoma selection medium supplemented with Azaserine (Sigma #A9666), high glucose DMEM medium with sodium pyruvate (Cellgro cat #15-017-CM) containing 15% Fetal Clone I serum (Hyclone), 10% BM Condimed (Roche Applied Sciences), 4 mM L-glutamine, 100 IU Penicillin-Streptomycin and 50 µM 2-mercaptoethanol and then plated in three T150 flasks in 50 mL selection medium per flask. The flasks were then placed in a humidified 37° C. incubator containing 5% CO2 and 95% air for 6-7 days.

After six days of growth the library consisting of the cells grown in bulk in the T150 flask was plated at 1 cell per well in Falcon 384 well flat-bottom plates using the Aria II cell sorter. The selected hybridomas were then grown in 90 µL of culture medium containing 15% Fetal Clone I serum (Hyclone), 10% BM-Condimed (Roche Applied Sciences), 1 mM sodium pyruvate, 4 mM L-glutamine, 100 IU Penicillin-Streptamycin, 50 µM 2-mercaptoethanol, and 100 µM hypoxanthine. Any remaining unused hybridoma library cells were frozen for future library testing. After ten days of growth supernatants from each well of the plated cells were assayed for antibodies reactive for δ1TCR by ELISA and FACS assays.

For screening by FACS-hybridoma wells secreting murine immunoglobulin were screened for human δ1/TCR specificity using a flow cytometry based assay. BE13 cells expressing δ1γ8TCR, or Zoledronic acid treated human PBMCs expressing δ2γ9TCR were incubated for δ0 minutes on ice with 25 µL hybridoma supernatant. Cells were washed with PBS, 2% FCS, twice and then incubated with 50 µL of a goat-anti-mouse IgG Fc fragment specific secondary conjugated to PE diluted 1:300 in PBS/2% FCS. After 15 minutes of incubation, cells were washed twice with PBS/2% FCS and re-suspended in PBS/2% FCS with DAPI and analyzed by flow cytometry using a FACS Canto per the manufacturer's instructions. Wells containing immunoglobulin that preferentially bound the BE13 cells were expanded and further tested for δ1 specificity by ELISA assay. Wells containing immunoglobulin that preferentially bound the Zoledronic acid activated PBMCs cells were expanded and further tested for δ2 specificity by ELISA assay.

High bond ELISA 96 well plates were coated with soluble γδTCR proteins generated by paring the following γδ TCR chains: γ8δ1, γ8δ2, γ9δ1 and γ9δ2. Soluble TCRs were diluted and used at 1 µg/ml in sodium carbonate buffer overnight at 4° C. The plates were washed and blocked with 3% BSA in PBS/Tween for one hour at 37° C. and used immediately or kept at 4° C. Undiluted hybridoma supernatants were incubated on the plates for one hour at RT. The plates were washed and probed with HRP labeled goat anti-mouse IgG diluted 1:10,000 in 3% BSA-PBS for one hour at RT. The plates were then incubated with substrate solution as described above and read at OD 450. Wells containing immunoglobulin that preferentially bound human δ1 TCR chain as determined by a signal above background, were transferred and expanded.

The resulting δ1 and δ2 TCR specific clonal hybridomas were cryopreserved in CS-10 freezing medium (Biolife Solutions) and stored in liquid nitrogen.

Example 40. Sequencing of δ1- and δ2-Specific Activators

Exemplary distinct monoclonal antibodies that specifically bind, activate, and expand δ1 T cells were selected for sequencing and further analysis. As shown in the tables below, sequence analysis of the heavy chain variable regions (FIG. 33) and light chain variable regions (FIG. 34) of selected δ1-γδ TCR specific monoclonal antibodies generated in Example 39 confirmed novel complementarity determining regions and display of novel VDJ arrangements. The complementarity determining regions set forth in FIGS. 33-34, are as defined by Kabat. Exemplary distinct monoclonal antibodies that specifically bind, activate, and expand δ2 T cells were separately selected for sequencing and further analysis. As shown in the tables below, sequence analysis of the heavy chain variable regions (FIG. 35) and light chain variable regions (FIG. 36) of selected δ2-γ6 TCR specific monoclonal antibodies generated in Example 39 confirmed novel complementarity determining regions and display of novel VDJ arrangements. The complementarity determining regions set forth in FIGS. 35-36, are as defined by Kabat.

Total RNA was extracted from selected hybridoma cells using the RNeasy isolation kit (RNeasy Mini Kit Qiagen #74106). $10^4$ hybridoma cells were lysed in 350 µl RLT Buffer, an equal volume of 70% ethanol was added, and the sample was loaded to RNeasy Mini spin column. Column was washed twice and RNA was eluted by 100 µl of RNase-free water loaded directly to the spin column membrane. The quality of the RNA preparations was determined by fractionating 3 µL in a 1% agarose gel before being stored at −80° C. until used.

The variable region of the Ig heavy chain of each hybridoma was amplified using a 5' primer mix comprising thirty-two mouse specific leader sequence primers, designed to target the complete mouse VH repertoire, in combination with a 3' mouse Cγ primer specific for all mouse Ig isotypes. A 400 bp PCR fragment of the VH was sequenced from both ends using the same PCR primers. Similarly, a mix of thirty-two 5' Vκ leader sequence primers designed to amplify each of the Vκ mouse families combined with a single reverse primer specific to the mouse kappa constant region were used to amplify and sequence the kappa light chain. The VH and VL transcripts were amplified from 100 ng total RNA using reverse transcriptase polymerase chain reaction (RT-PCR).

A total of eight RT-PCR reactions were run for each hybridoma: four for the Vκ light chain and four for the Vγ heavy chain. The One Step OneStep Ahead RT-PCR kit was used for amplification (Qiagen #220213). Reaction mixtures were prepared that included 5 µL of RNA, 0.5 of 100 µM of either heavy chain or κ light chain primers (custom synthesized by IDT), 12.5 µL of master mix with DNA polymerases, buffers, dNTPs, 1 µL of enzyme mix containing reverse transcriptase and DNA polymerase, and 0.4 µL of ribonuclease inhibitor RNasin (1 unit). The reaction mixture contains all of the reagents required for both reverse transcription and PCR. The thermal cycler program was set for an RT step 50° C. for 10 minutes, 95° C. for 5 minutes, followed by 30 cycles of PCR (95° C. for 30 seconds, 58° C. for 30 seconds, 72° C. for one minute). There was then a final incubation at 72° C. for 10 minutes.

PCR products were prepared for direct DNA sequencing, with the QIAquick™ PCR Purification Kit (Qiagen) according to the manufacturer's protocol. The DNA was eluted from the spin column using 50 μL of sterile water and then sequenced directly from both strands using specific V region primers. Nucleotide sequences were analyzed using VBase2 to identify germline V. D and J gene members with the highest sequence homology.

FIG. 33 depicts the contiguous amino acid sequences of heavy chain variable regions from δ1-specific antibodies. FIG. 34 depicts the corresponding contiguous amino acid sequences of the light chain variable regions. Taken together FIGS. 33-34 provide the annotated sequences of the identified operable anti δ1 TCR antibodies.

FIG. 35 depicts the contiguous amino acid sequences of heavy chain variable regions from δ2-specific antibodies. FIG. 36 depicts the corresponding contiguous amino acid sequences of the light chain variable regions. Taken together FIGS. 35-36 provide the annotated sequences of the identified operable anti δ2 TCR antibodies.

Example 41. Cross-Reactivity of 51-Specific Activators

The third gamma delta population is Vδ3 T cells, which take up about 0.2% of circulating T cells.

The Vδ3 T cells are rare in blood but are rich in liver and in patients with leukemias and some chronic viral infections. Other minor subsets include Vδ4, Vδ5, Vδ6, Vδ7, and Vδ8 γδ T cells, are composed of VJα genes spliced to the Cδ respectively, encoding distinct TCR alpha and delta proteins.

Cross reactivity and the ability of δ1-specific activators cross react with other γδ T cell populations was tested by binding assay to detect binding of δ1-specific activators to soluble TCRs composed of 8 different delta chains (Vδ1, Vδ2, Vδ3, Vδ4, Vδ5, Vδ6, Vδ7, and Vδ8). All eight delta chains were cloned as a C-terminal Fc-fusion and co-transfected with a γ-FC chain into 293 cells soluble TCRs-FC were secreted into the medium.

A day before the transfection 293 adherent cells 1×10$^5$ cells/well were plated in 12 well plate.

On the day of transfection, 0.5 μg of each plasmid (delta+ gamma chains) were co-transfected using 293Fectin™ Transfection Reagent (Thermo Fisher #12347019) in serum free media.

Secreted TCR was collected 3 days post transfection for binding analysis in ELISA assay.

ELISA binding assay.

Soluble TCRs-FC proteins were captured to the surface of ELISA plate coated with 1 μg/mL goat anti human FC (Goat Anti-Human IgG, Fcγ Fragment Specific-Jackson ImmunoResearch #109-005-098). Binding was perform overnight at 4° C. Binding of δ1-specific activators to soluble γδ TCRs captured on plates was tested by detection with HRP conjugated secondary antibody: Goat anti mouse FC specific (Jackson ImmunoResearch Laboratories, Inc. Peroxidase-AffiniPure Goat Anti-Mouse IgG, Fcγ Fragment Specific #115-035-008) diluted to 1:10,000 in blocking buffer, followed by adding TMB substrate per well. The results are shown in FIG. 37.

The ability to cross react and activate other subsets of γδ T cells in addition to the δ1 T cells may be of importance as clonally expanded TRDV4 and TRDV8 T cells were shown to contribute to the immune response directed against AML, while oligoclonal TRDV5 and TRDV6 might occur in patients who undergo relapse. (Jin et al. Journal of Hematology & Oncology (2016) 9:126).

Example 42. Activation and Proliferation Assay

δ1 and δ2 TCR specific antibodies were tested for induction of activation and proliferation of γδ T cells. Briefly, 48-well plates (Corning) were coated with goat-anti-mouse Fc-γ polyclonal antibodies at 5 μg/mL in 50 mM NaHCO$_3$ or PBS overnight. Wells were washed with PBS and further blocked with 1% BSA in PBS for 1 hr at 37 C and γδ-TCR specific antibodies were added at 1 μg/mL in 0.1% BSA for 2 hrs. For cell labeling, after overnight rest in complete medium fresh or frozen human PBMCs were washed and reconstituted in 5 μM CFSE (PBS) and incubated for 5 min in the dark at room temperature. Cells were washed with FBS containing media and reconstituted in RPMI-1640 culture media containing 10% FBS, 2 mM Glutamine, 25 mM HEPES and 200 IU/mL of rhIL-2 at 10$^6$/mL. CFSE-labeled PBMCs were plated at 0.5×10$^6$/well and cultured for 5 days.

Figure 39A:
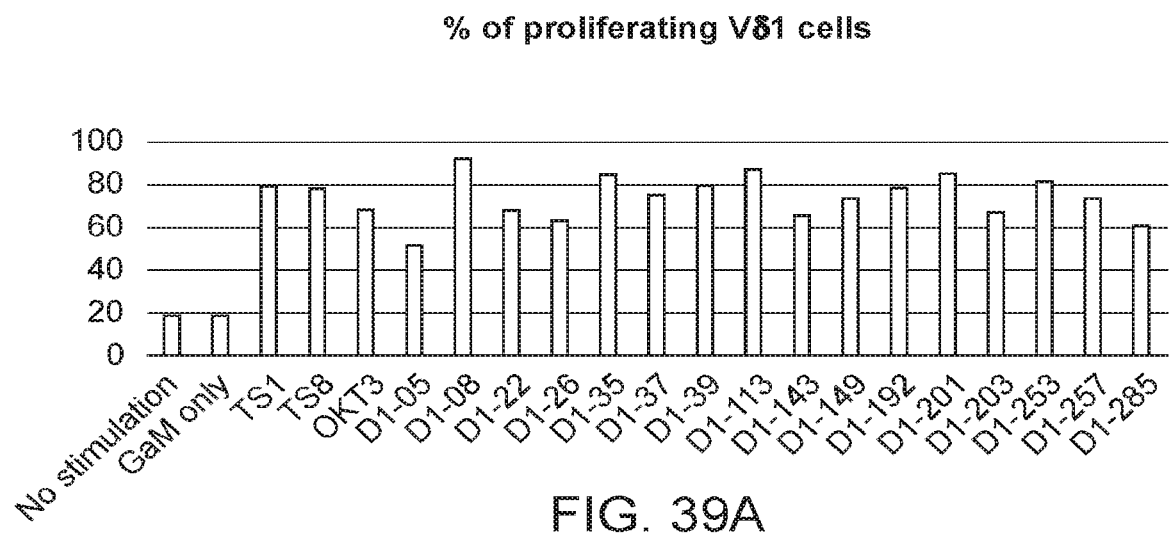
Figure 39B:
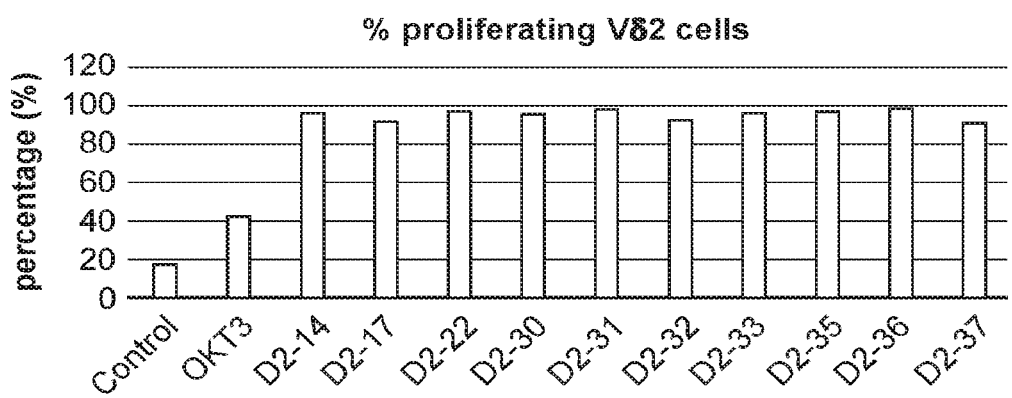

After 5 days, cells were harvested and stained with specific surface markers to pan-γδ, Vδ1, Vδ2 and αβ TCR and cell proliferation was assessed by progressive changes in CFSE fluorescence. Percentage of cells that divided during the 5 days as a result of activation is shown in FIG. 39 and served to rank antibodies for potency of activation.

Figure 40A:
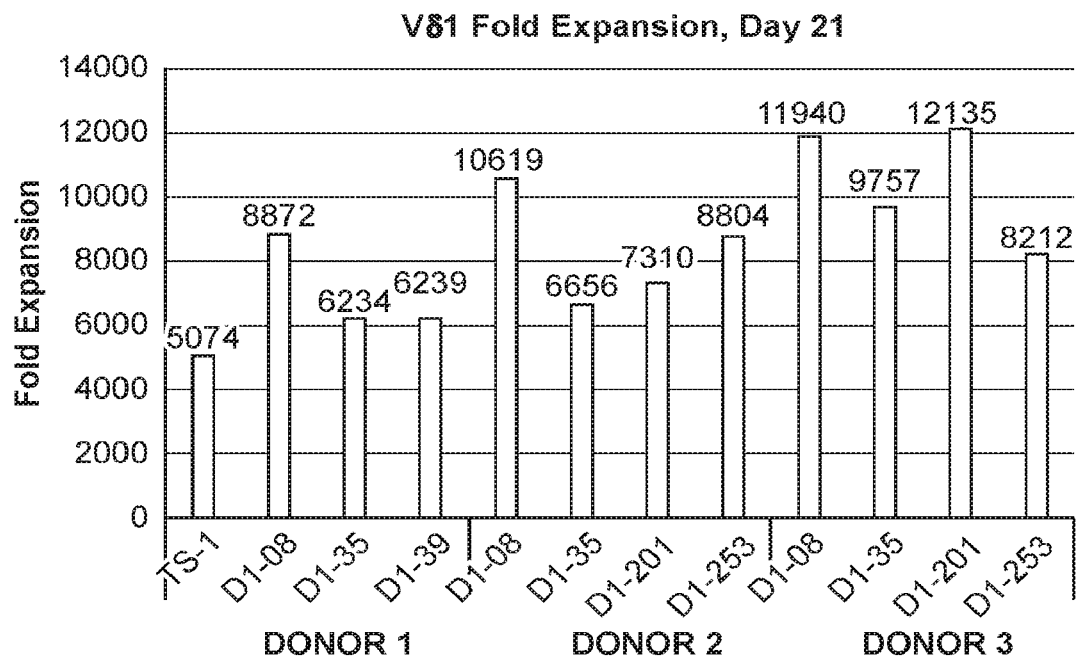
Figure 40B:
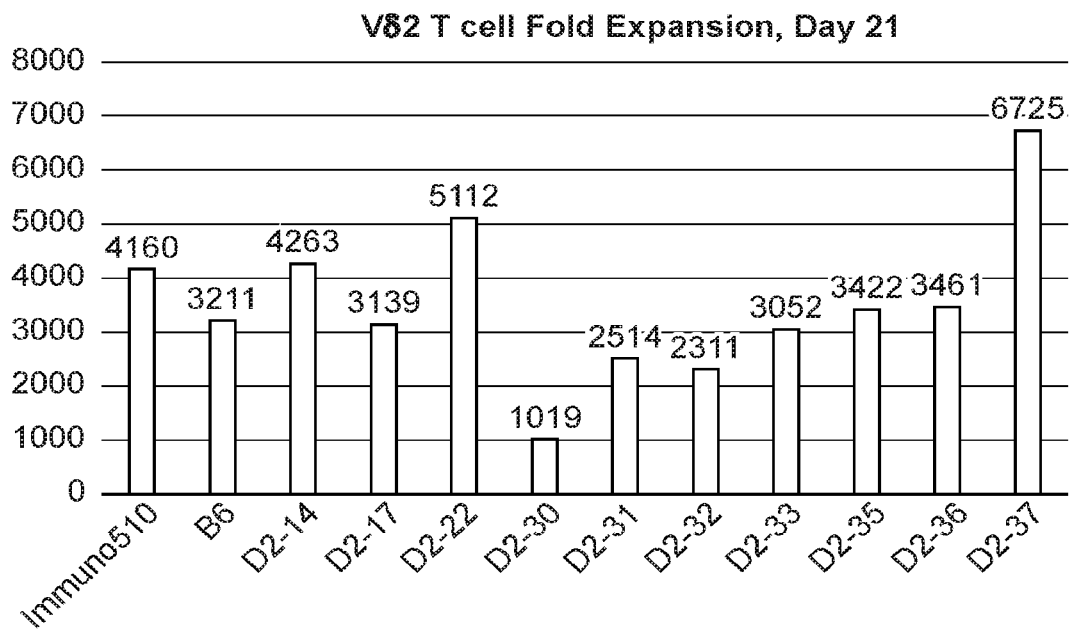

Example 43. One-Step Expansion of Vδ1 and Vδ2 T-Cells from Human PBMCs Using Specific MAbs Selected activating δ1-TCR and δ2-TCR antibodies (D1-08, D1-35, D1-39, D2-14, D2-17, D2-22, D2-30, D2-32, D2-33, D2-33, D2-35, D2-36, D2-37) and OKT3 were captured at 1 μg/mL in 2% FBS (PBS) by pre-coated goat-anti-mouse Fcγ antibodies in 24-well plates as in example 2 above. Human PBMCs from several donors having initial δ1 populations between 0.2-0.28% of total cells and Vδ2 population of ~0.2-4% of total cells were plated at 10$^6$/mL/well in RPMI-1640 media containing 10% FBS, 2 mM Glutamine, 100 IU/mL of rhIL-2. Cells in culture were fed every 2-3 days by media replenishment. On day 7 cells were harvested and re-plated at 10$^6$/mL into new plates without activating antibodies and further expanded by continued feeding and re-plating on Day 14 to 10$^6$/mL cell density. Cell analysis (counts and flow cytometry) was performed on Day 21 to determine purity and fold expansion of δ1 and δ2 cells. FIG. 40 shows fold expansion of δ1 (A) and δ2 (B) cells in PBMC cultures. Vδ1 and Vδ2 MAbs induced expansion of δ1 and δ2 T cells in 21 days up to ~12000 fold for Vδ1 and up to δ700 fold for Vδ2 T cells.

Figure 41:
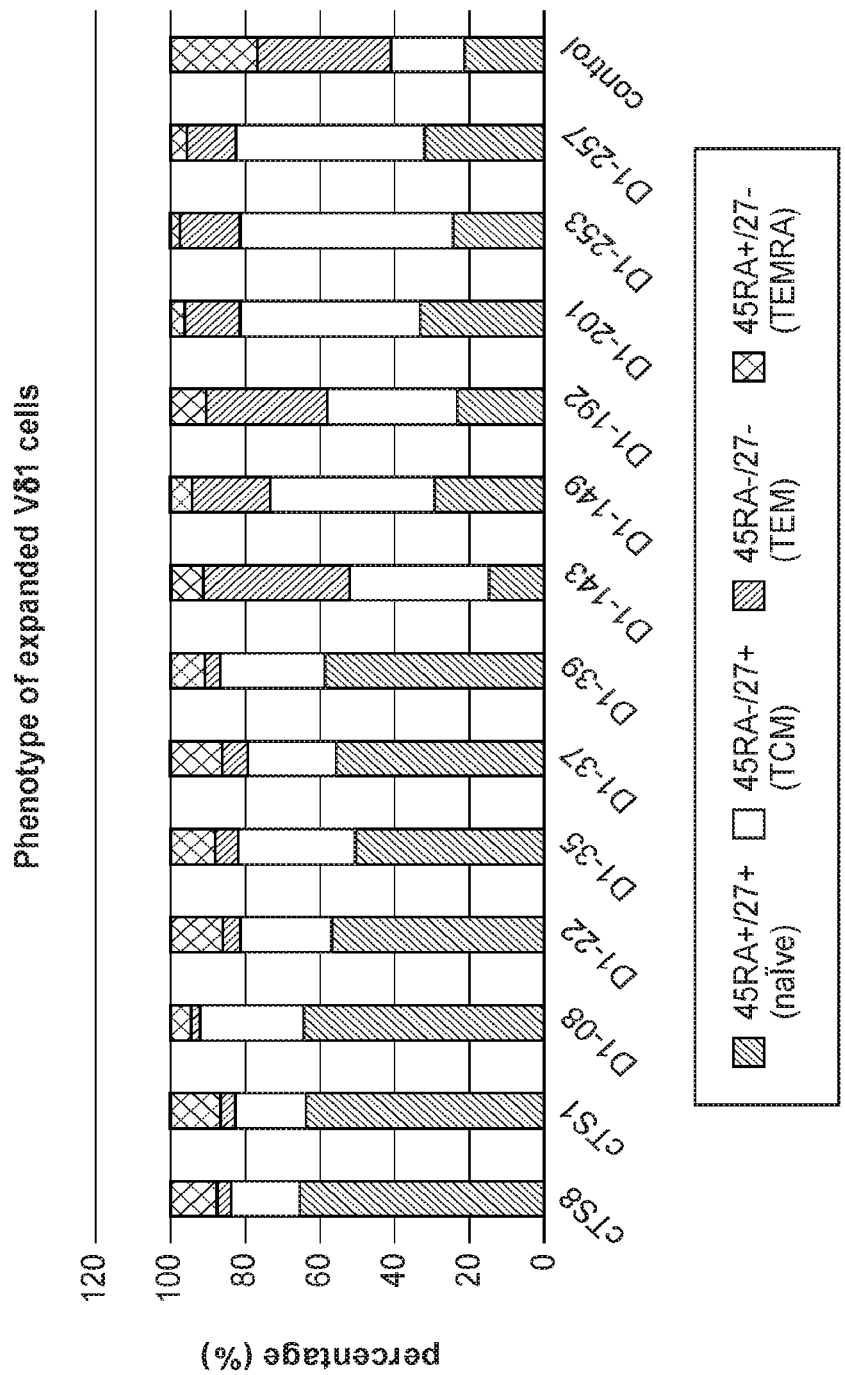

Phenotype of expanded δ1 cells on Day 21 was evaluated by CD27 surface marker expression. FIG. 41 shows that phenotype of Vδ1 T-cells activated with of MAbs on Day 21 is predominantly (>50%) CD27+CD45RA+ (naïve) and CD27+CD45RA− (central memory).

Example 44. One-Step Expansion of δ1-T Cells from Umbilical Cord Blood

Mononuclear cells from human umbilical cord blood containing 0.4% of Vδ1 cells were isolated by Ficoll density gradient and activated with captured δ1 TCR specific antibodies as described in example 43. As illustrated in the table below, Vδ1 T-cells expanded by up to 1503 fold in 21 days after activation with δ1 specific MAbs.

| D1 Antibody | Fold expansion, Day 21 |
|---|---|
| TS8.2 | 1062 |
| δ1-08 | 1104 |
| δ1-22 | 1503 |
| δ1-26 | 557 |
| δ1-35 | 918 |
| δ1-37 | 1017 |
| D1-39 | 1039 |
| Immuno510 | 460 |

Example 45. Two-Step Expansion of Vδ1 T Cells Using Feeder Cells

In this example, human PBMCs were activated and δ1 cells were expanded for 14 days following protocol described in Example 4. Briefly, Vδ1 antibodies TS-1, D1-08, D1-37, D1-39 were captured in 24-well plates via coated goat-anti-mouse Fcγ polyclonal antibodies and cells were activated and expanded as described. On Day 14 cell culture were harvested and δ1 T cells were enriched by depletion of αβ T cells using biotinylated anti-TCR αβ antibody and magnetic microbeads (Miltenyi Biotec). Enriched Vδ1 cells were subjected to a second step activation/expansion using irradiated PBMC feeder cells. Briefly, 130,000 total enriched cells were cultured in 20 mL of RPMI-1640 medium containing 10% FBS, 2 mM Glutamine, 100 IU/mL IL-2 and 30 ng/mL D1-35 MAb in the presence of irradiated human allogeneic PBMCs at a ratio of 200:1. The cultures were placed vertically in T25 flask. On Day 18 cells were fed by replacing 70% of the media. From then on, cells were fed every 2-3 days by exchanging 50% of the media and adjusting viable cell density to $1 \times 10^6$/mL and harvested on Day 28. As illustrated in the table below, δ1 cells were expanded up to about 28,000-fold in a 2-step expansion procedure.

| 1st Step activation, MAb | 2nd Step Activation after αβ T cell depletion/MAb | Vδ1 fold expansion |
|---|---|---|
| δ1-37 | iPBMCs/D1-35 | 11573 |
| δ1-08 | iPBMCs/D1-35 | 27965 |
| δ1-39 | iPBMCs/D1-35 | 15769 |

Example 46. Two-Step Expansion of Vδ1 T Cells Using Feeder Cells, without αβ T Cell Depletion In this example, human PBMCs with starting Vδ1 population of 0.2% were activated and δ1 cells were expanded for 7 days following a protocol described in Example 6. Briefly, Vδ1 antibodies TS-1, D1-08, D1-37, D1-39 were captured in 24-well plates via coated goat-anti-mouse Fcγ polyclonal antibodies and cells were activated and expanded as described. On Day 7 cell cultures were harvested and expanded cells were subjected to a second step activation/expansion using irradiated feeder cells. Briefly, 130,000 total cells were cultured in 20 mL of RPMI1640 medium containing 10% FBS, 2 mM Glutamine, 100 IU IL-2 and 30 ng/mL D1-35 MAb in the presence of irradiated human allogeneic PBMCs at a ratio of 200:1. The cultures were placed vertically in T25 flasks. On Day 12 cells were fed by replacing 70% of the media. From then on, cells were fed every 2-3 days by exchanging 50% of the media and adjusting viable cell density to $10^6$/mL until harvest on Day 21. As illustrated in the table below, δ1 cells were expanded up to about 114,000-fold in a 2-step expansion procedure.

| 1st Step activation, MAb | 2nd Step Activation/MAb | Vδ1 fold expansion |
|---|---|---|
| TS-1 | iPBMCs/D1-35 | 82298 |
| D1-37 | iPBMCs/D1-35 | 113764 |
| D1-08 | iPBMCs/D1-35 | 55348 |
| D1-39 | iPBMCs/D1-35 | 81391 |

Example 47. Two-Step Expansion of Vδ1 T Cells Using Feeder Cells with αβ T Cell Depletion In this example, human PBMCs with starting Vδ1 population of 0.36% were activated and Vδ1 cells were expanded for 14 days following protocol described in Example 4. On Day 14 cell culture was harvested and δ1 T cells were enriched by depletion of αβ T cells using biotinylated anti-TCR αβ antibody and magnetic microbeads (Miltenyi Biotec). Enriched Vδ1 cells were subjected to a second step activation/expansion using irradiated feeder cells. Briefly, enriched cells were cultured in 20 mL of RPMI-1640 medium containing 10% FBS, 2 mM Glutamine, 100 IU/mL IL-2 and 30 ng/mL D1-35 MAb in the presence of irradiated K562 cells at ratios of 49:1, 9:1 and 2:1. The cultures at the specified ratios ($25 \times 10^6$ each total live cells) were placed in 6-well G-Rex flask (Wilson Wolf). On Day 18 cells were fed by replacing 75% of the media and harvested on Day 21. As illustrated in the table below, δ1 cells were expanded up to about 31,000-fold in a 2-step expansion procedure.

| 1st Step activation, MAb | 2nd Step Activation/MAb | Vδ1 fold expansion, |
|---|---|---|
| D1-35 | iK562/D1-35 at 49:1 | 31121 |
| D1-35 | iK562/D1-35 at 9:1 | 18142 |
| D1-35 | iK562/D1-35 at 2:1 | 6346 |

Figure 42:
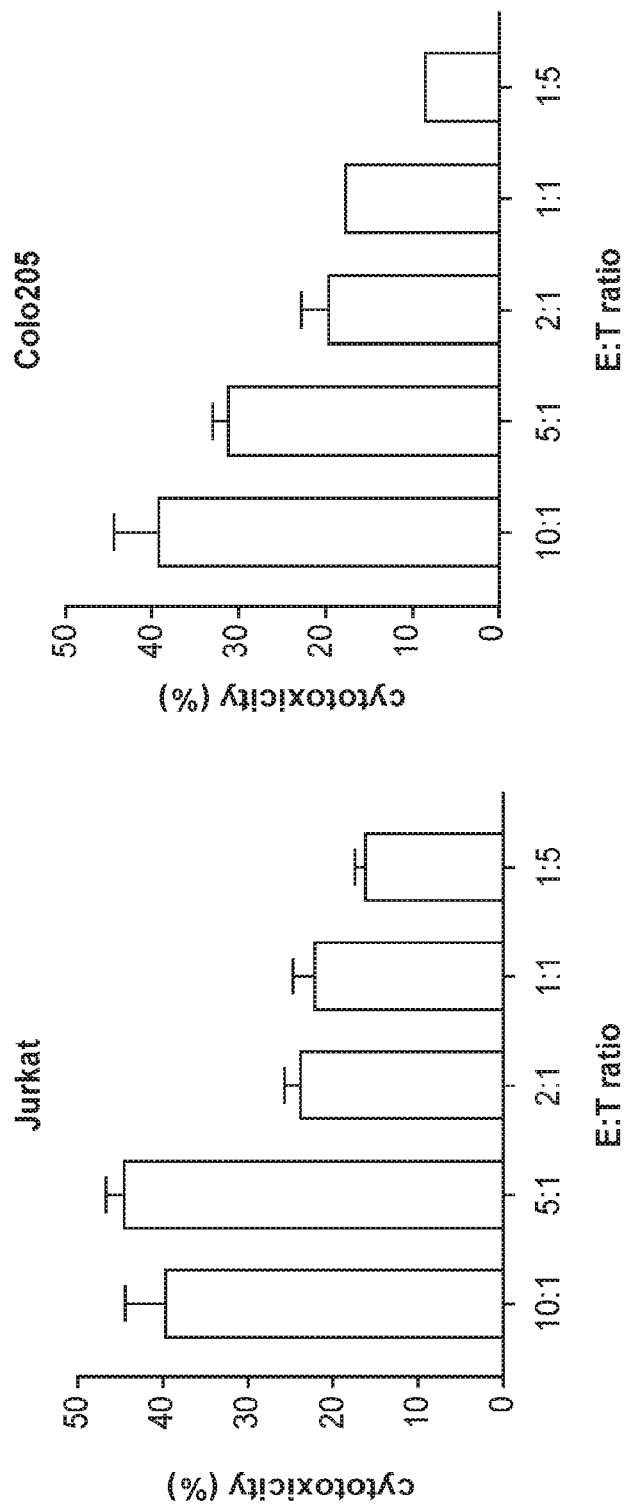

Example 48. δ1 T Cells Activated and Expanded with Vδ1 MAbs Show Robust Cytotoxicity Against Tumor Cell Lines Human PBMCs were activated with immobilized D1-08 MAb for 7 days and cultures were expanded by feeding every 2 days in static conditions. At the end of expansion, δ1 T cells were enriched by depletion of αβ T cells using anti-TCRαβ antibody and magnetic microbeads (Miltenyi). Purified δ1 cells were used in cytotoxicity assay against Jurkat (leukemia) and Colo205 (colon cancer) cell lines. Briefly, expanded δ1 T cells were incubated with CFSE labeled target cells at 10:1, 5:1, 2:1, 1:1 and 1:5 effector:target cell ratio for 4 hours in 96-well round bottom plates (suspension) in complete media containing 100 IU/mL IL-2. At the end of incubation, cell suspension was stained with Annexin-V-APC conjugate and Zombie Violet viability dye and analyzed by flow cytometry to detect dead/dying cells. As shown in FIG. 42, Vδ1 cells demonstrated cytotoxicity against both tumor cell lines at various ratios in 4 hr assay up to 45%.

Example 49. δ1 T Cells Activated and Expanded with a 2-Step Procedure Including a Second Step with Shaking Isolation of Peripheral Blood Mononuclear Cells Fresh blood product collected from an apheresis machine is diluted 1:3 with PBS without $Ca^{2+}$ and $Mg^{2+}$. Diluted blood product is then purify using the Ficoll-Paque™ PLUS (GE Healthcare) system using the Sepmate (STEMCELL). The enriched lymphocyte layer is then enriched washed twice, first with PBS without $Ca^{2+}$ and $Mg^{2+}$, then with 0.25% human serum albumin in PBS without $Ca^{2+}$ and $Mg^{2+}$. Finally, purified blood product is rested overnight in fetal bovine serum containing and serum free medium on ultra-low attachment 24-well plate, 6-well plate, and T-75 flasks at $1 \times 10^7$ cells/mL.

T-Cell Activation

The day before T-cell activation, the appropriate cell culture vessels, including tissue culture treated 24-well plate, 6-well plate, T75 flask, or gas permeable bags are coated with anti-Fc antibody. After initial coating, the vessels are stored at 2-8° C. in the dark overnight. After initial anti-Fc coating, the vessel is blocked with 5% fetal bovine serum in PBS without $Ca^{2+}$ and $Mg^{2+}$, and incubated for 1-hour at 37° C. $CO_2$ incubator. After the 1-hour incubation, the vessel is washed once with PBS without $Ca^{2+}$ and $Mg^{2+}$, then the vessel is captured with Vδ1 specific monoclonal antibodies. Then the vessel is incubated at room temperature for up to 4 hours with and without shaking. At the end of the capture, the vessel is washed twice with PBS without $Ca^{2+}$ and $Mg^{2+}$, and is ready for T-cell activation.

Overnight rested PBMC is diluted to $0.5 \times 10^6$ to $2 \times 10^6$ cells/cm² using either fetal bovine serum containing and serum free medium. Then the diluted PBMC is added to the Vδ1 specific monoclonal antibodies immobilized vessel. PBMC is maintained statically between 3 to 7 days. Fresh cell culture medium is added daily starting on day 3 to maintain sufficient nutrient level such as glucose and glutamine, and diluting the accumulation of toxic byproducts such as lactate and ammonium. At the end of the initial activation, cells are harvested by mechanical or chemical methods. Cells are then transferred to new flasks for subsequent expansion.

T-Cell Expansion

After initial T-cell activation, cell culture is maintained in 37° C. $CO_2$ incubator for up to 21 days. Initially, activated cell culture is diluted to 1e6 cells/mL in either fetal bovine serum containing or serum free medium. The T-cells can be cultivated in static T-flasks with ultra-low attachment or tissue culture treated surfaces, including T-25, T-75, T-150 and T-225 flasks, or in standard non-baffled or baffled shake flasks, including 125 mL, 250 mL, 500 mL, 1000 mL, 2000 mL, and 3000 mL total vessel volumes. In static T-flask, the working volume to surface area ratio is maintained at 0.5 mL/cm² or below to ensure sufficient culture oxygenation. In shake flask, the working volume to total vessel volume ratio is maintain at 1 to 2 or below on orbital shaking platforms to ensure sufficient mixing and aeration.

Viable cell culture density (VCD), metabolite, pH and gas measurements are taken daily. Metabolite measurements are taken of glucose, lactate, glutamine, glutamate, ammonium, sodium ion, potassium ion, and calcium ion. pH and gas measurements including partial pressure of oxygen, $CO^2$, and pH are also taken. Oxygen, $CO^2$, and pH measurement are taken with temperature compensation. Feeding based on VCD or metabolite can be both used to maintain cell cultures. For VCD-based feeding strategy, if VCD increased to $1.5 \times 10^6$ cells/mL or above, culture is diluted to $1 \times 10^6$ cells/mL using fresh medium. For metabolite-based feeding strategy, fresh medium is added when glucose level is below 1 g/L to increase to 1.5 g/L.

Cell Harvest and Banking

Cell viability of above 90% is always observed at the end of the 19 day or 21-day expansion. Post cell expansion, cell culture is washed and resuspended in cell banking medium. Cell is then aliquoted at more than $20 \times 10^6$ cells/mL cell density. Cryopreservation in the vapor phase of the liquid nitrogen is proceeded by control freezing using control rate freezer or freezing container.

Example 49a

Figure 43:
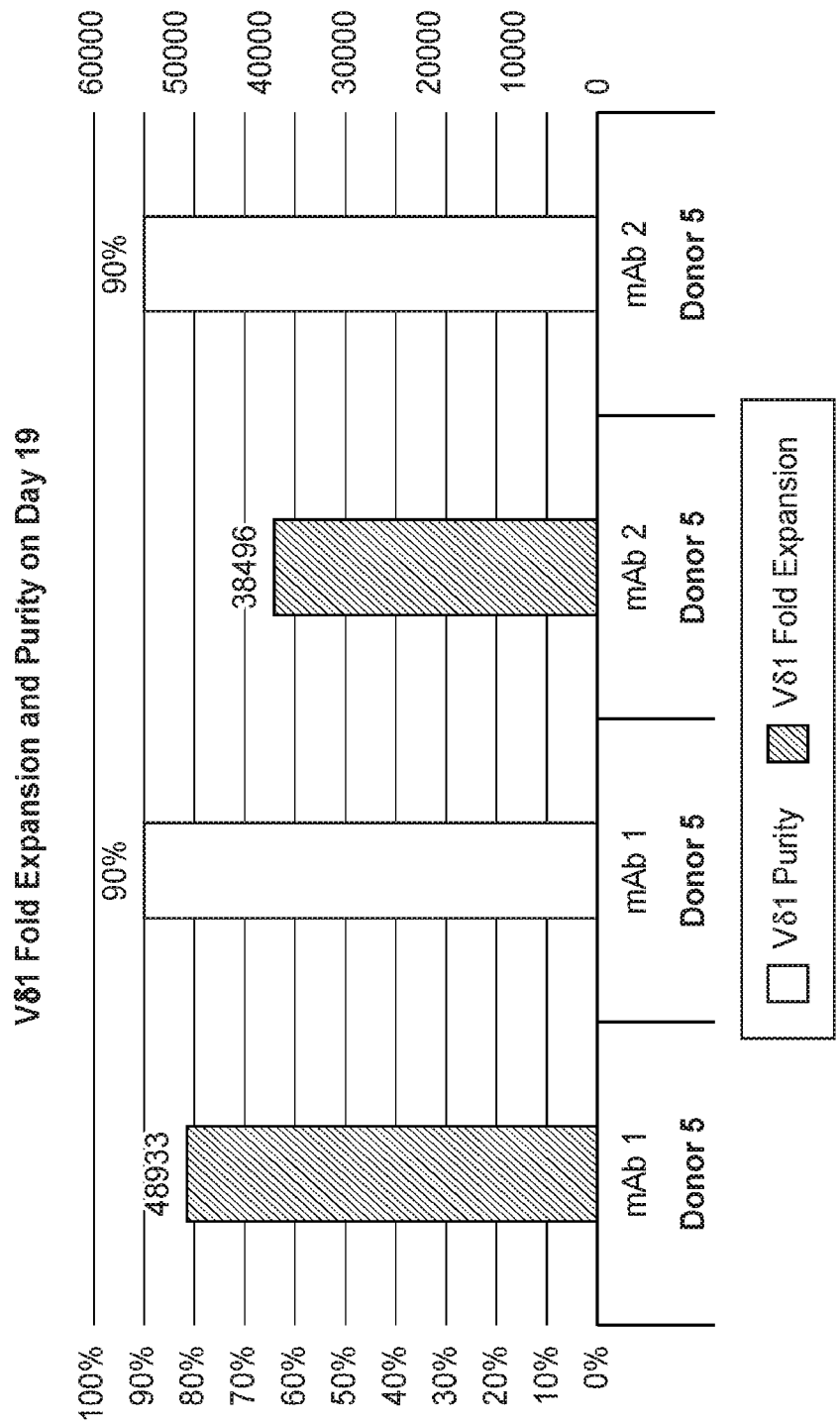

In this example, Donor A fresh blood product, which had a starting Vδ1 composition of 0.4%, was purified by Ficoll and rested overnight in ultra-low attachment T75 flask. After activation with immobilized δ1 specific monoclonal antibodies δ1-35 and δ1-08 from day 0 to day 5, the cultures were transferred to shake flasks. From day 5 to day 19, the cultures were sampled daily, and nutrient and waste concentrations were maintained by VCD-based feeding strategies using fresh serum medium. The Vδ1 fold expansion and purity for δ1-35 and δ1-08 activated cultures are illustrated in FIG. 43.

Example 49b

Figure 44:
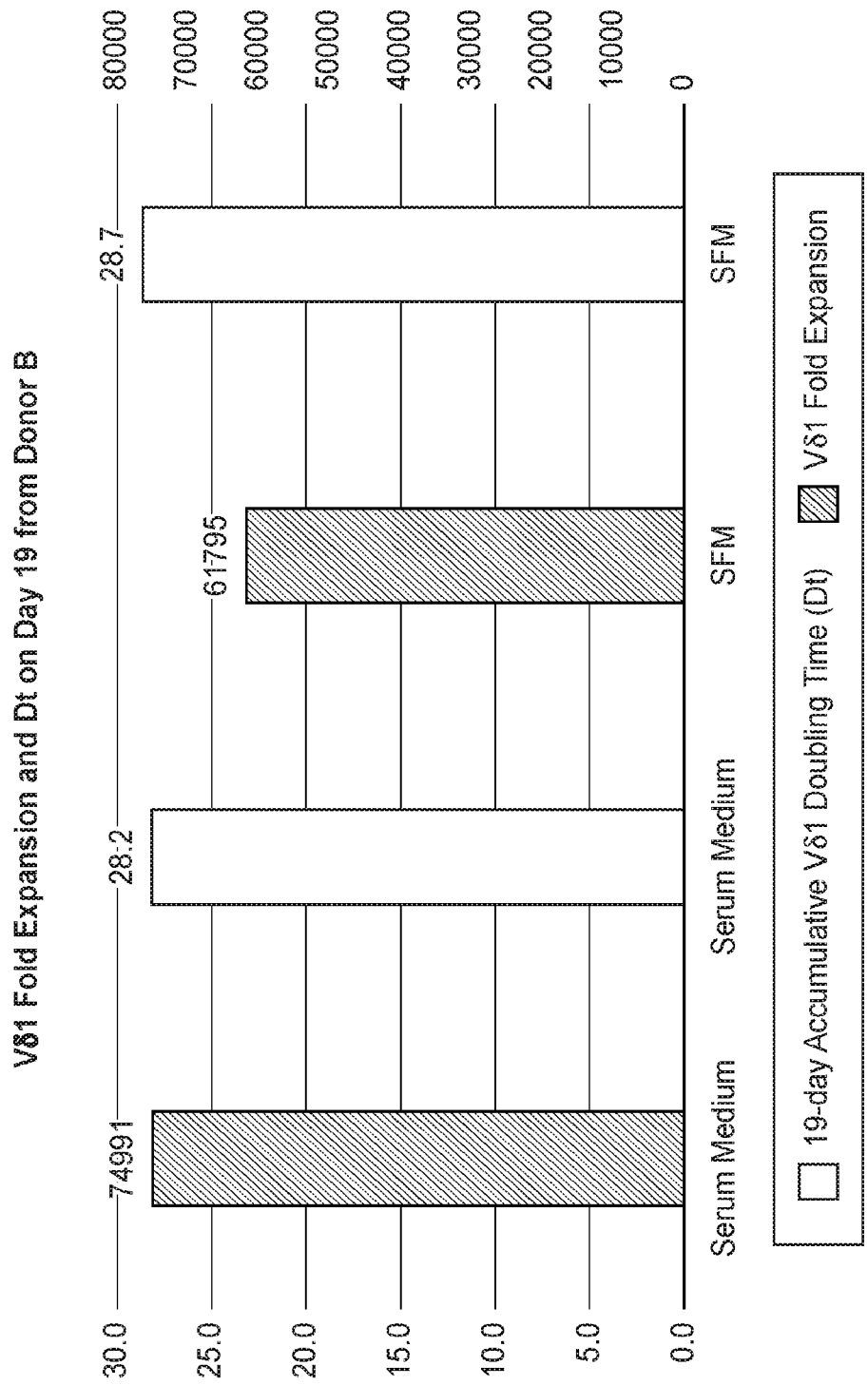

In this example, Donor B fresh blood product, which had a starting Vδ1 composition of 0.1%, was purified by Ficoll and rested overnight in ultra-low attachment T75 flask. After activation with immobilized δ1 specific monoclonal antibody δ1-08 from day 0 to day 5, the cultures were transferred to shake flasks. From day 5 to day 19, the cultures are sampled daily, and nutrient and waste concentrations were maintained by VCD-based feeding strategies using either fresh serum-containing medium or fresh serum free medium. The Vδ1 fold expansion and doubling time (DT) (accumulative from day 0 to day 19) in serum containing and serum free medium expanded cultures are illustrated in FIG. 44.

Example 49c

In this example, Donor C fresh blood product, which had a starting Vδ1 composition of 0.5%, was purified by Ficoll and rested overnight in ultra-low attachment T75 flask. After activation with immobilized δ1 specific monoclonal antibody δ1-08 from day 0 to day 7 (49c.1) and from day 0 to day 5, the cultures were transferred to shake flasks. From day 7 to day 19, the cultures were sampled daily, and nutrient and waste concentrations were maintained by glucose-based feeding strategies using fresh serum medium. And for the other two cultures, from day 7 to day 19, the cultures were sampled daily, and nutrient and waste concentrations were maintained by either VCD based feeding or glucose-based feeding strategies using fresh serum medium. The Vδ1 fold expansion and doubling time (DT) (accumulative from day 14 to day 19) are illustrated in FIG. 45.

Figure 45:
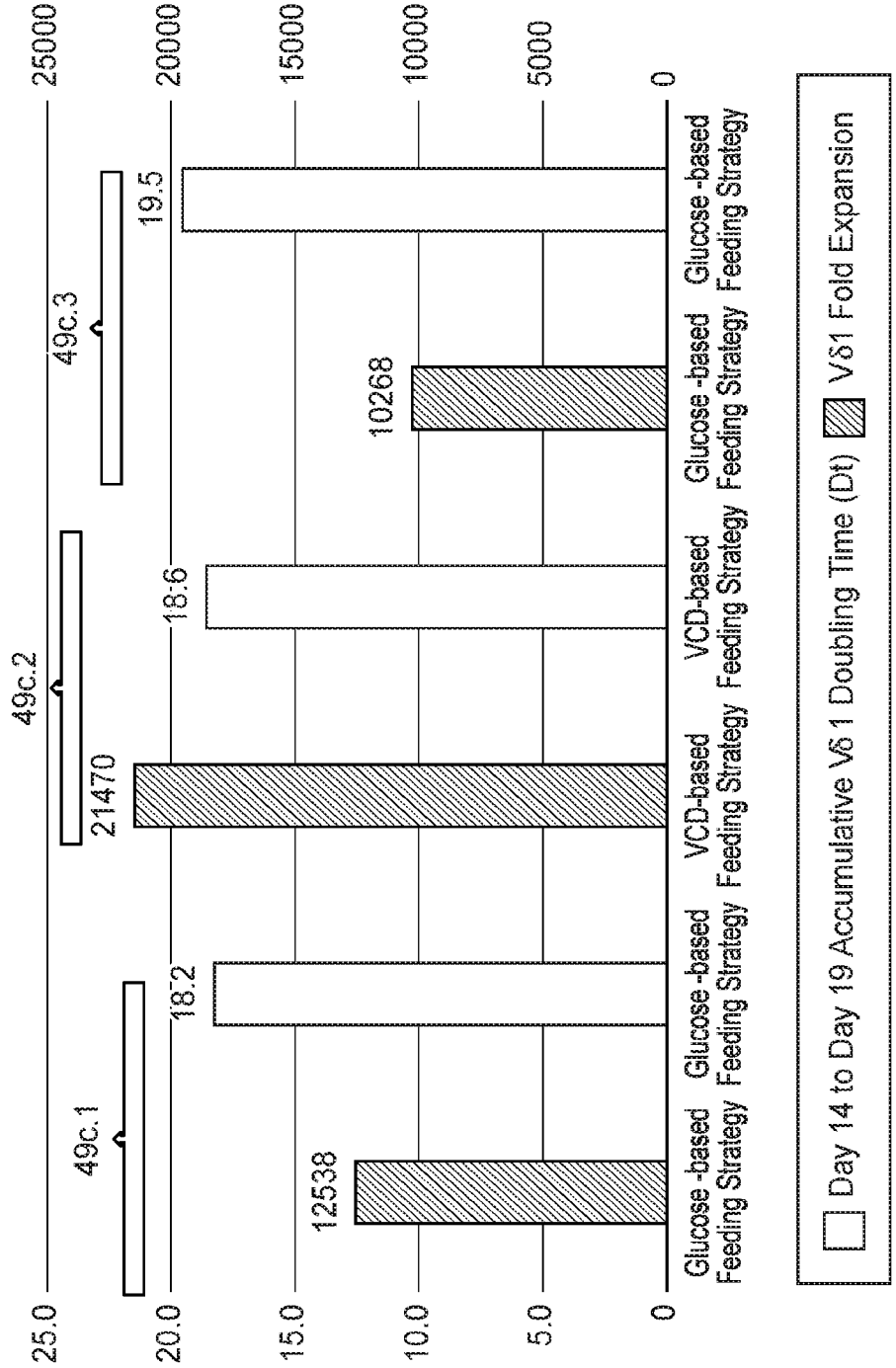

FIG. 45 section 49c.1 illustrates Vδ1 fold expansion and DT (accumulative from day 14 to day 19) from culture that was 7 day activated and then maintained using glucose-based feeding strategy from day 7 to day 19. FIG. 45 section 49c.2 illustrates Vδ1 fold expansion and DT (accumulative from day 14 to day 19) 5 day activated culture that was then maintained using VCD-based feeding strategy from day 7 to day 19. FIG. 45 section 49c.3 illustrates Vδ1 fold expansion and DT (accumulative from day 14 to day 19) 5 day activated culture that was then maintained using VCD-based feeding strategy from day 7 to day 19.

Figure 46:
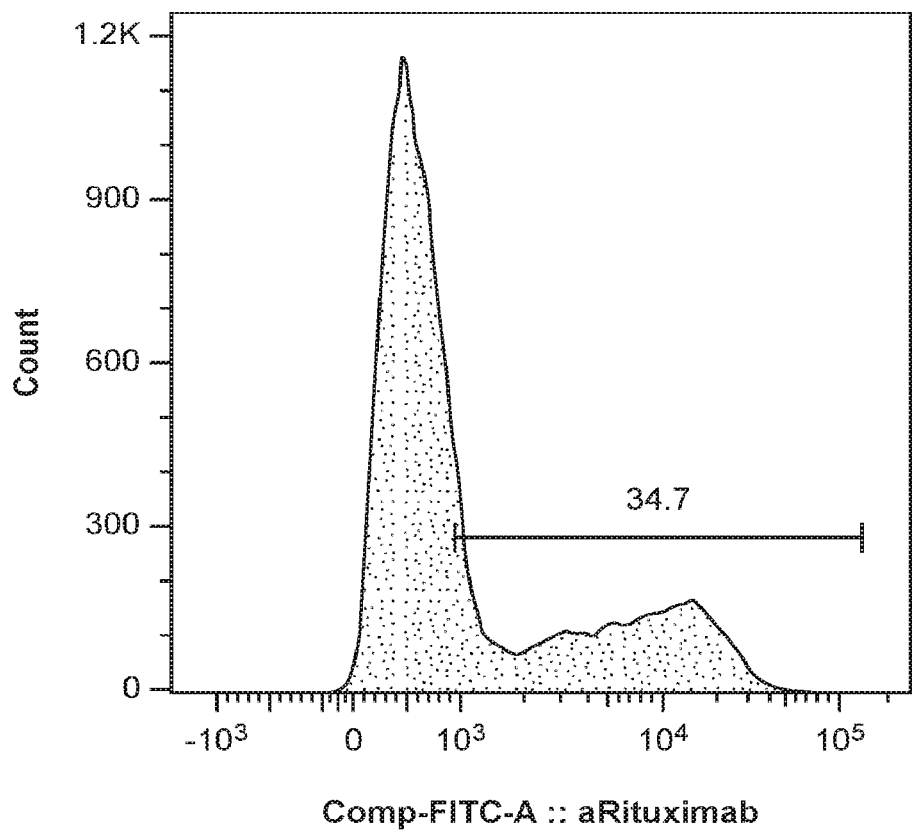

Example 50. Transduction of Vδ1 T Cells with Retroviral Chimeric Antigen Receptor Construct Peripheral blood mononuclear cells from a healthy donor were stimulated with an immobilized anti-Vδ1 specific monoclonal antibody (δ1-08) and cultured for 19 days in media supplemented with rhIL-2 as described in example 49a. Briefly, isolated PBMCs were activated in 24-well plates with D1-08 Vδ1 MAb captured via pre-coated goat-anti-mouse Fcγ antibodies. Cells were plated at $1e^6$/mL/well in RPMI1640 media containing 10% FBS, 25 mM HEPES, 2 mM Glutamine and 100 IU/mL IL-2. After five days cells were transferred to shake flasks and expanded as described in example 49a. On day 19 cells were harvested, washed and re-stimulated with PHA (2 μg/mL) for 2 days followed by transduction with a retroviral vector encoding an anti-CD20 (Rituximab) derived chimeric antigen receptor (scFv linked to CD28-CD3). Briefly, wells of 24-well plate were pre-coated with retronectin (TaKaRa Bio) and supernatant containing retrovirus (1 mL) was incubated for 4 hours at 32C to allow adhesion of viral particles, after which the supernatant was removed (retronectin plate). Expanded δ1 T cells were washed, resuspended in 1 mL of viral supernatant supplemented with 100 IU/mL of IL-2 at $0.5 \times 10^6$ cells/mL and plated into retronectin plate. Plate was centrifuged at 1800 rpm for 10 min and placed into 37C incubator. Cells were cultured for an additional 7 days with feeding every 2 days and then analyzed by flow cytometry for percent transduction using fluorescent rat anti-Rituximab idiotypic antibody (FITC conjugate) that recognizes the CD20-specific CAR expressed on the T-cell surface. More than 34% of the viable Vδ1+ cells expressed the CAR construct as shown in FIG. 46.

Example 51. Epitope Mapping of Antibodies to γδ T Cell TCRs

The aim was to map the epitope specificities of δ1-specific activators. All δ1-specific activators are directed against the δ1 chain of the γδ TCR. Mapping was done by using recombinant chimeric molecules of human and dolphin δ1 TCR chain. Despite of a high amino acid identity between the human and dolphin δ1 chain, δ1 specific activators did not bind dolphin δ1 chain. Therefore, we have utilized the similarities in sequence and conformation between human Vδ1 and dolphin Vδ1 (65% sequence similarity) to construct recombinant chimeric molecules in which we replaced different segments of the human residues with their homologous counterpart from the dolphin δ1 TCR chain.

All mAbs were confirmed to bind specifically to the variable region of the δ1 chain of γδ TCR by Flow cytometry analysis. The δ1γ8 TCR was expressed as soluble FC fusion protein in a correctly folded conformation, determined by binding of all panel of anti δ1 mouse monoclonal antibodies (mAbs). These mAbs were shown to target conformationally-dependent epitopes of the γδ TCR.

In-order to express discrete epitopes of human δ1 TCR, a set of 7 recombinant chimeric δ1 chains were cloned to produce human/dolphin δ1-FC TCR chains. Dolphin residues comprised amino acids 1-11, 1-21, 1-28, 1-47, 1-70, 1-80 and 1-95 respectively, according to IMGT unique numbering for T cell receptor variable domains (Lefranc et al., Developmental and Comparative Immunology 27 (2003) 55-77), as illustrated in FIG. 38.

These δ1 specific binding domains were identified by ELISA binding assay and detection of loss of binding without prior knowledge of potential contact residues. By overlaying key dolphin residues that impacted the binding of selected δ1 activators we have identified 8 possible binding bins within the V and J region of the δ1 TCR chain.

The expression vector used in this study is pCI-Neo Mammalian Expression Vector (Promega #E1841) Expression of soluble TCRs was derived from the CMV promoter. The mouse IgH signal peptide, was used for exporting the soluble TCR proteins to the medium, followed by human FC domain for capture of soluble TCR to ELISA plate.

The ECD of human δ1 chain was amplified from γδ1 BE-13 T cell line. The dolphin Vδ1 sequence was ordered as a synthetic gene base on the published sequence (*Tursiops truncatus* mRNA for T cell receptor delta chain (TRD gene), isolate 5R1D80) (GenBank: LN610748.1). Using these cDNAs as templates new chimeric molecules were cloned from synthetic fragments (IDT DNA) to be cloned into the 5' AgeI site at the signal peptide and 3' E.coRI at the delta constant region. Six constructs consisting of dolphin/humanδ1 chains were cloned and co transfected with a γ8-FC chain to express soluble δ1γ8 TCR proteins in 293 cells.

HEK-293 cells were cultured in 90-mm cell culture plates in a DMEM medium (Thermo Fisher Scientific) with 10% fetal calf serum (HyClone™ FetalClone™ I Serum (U.S.)—GE Healthcare Life Sciences). For every construct $1 \times 10^6$ HEK-293 cells were transfected with 10 μg of plasmid using 293 Fectin as transfection reagent. Supernatants were harvested 72 hours post transfection δ1 specific activators-monoclonal antibodies differed in their binding pattern to the chimeras and a distinct binding pattern could be identified for each monoclonal antibody, as tested in ELISA assay.

Polystyrene microtiter plates (Greiner bio-one #655061) were coated overnight at room temperature with 1 μg/well of Goat anti human FC specific antibody (Jackson ImmunoResearch #109-005-098) in ELISA coating buffer (50 mm Na2CO3, 0.05% NaH3, pH 9.6). The plates were washed three times with washing buffer (PBS 0.05% (v/v) Tween 20) and then blocked for 1 h at room temperature (RT) with 100 μl/well of ELISA blocking buffer (3% BSA in PBST). Binding of soluble TCRs to blocked plates was done by adding 100 ml of each supernatant and incubation for 1 hour at Room temperature. Each antibody was diluted to 1 μg/ml in ELISA blocking buffer, and tested for binding to each γδ TCR chimeric molecule.

Detection of binding was done by adding 100 μl/well of HRP conjugated secondary antibody: Goat anti mouse FC specific (Jackson ImmunoResearch Laboratories, Inc. Peroxidase-AffiniPure Goat Anti-Mouse IgG, Fcγ Fragment Specific #115-035-008) diluted to 1:10,000 in blocking buffer. The amount of bound antibodies was detected by the use of TMB substrate (Thermo Fisher #34029) Color development was measured spectrophotometrically at 450 nm after 10 minutes. All assays were done in duplicate.

Sequence of all Constructs

δ1-D3-J1 FC- Fully human TCR (SEQ ID NO: 101)
gcccagaaggttactcaagcccagtcatcagtatccatgccagtgaggaa
agcagtcaccctgaactgcctgtatgaaacaagttggtggtcatattata
ttttttggtacaagcaacttcccagcaaagagatgattttccttattcgc
cagggttctgatgaacagaatgcaaaagtggtcgctattctgtcaactt
caagaaagcagcgaaatccgtcgccttaaccatttcagccttacagctag
aagattcagcaaagtactttgtgctcttgggacggggtgaggggactc
caggacaccgataaactcatctttggaaaaggaacccgtgtgactgtgga
accaa (SEQ ID NO: 22)
AQKVTQAQSSVSMPVRKAVTLNCLYETSWWSYYIFWYKQLPSKEMIFLIR
QGSDEQNAKSGRYSVNFKKAAKSVALTISALQLEDSAKYFCALGTGVRGL
QDTDKLIFGKGTRVTVEP Dolphin TRD isolate 5R1D8

(SEQ ID NO: 102)
gcccagaaagttactcaagtccagcgagccatgtccagtcagctaggga
ggcggtcaccttgagctgtcagtatgaaacaagcttgagctggtacgata
tttttggtataagcagcttcccagtggagagatgactttccttattcat
cagatttcttctgaccaaaatgcaaagaatggccgctattctgtaaactt
tcaggaaagacataaattcatcagcctcaccatttcagccttactggtgg
aagattctgcaaactacttctgtgctctccgggagcgcgttgtccacgtc
gttttattcaatacgcgcaataagccactgctattcggcaaaggaaccta
tctgaacgttgaaccaa (SEQ ID NO: 103)
AQKVTQVQRAMSSQLGEAVTLSCQYETSLSWYDIFWYKQLPSGEMTFLIH
QISSDQNAKNGRYSVNFQERHKFISLTISALLVEDSANYFCALRERVVHV
VLFNTRNKPLLFGKGTYLNVEP Set of Dolphin/Human Chimera—Soluble TCRs were Cloned—Human Sequence in Blue Dolphin/Human 1-11

(SEQ ID NO: 104)
gcccagaaagttactcaagtccagcgagccatgtccatgccagtgaggaaagcagtcaccctgaactgcctgtatgaaacaa
gttggtggtcatattatattttttggtacaagcaacttcccagcaaagagatgattttccttattcgccagggttctgatga
acagaatgcaaaagtggtcgctattctgtcaacttcaagaaagcagcgaaatccgtcgccttaaccatttcagccttacag
ctagaagattcagcaaagtactttgtgctcttgggacgggggtgagggggactccaggacaccgataaactcatctttggaa
aaggaacccgtgtgactgtggaaccaa (SEQ ID NO: 105)
AQKVTQVQRAMSMPVRKAVTLNCLYETSWWSYYIFWYKQLPSKEMIFLIRQGSDE
QNAKSGRYSVNFKKAAKSVALTISALQLEDSAKYFCALGTGVRGLQDTDKLIFGKGTRVTV
EP Dolphin/Human 1-21

(SEQ ID NO: 106)
gcccagaaagttactcaagtccagcgagccatgtccagtcagctaggggaggcggtcaccttgaactgcctgtatgaaacaa
gttggtggtcatattatattttttggtacaagcaacttcccagcaaagagatgattttccttattcgccagggttctgatga
acagaatgcaaaagtggtcgctattctgtcaacttcaagaaagcagcgaaatccgtcgccttaaccatttcagccttacag
ctagaagattcagcaaagtactttgtgctcttgggacgggggtgagggggactccaggacaccgataaactcatctttggaa
aaggaacccgtgtgactgtggaaccaa (SEQ ID NO: 107)
AQKVTQVQRAMSSQLGEAVTLNCLYETSWWSYYIFWYKQLPSKEMIFLIRQGSDEQ
NAKSGRYSVNFKKAAKSVALTISALQLEDSAKYFCALGTGVRGLQDTDKLIFGKGTRVTVE
P Dolphin/Human 1-28

(SEQ ID NO: 108)
gcccagaaagttactcaagtccagcgagccatgtccagtcagctaggggaggcggtcaccttgagctgtcagtatgaaacaa
gctggtggtcatattatattttttggtacaagcaacttcccagcaaagagatgattttccttattcgccagggttctgatga
acagaatgcaaaagtggtcgctattctgtcaacttcaagaaagcagcgaaatccgtcgccttaaccatttcagccttacag
ctagaagattcagcaaagtactttgtgctcttgggacgggggtgagggggactccaggacaccgataaactcatctttggaa
aaggaacccgtgtgactgtggaaccaa -continued (SEQ ID NO: 109)
AQKVTQVQRAMSSQLGEAVTLSCQYETSWWSYYIFWYKQLPSKEMIFLIRQGSDEQ
NAKSGRYSVNFKKAAKSVALTISALQLEDSAKYFCALGTGVRGLQDTDKLIFGKGTRVTVE
P Dolphin/Human 1-47

(SEQ ID NO: 110)
gcccagaaagttactcaagtccagcgagccatgtccagtcagctaggggaggcggtcaccttgagctgtcagtatgaaacaa
gcttgagctggtacgatatttttttggtataagcagcttcccagtaaagagatgattttccttattcgccagggttctgatga
acagaatgcaaaaagtggtcgctattctgtcaacttcaagaaagcagcgaaatccgtcgccttaaccatttcagccttacag
ctagaagattcagcaaagtactttgtgctcttgggacgggggtgagggggactccaggacaccgataaactcatctttggaa
aaggaacccgtgtgactgtggaaccaa (SEQ ID NO: 111)
AQKVTQVQRAMSSQLGEAVTLSCQYETSLSWYDIFWYKQLPSKEMIFLIRQGSDEQ
NAKSGRYSVNFKKAAKSVALTISALQLEDSAKYFCALGTGVRGLQDTDKLIFGKGTRVTVE
P Dolphin/Human 1-70

(SEQ ID NO: 112)
gcccagaaagttactcaagtccagcgagccatgtccagtcagctaggggaggcggtcaccttgagctgtcagtatgaaacaa
gcttgagctggtacgatatttttttggtataagcagcttcccagtggagagatgactttccttattcatcagatttctgatga
acagaatgcaaaaagtggtcgctattctgtcaacttcaagaaagcagcgaaatccgtcgccttaaccatttcagccttacag
ctagaagattcagcaaagtactttgtgctcttgggacgggggtgagggggactccaggacaccgataaactcatctttggaa
aaggaacccgtgtgactgtggaaccaa (SEQ ID NO: 113)
AQKVTQVQRAMSSQLGEAVTLSCQYETSLSWYDIFWYKQLPSGEMTFLIHQISDEQ
NAKSGRYSVNFKKAAKSVALTISALQLEDSAKYFCALGTGVRGLQDTDKLIFGKGTRVTVE
P Dolphin/human 1-80

(SEQ ID NO: 114)
gcccagaaagttactcaagtccagcgagccatgtccagtcagctaggggaggcggtcaccttgagctgtcagtatgaaacaa
gcttgagctggtacgatatttttttggtataagcagcttcccagtggagagatgactttccttattcatcagatttcttctga
ccaaaatgcaaagaatggccgctattctgtaaactttaagaaagcagcgaaatccgtcgccttaaccatttcagccttacag
ctagaagattcagcaaagtactttgtgctcttgggacgggggtgagggggactccaggacaccgataaactcatctttggaa
aaggaacccgtgtgactgtggaaccaa (SEQ ID NO: 115)
AQKVTQVQRAMSSQLGEAVTLSCQYETSLSWYDIFWYKQLPSGEMTFLIHQISSDQ
NAKNGRYSVNFKKAAKSVALTISALQLEDSAKYFCALGTGVRGLQDTDKLIFGKGTRVTVE
P Dolphin/human 1-95

(SEQ ID NO: 116)
gcccagaaagttactcaagtccagcgagccatgtccagtcagctaggggaggcggtcaccttgagctgtcagtatgaaacaa
gcttgagctggtacgatatttttttggtataagcagcttcccagtggagagatgactttccttattcatcagatttcttctga
ccaaaatgcaaagaatggccgctattctgtaaactttcaggaaagacataaattcatcagcctcaccatttcagccttacag
ctagaagattcagcaaagtactttgtgctcttgggacgggggtgagggggactccaggacaccgataaactcatctttggaa
aaggaacccgtgtgactgtggaaccaa (SEQ ID NO: 38)
AQKVTQVQRAMSSQLGEAVTLSCQYETSLSWYDIFWYKQLPSGEMTFLIHQISSDQ
NAKNGRYSVNFQERHKFISLTISALQLEDSAKYFCALGTGVRGLQDTDKLIFGKGTRVTVEP Results Functional TCR genes are assembled from separate V, D and J region segments by genetic recombination. When the TCR delta chain gene is assembled a D gene segment is juxtaposed to a J segment and this is followed by rearrangement of a V segment to the assembled downstream DJ segment. The immunoglobulin-like fold of the TCR chains positions three loops or complementarity determining regions (CDRs) from each chain in close proximity to each other, creating a binding face that will contact antigen. Two of these CDR loops, namely 1 and 2, are encoded by the V gene segment and have only the diversity provided by the Vδ1 region gene segments. The third CDR loop is created by the juxtaposition of V(D)J segments and provides much more diversity, a result of the ability of each V segment to rearrange to any (D)J segment compounded by the fact that the joining of the coding sequences is imprecise. Nucleotides may be added or deleted at each of these junctions. Epitope binding specificity is shown by ELISA (FIGS. 47A-B).

We have identified activators that bind different epitopes on the framework region of the δ1 chain of the γδ TCR molecule. One group of monoclonal antibodies is reactive with δ1 variable region of the delta chain of the TCR. In particular, the invention provides monoclonal antibodies, such as d1-08, d1-39, d1-192, d1-201, d1-285 which bind the δ1 chain variable region, regardless of the junctional diversity (juxtaposition of all γδ TCR compositions (D)J1, V(D)J2 and V(D)J3). These monoclonal antibodies are reactive with the "variable region" of the delta TCR and therefore are monoclonal antibodies reactive with an epitope of the V region.

Other δ1 activators specifically recognize the δ1 chain variable region, and the CDR3 loop created by the restricted juxtaposition of V(D)J1 segments. These monoclonal antibodies are reactive with the "variable region" of the TCR in combination epitope of the V-D or V-D-J regions: d1-37, d1-113, d1-155, d1-182, d1-183, d1-191, d1-278 and d1-282.

Other δ1 activators specifically recognize the δ1 chain variable region, and the CDR3 loop created by the juxtaposition of V(D)J1 and V(D)J2 but not V(D)J3 segments: d1-35, d1-143, d1-149, d1-203.

Antibodies specific for δ1 were grouped into the following epitope Bins:
Bin1: VDJ Junction—JH1/JH2: TS-1; and δ1-18
Bin 1b: VDJ Junction—J1, not J3, loss of binding for K120T/A mutant: δ1-37
Bin2: (aa 11-21): δ1-285
Bin2b: (aa 11-21), loss of binding for R16N mutant: R9.12
Bin2c: (aa 11-21), cross reacts with δ3, δ4, and δ5 γδ TCRs: δ1-39
Bin3: (aa 80-95 or 70-95): δ1-08; δ1-23
Bin4: (aa 1-11), loss of binding for K120T/A mutant: δ1-35; δ1-203
Bin5: (aa 28-47+J1 region): δ1-113; δ1-155; δ1-183; δ1-191; δ1-278; δ1-282
Bin6: (aa 21-28+J1 region): TS8.2; δ1-143
Bin7: (aa 47-70+J1/J2 region): δ1-149; δ1-253, and δ1-257
Bing: (aa 70-80)+J1/J2: δ1-192
Bin9: (aa 80-95): δ1-201.

Similar to the d1 epitope mapping: based on Linguiti G. et al., 2016. Genomic and expression analyses of *Tursiops truncatus* T cell receptor gamma (TRG) and alpha/delta (TRA/TRD) loci reveal a similar basic public; repertoire in dolphin and human. BMC Genomics. A set of 5 recombinant chimeric δ2 chains were cloned to produce human/dolphin δ2-FC TCR chains. Dolphin residues comprised amino acids 28-94, 44-94, 72-94 and, 82-94 respectively, according to IMGT unique numbering for T cell receptor variable domains (Lefranc et al., Developmental and Comparative Immunology 27 (2003) 55-77), as illustrated in FIG. 15.

Transfection of δ2/γ9-FC Constructs

```
Human TRGV9-JP-FC
                                          (SEQ ID NO: 117)
GCAGGTCACCTAGAGCAACCTCAAATTTCCAGTACTAAAACGCTGTCAAA

AACAGCCCGCCTGGAATGTGTGGTGTCTGGAATAACAATTTCTGCAACAT

CTGTATATTGGTATCGAGAGAGACCTGGTGAAGTCATACAGTTCCTGGTG

TCCATTTCATATGACGGCACTGTCAGAAAGGAATCCGGCATTCCGTCAGG

CAAATTTGAGGTGGATAGGATACCTGAAACGTCTACATCCACTCTCACCA

TTCACAATGTAGAGAAACAGGACATAGCTACCTACTACTGTGCCTTGTGG

GAGGTAAAGCAAGAGTTGGGCAAAAAAATCAAGGTATTTGGTCCCGGAAC

AAAGCTTATCATTACAG (SEQ ID NO: 118)
AGHLEQPQISSTKTLSKTARLECVVSGITISATSVYWYRERPGEVIQFLV

SISYDGTVRKESGIPSGKFEVDRIPETSTSTLTIHNVEKQDIATYYCALW

EVKQELGKKIKVFGPGTKLIIT

Human Vδ21J1-FC
                                          (SEQ ID NO: 119)
GCCATTGAGTTGGTGCCTGAACACCAAACAGTGCCTGTGTCAATAGGGGT

CCCTGCCACCCTCAGGTGCTCCATGAAAGGAGAAGCGATCGGTAACTACT

ATATCAACTGGTACAGGAAGACCCAAGGTAACACAATGACTTTCATATAC

CGAGAAAAGGACATCTATGGCCCTGGTTTCAAAGACAATTTCCAAGGTGA

CATTGATATTGCAAAGAACCTGGCTGTACTTAAGATACTTGCACCATCAG

AGAGAGATGAAGGGTCTTACTACTGTGCCTGTGACCCTCTTGGCGGACCC

CCCGATAAACTCATCTTTGGAAAAGGAACCCGTGTGACTGTGGAACCAA (SEQ ID NO: 39)
AIELVPEHQTVPVSIGVPATLPCSMKGEAIGNYYINWYPKTQGNTMTFIY

REKDIYGPGFKDNFQGDIDIAKNLAVLKILAPSERDEGSYYCACDPLGGP

PDKLIFGKGTRVTVEP

Dolphin Vδ2J1-FC
                                          (SEQ ID NO: 120)
GCTGTCACGTTGGTGCCTCAAAACCAAGCAAGGAGTGTGTCTGTGGGGGA

ATCTGTCACCCTCAGGTGCTCCATGAAAGGAGACTCCATCAGTAACTATT

ATACCTTCTGGTACAGGAGAACACCGGGTAACACAATGACTCTCATATAC

CGAGAAGGGGGCACATATGGCCCTGGTTTCGAAGACAACCTCCAAGGTGA

AATTGATTTTTAAACAACCAGGCTGTGCTGAATATCCTGGAGGCATCAG

AGAGAGATGAAGGATCTTACTACTGTGCCTGTGACCCTCTTGGCGGACCC

CCCGATAAACTCATCTTTGGAAAA

GGAACCCGTGTGACTGTGGAACCAA
```

(SEQ ID NO: 47)
AVTLVPQNQARSVSVGESVTLRCSMKGDSISNYYTFWYRRTPGNTMTLIY
REGGTYGPGFEDNLQGEIDFLNNQAVLNILEASERDEGSYYCACDPLGGP
PDKLIFGKGTRVTVEP

Human/Dolphin Vδ2J1-FC (28-94)
(SEQ ID NO: 121)
GCCATTGAGTTGGTGCCTGAACACCAAACAGTGCCTGTGTCAATAGGGGT
CCCTGCCACCCTCAGGTGCTCCATGAAAGGAGACTCCATCAGTAACTATT
ATACCTTCTGGTACAGGAGAACACCGGGTAACACAATGACTCTCATATAC
CGAGAAGGGGGCACATATGGCCCTGGTTTCGAAGACAACCTCCAAGGTGA
AATTGATTTTTTAAACAACCAGGCTGTGCTGAATATCCTGGAGGCATCAG
AGAGAGATGAAGGATCTTACTACTGTGCCTGTGACCCTCTTGGCGGACCC
CCCGATAAACTCATCTTTGGAAAA
GGAACCCGTGTGACTGTGGAACCAA (SEQ ID NO: 43)
AIELVPEHQTVPVSIGVPATLRCSMKGDSISNYYTFWYRRTPGNTMTLIY
REGGTYGPGFEDNLQGEIDFLNNQAVLNILEASERDEGSYYCACDPLGGP
PDKLIFGKGTRVTVEP Human/Dolphin Vδ2J1-FC (44-94)
(SEQ ID NO: 122)
GCCATTGAGTTGGTGCCTGAACACCAAACAGTGCCTGTGTCAATAGGGGT
CCCTGCCACCCTCAGGTGCTCCATGAAAGGAGAAGCGATCGGTAACTACT
ATATCAACTGGTACAGGAGAACACCGGGTAACACAATGACTCTCATATAC
CGAGAAGGGGGCACATATGGCCCTGGTTTCGAAGACAACCTCCAAGGTGA
AATTGATTTTTTAAACAACCAGGCTGTGCTGAATATCCTGGAGGCATCAG
AGAGAGATGAAGGATCTTACTACTGTGCCTGTGACCCTCTTGGCGGACCC
CCCGATAAACTCATCTTTGGAAAAGGAACCCGTGTGACTGTGGAACCAA (SEQ ID NO: 123)
AIELVPEHQTVPVSIGVPATLRCSMKGEAIGNYYINWYRRTPGNTMTLIY
REGGTYGPGFEDNLQGEIDFLNNQAVLNILEASERDEGSYYCACDPLGGP
PDKLIFGKGTRVTVEP Human/Dolphin Vδ2J1-FC (72-94)
(SEQ ID NO: 124)
GCCATTGAGTTGGTGCCTGAACACCAAACAGTGCCTGTGTCAATAGGGGT
CCCTGCCACCCTCAGGTGCTCCATGAAAGGAGAAGCGATCGGTAACTACT
ATATCAACTGGTACAGGAAGACCCAAGGTAACACAATGACTTTCATATAC
CGAGAAAAGGACATCTATGGCCCTGGTTTCGAAGACAACCTCCAAGGTGA
AATTGATTTTTTAAACAACCAGGCTGTGCTGAATATCCTGGAGGCATCAG
AGAGAGATGAAGGATCTTACTACTGTGCCTGTGACCCTCTTGGCGGACCC
CCCGATAAACTCATCTTTGGAAAAGGAACCCGTGTGACTGTGGAACCAA (SEQ ID NO: 45)
AIELVPEHQTVPVSIGVPATLRCSMKGEAIGNYYINWYRKTQGNTMTFTY
REKDIYGPGFEDNLQGEIDFLNNQAVLNILEASERDEGSYYCACDPLGGP
PDKLIFGKGTRVTVEP Human Dolphin Vδ2J1-FC (82-94)
(SEQ ID NO: 125)
GCCATTGAGTTGGTGCCTGAACACCAAACAGTGCCTGTGTCAATAGGGGT
CCCTGCCACCCTCAGGTGCTCCATGAAAGGAGAAGCGATCGGTAACTACT
ATATCAACTGGTACAGGAAGACCCAAGGTAACACAATGACTTTCATATAC
CGAGAAAAGGACATCTATGGCCCTGGTTTCAAAGACAATTTCCAAGGTGA
CATTGATTTTTTAAACAACCAGGCTGTGCTGAATATCCTGGAGGCATCAG
AGAGAGATGAAGGATCTTACTACTGTGCCTGTGACCCTCTTGGCGGACCC
CCCGATAAACTCATCTTTGGAAAAGGAACCCGTGTGACTGTGGAACCAA (SEQ ID NO: 41)
AIELVPEHQTVPVSIGVPATLRCSMKGEAIGNYYINWYRKTQGNTMTFIY
PEKDIYGPGFKDNFQGDIDFLNNQAVLNILEASERDEGSYYCACDPLGGP
PDKLIFGKGTRVTVEP Human Vδ21J1-FC (CDR1-S)
(SEQ ID NO: 126)
GCCATTGAGTTGGTGCCTGAACACCAAACAGTGCCTGTGTCAATAGGGGT
CCCTGCCACCCTCAGGTGCTCCATGAAAGGAGAAGCGATCAGTAACTACT
ATATCAACTGGTACAGGAAGACCCAAGGTAACACAATGACTTTCATATAC
CGAGAAAAGGACATCTATGGCCCTGGTTTCAAAGACAATTTCCAAGGTGA
CATTGATATTGCAAAGAACCTGGCTGTACTTAAGATACTTGCACCATCAG
AGAGAGATGAAGGGTCTTACTACTGTGCCTGTGACCCTCTTGGCGGACCC
CCCGATAAACTCATCTTTGGAAAAGGAACCCGTGTGACTGTGGAACCAA (SEQ ID NO: 127)
AIELVPEHQTVPVSIGVPATLRCSMKGEAISNYYINWYRKTQGNTMTFIY
REKDIYGPGFKDNFQGDIDIAKNLAVLKILAPSERDEGSYYCACDPLGGP
PDKLIFGKGTRVTVEP Human Vδ21J1-FC (CDR2-G)
(SEQ ID NO: 128)
GCCATTGAGTTGGTGCCTGAACACCAAACAGTGCCTGTGTCAATAGGGGT
CCCTGCCACCCTCAGGTGCTCCATGAAAGGAGAAGCGATCGGTAACTACT
ATATCAACTGGTACAGGAAGACCCAAGGTAACACAATGACTTTCATATAC
CGAGAAAGGGCATCTATGGCCCTGGTTTCAAAGACAATTTCCAAGGTGA
CATTGATATTGCAAAGAACCTGGCTGTACTTAAGATACTTGCACCATCAG
AGAGAGATGAAGGGTCTTACTACTGTGCCTGTGACCCTCTTGGCGGACCC
CCCGATAAACTCATCTTTGGAAAAGGAACCCGTGTGACTGTGGAACCAA (SEQ ID NO: 129)
AIELVPEHQTVPVSIGVPATLRCSMKGEAIGNYYINWYRKTQGNTMTFIY
REKGIYGPGFKDNFQGDIDIAKNLAVLKILAPSERDEGSYYCACDPLGGP
PDKLIFGKGTRVTVEP Human Vδ21J1-FC (CDR3-S)
(SEQ ID NO: 130)
GCCATTGAGTTGGTGCCTGAACACCAAACAGTGCCTGTGTCAATAGGGGT
CCCTGCCACCCTCAGGTGCTCCATGAAAGGAGAAGCGATCGGTAACTACT
ATATCAACTGGTACAGGAAGACCCAAGGTAACACAATGACTTTCATATAC
CGAGAAAAGGACATCTATGGCCCTGGTTTCAAAGACAATTTCCAAGGTGA
CATTGATATTGCAAAGAACCTGGCTGTACTTAAGATACTTGCACCATCAG

```
AGAGAGATGAAGGGTCTTACTACTGTGCCTCTGACCCTCTTGGCGGACCC

CCCGATAAACTCATCTTTGGAAAAGGAACCCGTGTGACTGTGGAACCAA (SEQ ID NO: 131)
AIELVPEHQTVPVSIGVPATLRCSMKGEAIGNYYINWYRKTQGNTMTFIY

REKDIYGPGFKDNFQGDIDIAKNLAVLKILAPSERDEGSYYCASDPLGGP

PDKLIFGKGTRVTVEP
```

ELISA Results are Shown in FIG. 48, Identifying the Following Epitope Bins:

| Bin | 1 | 2 | 3 | 4 |
|---|---|---|---|---|
| Residues | 83-94 | 28-38 | 72-83 | 1-27 |
| mAbs | δ2-17 B6 | 15D | δ 2-32 | δ 2-14 |
|  |  |  |  | δ 2-22 |
|  |  |  |  | δ 2-30 |
|  |  |  |  | δ 2-31 |
|  |  |  |  | δ 2-36 |
|  |  |  |  | δ 2-37 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An ex vivo method for producing an enriched γδ T-cell population from an isolated mixed cell population, comprising directly contacting the mixed cell population with one or more agents which selectively expand δ2 γδ T-cells by binding to an activating epitope specific to a δ2 TCR to provide clinically-relevant levels of the enriched γδ T-cell population;

wherein the one or more agents which selectively expand δ2 γδ T-cells are selected from an antibody that specifically binds to an epitope comprising a δ2 variable region of a human δ2 TCR and comprising the six complementarity determining regions (CDRs) of δ2-14, δ2-17, δ2-30, δ2-31, δ2-32, δ2-33, δ2-35, δ2-36, or δ2-37.

2. The method of claim 1, wherein the one or more agents which selectively expand δ2 T-cells are selected from an antibody comprising a HCVR/LCVR sequence pair selected from the group consisting of SEQ ID NOs: 207/216, 208/217, 209/219, 210/220, 211/221, 212/222, 213/223, 214/224, and 215/225.

3. The method of claim 1, wherein the percentage of δ2 T-cells in the enriched γδ T-cell population is greater than 60% δ2 T-cells of total viable cells.

4. The method of claim 3, wherein the percentage of δ2 T-cells in the enriched γδ T-cell population is greater than 80% δ2 T-cells of total viable cells.

5. The method of claim 1, wherein:

(i) the enriched γδ T-cell population is not expanded by an antigen presenting cell or an aminophosphate;

(ii) the one or more agents which selectively expand δ2 T-cells are immobilized on a surface;

(iii) the isolated mixed cell population is selected from a peripheral blood sample, a cord blood sample or a tumor;

(iv) the enriched γδ T-cell population comprises polyclonal TCR diversity;

(v) the enriched γδ T-cell population is formulated for administration to a subject;

(vi) the enriched γδ T-cell population includes a therapeutically effective amount of γδ T-cells; and/or (vii) the enriched γδ T-cell population is engineered to stably express one or more antigen recognition moieties.

6. The method of claim 5, wherein the γδ T-cell population is engineered to express two or more antigen recognition moieties.

7. The method of claim 6, wherein the two or more antigen recognition moieties are different, and wherein each different antigen recognition moiety is engineered to recognize different epitopes of the same antigen or to recognize different epitopes of different antigens.

8. The method of claim 5, wherein the antigen recognition moiety recognizes a tumor antigen, an antigen associated with an autoimmune disease, or a pathogenic antigen.

9. The method of claim 8, wherein said antigen recognition moiety is selected from the group consisting of a TCR, αβ TCR, γδ TCR, a chimeric antigen receptor (CAR), whole antibody or their antigen-binding fragment, single-chain variable fragment (scFv), a heavy chain or a light chain single domain antibody (sdAb), a Fab, a F(ab)$_2$, or any combination thereof that binds to: (i) a cell surface tumor antigen, (ii) a peptide derived from a tumor antigen expressed on the cell surface as a complex with MHC (peptide-MHC complex), (iii) a cell surface antigen associated with an autoimmune disease or a pathogen, or (iv) a peptide derived from an antigen associated with an autoimmune disease or a pathogen expressed on the cell surface as a complex with MHC (peptide-MHC complex).

10. The method of claim 8, wherein the pathogenic antigen is a bacterial antigen or a viral antigen.

11. The method of claim 5, wherein the engineered γδ T-cells are further engineered to lack gene expression from at least one HLA loci.

12. The method of claim 5, wherein the engineered γδ T-cells are universal donor cells.

13. The method of claim 1, wherein the method comprises serum-free culture conditions and/or suspension cell culture conditions.

14. The method of claim 1, wherein the method achieves at least $10^8$ γδ T-cells expanded from the isolated mixed population of cells within less than 90 days, less than 60 days, less than 30 days, less than 21 days, or less than 19 days from:

initiation of a first expansion, a step of providing a donor sample, or a first step of directly contacting the mixed cell population with the one or more agents.

15. The method of claim 1, wherein the isolated mixed cell population comprises a whole PBMC population without prior depletion of monocytes, αβ T-cells, B-cells, and NK cells.

16. The method of claim 1, further comprising removing one or more of red blood cells, NK cells, αβ cells, B-cells, monocytes, and macrophages prior to selectively expanding the δ2 γδ T-cells.

17. The method of claim 1, wherein contacting the mixed cell population with one or more agents which selectively expand δ2 T-cells further comprises culture conditions comprising a cytokine selected from IL-2, IL-7, IL-9, IL-12, IL-15, IL-18, IL-21, IL-23, and IL-33.

18. The method of claim 17, wherein the cytokine is selected from the group consisting of IL-2, IL-7, and IL-15.

19. The method of claim 1, further comprising directly contacting at least a portion of the enriched γδ T-cell population with one or more agents that (a) expand γδ T-cells, and/or (b) deplete αβ T-cells.

20. The method of claim 19, comprising:

(i) selectively expanding δ2 T-cells by binding to an activating epitope specific of a δ2 TCR in a first γδ T-cell expansion, thereby producing a first enriched γδ T-cell population; and then (ii) directly contacting at least a portion of the first enriched γδ T-cell population with antigen presenting cells (APCs) in a second γδ T-cell expansion, thereby producing a second enriched γδ T-cell population, wherein the second enriched γδ T-cell population comprises a clinically relevant number of γδ T-cells.

21. The method of claim 1, wherein the activating epitope is selected from a δ2 TCR Bin 1 δ2 epitope, a Bin 3 δ2 epitope, and a Bin 4 δ2 epitope of a human δ2 TCR.

22. The method of claim 1, comprising:

(i) directly contacting the mixed cell population with one or more first activating agents which selectively expand δ2 T-cells by binding to an activating epitope specific of a δ2 TCR in a first γδ T-cell expansion, thereby producing a first enriched γδ T-cell population; and then (ii) directly contacting at least a portion of the first enriched γδ T-cell population with one or more second activating agents that (a) expand γδ T-cells, or (b) selectively expand δ1 T-cells by binding to an activating epitope specific of a δ1 TCR;

δ2 T-cells by binding to an activating epitope specific of a δ2 TCR;

δ1 T-cells, δ3 T-cells, δ4 T-cells, and δ5 T-cells by binding to an activating epitope specific of a δ1 TCR, a δ3 TCR, a δ4 TCR, and a δ5 TCR; or δ1 T-cells and δ4 T-cells by binding to an activating epitope specific of a δ1 TCR and a δ4 TCR in a second γδ T-cell expansion, thereby producing a second enriched γδ T-cell population.

23. The method of claim 20, wherein: (a) one or more of the second activating agents are structurally different from one or more of the activating agents of the first γδ T-cell expansion.

24. The method of claim 22, wherein: (a) one or more of the second activating agents are structurally different from one or more of the activating agents of the first γδ T-cell expansion.

25. The method of claim 1, comprising:

(i) directly contacting the mixed cell population with one or more activating agents which selectively expand δ2 T-cells by binding to an activating epitope specific of a δ2 TCR in a first γδ T-cell expansion, thereby producing a first enriched γδ T-cell population; and then (ii) directly contacting at least a portion of the enriched γδ T-cell population with one or more agents that deplete αβ T-cells, thereby producing a second enriched γδ T-cell population.

26. The method of claim 17, wherein the culture conditions do not comprise IL-4, and wherein the mixed cell population has not been exposed to exogenous IL-4 prior to expansion.

27. The method of claim 18, wherein the culture conditions do not comprise IL-4, and wherein the mixed cell population has not been exposed to exogenous IL-4 prior to expansion.

28. The method of claim 8, wherein the antigen recognition moiety recognizes an antigen selected from the group consisting of CD19, CD20, CD30, CD22, CD37, CD38, CD56, CD33, CD138, CD123, CD79b, CD70, CD75, CA6, GD2, alphafetoprotein (AFP), carcinoembryonic antigen (CEA), RON, CEACAM5, CA-125, MUC-16, ST4, NaPi2b, ROR1, ROR2, PLIF, Her2/Neu, EGFRvIII, GPMNB, LIV-1, glycolipidF77, fibroblast activation protein (FAP), PSMA, STEAP-1, STEAP-2, mesothelin, c-Met, CSPG4, PVRL-4, VEGFR2, PSCA, CLEC12a, LICAM, FPC2, GPC3, folate binding protein/receptor, SLC44A4, Cripto, CTAG1B, AXL, IL-13R, 13-3Rα2, SLTRK6, gp100, MARTI, Tyrosinase, SSX2, SSX4, NYESO-1, WT-1, PRAME, epithelial tumor antigen (ETA), MAGEA family genes, KKLC1, mutated ras, p53, MHC class I chain-related molecule A (MICA), or MHC class I chain-related molecule B (MICB), or one or more antigens of HPV, CMV, or EBV.

29. The method of claim 20, wherein the second γδ T-cell expansion further comprises directly contacting at least a portion of the enriched γδ T-cell population with one or more second activating agents which:

selectively expand δ1 T-cells by binding to an activating epitope specific of a δ1 TCR;

selectively expand δ1 T-cells, δ3 T-cells, δ4 T-cells, and δ5 T-cells by binding to an activating epitope specific of a δ1 TCR, a δ3 TCR, a δ4 TCR, and a δ5 TCR;

selectively expand δ1 T-cells and δ4 T-cells by binding to an activating epitope specific of a δ1 TCR and a δ4 TCR; or selectively expand δ2 T-cells by binding to an activating epitope specific of a δ2 TCR.

30. The method of claim 6, wherein the antigen recognition moiety recognizes a tumor antigen, an antigen associated with an autoimmune disease, or a pathogenic antigen.

31. The method of claim 30, wherein the pathogenic antigen is a bacterial antigen or a viral antigen.

* * * * *